(12) United States Patent
Song et al.

(10) Patent No.: US 8,597,630 B2
(45) Date of Patent: Dec. 3, 2013

(54) THERMAL-RESPONSIVE POLYMER NETWORKS, COMPOSITIONS, AND METHODS AND APPLICATIONS RELATED THERETO

(75) Inventors: Jie Song, Shrewsbury, MA (US); Jianwen Xu, Worcester, MA (US)

(73) Assignee: University of Massachusetts, Boston, MA (US)

( * ) Notice: Subject to any disclaimer, the term of this patent is extended or adjusted under 35 U.S.C. 154(b) by 746 days.

(21) Appl. No.: 12/748,301

(22) Filed: Mar. 26, 2010

(65) Prior Publication Data

US 2010/0280561 A1    Nov. 4, 2010

Related U.S. Application Data

(63) Continuation-in-part of application No. 12/450,872, filed as application No. PCT/US2008/005059 on Apr. 18, 2008.

(60) Provisional application No. 60/925,329, filed on Apr. 19, 2007.

(51) Int. Cl.
*A61K 47/30* (2006.01)
*C08G 63/08* (2006.01)

(52) U.S. Cl.
USPC ........ 424/78.08; 528/365; 528/367; 528/405; 528/425

(58) Field of Classification Search
USPC ......... 424/78, 78.08; 528/365, 367, 405, 425; 523/113
See application file for complete search history.

(56) References Cited

FOREIGN PATENT DOCUMENTS

JP    2006010829 A * 1/2006

OTHER PUBLICATIONS

Bozic (ACS Symposium Series, 916 New Polymeric Materials, Published 2005, pp. 201-214).*
Ropponen et al. (Journal of Polymer Science: Part A: Polymer Chemistry, vol. 42, pp. 5574-5586, Published 2004).*
Hult et al. (Macromolecules, 29, Published 1996, pp. 1222-1228).*

* cited by examiner

*Primary Examiner* — Richard Schnizer
*Assistant Examiner* — Alma Pipic
(74) *Attorney, Agent, or Firm* — Milstein Zhang & Wu LLC

(57) ABSTRACT

The invention relates to materials comprising polymer network containing siloxanes or organic-based core structures, preferably the materials have thermal-responsive properties. In some embodiments, the invention relates to an organic core functionalized with polymers. In another embodiment, organic core-polymer conjugates comprise polylactone segments. The organic core-polymer conjugates may be crosslinked together to form a material, and these materials may be functionalized with bioactive compounds so that the materials have desirable biocompatibility or bioactivity when used in medical devices. In some embodiments, the invention relates to silsesquioxane groups functionalized with polymers. In another embodiment, silsequioxane-polymer conjugates comprise polylactone segments. The silsesquioxane-polymer conjugates may be crosslinked together to form a material, and these materials may be functionalized with bioactive compounds so that the materials have desirable biocompatibility or bioactivity when used in medical devices. In further embodiments, the invention relates to composite materials that contain a polymer matrix and aggregates, and in some embodiments, methods of making, and methods of using these materials. Preferably, the aggregates are calcium phosphate aggregates. Preferably, the material is resistant to fracture. In further embodiments, the materials are used in surgical procedures of bone replacement. In further embodiments, the materials contain polyhedral silsesquioxanes and/or biodegradable segments.

9 Claims, 49 Drawing Sheets

A

B (a) Random structure (b) Ladder structure ($T_8$)
(c)

($T_{10}$)
(d)

($T_{12}$)
(e)

Cage structures

B

C

| | $M_n$ | Theoretical | GPC | NMR | PDI |
|---|---|---|---|---|---|
| n=10 | | 7245 | 7328 | 5587 | 1.20 |
| n=20 | | 13010 | 13576 | 9988 | 1.19 |
| n=40 | | 24541 | 25788 | 19576 | 1.36 |

D

E

F

G

| Shape memory polymer samples | Storage Modulus at 37 °C (MPa) | Storage Modulus at 80 °C (MPa) | Tan Delta | $T_{trans}$ (°C)* |
|---|---|---|---|---|
| 2, n=10 | 2196±56 | 4.156±0.084 | 2.407±0.051 | 52.7±0.81 |
| 2, n=20 | 2745.7±204.3 | 2.316±0.081 | 2.875±0.034 | 58.7±0.47 |
| 7, n=20 | 2581.7±108.7 | 1.482±0.098 | 2.768±0.068 | 53.4±0.43 |
| 2, n=40 | 2545.7±260.3 | 1.649±0.118 | 2.936±0.041 | 61.6±0.61 |

C

D

E

F

A

B

C

SEQUENCE LISTING

```
<160> NUMBER OF SEQ ID NOS: 2

<210> SEQ ID NO 1
<211> LENGTH: 5
<212> TYPE: PRT
<213> ORGANISM: Artificial Sequence
<220> FEATURE:
<223> OTHER INFORMATION: Synthetic

<400> SEQUENCE: 1

Gly Arg Gly Asp Ser
1               5

<210> SEQ ID NO 2
<211> LENGTH: 12
<212> TYPE: PRT
<213> ORGANISM: Artificial Sequence
<220> FEATURE:
<223> OTHER INFORMATION: Synthetic

<400> SEQUENCE: 2

Asn Pro Tyr His Pro Thr Ile Pro Gly Ser Val His
1               5                   10
```

THERMAL-RESPONSIVE POLYMER NETWORKS, COMPOSITIONS, AND METHODS AND APPLICATIONS RELATED THERETO

This application is a continuation-in-part of application Ser. No. 12/450,872 filed Nov. 24, 2009, which is a national stage entry of PCT/US08/05059 filed Apr. 18, 2008, which claims priority from provisional application 60/925,329 filed Apr. 19, 2007.

STATEMENT OF GOVERNMENT SUPPORT

This invention was made with government support under grants R01AR055615 and R01GM088678 awarded by the National Institutes of Health and under grant S10 RR021043 awarded by the National Center for Research Resources. The government has certain rights in the invention.

FIELD OF INVENTION

The present invention relates to shape memory compositions and methods of making and using these compositions. Such compositions are designed with inherent shape memory properties that remain fixed at specific temperatures. Some compositions comprise polymer mixtures providing tunable transition temperatures that allows a composition to change shape at predetermined temperatures. The structural components of the compositions may be based upon any multifunctional building block core, wherein the building blocks may be functionalized with a variety of reactive groups.

BACKGROUND

Thermal-responsive materials—shape memory alloys (SMA) and shape memory polymers (SMP)—are capable of switching between shapes upon exposure to a particular thermal environment. This unique property can be utilized to enhance the performance of many biomedical devices. However, known materials have certain physical property limitations that hinder broad use in biomedical applications. Some of these properties include low deformability (<8%), the necessity of high-temperature and time-consuming processing, as well as poor biocompatibility and degradability. Such properties are beneficial in, for example, the surgical removal of bone segments, a common treatment for osteosarcoma. The lack of a bone segment presents substantial problems for the patients, which are typically addressed by bone grafts. Bone cement such as Plexiglas, polymethylmethacrylate (PMMA), is used in joint, hip and shoulder replacement surgeries to bond metallic devices with bone. The benefits of such surgeries suffer from a relatively short lifetime due to PMMA's limited capacity to integrate with bony tissue and susceptibility to fatigue and fracture. Moreover, these organic scaffolds are intrinsically weak, and do not provide immediate solutions for large skeletal defects where moderate loads are expected. Thus, there is a need to develop materials that overcome both the limitations of currently employed materials and a need to develop bone substitutes that provide flexibility that facilitates surgical fitting, a degree of porosity to promote osteointegration, and strength and toughness against compressive forces.

SUMMARY OF THE INVENTION

The present invention relates to shape memory compositions and methods of making and using these compositions. Such compositions are designed with inherent shape memory properties that remain fixed at specific temperatures. Some compositions comprise polymer mixtures providing tunable transition temperatures that allows a composition to change shape at predetermined temperatures. The structural components of the compositions may be based upon any multifunctional building block core, wherein the building blocks may be functionalized with a variety of reactive groups.

In one embodiment, the present invention contemplates a generic organic core structure of $X-(Y-Z)_n$, where n is equal to or greater than 3. In one embodiment, X can include, but is not limited to, hydrocarbons, heteroatoms, alkyls, substituted alkyls, alkenyls, substituted alkenyls, alkynyls, substituted alkynyls, aryls, substituted aryls, heterocycles, substituted heterocycles, esters, amides, carbonates, orthoesters, and/or phosphates. In one embodiment, Y can include, but is not limited to hydrocarbons, heteroatoms, alkyls, substituted alkyls, alkenyls, substituted alkenyls, alkynyls, substituted alkynyls, aryls, substituted aryls, heterocycles, substituted heterocycles, esters, amides, carbonates, orthoesters, and/or phosphates. In one embodiment, Z can include, but is not limited to, hydroxyls, amines (i.e., for example, primary, secondary, tertiary amines etc.), sulfryl, carboxylic acids, azides, alkenyl, and/or alkynyl.

In one embodiment, the present invention contemplates compositions comprising a plurality of multifunctional building block cores wherein a) the building blocks can be, but are not limited to; i) hydrocarbon units, ii) aromatic units, iii) heterocycles (i.e., for example, porphoryin units), and/or iv) polyhedral oligomeric silsesquioxane (POSS) units; and b) functional groups attached to the building blocks can be, but are not limited to; i) hydroxyl, ii) amine, iii) sulfonyl, iv) carboxylic, v) alkenyl, vi) alkynyl, and/or vii) azido. In one embodiment, the present invention contemplates compositions with non-degradable polymer chains, wherein the polymer chain includes, but is not limited to, polystyrenes, polyacrylates, polyacrylamides, polymethacrylates, and/or polymethacrylamides. In one embodiment, the polymer chain may range in length from between approximately 2-10,000 polymer units. In one embodiment, the present invention contemplates compositions comprising a plurality of biodegradable polymer chains, wherein the polymers have poly (functional groups). In one embodiment, the biodegradable polymer chains are polyanhydrides. In one embodiment, the biodegradable polymer chains are polyesters. In one embodiment, the biodegradable polymer chains are polyorthoesters. In one embodiment, the biodegradable polymer chains are polyureas. In one embodiment, the biodegradable polymer chains are polyurethanes. In one embodiment, the biodegradable polymer chains are polycarbonates. In one embodiment, the biodegradable polymer chains are polyamides. In one embodiment, the biodegradable polymer chains are polyphosphazenes. In one embodiment, the composition further comprises covalent crosslinking between the polymers. In one embodiment, the covalent crosslinking is selected from the group including, but not limited to, isocyanate crosslinks, urethane crosslinks, ether crosslinks, ester crosslinks, amide crosslinks, anhydride crosslinks, epoxide crosslinks, maleimide crosslinks, alkyne crosslinks, and/or azido-derived triazole crosslinks. In one embodiment, the composition further comprises non-covalent crosslinking. In one embodiment, the non-covalent crosslinking comprises hydrogen-bonding (H-bonding) interactions. In one embodiment, the non-covalent crosslinking comprises electrostatic interactions. In one embodiment, the non-covalent crosslinking comprises pi-pi interactions. In one embodiment, the non-covalent crosslinking comprises hydrophobic interactions. In one embodiment, the non-covalent crosslinking comprises van der waals interactions.

In one embodiment, the present invention contemplates a composition comprising; a) at least one hydrocarbon chain with at least one functional group; b) at least one polymer group attached to said at least one functional group; and c) at least one linking group attached to said at least one polymer group. In one embodiment, the at least one hydrocarbon chain is substituted with three or more of said polymer groups to form a plurality of hydrocarbon-polymer conjugates. In one embodiment, the linking groups join two or more of said hydrocarbon-polymer conjugates. In one embodiment, the hydrocarbon chain functional group is selected from the group consisting of polyol, polyamine, polysulfryl, polycarbonate, polyester, and polylactone. In one embodiment, the composition has one-way or two-way shape memory. In one embodiment, the composition has a $T_g$ between −60° C. and 150° C. In one embodiment, the material has a $T_g$ between 37° C. and 70° C. In one embodiment, the hydrocarbon chain is 2,2'-oxybis(methylene)bis(2-ethylpropane-1,3-diol). In one embodiment, the linking groups are selected from the group consisting of alkyl, aryl, urethane, and polyethylene groups.

In one embodiment, the present invention contemplates a single shape memory polymer (SMP) composition comprising multiple tunable transition temperature ranges, wherein the composition changes shape at multiple predetermined temperatures. Although it is not necessary to understand the mechanism of an invention, it is believed that the multiple tunable transition temperatures are predetermined by the exact mixture (i.e., for example, a specific ratio of chemical composition and/or structure) of polymers and cores and respective quantities. In one embodiment, the mixtures of polymers include, but are not limited to, block co-polymers, homopolymers, and random co-polymers that may be used to modify the transition temperature. Furthermore, it is not intended that the present invention be limited to the classification of polymeric segments that comprise the invention; preferred embodiments include but are in no way limited to monomeric polymers or homopolymers, copolymers and block copolymers. In further embodiments, the end groups comprise alkenyl groups, including but not limited to acrylate or methacrylate. In further embodiments, the end groups or the side chain end groups of the polymeric segments are crosslinked with diisocyanate, diester, diacid, or diacyl by condensation chemistry when the end groups are nucleophilic groups (such as —OH, —NH$_2$, —SH, —COOH). In further embodiments, the end groups are crosslinked with high fidelity chemical ligation (such as the modified Staudinger ligation, the "Click" chemistry).

In one embodiment, the present invention contemplates a method comprising: a) providing; i) a shape memory polymer; and ii) an energy generation device capable of directing energy at the shape memory polymer; b) using the energy generation device, wherein the shape memory polymer is reshaped. In one embodiment, the device directs heat energy. In another embodiment, the device generates light energy. In one embodiment, the light energy is infrared light energy. In one embodiment, the light energy is ultraviolet light energy. In one embodiment, the light energy is visible light energy. In another embodiment, the light energy is electromagnetic energy.

In one embodiment, the present invention contemplates a composition comprising an Organic core with pendant polymers, wherein the polymer comprises a photo-active functional group. In one embodiment, the organic core pendant polymer comprises a photo-active functional group wherein the shape memory is initiated and related to the photo-active functional groups.

In additional embodiments, the invention relates to organic compound-based nanoparticles that are anchors for grafting polymer domains in bone grafts. One can crosslink any of the star-shaped macromers in the presence of varying percentages of calcium phosphate or apatite mineral (i.e., for example, hydroxyapatite, HA) and/or tricalcium phosphate (TCP) powders using appropriate crosslinkers. One chooses a crosslinker depending on the functional groups substituted on the macromers. For instance, with the Org-(PLA$_n$)$_8$ macromer, since the terminus of each arm is a free hydroxyl, one uses a diisocyanate crosslinker (via urethane linkages). For those macromers with additional polymer blocks grafted to each PLA arm via controlled polymerizations (i.e., for example, RAFT, ATRP), the crosslinker could depend on the functional groups, preferably the terminal functional group, displayed on the side chains on the grafted polymer blocks. In the case of Org-(PLA$_n$-co-pHEMA$_m$)$_8$, one can crosslink with a diisocyanate since the pHEMA block contains hydroxyl side chains. Alternatively, one can terminate Org-(PLA$_n$)$_8$ or Org-(PLA$_n$-co-pHEMA$_m$)$_8$, with alkylacrylates containing hydroxyl side chains. It is also contemplated that for macromers containing functional blocks displaying azido side chains, preferably terminal azido groups, one can use acetylene-based crosslinkers.

In one embodiment, the present invention contemplates a generic organic core structure with the formula of X—(Y)$_m$—(Z)$_n$.

In one embodiment, the present invention contemplates a material comprising: a) polyol moieties, b) polymer groups, and c) linking groups; wherein said polyol moieties are substituted with three or more of said polymer groups to form a plurality of polyol-polymer conjugates; and said linking groups join two or more of said polyol-polymer conjugates. In one embodiment, said polymer groups are polyester groups. In one embodiment, said material has one-way or two-way shape memory. In one embodiment, said material has a $T_g$ between 17° C. and 100° C. In one embodiment, said material has a $T_g$ between 37° C. and 70° C. In one embodiment, said polyol moiety is 2,2'-oxybis(methylene)bis(2-ethylpropane-1,3-diol). In one embodiment, said polyester groups are polylactones. In one embodiment, said linking groups comprise alkyl, aryl, or polyethylene groups. In one embodiment, said linking groups comprises urethane groups. In one embodiment, the present invention contemplates a method of supplementing or repairing a bone in a subject comprising: 1) providing a) the material above, and b) a subject suspected of or exhibiting symptoms associated with a bone disorder or dysfunction; and 2) administering said material to said subject under conditions such said symptoms are reduced. In one embodiment, said mode of administration is surgical implantation. In one embodiment, the present invention contemplates a method wherein the bone exhibiting said bone disorder or dysfunction is selected from the group consisting of cranial bones, mandible, ulna, humerus, radius, vertebrae, carpals, metacarpals, phalanges, ilium, ischium, pubis, femur, hip joint, patella, tibia, fibula, tarsals and metatarsals. In one embodiment, the present invention contemplates a method wherein said bone disorder or dysfunction is selected from the group consisting of bone fracture, bone cyst, bone spur, bone tumor, craniosynostosis, fibrodysplasia ossificans progressiva, fibrous dysplasia, giant cell tumor of bone, hypophosphatasia, Klippel-Feil syndrome, metabolic bone disease, osteitis deformans, osteitis fibrosa cystica, osteitis pubis, condensing osteitis, osteitis condensans ilii, osteochondritis dissecans, osteochondroma, osteogenesis imperfecta, osteomalacia, osteomyelitis, osteopenia, osteopetrosis, osteoporosis, osteosarcoma, porotic hyperostosis, primary hyperparathyroidism and renal osteodystrophy. In one embodiment, said subject is a mammal.

In yet another embodiment, the present invention contemplates an Organic core comprising a compound having the formula:
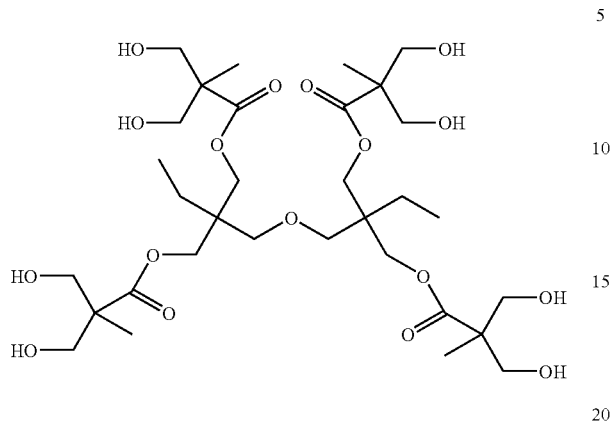
In yet another embodiment, the invention contemplates a composition comprising an Org-(PLA$_{10}$)$_8$ having the formula:
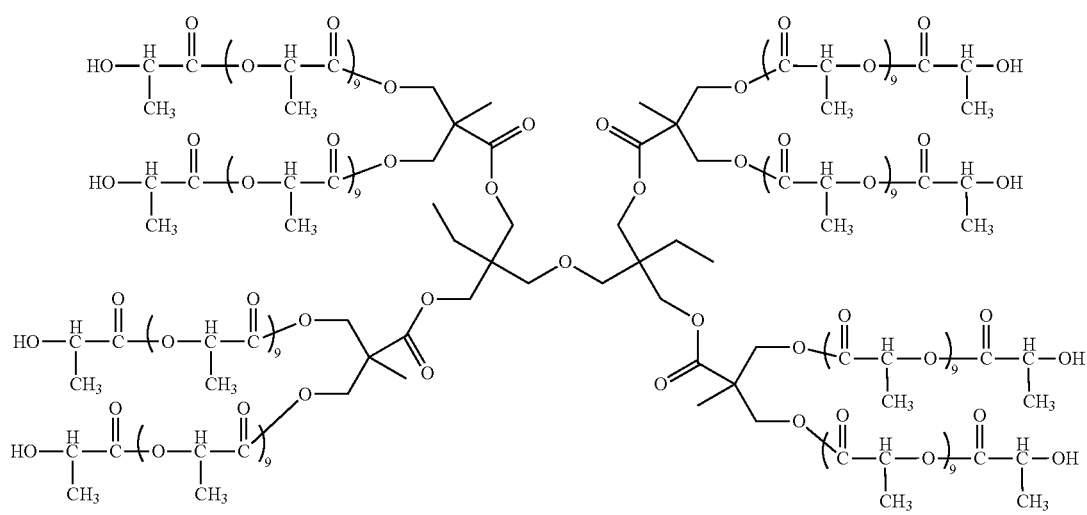
In yet another embodiment, the invention contemplates a composition comprising an Org-(PLA$_{20}$)$_8$ having the formula:
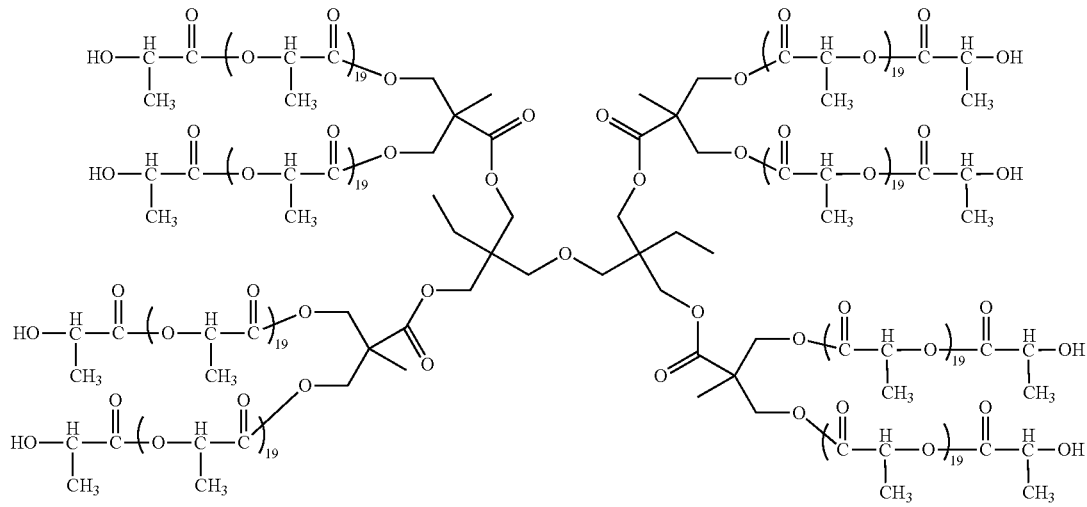

In yet another embodiment, the invention contemplates a composition comprising an Org-(PLA$_{40}$)$_8$ having the formula:
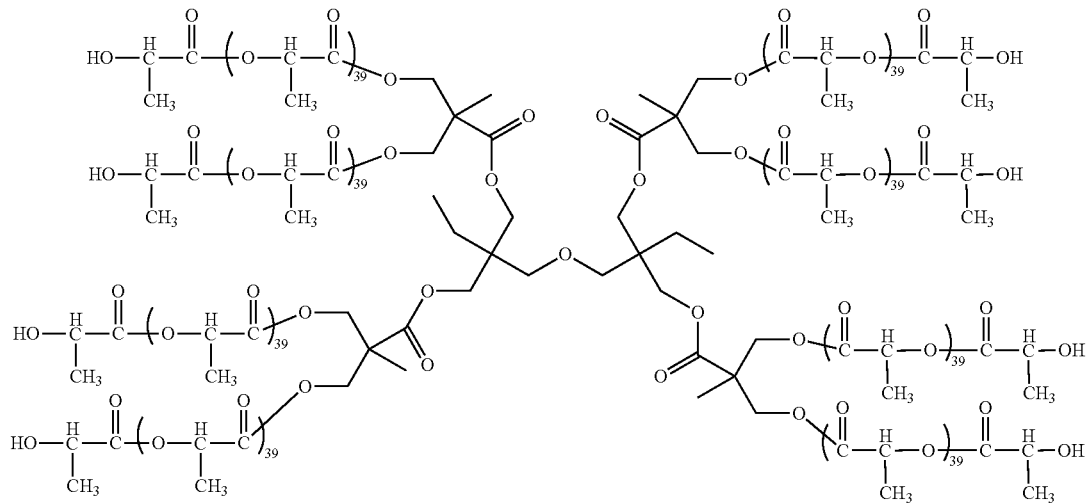
In yet another embodiment, the invention contemplates a composition comprising an Org-(PLA$_{10}$)$_{16}$ having the formula:
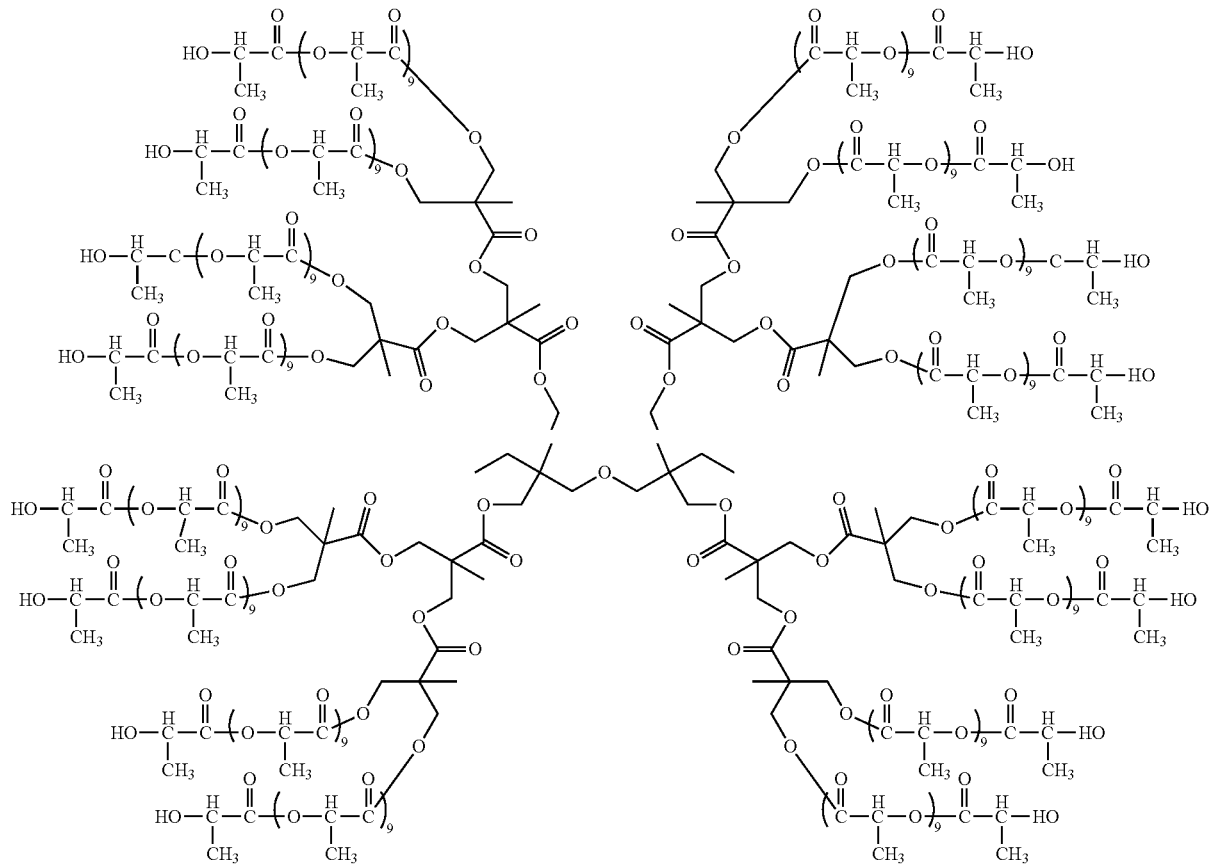

In yet another embodiment, the invention contemplates a composition comprising an Org-(PLA$_{20}$)$_{16}$ having the formula:
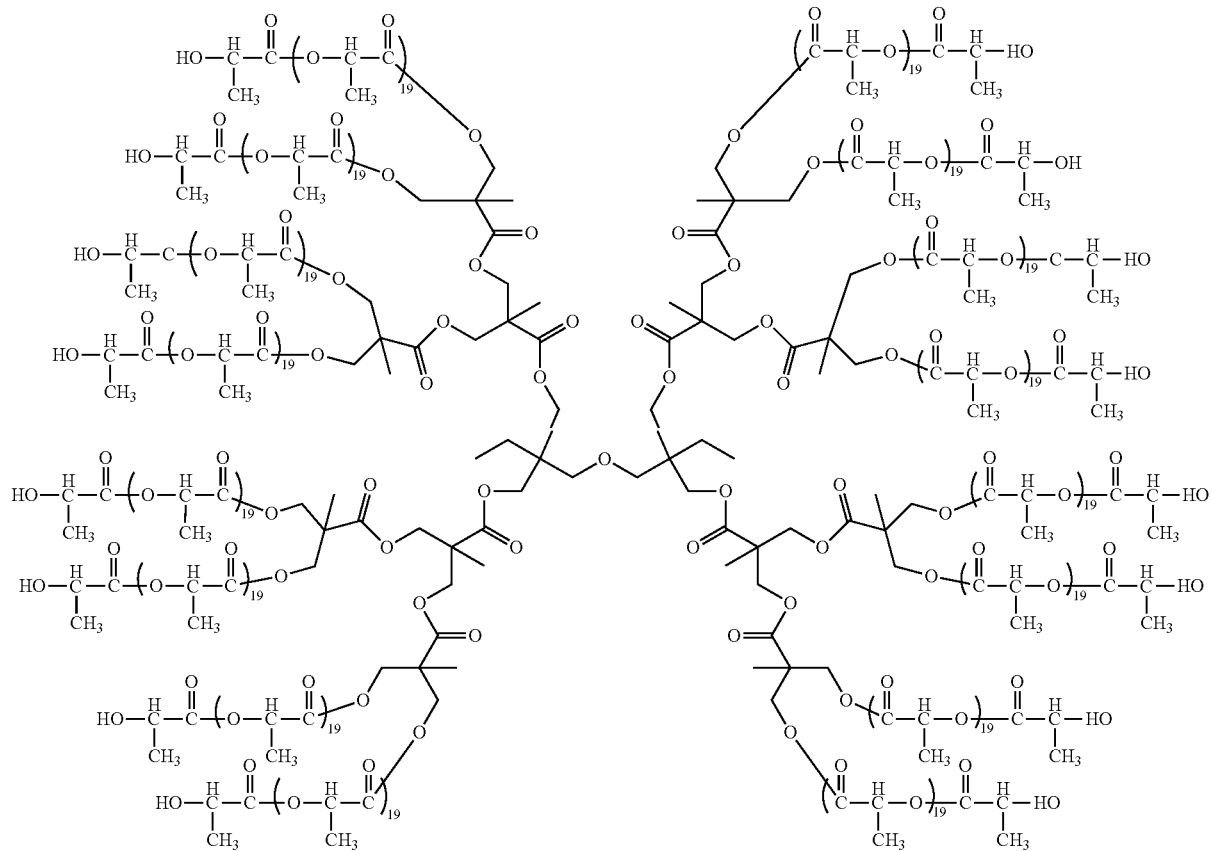
In yet another embodiment, the invention contemplates a composition comprising an Org-(PLA$_{40}$)$_{16}$ having the formula:
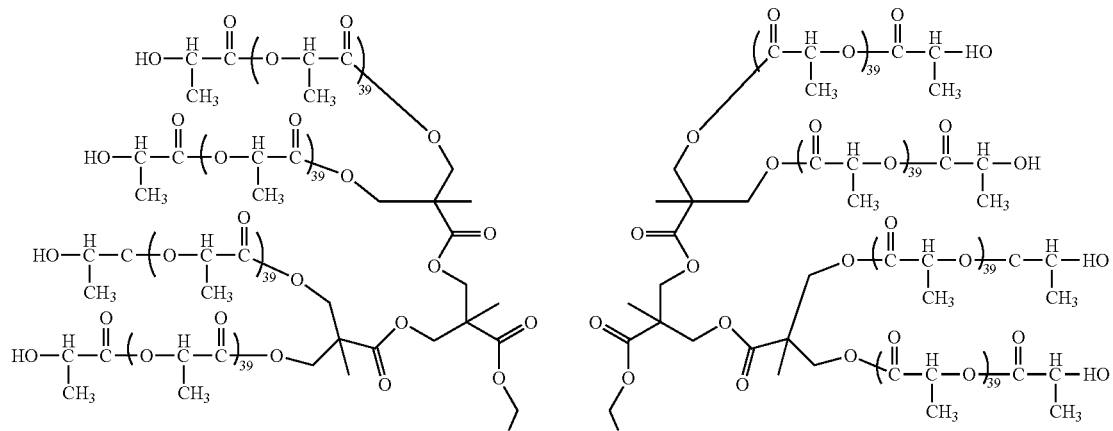

-continued
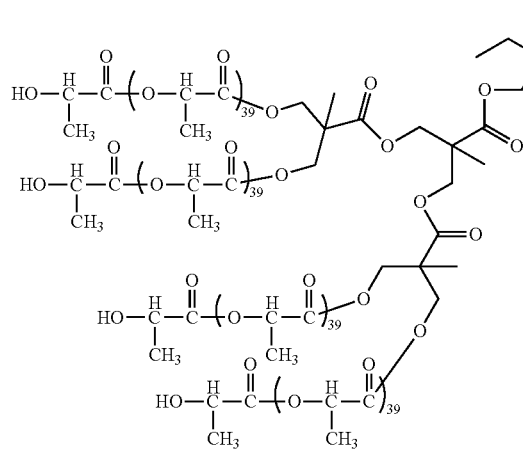
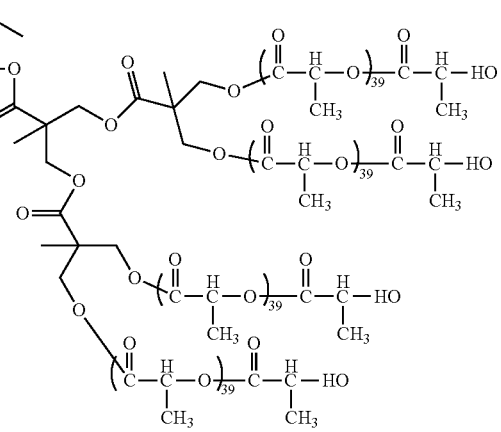
In yet another embodiment, the invention contemplates a composition comprising an Org-$(PLA_{10})_{32}$ having the formula:
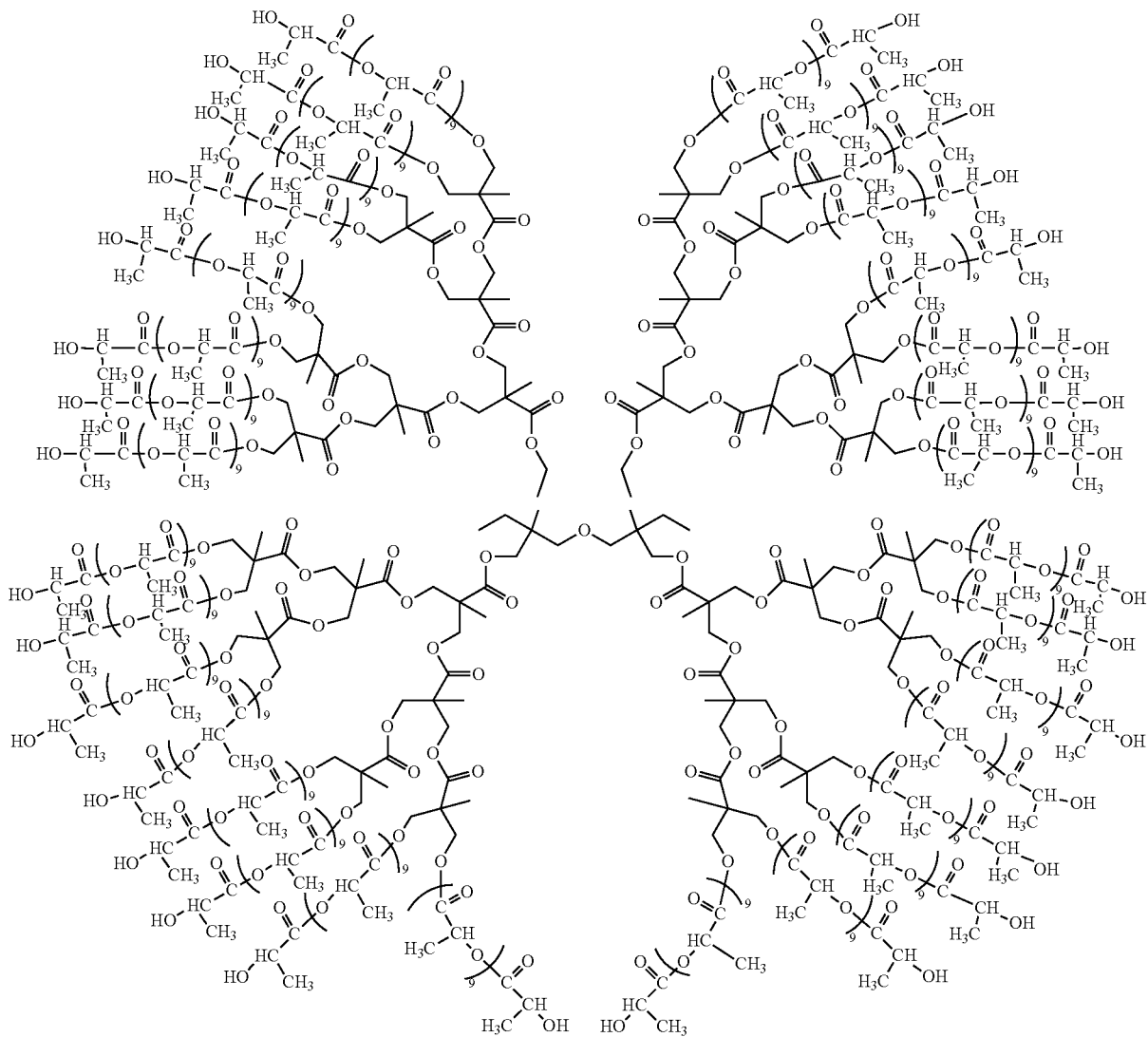

In yet another embodiment, the invention contemplates a composition comprising an Org-(PLA$_{20}$)$_{32}$ having the formula:
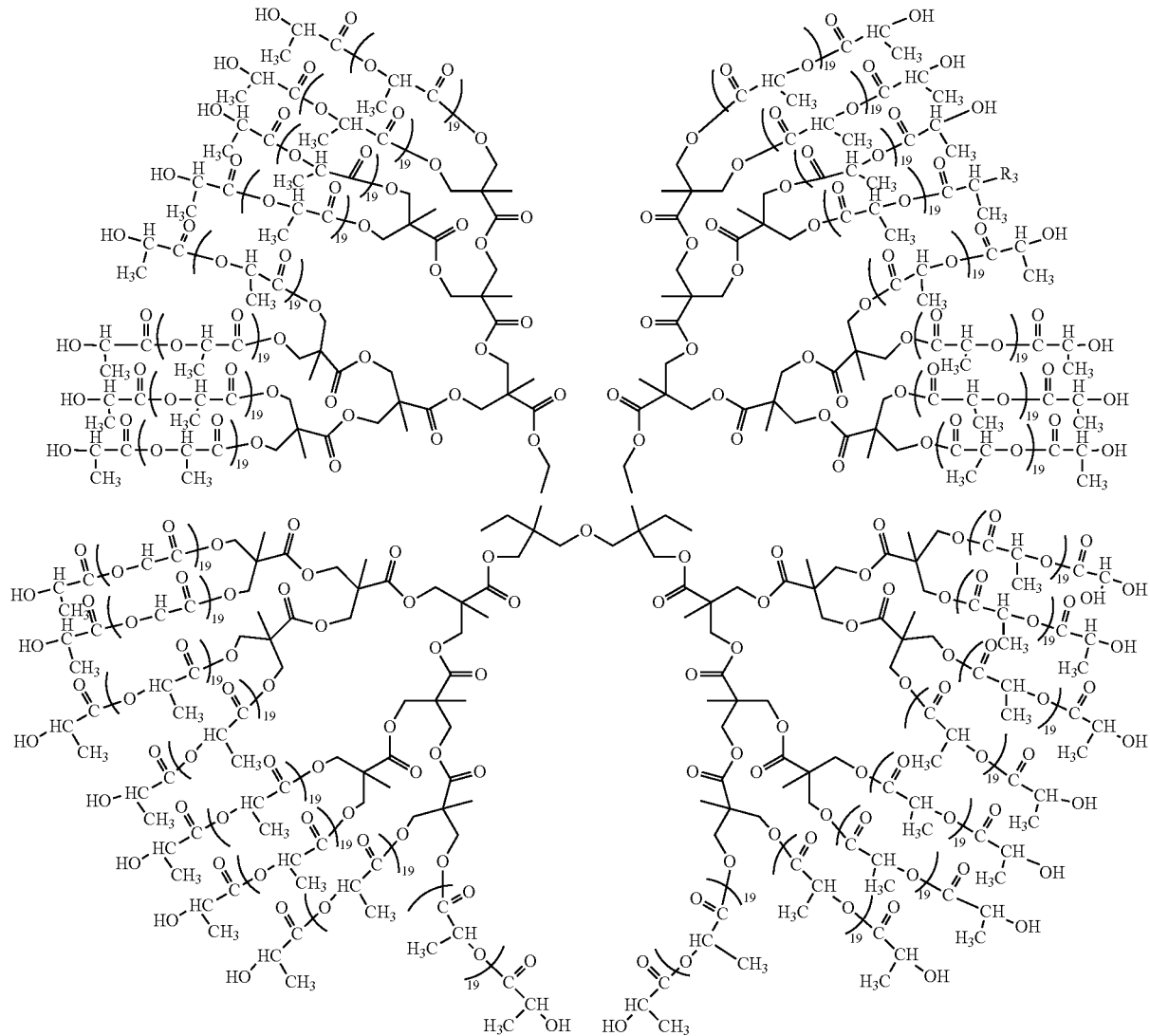

In yet another embodiment, the invention contemplates a composition comprising an Org-(PLA$_{40}$)$_{32}$ having the formula:
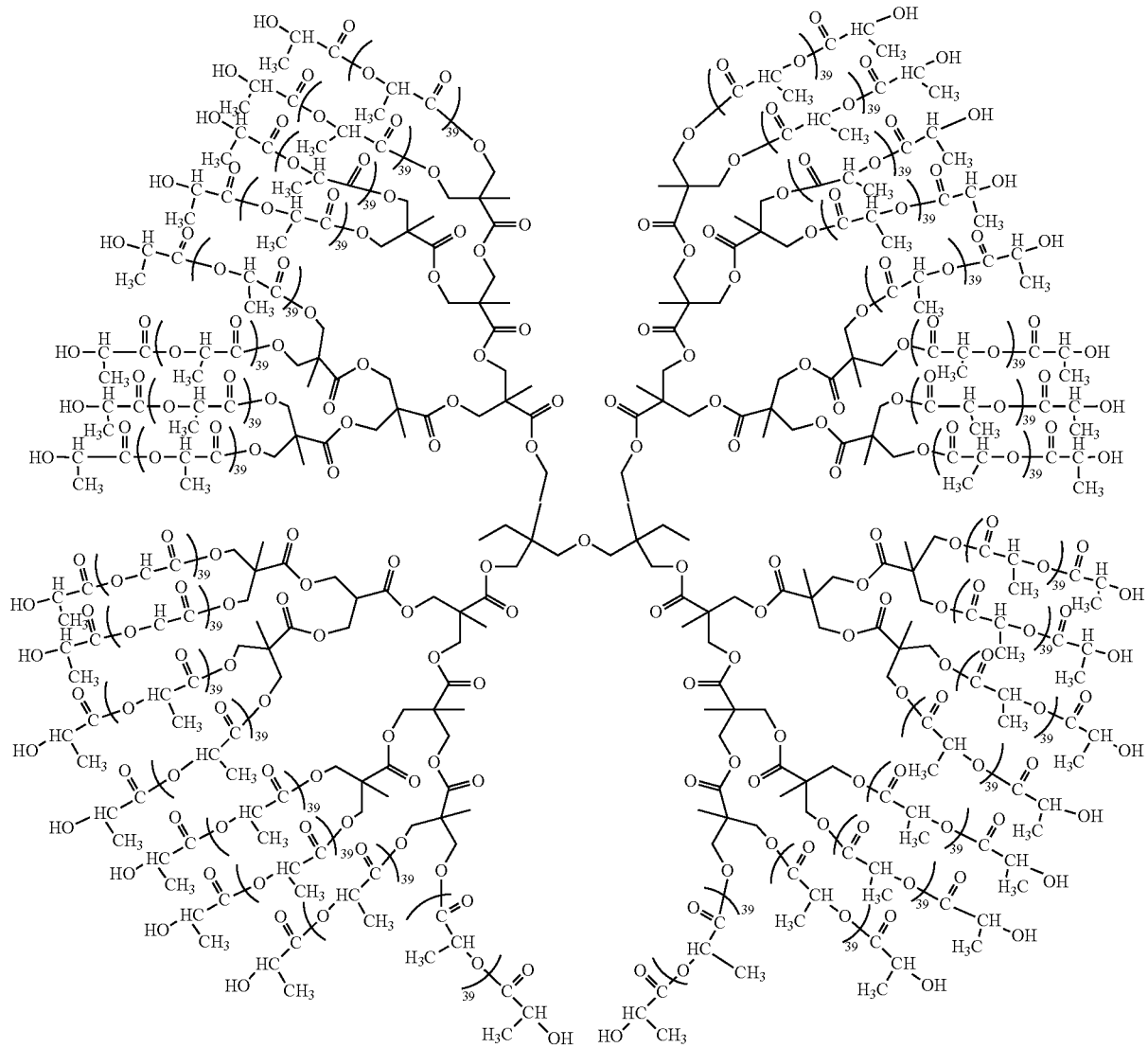
In yet another embodiment, the invention contemplates a composition comprising an Org-[Nordihydroguaiaretic acid]-(3-hydroxy-2-(hydroxymethyl)-2-methylpropanoic acid)$_8$ having the formula:
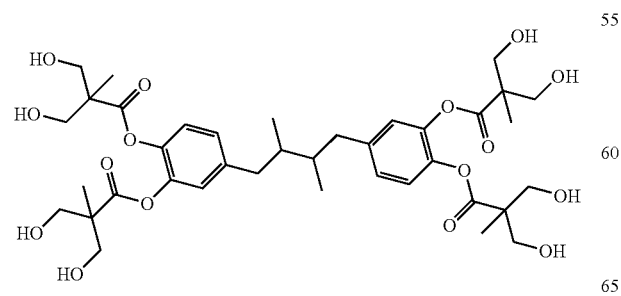

In yet another embodiment, the invention contemplates a composition comprising an Org-[Nordihydroguaiaretic acid]-(3-hydroxy-2-(hydroxymethyl)-2-methylpropanoic acid)$_{16}$ having the formula:

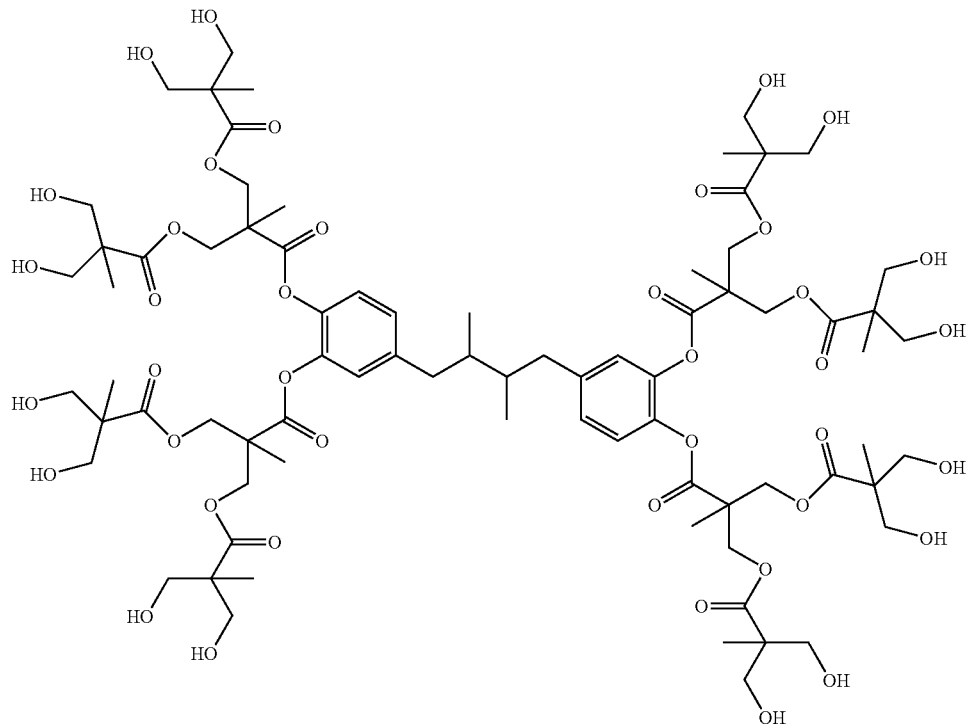 [SMILES: CC(Cc1ccc(OC(=O)C(C)(COC(=O)C(C)(CO)CO)COC(=O)C(C)(CO)CO)c(OC(=O)C(C)(COC(=O)C(C)(CO)CO)COC(=O)C(C)(CO)CO)c1)C(C)Cc1ccc(OC(=O)C(C)(COC(=O)C(C)(CO)CO)COC(=O)C(C)(CO)CO)c(OC(=O)C(C)(COC(=O)C(C)(CO)CO)COC(=O)C(C)(CO)CO)c1]

In yet another embodiment, the invention contemplates a composition comprising an Org-[Nordihydroguaiaretic acid]-(3-hydroxy-2-(hydroxymethyl)-2-methylpropanoic acid)$_{32}$ having the formula:

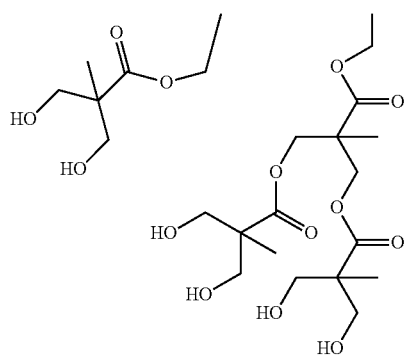

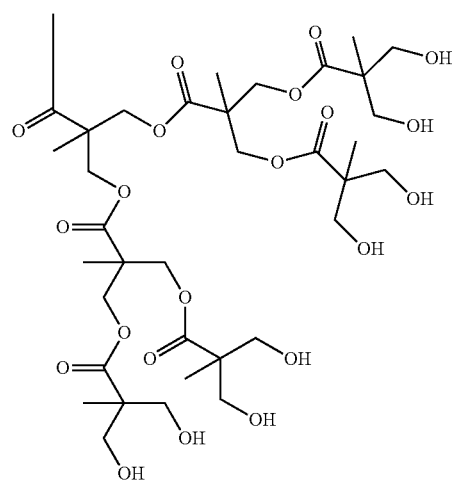

In yet another embodiment, the present invention contemplates a composition comprising a compound having the formula:

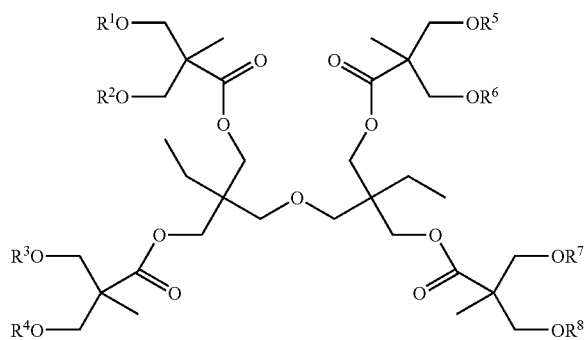

wherein, $R^1$, $R^2$, $R^3$, $R^4$, $R^5$, $R^6$, $R^7$, and $R^8$ are the same or different and, at each occurrence, independently —OH, —SH, —NH$_2$, —CO$_2$H, a substrate, or a group wherein, this compound is considered the modified Organic core. In one embodiment, the composition comprises salts including, but not limited to, $Ca^{2+}$, $Li^+$, $Na^+$, $K^+$, and/or $Mg^{2+}$ salts.

In one embodiment, the present invention contemplates a shape memory core comprising at least one biofunctionalized polymer. In one embodiment, the biofunctionalized polymer comprises at least one biological ligand. In one embodiment, the ligand comprises an amino acid sequence. In one embodiment, the amino acid sequence comprises an antibody. In one embodiment, the amino acid sequence comprises a biologically active protein. In one embodiment, the biologically active protein is an enzyme. In one embodiment, the biologically active protein is a peptide fragment. In one embodiment, the ligand comprises a nucleic acid sequence. In one embodiment, the nucleic acid sequence comprises messenger RNA. In one embodiment, the nucleic acid sequence comprises antisense. In one embodiment, the present invention contemplates a biofunctionalized shape memory core with an organic core. In one embodiment, the present invention contemplates a biofunctionalized shape memory core with an organic core wherein the transition temperature is reduced.

In some embodiments, the invention relates a macromer structure comprising a siloxane core, polymeric segments, and end groups. In preferred embodiments, the end groups and/or the side chain end groups of the polymeric segments may be crosslinked together using urethane chemistry or radical chemistry, both of which are synthetic techniques that are well known to those of ordinary skill in the art. While it is not intended that the present invention be limited by the chemical methods used to generate the present invention preferred methods include but are not limited to ring opening polymerization (ROP), reversible addition fragmentation transfer (RAFT) and atom transfer radical polymerization (ATRP). Furthermore, it is not intended that the present invention be limited to the classification of polymeric segments that comprise the invention; preferred embodiments include but are in no way limited to monomeric polymers or homopolymers, copolymers and block copolymers. In further embodiments, the end groups comprise alkenyl groups, e.g., acrylate or methacrylate. In further embodiments, the end groups or the side chain end groups of the polymeric segments are crosslinked with diisocyanate, diester, diacid, or diacyl by condensation chemistry when the end groups are nucleophilic groups (such as —OH, —NH2, —SH, —COOH). In further embodiments, the end groups are crosslinked with high fidelity chemical ligation (such as the modified Staudinger ligation, the "Click" chemistry).

In some embodiments, the invention relates to a medical device comprising a material comprising: a) siloxane moieties, b) polymer groups, and c) linking groups; wherein said siloxane moieties are substituted with three or more of said polymer groups to form a siloxane-polyester conjugate; and said linking groups are configured to join said conjugates through covalent bonds of said polymer groups. In further embodiments, said polymer groups are polyester groups. In further embodiments, said material has shape memory. In further embodiments, said siloxane moieties are selected from the group consisting of silsesquioxanes and metallasiloxanes. In further embodiments said material comprises a biocompatible or bioactive peptide. In further embodiment, said material surface comprises carboxylic acid groups. In further embodiments, said medical device is selected from the group consisting of cardiovascular stents, surgical guide wires, and orthodontic wires.

In some embodiments, the invention relates to a material comprising: a) siloxane moieties, b) polymer groups, and c) linking groups; wherein said siloxane moieties are substituted with three or more of said polymer groups to form a siloxane-polymer conjugate; and said linking groups join said conjugates through covalent bonds of said polymer groups. In further embodiments, said polymer groups are polyester groups. In further embodiments, said material has one-way or two-way shape memory. In further embodiments, said material has a Tg between 17° C. and 100° C. In further embodiments, said material has a Tg between 37° C. and 50° C. In further embodiments, said siloxane moieties are selected from the group consisting of silsesquioxanes and metallasiloxanes. In further embodiments, said siloxane moieties are caged structures. In further embodiments, said siloxane moieties are octakis(hydidodimethylsiloxy)octasesquioxanes. In further embodiments, said polyester groups are polylactones. In further embodiments, said linking groups comprise alkyl, aryl, or polyethylene groups. In further embodiments, said linking groups comprise urethane groups.

In yet another embodiment, the invention relates to a compound having the formula:

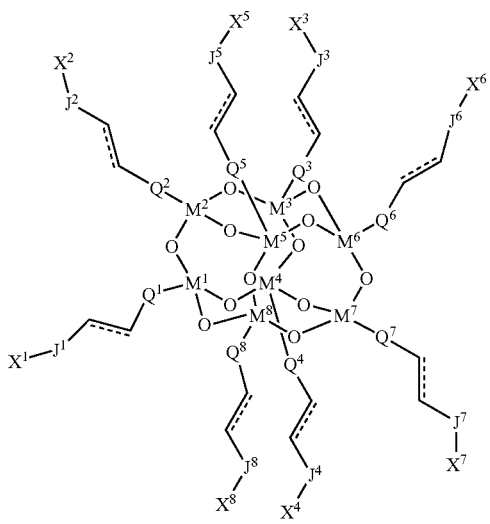

wherein, $X^1$, $X^2$, $X^3$, $X^4$, $X^5$, $X^6$, $X^7$, and $X^8$ are the same or different and, at each occurrence, independently nucleophilic groups; $J^1$, $J^2$, $J^3$, $J^4$, $J^5$, $J^6$, $J^7$, and $J^8$ are the same or different and, at each occurrence, independently joining groups; $=\!=\!=$ is a single or double bond; $Q^1$, $Q^2$, $Q^3$, $Q^4$, $Q^5$, $Q^6$, $Q^7$, $Q^8$ are the same or different and, at each occurrence, independently —O-$M^9R^1R^2$—, —O-$M^{10}R^3R^4$—, —O-$M^{11}R^5R^6$—, —O-$M^{12}R^7R^8$—, —O-$M^{13}R^9R^{10}$—, —O-$M^{14}R^{11}R^{12}$—, —O-$M^{15}R^{13}R^{14}$—, —O-$M^{16}R^{15}R^{16}$—, —O-$M^9R^1R^2$—, or absent forming a bond between adjacent atoms; $M^1$, $M^2$, $M^3$, $M^4$, $M^5$, $M^6$, $M^7$, $M^8$, $M^9$, $M^{10}$, $M^{11}$, $M^{12}$, $M^{13}$, $M^{14}$, $M^{15}$, and $M^{16}$ are the same or different and, at each occurrence, independently a metal or metalloid atom; $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ are the same or different and, at each occurrence, independently alkyl, substituted alkyl, aryl, substituted aryl, —Oalkyl, substituted —Oalkyl, —Oaryl, or substituted —Oaryl. In further embodiments, said nucleophilic groups are selected from the groups consisting of —OH, —SH, and —NH$_2$. In further embodiments, said metal or metalloid atom is selected from the group consisting of Si, Ti, Zr, Li, Co, and Cr. In further embodiments, said joining groups are selected from the group consisting of —(CH$_2$)$_n$—, —(OCH$_2$CH$_2$)$_n$—, —(C=O)—, and —((C=O)O(CH$_2$)$_n$)— wherein n is 1 to 22.

In still another embodiments, the invention relates to a compound having the formula:

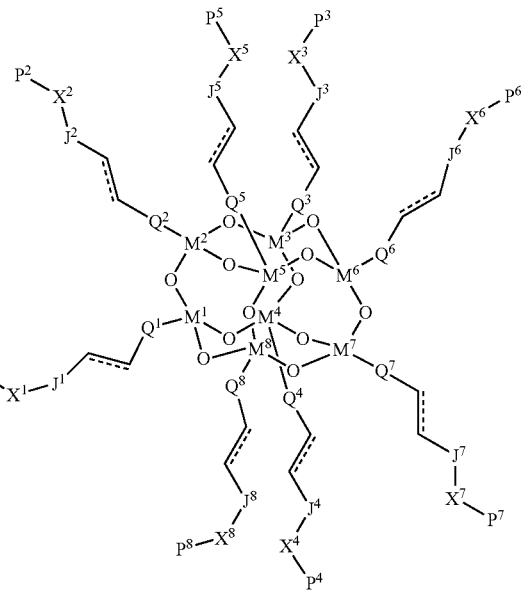

wherein $P^1$, $P^2$, $P^3$, $P^4$, $P^5$, $P^6$, $P^7$, and $P^8$ are the same or different and, at each occurrence, independently a polymer moiety; $X^1$, $X^2$, $X^3$, $X^4$, $X^5$, $X^6$, $X^7$, and $X^8$ are the same or different and, at each occurrence, independently —O—, —S—, —NH—, or —NR$^{19}$—; $J^1$, $J^2$, $J^3$, $J^4$, $J^5$, $J^6$, $J^7$, and $J^8$ are the same or different and, at each occurrence, independently joining groups; $=\!=\!=$ is a single or double bond; $Q^1$, $Q^2$, $Q^3$, $Q^4$, $Q^5$, $Q^6$, $Q^7$, $Q^8$ are the same or different and, at each occurrence, independently —O-$M^9R^1R^2$—, —O-$M^{10}R^3R^4$—, —O-$M^{11}R^5R^6$—, —O-$M^{12}R^7R^8$—, —O-$M^{13}R^9R^{10}$—, —O-$M^{14}R^{11}R^{12}$—, —O-$M^{15}R^{13}R^{14}$—, —O-$M^{16}R^{15}R^{16}$—, —O-$M^9R^1R^2$—, or absent forming a bond between adjacent atoms; $M^1$, $M^2$, $M^3$, $M^4$, $M^5$, $M^6$, $M^7$, $M^8$, $M^9$, $M^{10}$, $M^{11}$, $M^{12}$, $M^{13}$, $M^{14}$, $M^{15}$, and $M^{16}$ are the same or different and, at each occurrence, independently a metal or metalloid atom; $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ are the same or different and, at each occurrence, independently alkyl, substituted alkyl, aryl, substituted aryl, —Oalkyl, substituted —Oalkyl, —Oaryl, or substituted —Oaryl; and $R^{19}$ is alkyl. In further embodiments, three or more of said polymer moieties have the following structural formula:

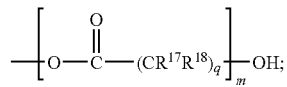

wherein $R^{17}$ and $R^{18}$ are the same or different and, at each occurrence, independently hydrogen, alkyl, or substituted alkyl; q is 1 to 4, 5, or 7; and m is 2 to 1000. In further embodiments, three or more of $P^1$, $P^2$, $P^3$, $P^4$, $P^5$, $P^6$, $P^7$, and $P^8$ have the following structural formula:

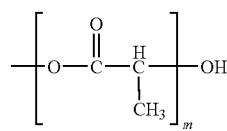

wherein m is 2 to 1000.

In another embodiment, the invention relates to a material made from reacting the compounds disclosed herein with a crosslinking agent. In further embodiments, said crosslinking agent is a diisocyanate. In further embodiments, said diisocyanate is hexamethylene diisocyanate In some embodiments, the invention relates to a compound having the following formula:

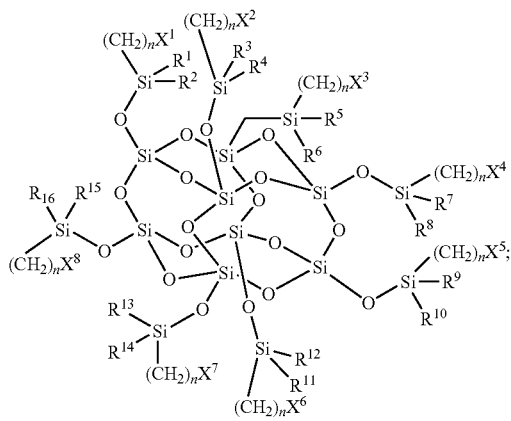

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ are the same or different and, at each occurrence, independently alkyl; n is 3 to 22; $X^1$, $X^2$, $X^3$, $X^4$, $X^5$, $X^6$, $X^7$, and $X^8$ are the same or different and, at each occurrence, independently —OH, —SH, —$NH_2$, or a group having the following structural formula;

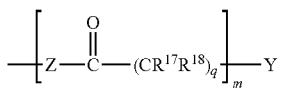

$R^{17}$ and $R^{18}$ are the same or different and, at each occurrence, independently hydrogen or alkyl; m is 2 to 1000; q is 1 to 4 or 5 or 7; Y and —OH, —SH, or —$NH_2$; and Z is —O—, —S—, or —NH—. In further embodiments, three or more of $X^1$, $X^2$, $X^3$, $X^4$, $X^5$, $X^6$, $X^7$, and $X^8$ have the structural formula:

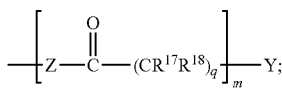

wherein m is 2 to 1000. In further embodiments, $X^1$, $X^2$, $X^3$, $X^4$, $X^5$, $X^6$, $X^7$, and $X^8$ are the same or different and, at each occurrence, independently —OH, —SH, —$NH_2$, or groups having the following formula:

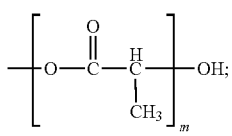

wherein m is 2 to 1000. In further embodiments, three or more of $X^1$, $X^2$, $X^3$, $X^4$, $X^5$, $X^6$, $X^7$, and $X^8$ have the structural formula:

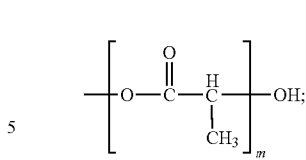

wherein m is 2 to 1000.

In further embodiments, the invention relates to a material comprising a polymer having a formula:

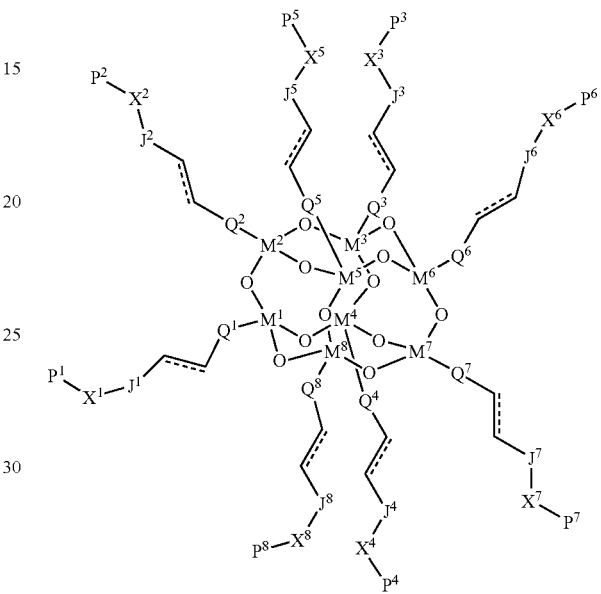

wherein $P^1$, $P^2$, $P^3$, $P^4$, $P^5$, $P^6$, $P^7$, and $P^8$ are the same or different and, at each occurrence, independently hydrogen, a polymer moiety, or a polymer moiety covalently bound to a group having the following structural formula:

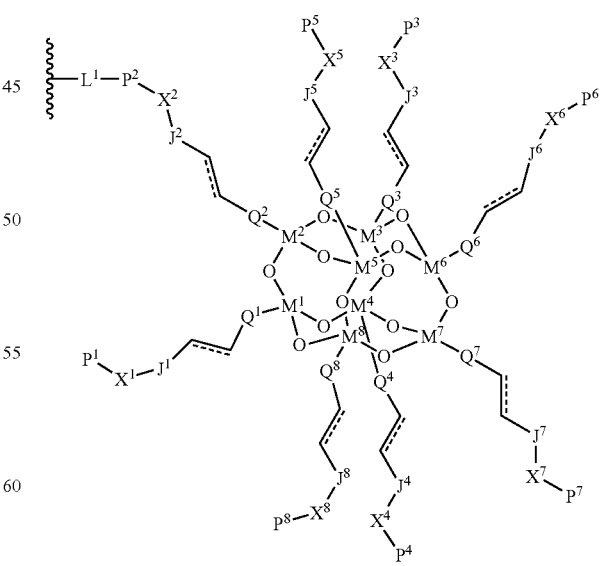

$L^1$ is a linking group, provided that at least three of said $P^1$, $P^2$, $P^3$, $P^4$, $P^5$, $P^6$, $P^7$, and $P^8$ have said polymer moieties covalently bound to said groups having said structural formula; $X^1$, $X^2$, $X^3$, $X^4$, $X^5$, $X^6$, $X^7$, and $X^8$ are the same or different and, at each occurrence, independently —O—, —S—, —NH—, —NR$^{21}$—; $J^1$, $J^2$, $J^3$, $J^4$, $J^5$, $J^6$, $J^7$, and $J^8$ are the same or different and, at each occurrence, independently joining groups; ═══ is a single or double bond; $Q^1$, $Q^2$, $Q^3$, $Q^4$, $Q^5$, $Q^6$, $Q^7$, $Q^8$ are the same or different and, at each occurrence, independently —O-$M^9R^1R^2$—, —O-$M^{10}R^3R^4$—, —O-$M^{11}R^5R^6$—, —O-$M^{12}R^7R^8$—, —O-$M^{13}R^9R^{10}$—, —O-$M^{14}R^{11}R^{12}$—, —O-$M^{15}R^{13}R^{14}$—, —O-$M^{16}R^{15}R^{16}$—, —O-$M^9R^1R^2$—, or absent forming a bond between adjacent atoms; $M^1$, $M^2$, $M^3$, $M^4$, $M^5$, $M^6$, $M^7$, $M^8$, $M^9$, $M^{10}$, $M^{11}$, $M^{12}$, $M^{13}$, $M^{14}$, $M^{15}$, and $M^{16}$ are the same or different and, at each occurrence, independently a metal or metalloid atom; $R^1$, $R^2$, $R^3$, $R^4$, $R^5$, $R^6$, $R^7$, $R^8$, $R^9$, $R^{10}$, $R^{11}$, $R^{12}$, $R^{13}$, $R^4$, $R^{15}$, and $R^{16}$ are the same or different and, at each occurrence, independently alkyl, —Oalkyl, or —Oaryl; and $R^{21}$ is alkyl. In further embodiments, said metal or metalloid atom is selected from the group consisting of Si, Ti, Zr, Li, Co, and Cr. In further embodiments, said joining groups are selected from the group consisting of —(CH$_2$)$_n$—, —(OCH$_2$CH$_2$)$_n$—, —(C═O), and —((C═O)O(CH$_2$)$_n$)— wherein n is 1 to 22. In further embodiments, said polymer moieties are covalently bound to -$L^1$- with a structure having the following structural formula:

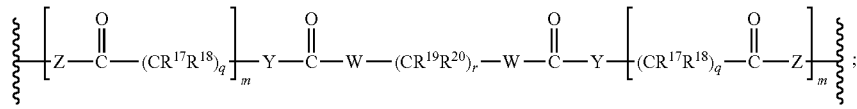

wherein r is 1 to 22, $R^{17}$, $R^{18}$, $R^{19}$ and $R^{20}$ are the same or different and, at each occurrence, independently hydrogen, alkyl, or substituted alkyl; q is 1 to 7; m is 2 to 1000; W is —O—, —S—, or —NH—; Y is —O—, —S—, or —NH—; and Z is —O—, —S—, or —NH—. In further embodiments, said polymer moieties are covalently bound to -$L^1$- with a structure having the following structural formula:

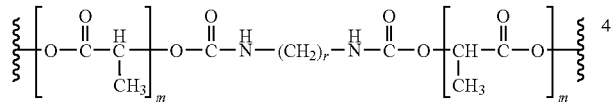

wherein r is 1 to 22, and m is 2 to 1000. In further embodiments, said polymer or polymer moiety has molecular weight over 1,000 and below 20,000, 20,000 and below 200,000; is over 200,000 and below 2,000,000; is over 2,000,000 and below, 20,000,000; or is over 20,000,000 and below 200,000,000.

In further embodiment, the invention relates to a method of making a material bioactive comprising: 1) providing: i) a material comprising: a) siloxane moieties, b) polymer groups, and c) linking groups; wherein said siloxane moieties are substituted with three or more of said polymer groups to form a siloxane-polyester conjugate; said linking groups join said conjugates through covalent bonds of said polymer groups, and wherein a portion of said linking groups comprise a first set of reactive groups; and ii) a bioactive substance comprising a second set of reactive groups; and 2) mixing said material and said bioactive substance under conditions such that a bioactive material formed by the reaction of said first reactive groups with said second reactive groups. In further embodiments, said first reactive groups are alkynyl groups. In further embodiments, said second reactive groups are —N$_3$ groups. In further embodiments, said first reactive groups are amine groups. In further embodiments, said second reactive groups are succinyl esters. In further embodiments, said bioactive substance comprises cationic or anionic moieties at physiological pH to form electrostatic interactions with target biomolecules. In further embodiments, said bioactive substance comprises hydrophilic moieties at physiological pH to form hydrogen-bonding interactions with target biomolecules. In further embodiments, said bioactive substance comprises a chemical moiety with acidic, basic, or neutral isoelectric points for the non-covalent adsorption of bioactive molecules with complementary isoelectric points (opposite net charges). In further embodiments, said chemical moiety is a peptide.

In some embodiments, the invention relates to a material comprising a polymer having the following structural formula:

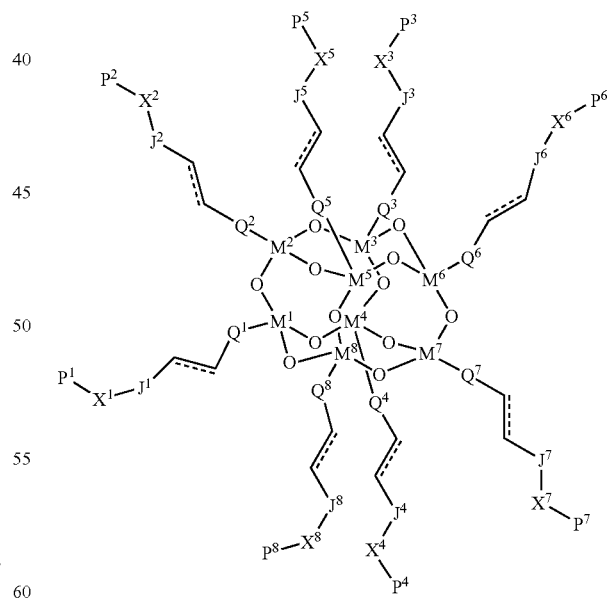

and salts thereof wherein, $P^1$, $P^2$, $P^3$, $P^4$, $P^5$, $P^6$, $P^7$, and $P^8$ are the same or different and, at each occurrence, independently hydrogen, a polymer moiety, a polymer linked to a bioactive substance or a polymer moiety covalently bound to a group having the following structural formula:

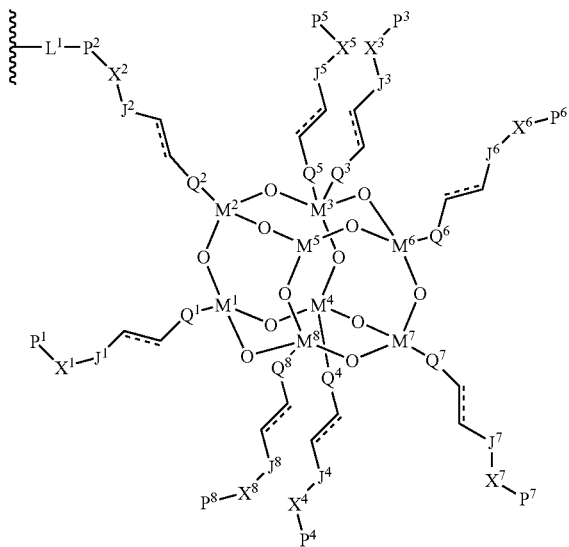

$L^1$ is a linking group, provided that at least three of said $P^1$, $P^2$, $P^3$, $P^4$, $P^5$, $P^6$, $P^7$, and $P^8$ have said polymer moieties covalently bound to said groups having said structural formula and provided that at least one $P^1$, $P^2$, $P^3$, $P^4$, $P^5$, $P^6$, $P^7$, and $P^8$ is a polymer moiety linked to a bioactive substance; $X^1$, $X^2$, $X^3$, $X^4$, $X^5$, $X^6$, $X^7$, and $X^8$ are the same or different and, at each occurrence, independently —O—, —S—, —NH—, —$NR^{21}$—, $J^1$, $J^2$, $J^3$, $J^4$, $J^5$, $J^6$, $J^7$, and $J^8$ are the same or different and, at each occurrence, independently joining groups; $=\!=\!=$ is a single or double bond; $Q^1$, $Q^2$, $Q^3$, $Q^4$, $Q^5$, $Q^6$, $Q^7$, $Q^8$ are the same or different and, at each occurrence, independently —O-$M^9R^1R^2$—, —O-$M^{10}R^3R^4$—, —O-$M^{11}R^5R^6$—, —O-$M^{12}R^7R^8$—, —O-$M^{13}R^9R^{10}$—, —O-$M^{14}R^{11}R^{12}$—, —O-$M^{15}R^{13}R^{14}$—, —O-$M^{16}R^{15}R^{16}$—, —O-$M^9R^1R^2$—, or absent forming a bond between adjacent atoms; $M^1$, $M^2$, $M^3$, $M^4$, $M^5$, $M^6$, $M^7$, $M^8$, $M^9$, $M^{10}$, $M^{11}$, $M^{12}$, $M^{13}$, $M^{14}$, $M^{15}$, and $M^{16}$ are the same or different and, at each occurrence, independently a metal or metalloid atom; $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ are the same or different and, at each occurrence, independently alkyl, —Oalkyl, or —Oaryl; and $R^{21}$ is alkyl. In further embodiments, said polymer moiety linked to said bioactive substance has the formula: $P^9$-$L^2$-Sub wherein, $P^9$ is a polymer moiety; $L^2$ is a linking group; and Sub is a bioactive substance. In further embodiments, said metal or metalloid atom is selected from the group consisting of Si, Ti, Zr, Li, Co, and Cr. In further embodiments, said joining groups are selected from the group consisting of —$(CH_2)_n$—, —$(OCH_2CH_2)_n$—, —(C=O)—, and —((C=O)O$(CH_2)_n$)— wherein n is 1 to 22. In further embodiments, $P^9$-$L^2$- has the following formula:

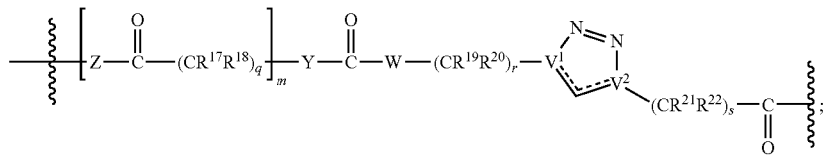

wherein $V^1$ is Nitrogen and $V^2$ is Carbon, or $V^1$ is Carbon and $V^2$ is Nitrogen; $=\!=\!=$ is a single or double bond s is 1 to 22, $R^{17}$, $R^{18}$, $R^{19}$, $R^{20}$, $R^{21}$, and $R^{22}$ are the same or different and, at each occurrence, independently hydrogen, alkyl, or substituted alkyl; q is 1 to 4, 5, or 7; m is 2 to 1000; W is —O—, —S—, or —NH—; Y is —O—, —S—, or —NH—; and Z is —O—, —S—, or —NH—. In further embodiments, said bioactive substance is a peptide. In further embodiments, $P^9$-$L^2$-Sub has the following structural formula:

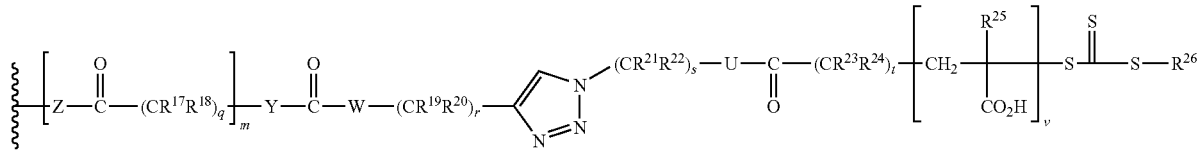

wherein, r is 1 to 22, s is 1 to 22, t is 1 to 22, $R^{17}$, $R^{18}$, $R^{19}$, $R^{20}$, $R^{21}$, $R^{22}$, $R^{23}$, $R^{24}$, $R^{25}$, and $R^{26}$ are the same or different and, at each occurrence, independently hydrogen, alkyl, or substituted alkyl; q is 1 to 4, 5, or 7; m is 2 to 1000; v is 1 to 1000; U is —O—, —S—, or —NH—; W is —O—, —S—, or —NH—; Y is —O—, —S—, or —NH—; and Z is —O—, —S—, or —NH—.

In some embodiments, the invention relates to composition comprising a polymer having the following structural formula:

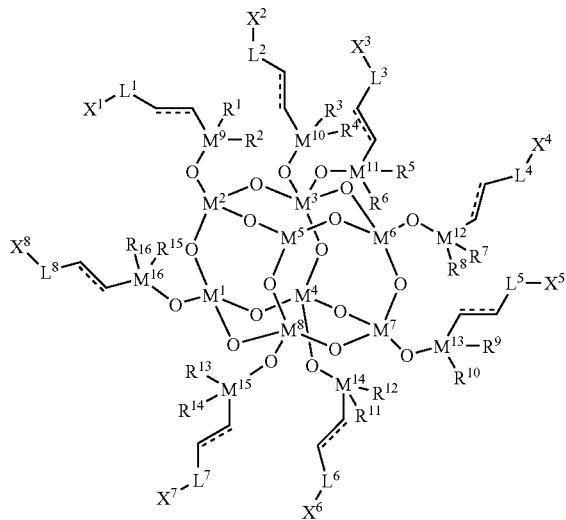

and salts thereof, wherein, $X^1$, $X^2$, $X^3$, $X^4$, $X^5$, $X^6$, $X^7$, and $X^8$ are the same or different and, at each occurrence, independently —OH, —SH, —NH$_2$, —CO$_2$H, a substrate, or a group having the following structural formula:

$L^1$, $L^2$, $L^3$, $L^4$, $L^5$, $L^6$, $L^7$, and $L^8$ are the same or different and, at each occurrence, independently linking groups; ═ is a single or double bond; $M^1$, $M^2$, $M^3$, $M^4$, $M^5$, $M^6$, $M^7$, $M^8$, $M^9$, $M^{10}$, $M^{11}$, $M^{12}$, $M^{13}$, $M^{14}$, $M^{15}$, and $M^{16}$ are the same or different and, at each occurrence, independently a metal or metalloid atom; $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ are the same or different and, at each occurrence, independently alkyl, —Oalkyl, or —Oaryl. In further embodiments, said metal or metalloid atom is selected from the group consisting of Si, Ti, Zr, Li, Co, and Cr. In still further embodiments, said linking groups are selected from the group consisting of —(CH$_2$)$_n$—, —(OCH$_2$CH$_2$)$_n$—, —(C═O)—, and —((C═O)O(CH$_2$)$_n$)— wherein n is 1 to 22. In certain embodiments, three or more $L^1$, $L^2$, $L^3$, $L^4$, $L^5$, $L^6$, $L^7$, and $L^8$ groups have the following structural formula:

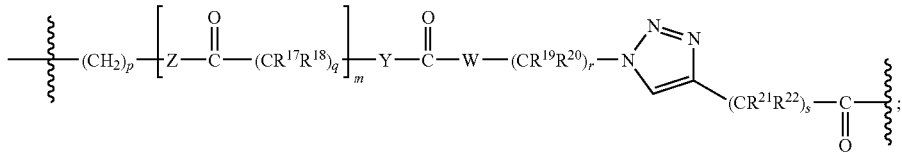

wherein p is 0 to 22, r is 1 to 22, s is 1 to 22, $R^{17}$, $R^{18}$, $R^{19}$, $R^{20}$, $R^{21}$, and $R^{22}$ are the same or different and, at each occurrence, independently hydrogen, alkyl, or substituted alkyl; q is 1 to 4; m is 10 to 100; W is —O—, —S—, or —NH—; Y is —O—, —S—, or —NH—; and Z is —O—, —S—, or —NH—. In further embodiments, said substrate is a peptide. In still further embodiments, said peptide is biocompatible or bioactive. In additional embodiments, at least three of -$L^1$-$X^1$, -$L^2$-$X^2$, -$L^3$-$X^3$, -$L^4$-$X^4$, -$L^5$-$X^5$, -$L^6$-$X^6$, -$L^7$-$X^7$, and -$L^8$-$X^8$ groups have the following structural formula:

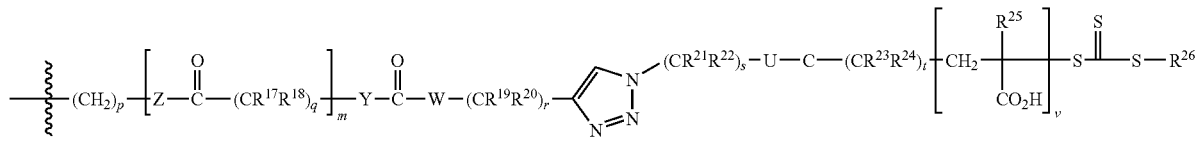

wherein p is 1 to 22, r is 1 to 22, s is 1 to 22, t is 1 to 22, $R^{17}$, $R^{18}$, $R^{19}$, $R^{20}$, $R^{21}$, $R^{22}$, $R^{23}$, $R^{24}$, $R^{25}$, and $R^{26}$ are the same or different and, at each occurrence, independently hydrogen, alkyl, or substituted alkyl; q is 1 to 4; m is 10 to 100; v is 1 to 100; U is —O—, —S—, or —NH—; W is —O—, —S—, or —NH—; Y is —O—, —S—, or —NH—; and Z is —O—, —S—, or —NH—. In certain embodiments, three or more $L^1$, $L^2$, $L^3$, $L^4$, $L^5$, $L^6$, $L^7$, and $L^8$ groups have the following structural formula:

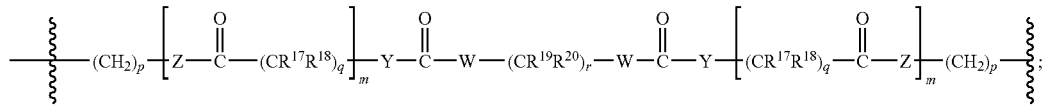

wherein p is 0 to 22, r is 1 to 22, $R^{17}$, $R^{18}$, $R^{19}$ and $R^{20}$ are the same or different and, at each occurrence, independently hydrogen, alkyl, or substituted alkyl; q is 1 to 4; m is 10 to 100; W is —O—, —S—, or —NH—; Y is —O—, —S—, or —NH—; and Z is —O—, —S—, or —NH—. In some embodiments, three or more $L^1$, $L^2$, $L^3$, $L^4$, $L^5$, $L^6$, $L^7$, and $L^8$ have the following structural formula:

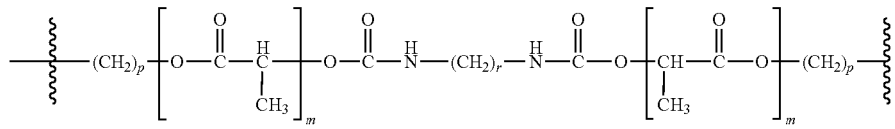

wherein p is 0 to 22, r is 1 to 22, and m is 10 to 100. In further embodiments, said polymer has molecular weight is over 100 and below 20,000; is over 20,000 and below 200,000; is over 200,000 and below 2,000,000; is over 2,000,000 and below, 20,000,000; or is over 20,000,000 and below 200,000,000.

In yet another embodiments, the invention relates to a material comprising: a) siloxane moieties substituted with polymer moieties b) a first set of linking groups, c) a second set of linking groups and d) a bioactive substance; wherein said first set of linking groups covalently join said siloxane moieties through said polymer moieties and said second set of linking groups join said bioactive substance to said polymer moieties through covalent or noncovalent bonds. In further embodiments, said bioactive substance is selected form the group consisting of a cell adhesive peptide, a nucleating ligand and growth factor. In further embodiments, said cell adhesive peptide comprises an RGD peptide sequence. In further embodiments, said nucleating ligand comprises a hydroxyapatite-binding peptide sequence. In further embodiments, said growth factor is an osteogenic growth factor. In further embodiments, said osteogenic growth factor comprises a bone morphogenetic protein 2 peptide sequence.

In some embodiments, the invention relates to a material comprising: a) siloxane moieties, b) linking groups, and c) a biocompatible or bioactive substance; said linking groups join said siloxane moieties and said biocompatible or bioactive biomolecule through covalent bonds. In other embodiments the material further comprises polymer groups, wherein said siloxane moieties are substituted with three or more of said polymer groups to form a siloxane-polymer conjugate; and said linking groups join said conjugates and said biocompatible or bioactive biomolecule through covalent bonds of said polymer groups. In further embodiments, said biocompatible or bioactive substance is selected form the group consisting of a cell adhesive peptide, a nucleating ligand and growth factor. In further embodiments, said cell adhesive peptide comprises an RGD peptide sequence. In further embodiments, said nucleating ligand comprises a hydroxyapatite-binding peptide sequence. In further embodiments, said growth factor is an osteogenic growth factor. In further embodiments, said osteogenic growth factor comprises a bone morphogenetic protein 2 peptide sequence.

In some embodiments, the invention relates to a degradable shape memory polymer composition comprising: a) POSS unit functionalized with a polylactone, and b) urethane crosslinks. In further embodiment, said polylactone has a stereocenter. In further embodiments, said polylactone is polylactide.

In other embodiments, the invention relates to a compound having the following formula:

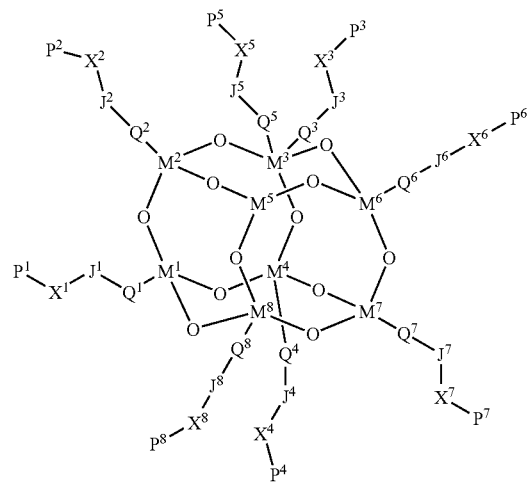

wherein, $Q^1$, $Q^2$, $Q^3$, $Q^4$, $Q^5$, $Q^6$, $Q^7$, $Q^8$ are the same or different and, at each occurrence, independently —O-$M^9R^1R^2$—, —O-$M^{10}R^3R^4$—, —O-$M^{11}R^5R^6$—, —O-$M^{12}R^7R^8$—, —O-$M^{13}R^9R^{10}$—, —O-$M^{14}R^{11}R^{12}$—, —O-$M^{15}R^{13}R^{14}$—, —O-$M^{16}R^{15}R^{16}$—, —O-$M^9R^1R^2$—, or absent forming a bond between adjacent atoms; $J^1$, $J^2$, $J^3$, $J^5$, $J^6$, $J^7$, and $J^8$ are the same or different and, at each occurrence, independently groups;

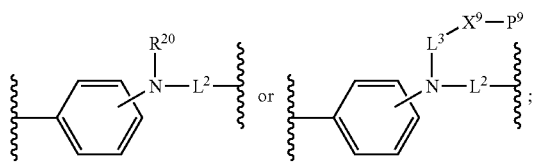

$L^2$, and $L^3$ are linking groups comprising an alkyl or substituted alkyl; $P^1$, $P^2$, $P^3$, $P^4$, $P^5$, $P^6$, $P^7$, $P^8$, and $P^9$ are the same or different and, at each occurrence, independently a hydrogen or a polymer moiety comprising a reactive group; $X^1$, $X^2$, $X^3$, $X^4$, $X^5$, $X^6$, $X^7$, $X^8$ and $X^9$ are the same or different and, at each occurrence, independently —O—, —S—, —NH—, or —$NR^{19}$—; $M^1$, $M^2$, $M^3$, $M^4$, $M^5$, $M^6$, $M^7$, $M^8$, $M^9$, $M^{10}$, $M^{11}$, $M^{12}$, $M^{13}$, $M^{14}$, $M^{15}$, and $M^{16}$ are the same or different and, at each occurrence, independently a metal or metalloid atom; $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ are the same or different and, at each occurrence, independently alkyl, substituted alkyl, aryl, substituted aryl, —Oalkyl, substituted —Oalkyl, —Oaryl, or substituted —Oaryl; $R^{19}$ is alkyl; and $R^{29}$ is hydrogen or alkyl.

In some embodiments, the invention relates to a material comprising a polymer having the following structural formula:

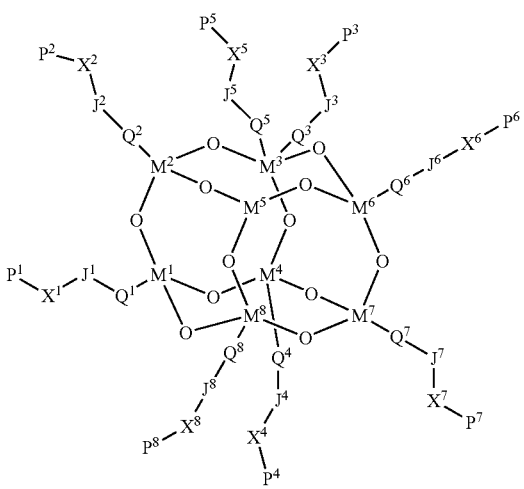

and salts thereof wherein, $Q^1$, $Q^2$, $Q^3$, $Q^4$, $Q^5$, $Q^6$, $Q^7$, $Q^8$ are the same or different and, at each occurrence, independently —O-$M^9R^1R^2$—, —O-$M^{10}R^3R^4$—, —O-$M^{11}R^5R^6$—, —O-$M^{12}R^7R^8$—, —O-$M^{13}R^9R^{10}$—, —O-$M^{14}R^{11}R^{12}$—, —O-$M^{15}R^{13}R^{14}$—, —O-$M^{16}R^{15}R^{16}$—, —O-$M^9R^1R^2$—, or absent forming a bond between adjacent atoms; $P^1$, $P^2$, $P^3$, $P^4$, $P^5$, $P^6$, $P^7$, $P^8$ and $P^9$ are the same or different and, at each occurrence, independently hydrogen, a polymer moiety, a polymer linked to a bioactive substance or a polymer moiety covalently bound to a group having the following structural formula:

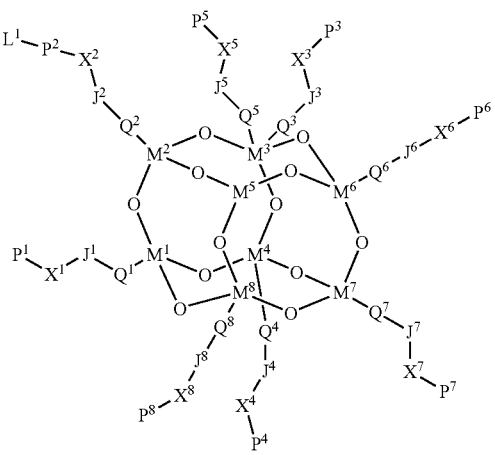

$L^1$ is a linking group, provided that at least three of said $P^1$, $P^2$, $P^3$, $P^4$, $P^5$, $P^6$, $P^7$, and $P^8$ have said polymer moieties covalently bound to said groups having said structural formula and provided that at least one $P^1$, $P^2$, $P^3$, $P^4$, $P^5$, $P^6$, and $P^8$ is a polymer moiety linked to a bioactive substance; $X^1$, $X^2$, $X^3$, $X^4$, $X^5$, $X^6$, $X^7$, $X^8$ and $X^9$ are the same or different and, at each occurrence, independently —O—, —S—, —NH—, or —$NR^{21}$—, $J^1$, $J^2$, $J^3$, $J^4$, $J^5$, $J^6$, $J^7$, and $J^8$ are the same or different and, at each occurrence, independently joining groups or joining group having the following structure;

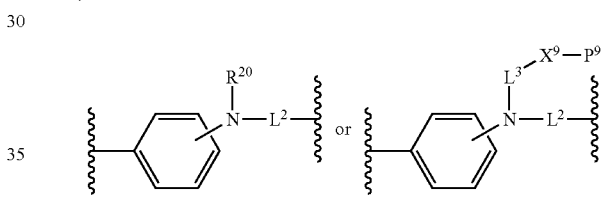

$L^2$, and $L^3$ are linking groups; $M^1$, $M^2$, $M^3$, $M^4$, $M^5$, $M^6$, $M^7$, $M^8$, $M^9$, $M^{10}$, $M^{11}$, $M^{12}$, $M^{13}$, $M^{14}$, $M^{15}$, and $M^{16}$ are the same or different and, at each occurrence, independently a metal or metalloid atom; $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ are the same or different and, at each occurrence, independently alkyl, —Oalkyl, or —Oaryl; and $R^{21}$ is alkyl. In further embodiments, more than half of the metal and metalloid atoms are Si.

In yet other embodiments, the invention relates to a compound of the formula:

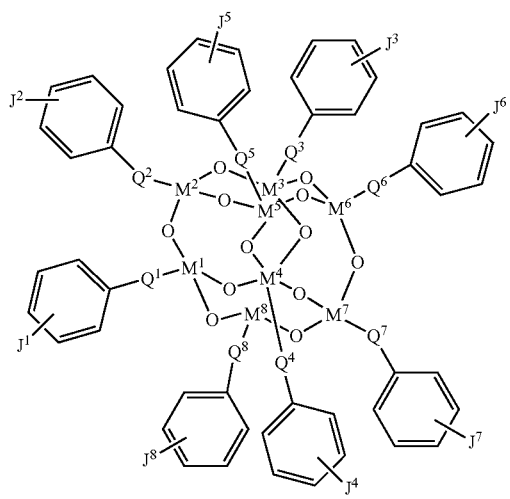

wherein, $Q^1$, $Q^2$, $Q^3$, $Q^4$, $Q^5$, $Q^6$, $Q^7$, $Q^8$ are the same or different and, at each occurrence, independently —O-$M^9R^1R^2$—, —O-$M^{10}R^3R^4$—, —O-$M^{11}R^5R^6$—, —O-$M^{12}R^7R^8$—, —O-$M^{13}R^9R^{10}$—, —O-$M^{14}R^{11}R^{12}$—, —O-$M^{15}R^{13}R^{14}$—, —O-$M^{16}R^{15}R^{16}$—, —O-$M^9R^1R^2$—, or absent forming a bond between adjacent atoms; $M^1$, $M^2$, $M^3$, $M^4$, $M^5$, $M^6$, $M^7$, $M^8$, $M^9$, $M^{10}$, $M^{11}$, $M^{12}$, $M^{13}$, $M^{14}$, $M^{15}$, and $M^{16}$ are the same or different and, at each occurrence, independently a metal or metalloid atom; $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ are the same or different and, at each occurrence, independently alkyl, substituted alkyl, aryl, substituted aryl, —Oalkyl, substituted —Oalkyl, —Oaryl, or substituted —Oaryl; $J^1$, $J^2$, $J^3$, $J^4$, $J^5$, $J^6$, $J^7$, and $J^8$ are the same or different and, at each occurrence, independently groups;

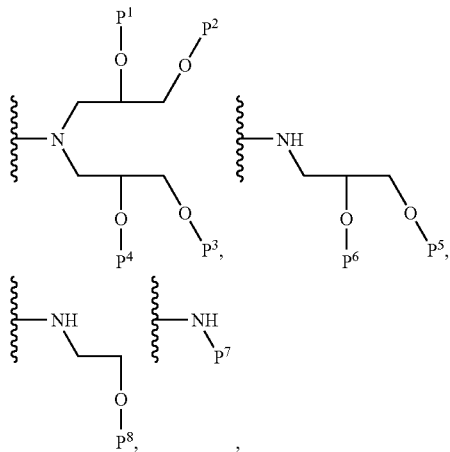

or —$X^1$-$L^1$-$P^9$; $X^1$ is —O—, —S—, —NH—, or —$NR^{21}$; $L^1$ is a linking group; $R^{21}$ is hydrogen or alkyl; and $P^1$, $P^2$, $P^3$, $P^4$, $P^5$, $P^6$, $P^7$, $P^8$ and $P^9$ are the same or different and, at each occurrence, independently hydrogen or a polymer moiety with a reactive group. In further embodiments, three or more of said polymer moieties have the following structural formula:

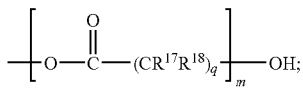

wherein, $R^{17}$ and $R^{18}$ are the same or different and, at each occurrence, independently hydrogen, alkyl, or substituted alkyl; q is 1 to 4, 5, or 7; and m is 2 to 1000. In further embodiments, three or more of $P^1$, $P^2$, $P^3$, $P^4$, $P^5$, $P^6$, $P^7$, and $P^8$ have the following structural formula:

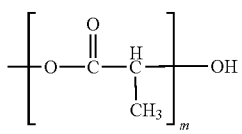

wherein m is 2 to 1000.

In some embodiments, the invention relates to compounds, polymers, and materials disclosed herein that have three or more of said polymer moieties having a terminal alkenyl group for crosslinking by radical polymerization such as those with the following structural formula:

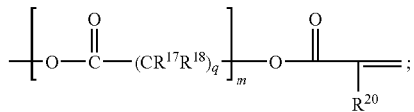

wherein, $R^{17}$ and $R^{18}$ are the same or different and, at each occurrence, independently hydrogen, alkyl, or substituted alkyl; $R^{20}$ is hydrogen or alkyl; q is 1 to 4, 5, or 7; and m is 2 to 1000.

In some embodiments, the invention relates to materials made by crosslinking the compounds disclosed herein.

In other embodiments, the invention relates to the use of compositions and materials disclosed herein for medical devices, such as self-expanding stents, intravascular thrombectomy devices, sutures, replacements for ocular tissue, scaffolds for tissue regeneration, orthopedic implants for the fixation of bone fragments and fractures, tubular vascular implants for the prophlaxis of restenosis, actuators and catheters to remove matter from a vessel, biostable catheter distal tips and actuators for intravascular use and other minimally invasive operations, to fortify an intervertebral disc having an annulus fibrosis with an inner ball, as a self-expanding frame to be fastened to the inner wall of the annulus, self-tightening sutures to close a wound of body scission.

In some embodiments, the invention relates to the use of compositions and materials disclosed herein for to eyeglass frames, sporting goods, toys, automobile parts, space structures, fabrics, rewritable digital storage media.

In some embodiments, the invention relates to the use of compositions and materials disclosed herein for the reconstruction of functional tissues by the degration or release of bioactive substances on demand, inducing forces on seeded cells, or inducing proliferation and differentiation of cells.

In some embodiments, the invention relates to the use of compositions and materials disclosed herein for the prevention or treatment of diseases and disorders associated with the gastrointestinal tract. In further embodiments, a device is configured to reduce the volume of the stomach, esophagus, or intestine without interfering with the flow of food through the gastrointestinal tract. In further embodiments, a device comprising materials and compositions disclosed herein is used to facilitate weightloss. In further embodiments, a device comprising materials and compositions disclosed herein is used to deliver a drug.

In some embodiments, the invention relates to the compositions and materials disclosed herein in a pharmaceutical composition.

In some embodiments, the invention relates to a material comprising: siloxane moieties, polymer groups, linking groups, and at least one inorganic mineral wherein said siloxane moieties are substituted with three or more of said polymer groups to form a siloxane-polymer conjugate; said linking groups join said conjugates through covalent bonds of said polymer groups, and said inorganic mineral intercalated within said siloxane, said polymer and said linking groups to form a siloxane-polymer-inorganic mineral conjugate. The inorganic mineral is interspersed within the framework of the conjugate material in a non-covalently bound arrangement. In further embodiments, said siloxane moieties are octakis(hydridodimethylsiloxy)octasesquioxanes. In still further embodiments, said polymer groups are polyester groups. In additional embodiments, said material has one-way or two-way shape memory. In additional embodiments, the inorganic mineral is selected from the group consisting of calcium carbonate, calcium phosphate, calcium hydroxyapatite, carbonated hydroxyapatite and beta-tricalcium phosphate. In some embodiments, said inorganic mineral comprises between 0.1% and 90% by weight of said material.

In some embodiments, the invention relates to a method of making a material suitable for biomedical use comprising: providing at least one inorganic mineral and a first compound, said first compound comprising siloxane moieties, polymer groups and linking groups wherein said siloxane moieties are substituted, with three or more of said polymer groups to form a siloxane-polyester conjugate; said linking groups join said conjugates through covalent bonds of said polymer groups and wherein a portion of said linking groups comprise a first set of reactive groups; mixing said inorganic mineral with said compound under conditions such that said inorganic mineral intercalates. In further embodiments, said siloxane moieties are octakis(hydridodimethylsiloxy)octasesquioxanes. In still further embodiments, said polymer groups are polyester groups. In additional embodiments, said first reactive groups are alkynyl groups. In some embodiments, said first reactive groups are amine groups. In further embodiments, said material has one-way or two-way shape memory. In still further embodiments, said biomedical use is bone substitution.

In some embodiments, the invention relates to a method of making a material suitable for biomedical use comprising: providing siloxane moieties, polymer groups, and linking groups and substituting said siloxane moieties with three or more of said polymer groups to form a siloxane-polyester conjugate; said linking groups joining said conjugates through covalent bonds of said polymer groups, and wherein a portion of said linking groups comprise a first set of reactive groups. In further embodiments, said siloxane moieties are octakis(hydridodimethylsiloxy)octasesquioxanes. In still further embodiments, said first reactive groups are alkynyl groups. In additional embodiments, said first reactive groups are amine groups. In additional embodiments, said material has one-way or two-way shape memory. In some embodiments, said material suitable for biomedical use is selected from the group consisting of stitches, stents, sutures, orthopedic supports and surgical supports. In further embodiments, said polymer groups are polyester groups. In additional embodiments, said material has a $T_g$ between 17° C. and 100° C. In some embodiments, said material has a $T_g$ between 37° C. and 50° C. In further embodiments, said siloxane moieties are selected from the group consisting of silsesquioxanes and metallasiloxanes. In some embodiments, said siloxane moieties are caged structures. In further embodiments, said siloxane moieties are octakis(hydridodimethylsiloxy)octasesquioxanes. In still further embodiments, said polyester groups are polylactones. In additional embodiments, said linking groups comprise alkyl, aryl, or polyethylene groups. In some embodiments, said linking groups comprise urethane groups. In further embodiments, said material is porous. In still further embodiments, said porosity is between 0.1% and 90%. It is not intended that the present invention be limited to the method of fabrication by which said porosity is incorporated into the present invention. Preferred methods of fabrication include but are in no way limited to salt-leaching, porogen leaching, thermally induced phase separation, and solid freeform fabrication techniques.

In some embodiments, the invention relates to a method of supplementing or repairing a bone in a subject comprising: providing a material comprising: siloxane moieties, polymer groups, linking groups, and at least one inorganic mineral wherein said siloxane moieties are substituted with three or more of said polymer groups to form a siloxane-polymer conjugate, said linking groups join said conjugates through covalent bonds of said polymer groups, said inorganic mineral intercalated within said siloxane, and said polymer and said linking groups to form a siloxane-polymer-inorganic mineral conjugate; a subject suspected of or exhibiting symptoms associated with a bone disorder or dysfunction and administering said material to said subject under conditions such that said bone disorder or dysfunction is reduced. In further embodiments, said siloxane moieties are octakis(hydridodimethylsiloxy)octasesquioxanes. In still further embodiments, said polymer groups are polyester groups. In additional embodiments, said polyester groups are polylactones. In some embodiments, said linking groups comprise alkyl, aryl, or polyethylene groups. In further embodiments, said linking groups comprises urethane groups. In still further embodiments, said mode of administration is surgical implantation. In additional embodiments, the bone exhibiting said bone disorder or dysfunction is selected from the group consisting of cracnial bones, mandible, ulna, humerus, radius, vertebrae, carpals, metacarpals, phalanges, ilium, ischium, pubis, femur, hip joint, patella, tibia, fibula, tarsals and metatarsals. In some embodiments, said bone disorder or dysfunction is selected from the group consisting of bone fracture, bone cyst, bone spur, bone tumor, craniosynostosis, fibrodysplasia ossificans progressiva, fibrous dysplasia, giant cell tumor of bone, hypophosphatasia, Klippel-Feil syndrome, metabolic bone disease, osteitis deformans, osteitis fibrosa cystica, osteitis pubis, condensing osteitis, osteitis condensans ilii, osteochondritis dissecans, osteochondroma, osteogenesis imperfecta, osteomalacia, osteomyelitis, osteopenia, osteopetrosis, osteoporosis, osteosarcoma, porotic hyperostosis, primary hyperparathyroidism and renal osteodystrophy. In further embodiments, said subject is a mammal.

In one embodiment, the present invention contemplates a method of treating a cardiovascular disease in a subject comprising: a) providing; i) a medical device comprising a shape memory polymer composition, and ii) a subject suspected of or exhibiting symptoms associated with a cardiovascular disease; and b) implanting said device to said subject under conditions such said symptoms are reduced. In one embodiment, the implanting is surgical. In one embodiment, the implanting is endoscopic. In one embodiment, the medical device is selected from the group consisting of cardiovascular stents, surgical guide wires, orthodontic wires, actuators, catheters, self-tightening sutures, and resorbable drug-delivery scaffolds. In one embodiment, the composition is resorbable. In one embodiment, the composition is non-resorbable.

In some embodiments, the invention relates to a method, comprising hydrosilyating octakis(dimethylsiloxy)octasilsesquioxane (POSS) by allyl alcohol under conditions such that an octahedral hydroxylated POSS core is formed; and grafting a biodegradable polylactide to said core to create a macromer. In further embodiments, said conditions of step a) comprise a catalyst. In still further embodiments, said catalyst is platinum divinyltetramethyldisiloxane. In additional embodiments, said grafting is achieved by ring opening polymerization of cyclic racemic lactide. In some embodiments, said polymerization is catalyzed by stannous octoate.

DEFINITIONS

As used herein, a "material" means a physical substance preferably a solid, but it is not intended to be limited to a solid material. It is also not intended to be limited to those substances that are actually used in the manufacture or production of a device.

As used herein, a material that exhibits "shape memory" refers to a material that will, without the prevention of another outside physical barrier, change to a previously adpted shape upon exposure to a certain temperature. Shape memory materials may have different kinds of shape memory effects. The two common memory effects are the one-way and two-way shape memory. With the one-way effect, cooling from high temperatures does not cause a shape change. One can physically deform the material. Subsequent heating transforms the material into its original shape. The two-way shape memory effect is the effect that the material remembers two different shapes—one at low temperatures, and one at the high temperature shape—preferably without the application of an external force (intrinsic two-way effect).

The term "conjugate", as used herein, refers to any compound that has been formed by the joining of two or more moieties.

A "moiety" or "group" is any type of molecular arrangement designated by formula, chemical name, or structure. Within the context of certain embodiments, a conjugate is said to comprise one or more moieties or chemical groups. This means that the formula of the moiety is substituted at some place in order to be joined and be a part of the molecular arrangement of the conjugate. Although moieties may be directly covalently joined, it is not intended that the joining of two or more moieties must be directly to each other. A linking group, crosslinking group, or joining group refers any molecular arrangement that will connect the moieties by covalent bonds such as, but are not limited to, one or more amide group(s), may join the moieties. Additionally, although the conjugate may be unsubstituted, the conjugate may have a variety of additional substituents connected to the linking groups and/or connected to the moieties. Siloxanes moieties are molecular arrangements containing silicon-oxygen bonds. Preferably, within certain embodiments, the siloxane moieties are caged structures.

A "polymer" or "polymer group" means a chemical species or group made up of repeatedly linked moieties. In some embodiments, the number of repeatedly linked moieties range between approximately 2-10,000, preferably between approximately 5-1,000, more preferably between Within certain embodiments, it is preferred that the number repeating moieties is three or more or greater than 10. The linked moieties may be identical in structure or may have variation of moiety structure. In a preferred embodiment, the polymer is made up of moieties linked by ester groups, i.e., polyester. Polyesters include polymer architecture obtained through stereoselective polymerizations. Polylactone means a polyester of any cyclic diester preferably the glycolide the diester of glycolic acid, lactide the diester of 2-hydroxypropionic acid, ethylglycolide, hexylglycolide, and isobutylglycolide which can be produced in chiral and racemic forms by, e.g., fermentation of corn. Metal alkoxide catalysts may be used for the ring-opening polymerization (ROP) of lactones. In the presence of chiral catalysts, each catalyst enantiomer preferentially polymerizes one lactone stereoisomer to give polymer chains with isotactic domains. A "monomeric polymer" or "homopolymer" is a polymer that contains the same repeating, asymmetric subunit. A "copolymer" is a polymer that is derived from two or more types of monomeric species, i.e. two or more different chemical asymmetric subunits. "Block copolymers" are polymers comprised of two or more species of polymer subunits linked by covalent bonds. FIGS. 8E and 8H provide for suitable block copolymers that may be incorporated into the present invention.

The term "substituted", as used herein, means at least one hydrogen atom of a molecular arrangement is replaced with a substituent. In the case of an oxo substituent ("=O"), two hydrogen atoms are replaced. When substituted, one or more of the groups below are "substituents." Substituents include, but are not limited to, halogen, hydroxy, oxo, cyano, nitro, amino, alkylamino, dialkylamino, alkyl, alkoxy, alkylthio, haloalkyl, aryl, arylalkyl, heteroaryl, heteroarylalkyl, heterocycle, and heterocyclealkyl, as well as, $-NR_aR_b$, $-NR_aC(=O)R_b$, $-NR_aC(=O)NR_aNR_b$, $-NR_aC(=O)OR_b-$ $NR_aSO_2R_b$, $-C(=O)R_a$, $C(=O)OR_a$, $-C(=O)NR_aR_b$, $-OC(=O)NR_aR_b$, $-OR_a$, $-SR_a$, $-SOR_a$, $-S(=O)_2R_a$, $-OS(=O)_2R_a$ and $-S(=O)_2OR_a$. In addition, the above substituents may be further substituted with one or more of the above substituents, such that the substituent comprises a substituted alky, substituted aryl, substituted arylalkyl, substituted heterocycle, or substituted heterocyclealkyl. $R_a$ and $R_b$ in this context may be the same or different and, independently, hydrogen, alkyl, haloalkyl, substituted alkyl, aryl, substituted aryl, arylalkyl, substituted arylalkyl, heterocycle, substituted heterocycle, heterocyclealkyl or substituted heterocyclealkyl.

The term "unsubstituted", as used herein, refers to any compound does not contain extra substituents attached to the compound. An unsubstituted compound refers to the chemical makeup of the compound without extra substituents, e.g., the compound does not contain protecting group(s). For example, unsubstituted proline is a proline amino acid even though the amino group of proline may be considered disubstituted with alkyl groups.

The term "alkyl", as used herein, means any straight chain or branched, non-cyclic or cyclic, unsaturated or saturated aliphatic hydrocarbon containing from 1 to 10 carbon atoms, while the term "lower alkyl" has the same meaning as alkyl but contains from 1 to 6 carbon atoms. The term "higher alkyl" has the same meaning as alkyl but contains from 2 to 10 carbon atoms. Representative saturated straight chain alkyls include, but are not limited to, methyl, ethyl, n-propyl, n-butyl, n-pentyl, n-hexyl, n-septyl, n-octyl, n-nonyl, and the like; while saturated branched alkyls include, but are not limited to, isopropyl, sec-butyl, isobutyl, tert-butyl, isopentyl, and the like. Cyclic alkyls may be obtained by joining two alkyl groups bound to the same atom or by joining two alkyl groups each bound to adjoining atoms. Representative saturated cyclic alkyls include, but are not limited to, cyclopropyl, cyclobutyl, cyclopentyl, cyclohexyl, and the like; while unsaturated cyclic alkyls include, but are not limited to, cyclopentenyl and cyclohexenyl, and the like. Cyclic alkyls are also referred to herein as a "homocycles" or "homocyclic rings." Unsaturated alkyls contain at least one double or triple bond between adjacent carbon atoms (referred to as an "alkenyl" or "alkynyl", respectively). Representative straight chain and branched alkenyls include, but are not limited to, ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include, but are not limited to, acetylenyl, propynyl, 1-butynyl, 2-butynyl, 1-pentynyl, 2-pentynyl, 3-methyl-1-butynyl, and the like.

The term "aryl", as used herein, means any aromatic carbocyclic moiety such as, but not limited to, phenyl or naphthyl.

The term "arylalkyl", as used herein, means any alkyl having at least one alkyl hydrogen atoms replaced with an aryl moiety, such as benzyl, but not limited to, —(CH$_2$)$_2$phenyl, —(CH$_2$)$_3$phenyl, —CH(phenyl)$_2$, and the like.

The term "halogen", as used herein, refers to any fluoro, chloro, bromo, or iodo moiety.

The term "haloalkyl", as used herein, refers to any alkyl having at least one hydrogen atom replaced with halogen, such as trifluoromethyl, and the like.

The term "heteroaryl", as used herein, refers to any aromatic heterocycle ring of 5- to 10 members and having at least one heteroatom selected from nitrogen, oxygen and sulfur, and containing at least 1 carbon atom, including, but not limited to, both mono- and bicyclic ring systems. Representative heteroaryls include, but are not limited to, furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, or quinazolinyl.

The term "heteroarylalkyl", as used herein, means any alkyl having at least one alkyl hydrogen atom replaced with a heteroaryl moiety, such as —CH$_2$pyridinyl, —CH$_2$pyrimidinyl, and the like.

The term "heterocycle" or "heterocyclic ring", as used herein, means any 4- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles may include heteroaryls exemplified by those defined above. Thus, in addition to the heteroaryls listed above, heterocycles may also include, but are not limited to, morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The term "heterocyclealkyl", as used herein, means any alkyl having at least one alkyl hydrogen atom replaced with a heterocycle, such as —CH$_2$morpholinyl, and the like.

The term "homocycle" or "homocyclic ring", as used herein, means any saturated or unsaturated (but not aromatic) carbocyclic ring containing from 3-7 carbon atoms, such as, but not limited to, cyclopropane, cyclobutane, cyclopentane, cyclohexane, cycloheptane, cyclohexene, and the like.

The term "alkylamino", as used herein, means at least one alkyl moiety attached through a nitrogen bridge (i.e., —N-(alkyl)$_N$, such as a dialkylamino)) including, but not limited to, methylamino, ethylamino, dimethylamino, diethylamino, and the like.

The term "alkyloxy", as used herein, means any alkyl moiety attached through an oxygen bridge (i.e., —O-alkyl) such as, but not limited to, methoxy, ethoxy, and the like.

The term "alkylthio", as used herein, means any alkyl moiety attached through a sulfur bridge (i.e., —S— alkyl) such as, but not limited to, methylthio, ethylthio, and the like The term "alkenyl" means a unbranched or branched hydrocarbon chain having one or more double bonds therein. The double bond of an alkenyl group can be unconjugated or conjugated to another unsaturated group. Suitable alkenyl groups include, but are not limited to (C$_2$-C$_8$)alkenyl groups, such as vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl. An alkenyl group can be unsubstituted or substituted with one or two suitable substituents.

The term "alkynyl" means unbranched or branched hydrocarbon chain having one or more triple bonds therein. The triple bond of an alkynyl group can be unconjugated or conjugated to another unsaturated group. Suitable alkynyl groups include, but are not limited to, (C$_2$-C$_8$)alkynyl groups, such as ethynyl, propynyl, butynyl, pentynyl, hexynyl, methylpropynyl, 4-methyl-1-butynyl, 4-propyl-2-pentynyl-, and 4-butyl-2-hexynyl. An alkynyl group can be unsubstituted or substituted with one or two suitable substituents The term "salts", as used herein, refers to any salt that complexes with identified compounds contained herein. Examples of such salts include, but are not limited to, acid addition salts formed with inorganic acids (e.g. hydrochloric acid, hydrobromic acid, sulfuric acid, phosphoric acid, nitric acid, and the like), and salts formed with organic acids such as, but not limited to, acetic acid, oxalic acid, tartaric acid, succinic acid, malic acid, fumaric acid, maleic acid, ascorbic acid, benzoic acid, tannic acid, pamoic acid, alginic acid, polyglutamic, acid, naphthalene sulfonic acid, naphthalene disulfonic acid, and polygalacturonic acid. Salt compounds can also be administered as pharmaceutically acceptable quaternary salts known by a person skilled in the art, which specifically include the quaternary ammonium salts of the formula —NR,R',R"$^+$Z$^-$, wherein R, R', R" is independently hydrogen, alkyl, or benzyl, and Z is a counter ion, including, but not limited to, chloride, bromide, iodide, alkoxide, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate). Salt compounds can also be administered as pharmaceutically acceptable pyridine cation salts having a substituted or unsubstituted partial formula:

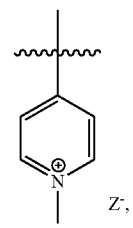

wherein Z is a counter ion, including, but not limited to, chloride, bromide, iodide, alkoxide, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate).

As used herein, reactive groups refer to nucleophiles, electrophiles, or radically active groups, i.e., groups that react in the presence of radicals. A nucleophile is a moeity that forms a chemical bond to its reaction partner (the electrophile) by donating both bonding electrons. Electrophile accept these electrons. Nucleophiles may take part in nucleophilic substitution, whereby a nucleophile becomes attracted to a full or partial positive charge on an element and displaces the group it is bonded to. Alternatively nucleophiles may take part in substitution of carbonyl group. Carboxylic acids are often made electrophilic by creating succinyl esters and reacting these esters with aminoalkyls to form amides. Other common nucleophilic groups are thiolalkyls, hydroxylalkys, primary and secondary amines, and carbon nucleophiles such as enols and alkyl metal complexes. Other preferred methods of ligating proteins, oligosaccharides and cells using reactive groups are disclosed in Lemieux & Bertozzi, *Trends in Biotechnology* 16 (12): 506-513 (1998), incorporated herein by reference. In yet another preferred method, one provides reactive groups for the Staudinger ligation, i.e., "click chemistry" with an azide comprising moiety and an alkynyl reactive groups to form triazoles. Micheal additions of a carbon nucleophile enolate with an electrophilic carbonyl, or the Schiff base formation of a nucleophilic primary or secondary amine with an aldehyde or ketone may also be utilized. Other methods of bioconjugation are provided in Hang & Bertozzi, *Accounts of Chemical Research* 34, 727-73 (2001) and Kiick et al., *Proc. Natl. Acad. Sci. USA* 99, 2007-2010 (2002), both of which are incorporated by reference.

"Epimers" refer to diastereomers that differ in configuration of only one stereogenic center. Diastereomers are a class of stereoisomers that are non-superposable, non-mirror images of one another, unlike enantiomers that are non-superposable mirror images of one another.

The term "salts", as used herein, refers to any salt that complexes with identified compounds contained herein while retaining a desired function, e.g., biological activity. Examples of such salts include, but are not limited to, acid addition salts formed with inorganic acids (e.g. hydrochloric acid, hydrobromic acid, sulfuric acid, phosphoric acid, nitric acid, and the like), and salts formed with organic acids such as, but not limited to, acetic acid, oxalic acid, tartaric acid, succinic acid, malic acid, fumaric acid, maleic acid, ascorbic acid, benzoic acid, tannic acid, pamoic acid, alginic acid, polyglutamic, acid, naphthalene sulfonic acid, naphthalene disulfonic acid, and polygalacturonic acid.

As used herein, "hydrogen" means —H; "hydroxy" means —OH; "oxo" means =O; "halo" means independently —F, —Cl, —Br or —I; "amino" means —NH$_2$ (see below for definitions of groups containing the term amino, e.g., alkylamino); "hydroxyamino" means —NHOH; "nitro" means —NO$_2$; imino means =NH (see below for definitions of groups containing the term imino, e.g., alkylamino); "cyano" means —CN; "azido" means —N$_3$; "mercapto" means —SH; "thio" means =S; "sulfonamido" means —NHS(O)$_2$— (see below for definitions of groups containing the term sulfonamido, e.g., alkylsulfonamido); "sulfonyl" means —S(O)$_2$— (see below for definitions of groups containing the term sulfonyl, e.g., alkylsulfonyl); and "silyl" means —SiH$_3$ (see below for definitions of group(s) containing the term silyl, e.g., alkylsilyl).

For the groups below, the following parenthetical subscripts further define the groups as follows: "(Cn)" defines the exact number (n) of carbon atoms in the group; "(C≤n)" defines the maximum number (n) of carbon atoms that can be in the group; (Cn–n') defines both the minimum (n) and maximum number (n') of carbon atoms in the group. For example, "alkoxy$_{(C≤10)}$" designates those alkoxy groups having from 1 to 10 carbon atoms (e.g., 1, 2, 3, 4, 5, 6, 7, 8, 9, or 10, or any range derivable therein (e.g., 3-10 carbon atoms)). Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3-10 carbon atoms)).

The term "alkyl" when used without the "substituted" modifier refers to a non-aromatic monovalent group with a saturated carbon atom as the point of attachment, a linear or branched, cyclo, cyclic or acyclic structure, no carbon-carbon double or triple bonds, and no atoms other than carbon and hydrogen. The groups, —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neo-pentyl), cyclobutyl, cyclopentyl, cyclohexyl, and cyclohexylmethyl are non-limiting examples of alkyl groups. The term "substituted alkyl" refers to a non-aromatic monovalent group with a saturated carbon atom as the point of attachment, a linear or branched, cyclo, cyclic or acyclic structure, no carbon-carbon double or triple bonds, and at least one atom independently selected from the group consisting of N, O, F, Cl, Br, I, Si, P, and S. The following groups are non-limiting examples of substituted alkyl groups: —CH$_2$OH, —CH$_2$Cl, —CH$_2$Br, —CH$_2$SH, —CF$_3$, —CH$_2$CN, —CH$_2$C(O)H, —CH$_2$C(O)OH, —CH$_2$C(O)OCH$_3$, —CH$_2$C(O)NH$_2$, —CH$_2$C(O)NHCH$_3$, —CH$_2$C(O)CH$_3$, —CH$_2$OCH$_3$, —CH$_2$OCH$_2$CF$_3$, —CH$_2$OC(O)CH$_3$, —CH$_2$NH$_2$, —CH$_2$NHCH$_3$, —CH$_2$N(CH$_3$)$_2$, —CH$_2$CH$_2$Cl, —CH$_2$CH$_2$OH, —CH$_2$CF$_3$, —CH$_2$CH$_2$OC(O)CH$_3$, —CH$_2$CH$_2$NHCO$_2$C(CH$_3$)$_3$, and —CH$_2$Si(CH$_3$)$_3$.

The term "alkanediyl" when used without the "substituted" modifier refers to a non-aromatic divalent group, wherein the alkanediyl group is attached with two σ-bonds, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, —CH$_2$CH$_2$CH$_2$—, and

are non-limiting examples of alkanediyl groups. The term "substituted alkanediyl" refers to a non-aromatic monovalent group, wherein the alkynediyl group is attached with two σ-bonds, with one or two saturated carbon atom(s) as the point(s) of attachment, a linear or branched, cyclo, cyclic or acyclic structure, no carbon-carbon double or triple bonds, and at least one atom independently selected from the group consisting of N, O, F, Cl, Br, I, Si, P, and S. The following groups are non-limiting examples of substituted alkanediyl groups: —CH(F)—, —CF$_2$—, —CH(Cl)—, —CH(OH)—, —CH(OCH$_3$)—, and —CH$_2$CH(Cl)—.

The term "alkenyl" when used without the "substituted" modifier refers to a monovalent group with a nonaromatic carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CH—C$_6$H$_5$. The term "substituted alkenyl" refers to a monovalent group with a nonaromatic carbon atom as the point of attachment, at least one nonaromatic carbon-carbon double bond, no carbon-carbon triple bonds, a linear or branched, cyclo, cyclic or acyclic structure, and at least one atom independently selected from the group consisting of N, O, F, Cl, Br, I, Si, P, and S. The groups, —CH=CHF, —CH=CHCl and —CH=CHBr, are non-limiting examples of substituted alkenyl groups.

The term "alkenediyl" when used without the "substituted" modifier refers to a non-aromatic divalent group, wherein the alkenediyl group is attached with two σ-bonds, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$)CH$_2$—, —CH=CHCH$_2$—, and

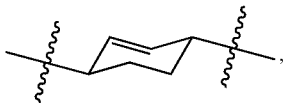 [SMILES: *C1C=CC(*)CC1]

are non-limiting examples of alkenediyl groups. The term "substituted alkenediyl" refers to a non-aromatic divalent group, wherein the alkenediyl group is attached with two σ-bonds, with two carbon atoms as points of attachment, a linear or branched, cyclo, cyclic or acyclic structure, at least one nonaromatic carbon-carbon double bond, no carbon-carbon triple bonds, and at least one atom independently selected from the group consisting of N, O, F, Cl, Br, I, Si, P, and S. The following groups are non-limiting examples of substituted alkenediyl groups: —CF=CH—, —C(OH)=CH—, and —CH$_2$CH=C(Cl)—.

The term "alkynyl" when used without the "substituted" modifier refers to a monovalent group with a nonaromatic carbon atom as the point of attachment, a linear or branched, cyclo, cyclic or acyclic structure, at least one carbon-carbon triple bond, and no atoms other than carbon and hydrogen. The groups, —C≡CH, —C≡CCH$_3$, —C≡CC$_6$H$_5$ and —CH$_2$C≡CCH$_3$, are non-limiting examples of alkynyl groups. The term "substituted alkynyl" refers to a monovalent group with a nonaromatic carbon atom as the point of attachment and at least one carbon-carbon triple bond, a linear or branched, cyclo, cyclic or acyclic structure, and at least one atom independently selected from the group consisting of N, O, F, Cl, Br, I, Si, P, and S. The group, —C≡CSi(CH$_3$)$_3$, is a non-limiting example of a substituted alkynyl group.

The term "alkynediyl" when used without the "substituted" modifier refers to a non-aromatic divalent group, wherein the alkynediyl group is attached with two σ-bonds, with two carbon atoms as points of attachment, a linear or branched, cyclo, cyclic or acyclic structure, at least one carbon-carbon triple bond, and no atoms other than carbon and hydrogen. The groups, —C≡C—, —C≡CCH$_2$—, and —C≡CCH(CH$_3$)— are non-limiting examples of alkynediyl groups. The term "substituted alkynediyl" refers to a non-aromatic divalent group, wherein the alkynediyl group is attached with two σ-bonds, with two carbon atoms as points of attachment, a linear or branched, cyclo, cyclic or acyclic structure, at least one carbon-carbon triple bond, and at least one atom independently selected from the group consisting of N, O, F, Cl, Br, I, Si, P, and S. The groups —C≡CCFH— and —C≡CHCH(Cl)— are non-limiting examples of substituted alkynediyl groups.

The term "aryl" when used without the "substituted" modifier refers to a monovalent group with an aromatic carbon atom as the point of attachment, said carbon atom forming part of a six-membered aromatic ring structure wherein the ring atoms are all carbon, and wherein the monovalent group consists of no atoms other than carbon and hydrogen. Non-limiting examples of aryl groups include phenyl (Ph), methylphenyl, (dimethyl)phenyl, —C$_6$H$_4$CH$_2$CH$_3$ (ethylphenyl), —C$_6$H$_4$CH$_2$CH$_2$CH$_3$ (propylphenyl), —C$_6$H$_4$CH(CH$_3$)$_2$, —C$_6$H$_4$CH(CH$_2$)$_2$, —C$_6$H$_3$(CH$_3$)CH$_2$CH$_3$ (methylethylphenyl), —C$_6$H$_4$CH=CH$_2$ (vinylphenyl), —C$_6$H$_4$CH=CHCH$_3$, —C$_6$H$_4$C≡CH, —C$_6$H$_4$C≡CCH$_3$, naphthyl, and the monovalent group derived from biphenyl. The term "substituted aryl" refers to a monovalent group with an aromatic carbon atom as the point of attachment, said carbon atom forming part of a six-membered aromatic ring structure wherein the ring atoms are all carbon, and wherein the monovalent group further has at least one atom independently selected from the group consisting of N, O, F, Cl, Br, I, Si, P, and S. Non-limiting examples of substituted aryl groups include the groups: —C$_6$H$_4$F, —C$_6$H$_4$Cl, —C$_6$H$_4$Br, —C$_6$H$_4$I, —C$_6$H$_4$OH, —C$_6$H$_4$OCH$_3$, —C$_6$H$_4$OCH$_2$CH$_3$, —C$_6$H$_4$OC(O)CH$_3$, —C$_6$H$_4$NH$_2$, —C$_6$H$_4$NHCH$_3$, —C$_6$H$_4$N(CH$_3$)$_2$, —C$_6$H$_4$CH$_2$OH, —C$_6$H$_4$CH$_2$OC(O)CH$_3$, —C$_6$H$_4$CH$_2$NH$_2$, —C$_6$H$_4$CF$_3$, —C$_6$H$_4$CN, —C$_6$H$_4$CHO, —C$_6$H$_4$CHO, —C$_6$H$_4$C(O)CH$_3$, —C$_6$H$_4$C(O)C$_6$H$_5$, —C$_6$H$_4$CO$_2$H, —C$_6$H$_4$CO$_2$CH$_3$, —C$_6$H$_4$CONH$_2$, —C$_6$H$_4$CONHCH$_3$, and —C$_6$H$_4$CON(CH$_3$)$_2$.

The term "arenediyl" when used without the "substituted" modifier refers to a divalent group, wherein the arenediyl group is attached with two σ-bonds, with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. Non-limiting examples of arenediyl groups include:

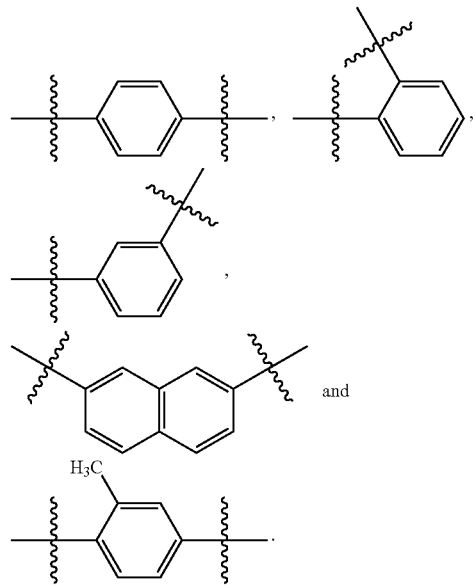

and

The term "substituted arenediyl" refers to a divalent group, wherein the arenediyl group is attached with two σ-bonds, with two aromatic carbon atoms as points of attachment, said carbon atoms forming part of one or more six-membered aromatic rings structure(s), wherein the ring atoms are all carbon, and wherein the divalent group further has at least one atom independently selected from the group consisting of N, O, F, Cl, Br, I, Si, P, and S.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn), 1-phenyl-ethyl, 2-phenyl-ethyl, indenyl and 2,3-dihydro-indenyl, provided that indenyl and 2,3-dihydro-indenyl are only examples of aralkyl in so far as the point of attachment in each case is one of the saturated carbon atoms. When the term "aralkyl" is used with the "substituted" modifier, either one or both the alkanediyl and the aryl is substituted. Non-limiting examples of substituted aralkyls are: (3-chlorophenyl)-methyl, 2-oxo-2-phenyl-ethyl (phenylcarbonylmethyl), 2-chloro-2-phenyl-ethyl, chromanyl where the point of attachment is one of the saturated carbon atoms, and tetrahydroquinolinyl where the point of attachment is one of the saturated atoms.

The term "heteroaryl" when used without the "substituted" modifier refers to a monovalent group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the monovalent group consists of no atoms other than carbon, hydrogen, aromatic nitrogen, aromatic oxygen and aromatic sulfur. Non-limiting examples of aryl groups include acridinyl, furanyl, imidazoimidazolyl, imidazopyrazolyl, imidazopyridinyl, imidazopyrimidinyl, indolyl, indazolinyl, methylpyridyl, oxazolyl, phenylimidazolyl, pyridyl, pyrrolyl, pyrimidyl, pyrazinyl, quinolyl, quinazolyl, quinoxalinyl, tetrahydroquinolinyl, thienyl, triazinyl, pyrrolopyridinyl, pyrrolopyrimidinyl, pyrrolopyrazinyl, pyrrolotriazinyl, pyrroloimidazolyl, chromenyl (where the point of attachment is one of the aromatic atoms), and chromanyl (where the point of attachment is one of the aromatic atoms). The term "substituted heteroaryl" refers to a monovalent group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the monovalent group further has at least one atom independently selected from the group consisting of non-aromatic nitrogen, non-aromatic oxygen, non aromatic sulfur F, Cl, Br, I, Si, and P.

The term "heteroarenediyl" when used without the "substituted" modifier refers to a divalent group, wherein the heteroarenediyl group is attached with two σ-bonds, with an aromatic carbon atom or nitrogen atom as the point of attachment, said carbon atom or nitrogen atom two aromatic atoms as points of attachment, said carbon atoms forming part of one or more six-membered aromatic ring structure(s) wherein the ring atoms are all carbon, and wherein the monovalent group consists of no atoms other than carbon and hydrogen. Non-limiting examples of heteroarenediyl groups include:

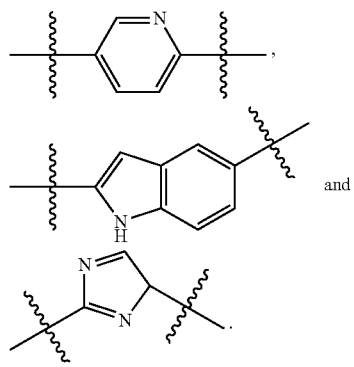

and

The term "substituted heteroarenediyl" refers to a divalent group, wherein the heteroarenediyl group is attached with two σ-bonds, with two aromatic carbon atoms as points of attachment, said carbon atoms forming part of one or more six-membered aromatic rings structure(s), wherein the ring atoms are all carbon, and wherein the divalent group further has at least one atom independently selected from the group consisting of N, O, F, Cl, Br, I, Si, P, and S.

The term "heteroaralkyl" when used without the "substituted" modifier refers to the monovalent group -alkanediyl-heteroaryl, in which the terms alkanediyl and heteroaryl are each used in a manner consistent with the definitions provided above. Non-limiting examples of aralkyls are: pyridylmethyl, and thienylmethyl. When the term "heteroaralkyl" is used with the "substituted" modifier, either one or both the alkanediyl and the heteroaryl is substituted.

The term "acyl" when used without the "substituted" modifier refers to a monovalent group with a carbon atom of a carbonyl group as the point of attachment, further having a linear or branched, cyclo, cyclic or acyclic structure, further having no additional atoms that are not carbon or hydrogen, beyond the oxygen atom of the carbonyl group. The groups, —CHO, —C(O)CH$_3$, —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)C$_6$H$_4$CH$_2$CH$_3$, —COC$_6$H$_3$(CH$_3$)$_2$, and —C(O)CH$_2$C$_6$H$_5$, are non-limiting examples of acyl groups. The term "acyl" therefore encompasses, but is not limited to groups sometimes referred to as "alkyl carbonyl" and "aryl carbonyl" groups. The term "substituted acyl" refers to a monovalent group with a carbon atom of a carbonyl group as the point of attachment, further having a linear or branched, cyclo, cyclic or acyclic structure, further having at least one atom, in addition to the oxygen of the carbonyl group, independently selected from the group consisting of N, O, F, Cl, Br, I, Si, P, and S. The groups, —C(O)CH$_2$CF$_3$, —CO$_2$H (carboxyl), —CO$_2$CH$_3$ (methylcarboxyl), —CO$_2$CH$_2$CH$_3$, —CO$_2$CH$_2$CH$_2$CH$_3$, —CO$_2$C$_6$H$_5$, —CO$_2$CH(CH$_3$)$_2$, —CO$_2$CH(CH$_2$)$_2$, —C(O)NH$_2$ (carbamoyl), —C(O)NHCH$_3$, —C(O)NHCH$_2$CH$_3$, —CONHCH(CH$_3$)$_2$, —CONHCH(CH$_2$)$_2$, —CON(CH$_3$)$_2$, —CONHCH$_2$CF$_3$, —CO-pyridyl, —CO-imidazoyl, and —C(O)N$_3$, are non-limiting examples of substituted acyl groups. The term "substituted acyl" encompasses, but is not limited to, "heteroaryl carbonyl" groups.

The term "alkylidene" when used without the "substituted" modifier refers to the divalent group =CRR', wherein the alkylidene group is attached with one σ-bond and one π-bond, in which R and R' are independently hydrogen, alkyl, or R and R' are taken together to represent alkanediyl. Non-limiting examples of alkylidene groups include: =CH$_2$, =CH(CH$_2$CH$_3$), and =C(CH$_3$)$_2$. The term "substituted alkylidene" refers to the group =CRR', wherein the alkylidene group is attached with one σ-bond and one π-bond, in which R and R' are independently hydrogen, alkyl, substituted alkyl, or R and R' are taken together to represent a substituted alkanediyl, provided that either one of R and R' is a substituted alkyl or R and R' are taken together to represent a substituted alkanediyl.

The term "alkoxy" when used without the "substituted" modifier refers to the group —OR, in which R is an alkyl, as that term is defined above. Non-limiting examples of alkoxy groups include: —OCH$_3$, —OCH$_2$CH$_3$, —OCH$_2$CH$_2$CH$_3$, —OCH(CH$_3$)$_2$, —OCH(CH$_2$)$_2$, —O-cyclopentyl, and —O-cyclohexyl. The term "substituted alkoxy" refers to the group —OR, in which R is a substituted alkyl, as that term is defined above. For example, —OCH$_2$CF$_3$ is a substituted alkoxy group.

Similarly, the terms "alkenyloxy", "alkynyloxy", "aryloxy", "aralkoxy", "heteroaryloxy", "heteroaralkoxy" and "acyloxy", when used without the "substituted" modifier, refers to groups, defined as —OR, in which R is alkenyl, alkynyl, aryl, aralkyl, heteroaryl, heteroaralkyl and acyl, respectively, as those terms are defined above. When any of the terms alkenyloxy, alkynyloxy, aryloxy, aralkyloxy and acyloxy is modified by "substituted," it refers to the group —OR, in which R is substituted alkenyl, alkynyl, aryl, aralkyl, heteroaryl, heteroaralkyl and acyl, respectively.

The term "alkylamino" when used without the "substituted" modifier refers to the group —NHR, in which R is an alkyl, as that term is defined above. Non-limiting examples of alkylamino groups include: —NHCH$_3$, —NHCH$_2$CH$_3$, —NHCH$_2$CH$_2$CH$_3$, —NHCH(CH$_3$)$_2$, —NHCH(CH$_2$)$_2$, —NHCH$_2$CH$_2$CH$_2$CH$_3$, —NHCH(CH$_3$)CH$_2$CH$_3$, —NHCH$_2$CH(CH$_3$)$_2$, —NHC(CH$_3$)$_3$, —NH-cyclopentyl, and —NH-cyclohexyl. The term "substituted alkylamino" refers to the group —NHR, in which R is a substituted alkyl, as that term is defined above. For example, —NHCH$_2$CF$_3$ is a substituted alkylamino group.

The term "dialkylamino" when used without the "substituted" modifier refers to the group —NRR', in which R and R' can be the same or different alkyl groups, or R and R' can be taken together to represent an alkanediyl having two or more saturated carbon atoms, at least two of which are attached to the nitrogen atom. Non-limiting examples of dialkylamino groups include: —NHC(CH$_3$)$_3$, —N(CH$_3$)CH$_2$CH$_3$, —N(CH$_2$CH$_3$)$_2$, N-pyrrolidinyl, and N-piperidinyl. The term "substituted dialkylamino" refers to the group —NRR', in which R and R' can be the same or different substituted alkyl groups, one of R or R' is an alkyl and the other is a substituted alkyl, or R and R' can be taken together to represent a substituted alkanediyl with two or more saturated carbon atoms, at least two of which are attached to the nitrogen atom.

The terms "alkoxyamino", "alkenylamino", "alkynylamino", "arylamino", "aralkylamino", "heteroarylamino", "heteroaralkylamino", and "alkylsulfonylamino" when used without the "substituted" modifier, refers to groups, defined as —NHR, in which R is alkoxy, alkenyl, alkynyl, aryl, aralkyl, heteroaryl, heteroaralkyl and alkylsulfonyl, respectively, as those terms are defined above. A non-limiting example of an arylamino group is —NHC$_6$H$_5$. When any of the terms alkoxyamino, alkenylamino, alkynylamino, arylamino, aralkylamino, heteroarylamino, heteroaralkylamino and alkylsulfonylamino is modified by "substituted," it refers to the group —NHR, in which R is substituted alkoxy, alkenyl, alkynyl, aryl, aralkyl, heteroaryl, heteroaralkyl and alkylsulfonyl, respectively.

The term "amido" (acylamino), when used without the "substituted" modifier, refers to the group —NHR, in which R is acyl, as that term is defined above. A non-limiting example of an acylamino group is —NHC(O)CH$_3$. When the term amido is used with the "substituted" modifier, it refers to groups, defined as —NHR, in which R is substituted acyl, as that term is defined above. The groups —NHC(O)OCH$_3$ and —NHC(O)NHCH$_3$ are non-limiting examples of substituted amido groups.

The term "alkylimino" when used without the "substituted" modifier refers to the group =NR, wherein the alkylimino group is attached with one σ-bond and one π-bond, in which R is an alkyl, as that term is defined above. Non-limiting examples of alkylimino groups include: =NCH$_3$, =NCH$_2$CH$_3$ and =N-cyclohexyl. The term "substituted alkylimino" refers to the group =NR, wherein the alkylimino group is attached with one σ-bond and one π-bond, in which R is a substituted alkyl, as that term is defined above. For example, =NCH$_2$CF$_3$ is a substituted alkylimino group.

Similarly, the terms "alkenylimino", "alkynylimino", "arylimino", "aralkylimino", "heteroarylimino", "heteroaralkylimino" and "acylimino", when used without the "substituted" modifier, refers to groups, defined as =NR, wherein the alkylimino group is attached with one σ-bond and one π-bond, in which R is alkenyl, alkynyl, aryl, aralkyl, heteroaryl, heteroaralkyl and acyl, respectively, as those terms are defined above. When any of the terms alkenylimino, alkynylimino, arylimino, aralkylimino and acylimino is modified by "substituted," it refers to the group =NR, wherein the alkylimino group is attached with one σ-bond and one π-bond, in which R is substituted alkenyl, alkynyl, aryl, aralkyl, heteroaryl, heteroaralkyl and acyl, respectively.

The term "alkylthio" when used without the "substituted" modifier refers to the group —SR, in which R is an alkyl, as that term is defined above. Non-limiting examples of alkylthio groups include: —SCH$_3$, —SCH$_2$CH$_3$, —SCH$_2$CH$_2$CH$_3$, —SCH(CH$_3$)$_2$, —SCH(CH$_2$)$_2$, —S-cyclopentyl, and —S-cyclohexyl. The term "substituted alkylthio" refers to the group —SR, in which R is a substituted alkyl, as that term is defined above. For example, —SCH$_2$CF$_3$ is a substituted alkylthio group.

Similarly, the terms "alkenylthio", "alkynylthio", "arylthio", "aralkylthio", "heteroarylthio", "heteroaralkylthio", and "acylthio", when used without the "substituted" modifier, refers to groups, defined as —SR, in which R is alkenyl, alkynyl, aryl, aralkyl, heteroaryl, heteroaralkyl and acyl, respectively, as those terms are defined above. When any of the terms alkenylthio, alkynylthio, arylthio, aralkylthio, heteroarylthio, heteroaralkylthio, and acylthio is modified by "substituted," it refers to the group —SR, in which R is substituted alkenyl, alkynyl, aryl, aralkyl, heteroaryl, heteroaralkyl and acyl, respectively.

The term "thioacyl" when used without the "substituted" modifier refers to a monovalent group with a carbon atom of a thiocarbonyl group as the point of attachment, further having a linear or branched, cyclo, cyclic or acyclic structure, further having no additional atoms that are not carbon or hydrogen, beyond the sulfur atom of the carbonyl group. The groups, —CHS, —C(S)CH$_3$, —C(S)CH$_2$CH$_3$, —C(S)CH$_2$CH$_2$CH$_3$, —C(S)CH(CH$_3$)$_2$, —C(S)CH(CH$_2$)$_2$, —C(S)C$_6$H$_5$, —C(S)C$_6$H$_4$CH$_3$, —C(S)C$_6$H$_4$CH$_2$CH$_3$, —C(S)C$_6$H$_3$(CH$_3$)$_2$, and —C(S)CH$_2$C$_6$H$_5$, are non-limiting examples of thioacyl groups. The term "thioacyl" therefore encompasses, but is not limited to, groups sometimes referred to as "alkyl thiocarbonyl" and "aryl thiocarbonyl" groups. The term "substituted thioacyl" refers to a radical with a carbon atom as the point of attachment, the carbon atom being part of a thiocarbonyl group, further having a linear or branched, cyclo, cyclic or acyclic structure, further having at least one atom, in addition to the sulfur atom of the carbonyl group, independently selected from the group consisting of N, O, F, Cl, Br, I, Si, P, and S. The groups, —C(S)CH$_2$CF$_3$, —C(S)O$_2$H, —C(S)OCH$_3$, —C(S)OCH$_2$CH$_3$, —C(S)OCH$_2$CH$_2$CH$_3$, —C(S)OC$_6$H$_5$, —C(S)OCH(CH$_3$)$_2$, —C(S)OCH(CH$_2$)$_2$, —C(S)NH$_2$, and —C(S)NHCH$_3$, are non-limiting examples of substituted thioacyl groups. The term "substituted thioacyl" encompasses, but is not limited to, "heteroaryl thiocarbonyl" groups.

The term "alkylsulfonyl" when used without the "substituted" modifier refers to the group —S(O)$_2$R, in which R is an alkyl, as that term is defined above. Non-limiting examples of alkylsulfonyl groups include: —S(O)$_2$CH$_3$, —S(O)$_2$CH$_2$CH$_3$, —S(O)$_2$CH$_2$CH$_2$CH$_3$, —S(O)$_2$CH(CH$_3$)$_2$, —S(O)$_2$CH(CH$_2$)$_2$, —S(O)$_2$-cyclopentyl, and —S(O)$_2$-cyclohexyl. The term "substituted alkylsulfonyl" refers to the group —S(O)$_2$R, in which R is a substituted alkyl, as that term is defined above. For example, —S(O)$_2$CH$_2$CF$_3$ is a substituted alkylsulfonyl group.

Similarly, the terms "alkenylsulfonyl", "alkynylsulfonyl", "arylsulfonyl", "aralkylsulfonyl", "heteroarylsulfonyl", and "heteroaralkylsulfonyl" when used without the "substituted" modifier, refers to groups, defined as —S(O)$_2$R, in which R is alkenyl, alkynyl, aryl, aralkyl, heteroaryl, and heteroaralkyl, respectively, as those terms are defined above. When any of the terms alkenylsulfonyl, alkynylsulfonyl, arylsulfonyl, aralkylsulfonyl, heteroarylsulfonyl, and heteroaralkylsulfonyl is modified by "substituted," it refers to the group —S(O)$_2$R, in which R is substituted alkenyl, alkynyl, aryl, aralkyl, heteroaryl and heteroaralkyl, respectively.

The term "alkylammonium" when used without the "substituted" modifier refers to a group, defined as —NH$_2$R$^+$, —NHRR'$^+$, or —NR'R''$^+$, in which R, R' and R'' are the same or different alkyl groups, or any combination of two of R, R' and R'' can be taken together to represent an alkanediyl. Non-limiting examples of alkylammonium cation groups include: —NH$_2$(CH$_3$)$^+$, —NH$_2$(CH$_2$CH$_3$)+, —NH$_2$(CH$_2$CH$_2$CH$_3$)+, —NH(CH$_3$)$_2$$^+$, —NH(CH$_2$CH$_3$)$_2$$^+$, —NH(CH$_2$CH$_2$CH$_3$)$_2$$^+$, —N(CH$_3$)$_3$$^+$, —N(CH$_3$)(CH$_2$CH$_3$)$_2$$^+$, —N(CH$_3$)$_2$(CH$_2$CH$_3$)$^+$, —NH$_2$C(CH$_3$)$_3$$^+$, —NH(cyclopentyl)$_2$$^+$, and —NH$_2$(cyclohexyl)$^+$. The term "substituted alkylammonium" refers —NH$_2$R$^+$, —NHRR'$^+$, or —NRR'R''$^+$, in which at least one of R, R' and R'' is a substituted alkyl or two of R, R' and R'' can be taken together to represent a substituted alkanediyl. When more than one of R, R' and R'' is a substituted alkyl, they can be the same of different. Any of R, R' and R'' that are not either substituted alkyl or substituted alkanediyl, can be either alkyl, either the same or different, or can be taken together to represent a alkanediyl with two or more carbon atoms, at least two of which are attached to the nitrogen atom shown in the formula.

The term "alkylsulfonium" when used without the "substituted" modifier refers to the group —SRR'$^+$, in which R and R' can be the same or different alkyl groups, or R and R' can be taken together to represent an alkanediyl. Non-limiting examples of alkylsulfonium groups include: —SH(CH$_3$)$^+$, —SH(CH$_2$CH$_3$)$^+$, —SH(CH$_2$CH$_2$CH$_3$)$^+$, —S(CH$_3$)$_2$$^+$, —S(CH$_2$CH$_3$)$_2$$^+$, —S(CH$_2$CH$_2$CH$_3$)$_2$$^+$, —SH(cyclopentyl)$^+$, and —SH(cyclohexyl)$^+$. The term "substituted alkylsulfonium" refers to the group —SRR'$^+$, in which R and R' cane be the same or different substituted alkyl groups, one of R or R' is an alkyl and the other is a substituted alkyl, or R and R' can be taken together to represent a substituted alkanediyl. For example, —SH(CH$_2$CF$_3$)$^+$ is a substituted alkylsulfonium group.

The term "alkylsilyl" when used without the "substituted" modifier refers to a monovalent group, defined as —SiH$_2$R, —SiHRR', or —SiRR'R'', in which R, R' and R'' can be the same or different alkyl groups, or any combination of two of R, R' and R'' can be taken together to represent an alkanediyl. The groups, —SiH$_2$CH$_3$, —SiH(CH$_3$)$_2$, —Si(CH$_3$)$_3$ and —Si(CH$_3$)$_2$C(CH$_3$)$_3$, are non-limiting examples of unsubstituted alkylsilyl groups. The term "substituted alkylsilyl" refers —SiH$_2$R, —SiHRR', or —SiRR'R'', in which at least one of R, R' and R'' is a substituted alkyl or two of R, R' and R'' can be taken together to represent a substituted alkanediyl. When more than one of R, R' and R'' is a substituted alkyl, they can be the same of different. Any of R, R' and R'' that are not either substituted alkyl or substituted alkanediyl, can be either alkyl, either the same or different, or can be taken together to represent a alkanediyl with two or more saturated carbon atoms, at least two of which are attached to the silicon atom.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}$C and $^{14}$C. Similarly, it is contemplated that one or more carbon atom(s) of a compound of the present invention may be replaced by a silicon atom(s). Furthermore, it is contemplated that one or more oxygen atom(s) of a compound of the present invention may be replaced by a sulfur or selenium atom(s).

A compound having a formula that is represented with a dashed bond is intended to include the formulae optionally having zero, one or more double bonds. Thus, for example, the structure

includes the structures

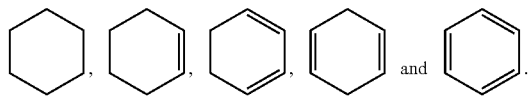

As will be understood by a person of skill in the art, no one such ring atom forms part of more than one double bond.

Any undefined valency on an atom of a structure shown in this application implicitly represents a hydrogen atom bonded to the atom.

A ring structure shown with an unconnected "R" group, indicates that any implicit hydrogen atom on that ring can be replaced with that R group. In the case of a divalent R group (e.g., oxo, imino, thio, alkylidene, etc.), any pair of implicit hydrogen atoms attached to one atom of that ring can be replaced by that R group. This concept is as exemplified below:

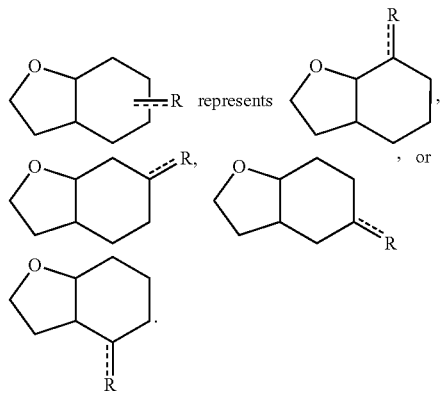

As used herein, a "chiral auxiliary" refers to a removable chiral group that is capable of influencing the stereoselectivity of a reaction. Persons of skill in the art are familiar with such compounds, and many are commercially available.

The term "protecting group," as that term is used in the specification and/or claims, is used in the conventional chemical sense as a group, which reversibly renders unreactive a functional group under certain conditions of a desired reaction and is understood not to be H. After the desired reaction, protecting groups may be removed to deprotect the protected functional group. All protecting groups should be removable (and hence, labile) under conditions which do not degrade a substantial proportion of the molecules being synthesized. In contrast to a protecting group, a "capping group" permanently binds to a segment of a molecule to prevent any further chemical transformation of that segment. It should be noted that the functionality protected by the protecting group may or may not be a part of what is referred to as the protecting group.

The term "leaving group," as that term is used in the specification and/or claims, is an atom or group (charged or uncharged) that becomes detached from an atom in what is considered to be the residual or main part of the substrate in a specified reaction.

Leaving groups include, but are not limited to: $NH_2^-$ (amine), $CH_3O^-$ (methoxy), $HO^-$ (hydroxyl), $CH_3COO^-$ (carboxylate), $H_2O$ (water), $F^-$, $Cl^-$, $Br^-$, $I^-$, $N_3^-$ (azide), $SCN^-$ (thiocyanate), $NO_2$ (nitro), and protecting groups.

Polyols include, but are not limited to: Boric acid, 2,2'-oxybis(methylene)bis(2-ethylpropane-1,3-diol), 2-Bromo-2-nitro-1,3-propanediol, 1,3-Dibromo-2-propanol, 3-Bromo-1,2-propanediol, (±)-3-Chloro-1,2-propanediol, 1,3-Propanediol, 2,2,3,3-Tetrafluoro-1,4-butanediol, (±)-2,3-Dibromo-1,4-butanediol, 1,4-Dibromo-2,3-butanediol, Tris (hydroxymethyl)nitromethane, (±)-1,3-Butanediol, 1,2-Butanediol, 1,4-Butanediol, 2,3-Butanediol, meso-2,3-Butanediol, (±)-1,2,4-Butanetriol, 2-Hydroxymethyl-1,3-propanediol, Diethylene glycol, Threitol, 2,2,3,3,4,4-Hexafluoro-1,5-pentanediol, 1,1,1,5,5,5-Hexafluoro-2,2,4,4-pentanetetrol, (±)-trans-1,2-Cyclopentanediol, 1,1-Bis (hydroxymethyl)cyclopropane, 1,3-Cyclopentanediol, cis-1,2-Cyclopentanediol, 1,2-Pentanediol, 1,4-Pentanediol, 1,5-Pentanediol, 2,2-Dimethyl-1,3-propanediol, 2,4-Pentanediol, 3-Methyl-1,3-butanediol, 1,1,1-Tris (hydroxymethyl)ethane, Pentaerythritol, Tetrabromocatechol, Tetrabromohydroquinone, Hexafluoro-2,3-bis(trifluoromethyl)-2,3-butanediol, 2,4,6-Tribromoresorcinol, 4-Nitrocatechol, 2,5-Dichlorohydroquinone, 3,5-Dichlorocatechol, 4,5-Dichlorocatechol, 4,6-Dichlororesorcinol, 2,4-Difluororesorcinol, 4-Bromoresorcinol, Bromohydroquinone, 4-Chlororesorcinol, Chlorohydroquinone, 4-Fluororesorcinol, Fluorohydroquinone, 4-Nitrocatechol, 2-Nitrophloroglucinol, 2-Amino-4-bromophenol, Hydroquinone, Pyrocatechol, Resorcinol, 1,3,5-Trihydroxybenzene dehydrate, Phloroglucinol, Phloroglucinol dehydrate, Pyrogallol, 4-Aminoresorcinol hydrochloride, 2,5-Diaminohydroquinone dihydrochloride, 4,6-Diaminoresorcinol dihydrochloride, (±)-trans-1,2-Cyclohexanediol, 1,3-Cyclohexanediol, 1,4-Cyclohexanediol, cis-1,2-Cyclohexanediol, 3-Allyloxy-1,2-propanediol, cis,cis-1,3,5-Cyclohexanetriol dehydrate, 1,2-Hexanediol, 1,5-Hexanediol, 1,6-Hexanediol, 2,5-Hexanediol, 3-Methyl-1,5-pentanediol, Hexylene glycol, Pinacol, 3,6-Dithiaoctane-1,8-diol, 1,1,1-Tris(hydroxymethyl)propane, 1,2,6-Hexanetriol, Dipropylene glycol, Triethylene glycol, a,a'-Diglycerol, 3-(Trimethylsilyl)-1,2-propanediol, 2-Methylresorcinol, 3-Methylcatechol, 4-Methylcatechol, 4-Methylresorcinol, Methylhydroquinone, Orcinol, 3-Methoxycatechol, 5-Methoxyresorcinol, 1,7-Heptanediol, 2,2-Diethyl-1,3-propanediol, 2,4-Dimethyl-2,4-pentanediol, 2-Methyl-2-propyl-1,3-propanediol, (±)-3-tert-Butoxy-1,2-propanediol, 3,7-Dioxa-1,9-nonanediol, 5-Nitro-m-xylene-a,a'-diol, (±)-1-Phenyl-1,2-ethanediol, 1,2-Benzenedimethanol, 1,3-Benzenedimethanol, 1,4-Benzenedimethanol, 1-Phenyl-1,2-ethanediol, 4-Ethylcatechol, 4-Ethylresorcinol, 1,4-Dihydroxy-2,6-dimethoxybenzene, Dopamine hydrochloride, 1,4-Cyclohexanedimethanol, 2,2,4,4-Tetramethyl-1,3-cyclobutanediol, cis-1,2-Cyclohexanedimethanol, cis-1,2-Cyclooctanediol, cis-1,5-Cyclooctanediol, Cyclohexane-1,4-dimethanol, 1,2-Octanediol, 1,8-Octanediol, 2,2,4-Trimethyl-1,3-pentanediol, 2,5-Dimethyl-2,5-hexanediol, 2-Ethyl-1,3-hexanediol, 1,2,7,8-Octanetetrol, 1-(4-Nitrophenoxy)-2,3-propanediol, 2-Phenyl-1,3-propanediol, Trimethylhydroquinone, 2,6-Bis(hydroxymethyl)-p-cresol, 4-Methoxy-1,3-benzenedimethanol, 5-Methoxy-1,3-benzenedimethanol, 4-Hydroxy-3-methoxyphenylglycol, 1,9-Nonanediol, 2-Butyl-2-ethyl-1,3-propanediol, Triglycerol80, 2,2,3,3,4,4,5,5,6,6,7,7,8,8,9,9-Hexadecafluoro-1,10-decanediol, 1,2-Dihydroxynaphthalene, 1,4-Dihydroxynaphthalene, 1,5-Dihydroxynaphthalene, 1,6-Dihydroxynaphthalene, 1,7-Dihydroxynaphthalene, 2,3-Dihydroxynaphthalene, 2,6-Dihydroxynaphthalene, 2,7-Dihydroxynaphthalene, 4-tert-Butylcatechol, tert-Butylhydroquinone, (±)-3-Benzyloxy-1,2-propanediol, 2-Benzyloxy-1,3-propanediol, Mephenesin, 1,3-Adamantanediol, (±)-exo,exo-2,3-Camphanediol, [1,1'-Bicyclopentyl]-1,1'-diol, p-Menthane-1,8-diol monohydrate, 2,2,6,6-Tetrakis(hydroxymethyl)cyclohexanol, 1,10-Decanediol, Pentaethylene glycol, Dipentaerythritol, Olivetol, 3-t-Butyl-5-methoxycatechol, 4-tert-Butyl-5-methoxycatechol, 2,2-Dibutyl-1,3-propanediol, a,a,a',a'-Tetrakis(trifluoromethyl)-1,3-benzenedimethanol, a,a,a',a'-Tetrakis(trifluoromethyl)-1,4-benzenedimethanol, 2-(2-Chlorophenyl)hydroquinone hydrate, 2,2'-Dihydroxybiphenyl, 2-Phenylhydroquinone, 4,4'-Dihydroxybiphenyl, 1,8-Naphthalenedimethanol, 3,5-Diisopropylcatechol, 4-Hexylresorcinol, a,a,a',a'-Tetramethyl-1,3-benzenedimethanol, 4,8-Bis(hydroxymethyl)tricyclo[5.2.1.02,6]decane, 1,2-Dodecanediol, Hexaethylene glycol, Hexachlorophene, Bis(5-chloro-2-hydroxyphenyl) methane, 4,4'-Methylenediphenol, Bis(2-hydroxyphenyl) methane, Bis(4-hydroxyphenyl)methane, 1,1,1-Trichloro-2,2-bis(4-hydroxyphenyl)ethane, meso-Hydrobenzoin, 2,5-Di-tert-butylhydroquinone, 3,5-Di-tert-butylcatechol, 4,6-Di-tert-butylresorcinol, 1,14-Tetradecanediol, 4,4'-(Hexafluoroisopropylidene)diphenol, 3,3',5,5'-Tetrabromobisphenol A, 9H-Fluorene-9,9-dimethanol, 4,4'-Isopropylidenediphenol, Bisphenol A, Tripentaerythritol, 2,3-Diphenyl-2,3-butanediol, 1,16-Hexadecanediol, 1,2-Hexadecanediol, 2,2-Bis(4-hydroxy-3-methylphenyl)propane, 2,2-Dibenzyl-1,3-propanediol, 2-Methoxy-5-(2'-ethylhexyloxy)-1,4-bis(hydroxymethyl)benzene, trans-9,10-Dihydro-9,10-ethanoanthracene-11,12-dimethanol, Nordihydroguaiaretic acid, 4-Dodecylresorcinol, 1-O-Palmityl-rac-glycerol, 6,6'-Dibromo-1,1'-bi-2-naphthol, (±)-1,1'-Bi(2-naphthol), 5,5',6,6',7,7',8,8'-Octahydro-1,1'-bi-2-naphthol, Batyl alcohol, 4,4'-(9-Fluorenylidene)diphenol, 1,1,2,2-Tetraphenyl-1,2-ethanediol, and 1,1,2,2-Tetrakis(p-hydroxyphenyl)ethane.

As used herein, a crosslinking refers to joining moieties together by covalent bonding using a crosslinking agent, i.e., forming a linking group, or by the radical polymerization of monomers such as, but not limited to methacrylates, methacrylamides, acrylates, or acrylamides. In some embodiment, the linking groups are grown to the end of the polymer arms. In preferred embodiments, siloxane-polymers conjugates have alkenyl groups and are crosslinked by radical polymerization the absence or presence of other molecules that contain alkenyl groups, such as, but not limited to, methacrylates, methacrylamides, acrylates, or acrylamides and crosslinkers and radical initiators.

As used herein, a radical refers are species with a single, unpaired electron. Radical species can be electrically neutral, but it is not intended that the term be limited to electrically neutral species, in which case they are referred to as free radicals. Pairs of electrically neutral radicals may be formed via homolytic bond breakage. Molecular chlorine, $Cl_2$, forms chlorine radicals (Cl.) upon heating. Similarly peroxides form oxygen radicals and per-esters fragment to acyl radicals, which may decompose to lose carbon dioxide to give carbon radicals. Azo compounds eject nitrogen to give a pair of carbon radicals. Many polymers may be made by the chain radical addition of substituted alkenyl moieties with radicals.

As used herein, "$T_g$" and "glass transition temperature" refers to the temperature at which the Gibbs free energy is such that the activation energy for the cooperative movement of a substantial number of elements of the polymer is exceeded. $T_g$ is typically experimentally determined by measuring the stiffness of the material verses the temperature, i.e., as one increased the temperature, $T_g$ has been reached when the stiffness stays substantially the same, plateaus, for a while, until the material melts, $T_m$.

The term "effective amount" as used herein, refers to a particular amount of a pharmaceutical composition comprising a therapeutic agent that achieves a clinically beneficial result (i.e., for example, a reduction of symptoms). Toxicity and therapeutic efficacy of such compositions can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The term "symptom", as used herein, refers to any subjective or objective evidence of disease or physical disturbance observed by the patient. For example, subjective evidence is usually based upon patient self-reporting and may include, but is not limited to, pain, headache, visual disturbances, nausea and/or vomiting. Alternatively, objective evidence is usually a result of medical testing including, but not limited to, body temperature, complete blood count, lipid panels, thyroid panels, blood pressure, heart rate, electrocardiogram, tissue and/or body imaging scans.

The term "disease", as used herein, refers to any impairment of the normal state of the living animal or plant body or one of its parts that interrupts or modifies the performance of the vital functions. Typically manifested by distinguishing signs and symptoms, it is usually a response to: i) environmental factors (as malnutrition, industrial hazards, or climate); ii) specific infective agents (as worms, bacteria, or viruses); iii) inherent defects of the organism (as genetic anomalies); and/or iv) combinations of these factors The terms "reduce," "inhibit," "diminish," "suppress," "decrease," "prevent" and grammatical equivalents (including "lower," "smaller," etc.) when in reference to the expression of any symptom in an untreated subject relative to a treated subject, mean that the quantity and/or magnitude of the symptoms in the treated subject is lower than in the untreated subject by any amount that is recognized as clinically relevant by any medically trained personnel. In one embodiment, the quantity and/or magnitude of the symptoms in the treated subject is at least 10% lower than, at least 25% lower than, at least 50% lower than, at least 75% lower than, and/or at least 90% lower than the quantity and/or magnitude of the symptoms in the untreated subject.

The term "injury" as used herein, denotes a bodily disruption of the normal integrity of tissue structures. In one sense, the term is intended to encompass surgery. In another sense, the term is intended to encompass irritation, inflammation, infection, and skeletal/muscular defects. In another sense, the term is intended to encompass skeletal injuries including, but not limited to, craniofacial injuries, bone cracks, bone breaks, osteoporotic defects, congenital defects, spinal defects etc.

The term "attached" as used herein, refers to any interaction between a polymer and a compound (i.e., for example, a therapeutic drug and/or a microparticle). Attachment may be reversible or irreversible. Such attachment includes, but is not limited to, covalent bonding, ionic bonding, Van der Waals forces or friction, and the like.

The term "binding" as used herein, refers to any interaction between any material (i.e., for example, an SMP material) and a surface. Such as surface is defined as a "binding surface". Binding may be reversible or irreversible. Such binding may be, but is not limited to, non-covalent binding, covalent bonding, ionic bonding, Van de Waal forces or friction, and the like. A material is bound to a surface if it is impregnated, incorporated, coated, in suspension with, in solution with, mixed with, etc.

The term "therapeutic drug" or "compound" as used herein, refers to any pharmacologically active substance capable of being administered which achieves a desired effect. Drugs or compounds can be synthetic or naturally occurring, non-peptide, proteins or peptides, oligonucleotides or nucleotides, polysaccharides or sugars.

As used herein, a "bioactive substance" refers to any of a variety of chemical moieties and that binds with a biomolecule such as, but not limited to, peptides, proteins, enzymes, receptors, substrates, lipids, antibodies, antigens, and nucleic acids. In certain preferred embodiments, the bioactive substance is a biomolecule but it not intended that the bioactive substance be limited to biomolecules. In other preferred embodiments, the bioactive substances provide hydrophobic, hydrophilic or electrostatic interactions, such as polycarboxylic acids that are anionic at physiological pH. In other preferred embodiment, the alkaline growth factors (with isoelectric point above 7) are retained via. favorable electrostatic interactions by the polycarboxylates, and subsequently released in a controlled and sustained manner.

The term "administered" or "administering", as used herein, refers to any method of providing a composition to a patient such that the composition has its intended effect on the patient. For example, one method of administering is by an indirect mechanism using at least one surgical device such as, but not limited to a clamps, probes, scissors, syringe, catheter, or endoscope etc.

The term "anti-osteoporosis drug" or "osteogenic drug, as used herein, refers to any drug that stimulates bone formation. For example, an anti-osteoporosis drug may include, but is not limited to; bisphosphonates such as alendronate (Fosamax), ibandronate (Boniva), and risedronate (Actonel). calcitonin, parathyroid hormone (Teriparatide; Forteo), and/or raloxifene.

The term "antiplatelets" or "antiplatelet drug" as used herein, refers to any drug that prevents aggregation of platelets or fibrin formation (i.e., for example as a prior event to adhesion formation). For example, an antiplatelet drug comprises an inhibitor of glycoprotein IIb/IIIa (GPIIb/IIIa). Further a GPIIb/IIIa inhibitor includes, but is not limited to, xemilofiban, abciximab (ReoPro®) cromafiban, elarofiban, orbofiban, roxifiban, sibrafiban, RPR 109891, tirofiban (Aggrastat®), eptifibatide (Integrilin®), UR-4033, UR-3216 or UR-2922.

The term, "antithrombins" or "antithrombin drug" as used herein, refers to any drug that inhibits or reduces thrombi formation and include, but are not limited to, bivalirudin, ximelagatran, hirudin, hirulog, argatroban, inogatran, efegatran, or thrombomodulin.

The term, "anticoagulants" or "anticoagulant drug" as used herein, refers to any drug that inhibits the blood coagulation cascade. A typical anticoagulant comprises heparin, including but not limited to, low molecular weight heparin (LMWH) or unfractionated heparin (UFH). Other anticoagulants include, but are not limited to, tinzaparin, certoparin, parnaparin, nadroparin, ardeparin, enoxaparin, reviparin or dalteparin. Specific inhibitors of the blood coagulation cascade include, but are not limited to, Factor Xa (FXa) inhibitors (i.e., for example, fondaparinux), Factor IXa (FM) inhibitors, Factor XIIIa (FXIIIa) inhibitors, and Factor VIIa (FVIIa) inhibitors.

The term "patient", as used herein, is a human or animal and need not be hospitalized. For example, out-patients, persons in nursing homes are "patients." A patient may comprise any age of a human or non-human animal and therefore includes both adult and juveniles (i.e., children). It is not intended that the term "patient" connote a need for medical treatment, therefore, a patient may voluntarily or involuntarily be part of experimentation whether clinical or in support of basic science studies.

The term "derived from" as used herein, refers to the source of a compound or sequence. In one respect, a compound or sequence may be derived from an organism or particular species. In another respect, a compound or sequence may be derived from a larger complex or sequence.

The term "peptide" as used herein, refers to any of various amides that are derived from two or more amino acids by combination of the amino group of one acid with the carboxyl group of another and are usually obtained by partial hydrolysis of proteins. In general, a peptide comprises amino acids having an order of magnitude with the tens.

The term "pharmaceutically" or "pharmacologically acceptable", as used herein, refer to molecular entities and compositions that do not produce adverse, allergic, or other untoward reactions when administered to an animal or a human.

The term, "pharmaceutically acceptable carrier", as used herein, includes any and all solvents, or a dispersion medium including, but not limited to, water, ethanol, polyol (for example, glycerol, propylene glycol, and liquid polyethylene glycol, and the like), suitable mixtures thereof, and vegetable oils, coatings, isotonic and absorption delaying agents, liposome, commercially available cleansers, and the like. Supplementary bioactive ingredients also can be incorporated into such carriers.

The term, "purified" or "isolated", as used herein, may refer to a peptide composition that has been subjected to treatment (i.e., for example, fractionation) to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the composition (i.e., for example, weight/weight and/or weight/volume). The term "purified to homogeneity" is used to include compositions that have been purified to "apparent homogeneity" such that there is single protein species (i.e., for example, based upon SDS-PAGE or HPLC analysis). A purified composition is not intended to mean that some trace impurities may remain.

As used herein, the term "substantially purified" refers to molecules, either nucleic or amino acid sequences, that are removed from their natural environment, isolated or separated, and are at least 60% free, preferably 75% free, and more preferably 90% free from other components with which they are naturally associated. An "isolated polynucleotide" is therefore a substantially purified polynucleotide.

The term "biocompatible", as used herein, refers to any material does not illicit a substantial detrimental response in the host. There is always concern, when a foreign object is introduced into a living body, that the object will induce an immune reaction, such as an inflammatory response that will have negative effects on the host. In the context of this invention, biocompatibility is evaluated according to the application for which it was designed: for example; a bandage is regarded a biocompatible with the skin, whereas an implanted medical device is regarded as biocompatible with the internal tissues of the body. Preferably, biocompatible materials include, but are not limited to, biodegradable and biostable materials. A substantial detrimental response has not occurred if an implant comprising the material is in close association to its implant site within the host animal and the response is better than a tissue response recognized and established as suitable from a materials provided in an ASTM. ASTM subcommittee F04.16 on Biocompatibility Test Methods has developed biocompatibility standards for medical and surgical materials and devices. For example, materials that are to be used in contact with the blood stream must be composed of materials that meet hemocompatibility standards. One of these tests is for damage to red blood cells, which can result in hemolysis, that is, rupturing of the cells, as described in F 756, Practice for Assessment of Hemolytic Properties of Materials, incorporated herein by reference.

The term "biodegradable" as used herein, refers to any material that can be acted upon biochemically by living cells or organisms, or processes thereof, including water, and broken down into lower molecular weight products such that the molecular structure has been altered.

The term "bioerodible" as used herein, refers to any material that is mechanically worn away from a surface to which it is attached without generating any long term inflammatory effects such that the molecular structure has not been altered. In one sense, bioerosin represents the final stages of "biodegradation" wherein stable low molecular weight products undergo a final dissolution.

The term "bioresorbable" as used herein, refers to any material that is assimilated into or across bodily tissues. The bioresorption process may utilize both biodegradation and/or bioerosin.

The term "biostable" as used herein, refers to any material that remains within a physiological environment for an intended duration resulting in a medically beneficial effect.

The term "Nucleic acid sequence" and "nucleotide sequence" as used herein, refer to an oligonucleotide or polynucleotide, and fragments or portions thereof, and to DNA or RNA of genomic or synthetic origin which may be single- or double-stranded, and represent the sense or antisense strand.

The term "an isolated nucleic acid", as used herein, refers to any nucleic acid molecule that has been removed from its natural state (e.g., removed from a cell and is, in a preferred embodiment, free of other genomic nucleic acid).

The terms "amino acid sequence" and "polypeptide sequence" as used herein, are interchangeable and to refer to a sequence of amino acids.

As used herein the term "portion" when in reference to a protein (as in "a portion of a given protein") refers to fragments of that protein. The fragments may range in size from four amino acid residues to the entire amino acid sequence minus one amino acid.

The term "portion" when used in reference to a nucleotide sequence refers to fragments of that nucleotide sequence. The fragments may range in size from 5 nucleotide residues to the entire nucleotide sequence minus one nucleic acid residue.

The term "antibody" refers to immunoglobulin evoked in animals by an immunogen (antigen). It is desired that the antibody demonstrates specificity to epitopes contained in the immunogen. The term "polyclonal antibody" refers to immunoglobulin produced from more than a single clone of plasma cells; in contrast "monoclonal antibody" refers to immunoglobulin produced from a single clone of plasma cells.

The term "patient" or "subject", as used herein, is a human or animal and need not be hospitalized. An animal may including but not limited to, a mammal including but not limited to caprine, ovine, bovine, reptile or avian. For example, out-patients, persons in nursing homes are "patients." A patient may comprise any age of a human or non-human animal and therefore includes both adult and juveniles (i.e., children). It is not intended that the term "patient" connote a need for medical treatment, therefore, a patient may voluntarily or involuntarily be part of experimentation whether clinical or in support of basic science studies.

The terms "specific binding" or "specifically binding" when used in reference to the interaction of an antibody and a protein or peptide means that the interaction is dependent upon the presence of a particular structure (i.e., for example, an antigenic determinant or epitope) on a protein; in other words an antibody is recognizing and binding to a specific protein structure rather than to proteins in general. For example, if an antibody is specific for epitope "A", the presence of a protein containing epitope A (or free, unlabelled A) in a reaction containing labeled "A" and the antibody will reduce the amount of labeled A bound to the antibody.

The term "small organic molecule" as used herein, refers to any molecule of a size comparable to those organic molecules generally used in pharmaceuticals. The term excludes biological macromolecules (e.g., proteins, nucleic acids, etc.). Preferred small organic molecules range in size from approximately 10 Da up to about 5000 Da, more preferably up to 2000 Da, and most preferably up to about 1000 Da.

As used herein, the term "antisense" is used in reference to RNA sequences which are complementary to a specific RNA sequence (e.g., mRNA). Antisense RNA may be produced by any method, including synthesis by splicing the gene(s) of interest in a reverse orientation to a viral promoter which permits the synthesis of a coding strand. Once introduced into a cell, this transcribed strand combines with natural mRNA produced by the cell to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

As used herein, the terms "siRNA" refers to either small interfering RNA, short interfering RNA, or silencing RNA. Generally, siRNA comprises a class of double-stranded RNA molecules, approximately 20-25 nucleotides in length. Most notably, siRNA is involved in RNA interference (RNAi) pathways and/or RNAi-related pathways. wherein the compounds interfer with gene expression.

As used herein, the term "shRNA" refers to any small hairpin RNA or short hairpin RNA. Although it is not necessary to understand the mechanism of an invention, it is believed that any sequence of RNA that makes a tight hairpin turn can be used to silence gene expression via RNA interference. Typically, shRNA uses a vector stably introduced into a cell genome and is constitutively expressed by a compatible promoter. The shRNA hairpin structure may also cleaved into siRNA, which may then become bound to the RNA-induced silencing complex (RISC). This complex binds to and cleaves mRNAs which match the siRNA that is bound to it.

As used herein, the term "microRNA", "miRNA", or "μRNA" refers to any single-stranded RNA molecules of approximately 21-23 nucleotides in length, which regulate gene expression. miRNAs may be encoded by genes from whose DNA they are transcribed but miRNAs are not translated into protein (i.e. they are non-coding RNAs). Each primary transcript (a pri-miRNA) is processed into a short stem-loop structure called a pre-miRNA and finally into a functional miRNA. Mature miRNA molecules are partially complementary to one or more messenger RNA (mRNA) molecules, and their main function is to down-regulate gene expression.

The term "medical device", as used herein, refers broadly to any apparatus used in relation to a medical procedure. Specifically, any apparatus that contacts a patient during a medical procedure or therapy is contemplated herein as a medical device. Similarly, any apparatus that administers a compound or drug to a patient during a medical procedure or therapy is contemplated herein as a medical device. "Direct medical implants" include, but are not limited to, urinary and intravascular catheters, dialysis shunts, wound drain tubes, skin sutures, vascular grafts and implantable meshes, intraocular devices, implantable drug delivery systems and heart valves, and the like. "Wound care devices" include, but are not limited to, general wound dressings, non-adherent dressings, burn dressings, biological graft materials, tape closures and dressings, and surgical drapes. "Surgical devices" include, but are not limited to, endoscope systems (i.e., catheters, vascular catheters, surgical tools such as scalpels, retractors, and the like) and temporary drug delivery devices such as drug ports, injection needles etc. to administer the medium. A medical device is "coated" when a medium comprising a cytostatic or antiproliferative drug (i.e., for example, sirolimus or an analog of sirolimus) becomes attached to the surface of the medical device. This attachment may be permanent or temporary. When temporary, the attachment may result in a controlled release of a cytostatic or antiproliferative drug.

BRIEF DESCRIPTION OF THE FIGURES

FIG. 7F illustrates a proposed shape memory mechanism even though the applicant does not intend that the invention be limited to any particular mechanism.

FIG. 16A: Synthesis and crosslinking of macromers to make either a POSS-SMP or an Org-SMP.

FIG. 16B: Comparison of storage modulus (E')-temperature and loss angle (Tan δ)-temperature (denoted by black arrows) curves of POSS-SMP-20 vs. Org-SMP-20.

FIG. 17 presents exemplary data showing thermal mechanical properties of POSS-SMPs with varying PLA arm lengths.

FIG. 18 presents exemplary data of POSS-SMP after chemical modification with a bioactive peptide.

FIG. 20A: Total energy contours of systemic grid scans of torsion angles 1 (O—Si—O—Si), 2 (Si—O—Si—C), 3 (C—C—C—O), 4 (C—C—O—H), and 5 (O—Si—C—C) of the POSS core.

FIG. 20B: Total energy contours of systemic grid scans of torsion angles 1 (C—C—C—O), 2 (C—C—O—C), 3 (C—C—C—O), and 4 (C—C—O—H) of the Organic core.

FIG. 24A: % Mass residue of POSS-SMPs in PBS (pH 7.4) as a function of time and PLA arm length. A sample size of 3 was applied.

FIG. 24B: SEM micrographs of POSS-SMPs before and after 73-day incubation in PBS at 37° C.

FIG. 28 presents exemplary data regarding in vivo POSS-SMP immunogenicity following subcutaneous implantation in rats.

DETAILED DESCRIPTION OF THE INVENTION

Figure 1:
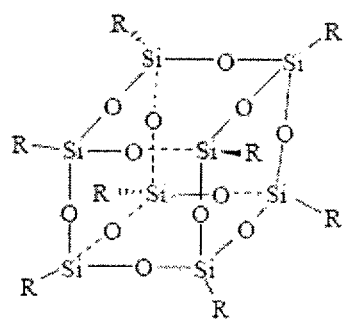
FIG. 1A shows an illustration of an embodiment of the invention wherein a POSS is functionalized with groups, R.
FIG. 1B shows an illustration of alternative POSS functionalized embodiments.
Figure 1:
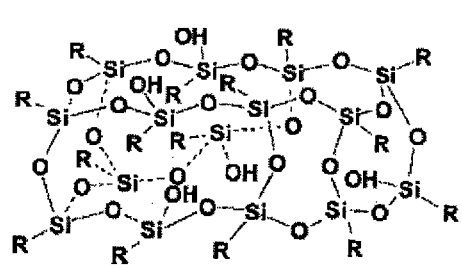
Figure 1:
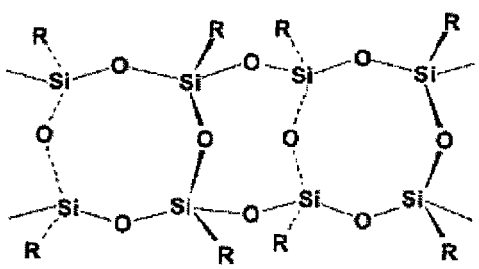
Figure 1:
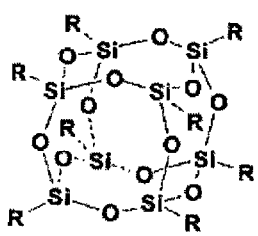
Figure 1:
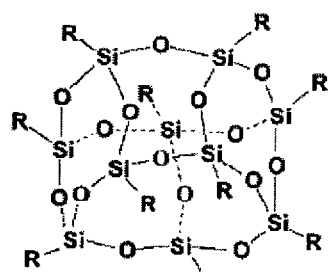
Figure 1:
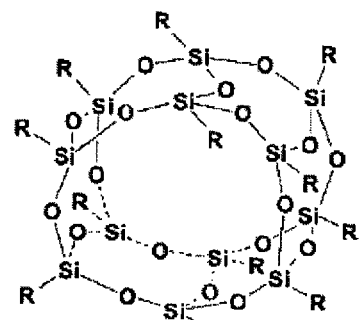

The present invention relates to shape memory compositions and methods of making and using these compositions. Such compositions are designed with inherent shape memory properties that remain fixed at specific temperatures. Some compositions comprise polymer mixtures providing tunable transition temperatures that allows a composition to change shape at predetermined temperatures. The structural components of the compositions may be based upon any multifunctional building block core, wherein the building blocks may be functionalized with a variety of reactive groups.

One structural feature of a shape memory network is a well-defined star-branched macromer comprising building blocks containing identical polymer chains which enabled high-density crosslinking, selective biofunctionalization, and more uniform response of the polymer chains to thermal stimuli. Compared to organic polyhydroxyl cores, a bulkier and more rigid POSS nanoparticle core is more effective in minimizing excessive global entanglement of the tethered network chains and in maximizing their participation in the shape memory process. Although it is not necessary to understand the mechanism of an invention, it is believed that a strategic use of well-defined nanoparticles to mediate polymer chain-chain interactions coupled with a bottom-up approach towards control over the structure, mechanical properties and chemical functionalities may allow optimization of SMP multiple properties for alternative applications other than those described herein.

In one embodiment, the present invention contemplates compositions comprising hydrocarbon subunits, preferably hydrocarbon subunits having thermal-responsive properties. In some embodiments, the hydrocarbon subunits are functionalized with polymers to create hydrocarbon-polymer conjugates. In another embodiment, hydrocarbon-polymer conjugates comprise polylactone segments. The hydrocarbon-polymer conjugates may be crosslinked together to form, a material, and these materials may be functionalized with bioactive compounds so that the materials have desirable biocompatibility or bioactivity when used in medical devices. In further embodiments, the invention relates to composite materials that contain a polymer matrix and aggregates, and in some embodiments, methods of making, and methods of using these materials. Preferably, the aggregates are calcium phosphate aggregates. Preferably, the material is resistant to fracture. In further embodiments, the materials are used in surgical procedures of bone replacement. In further embodiments, the materials contain polyhedral hydrocarbons and/or biodegradable segments.

In one embodiment, the present invention contemplates compositions comprising siloxanes, preferably siloxanes having thermal-responsive properties. In some embodiments, silsesquioxane groups are functionalized with polymers to create silsequioxane-polymer conjugates. In another embodiment, silsequioxane-polymer conjugates comprise polylactone segments. The silsequioxane-polymer conjugates may be crosslinked together to form a material, and these materials may be functionalized with bioactive compounds so that the materials have desirable biocompatibility or bioactivity when used in medical devices. In further embodiments, the invention relates to composite materials that contain a polymer matrix and aggregates, and in some embodiments, methods of making, and methods of using these materials. Preferably, the aggregates are calcium phosphate aggregates. Preferably, the material is resistant to fracture. In further embodiments, the materials are used in surgical procedures of bone replacement. In further embodiments, the materials contain polyhedral silsesquioxanes and/or biodegradable segments.

I. Shape Memory Polymers

Figure 12:
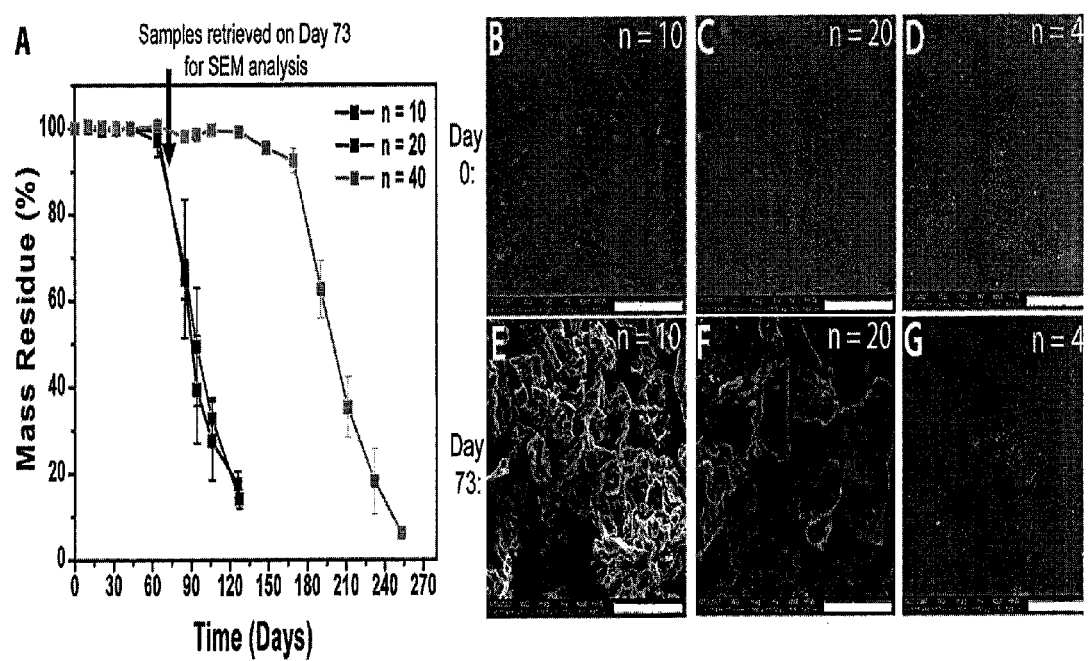
FIG. 12 shows in vitro degradation of a urethane-crosslinked macromer of the present invention, POSS-(PLA$_n$)$_8$, as a function of PLA chain length, wherein n=10, 20, 40. Panel A shows the percentage of mass reduction of crosslinked macromer 2 in PBS (pH 7.4) as a function of time. Panels B-G show SEM micrographs of the smooth surfaces prior to hydrolytic degradation (B: n=10; C: n=20; D: n=40) and the morphology of the materials after 73 days in PBS (E: n=10; F: n=20; G: n=40). Scale bars: 50 µm. A sample size of 3 was applied (N=3).

Embodiments of the invention concern a class of POSS-strengthened biodegradable shape memory polyester-urethanes that exhibit desired characteristics. A system is designed to provide a chemically crosslinked thermoset, which exhibits a transition of storage modulus around its glass transition temperature. The materials are prepared by the chemical crosslinking, i.e., preferably by the formation of urethane linkages with hexamethylene diisocyanate of multifunctional hybrid polyester, which are synthesized by ring opening polymerization of cyclic monomers such as, but not limited to, lactide, glycolide and caprolactone. The polyester-urethane solution can be cast into molds and crosslinked to form films or bulk materials with desired shapes (FIG. 12). The permanent shape can be easily deformed when heated above the transformation temperature; the deformed shape can be fixed at room temperature and preserved for a sufficient time, e.g., greater than 1 month. When heated again the deformed shape can recover to its original shape rapidly, e.g., within 1 second (FIG. 12). Responsive shape recovery times of this material is 300 times less than those disclosed in Lendlein et al., *Journal of Polymer Science Part A—Polymer Chemistry* 43, 1369 (2005), incorporated herein by reference. A number of methods can be used to trigger the transition of the polymer from its temporary shape to its permanent shape. For example, a resistive heater of radio frequency (RF) heater can be used. Alternatively or in addition, the polymer can be formulated to incorporate magnetic particles that are susceptible to heating by magnetic effects. The incorporation of the POSS cores reduces the crystallinity of the polyesters and results in the formation of amorphous polyester-urethane network with adjustable glass transition temperature and a transparent appearance.

In some embodiments of the invention have the advantages to known materials in that they have 1) lighter weights and larger recoverable deformation ranges (up to several hundred percent strain), 2) more tunable mechanical properties and glass transition temperatures ($T_g$'s) that are suitable for biological applications, and 3) better chemical functionalizability to improve their biodegradability and biocompatibility or bioactivity. Tunable biodegradability with any single shape-memory material having substantial shape memory effect has not been previously reported.

Figure 7A:
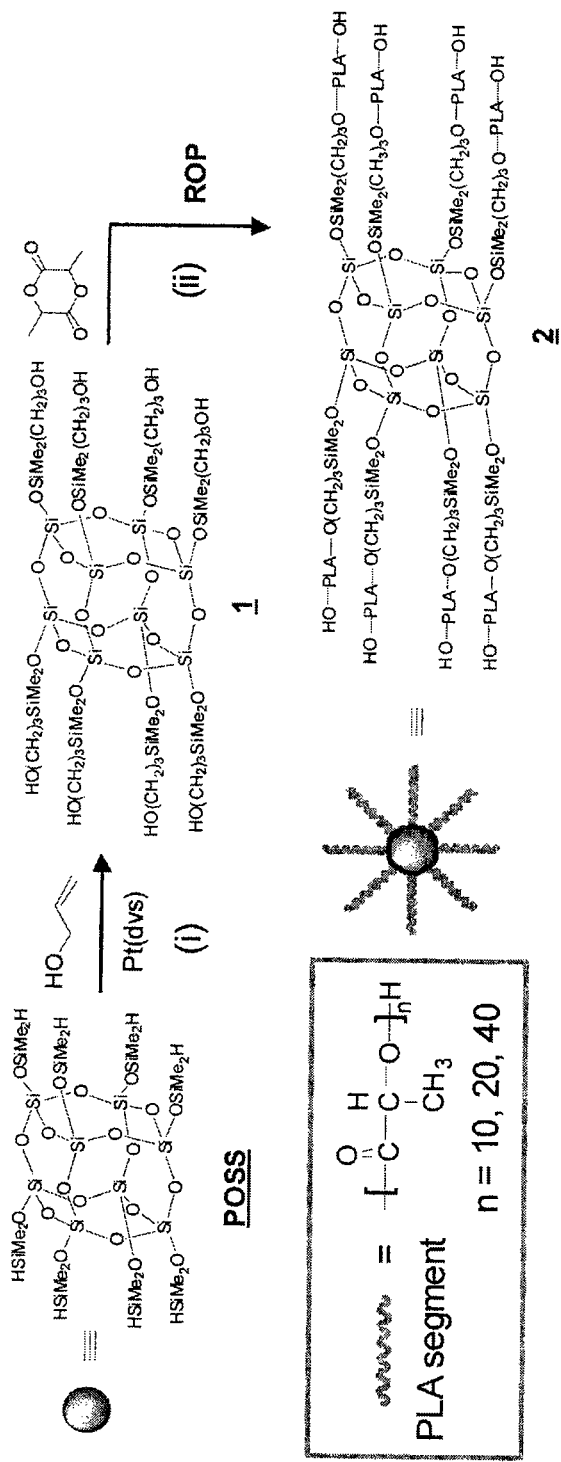
FIG. 7A shows a preferred method of making embodiments. It illustrates the synthesis of macromer 2 wherein (i) is carried out using 15 eq. allyl alcohol, 6×10$^{-4}$ eq. Pt(dvs), 20° C., 1 h, followed by 90° C., 1.5 h, N$_2$; and (ii) is carried out as follows: 40, 80 or 160 eq. rac-lactide, 200 ppm stannous octoate, 115° C., N$_2$, 20 h.
Figure 7:
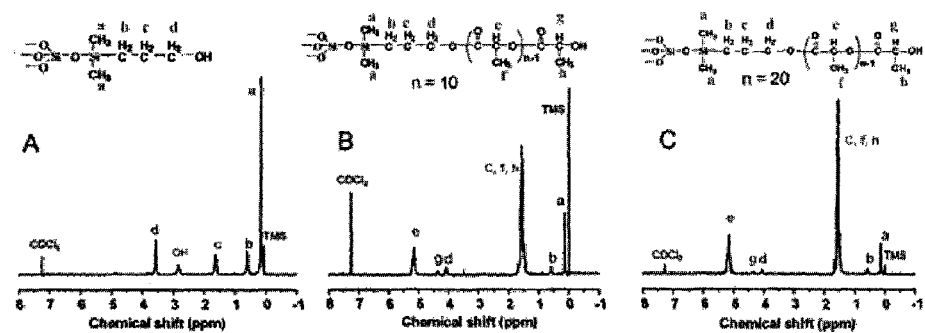
FIG. 7B shows the $^1$H NMR spectra for a monomer (A) and n=10 (B) and n=20 (C) macromers of the invention.
FIG. 7C shows the estimated and determined molecular mass for the n=10 and n=20 macromers disclosed in FIG. 7B as well as an n=40 macromer. Table Legend: "Theoretical"=theoretical molecular mass of the disclosed macromers; "GPC"=molecular mass of the disclosed macromers as determined by gel permeation chromatography; "NMR"=calculated molecular mass of the disclosed macromers as determined by NMR peak area integration; "PDI"=polymer dispersion index of the disclosed macromers.
FIG. 7D shows differential scanning calorimetry (DSC) traces of crosslinked POSS-(PLA$_n$)$_8$ urethane with a heating rate of 10° C./min.
FIG. 7E shows data of flexural moduli of urethane-crosslinked POSS-(PLA$_n$)$_8$ as a function of PLA chain length in preferred embodiments.
FIG. 7F shows data of flexural moduli as a function of temperature in preferred embodiments.
FIGS. 7G and 7H show dynamic mechanical properties (storage moduli and tan delta) of the urethane-crosslinked macromer 2 (FIG. 7A) and 7 (FIG. 8C) as a function of PLA chain length and temperature.
FIG. 7I summarizes some of the properties of the present invention as described in FIGS. 7G and 7H. The dynamical mechanical properties were measured on a DMA Q800 (TA Instrument), which has a force resolution of 0.00001N and a displacement resolution of 1.0 nm. With temperature sweeping from 25.0° C. to 110° C. at a rate of 2.0° C./min, the samples were subjected to an oscillated deformation with constant strain of 0.02% at 1 Hz. The storage modulus, loss modulus and loss angel (Tan delta) were recorded with temperature.
FIG. 7J shows shape memory behavior.
Figure 7:
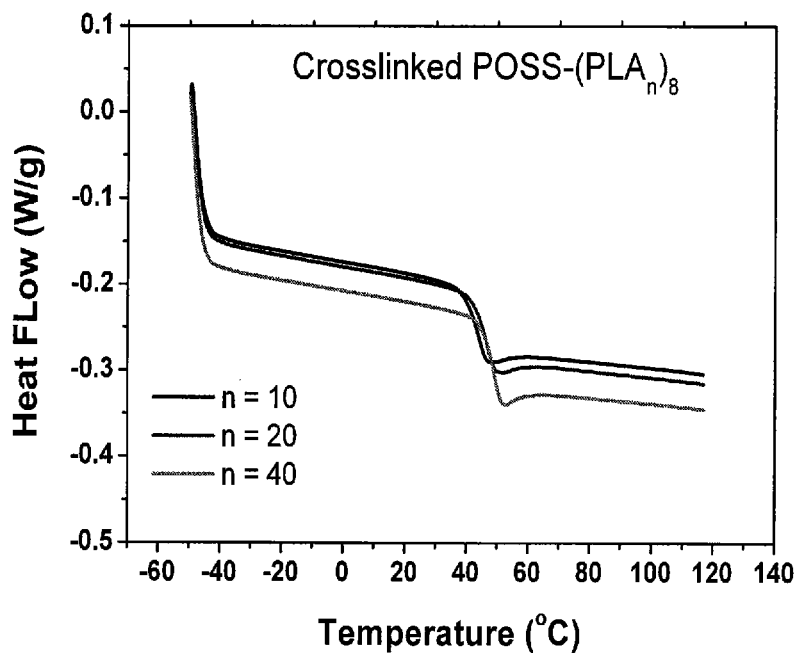
Figure 7:
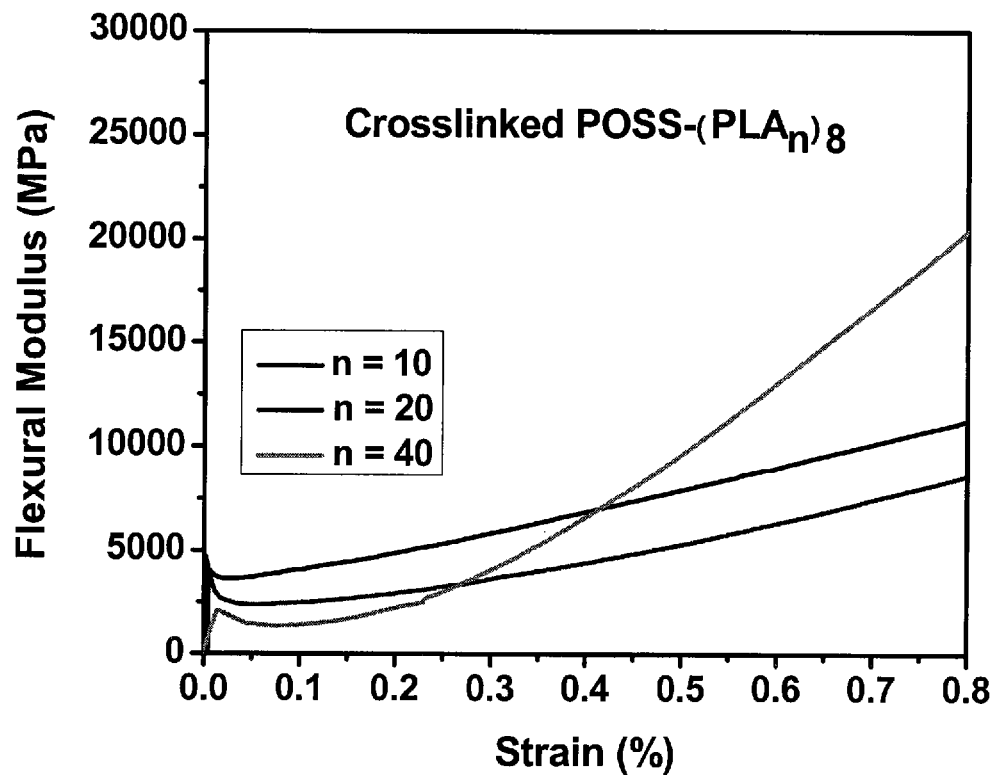
Figure 7:
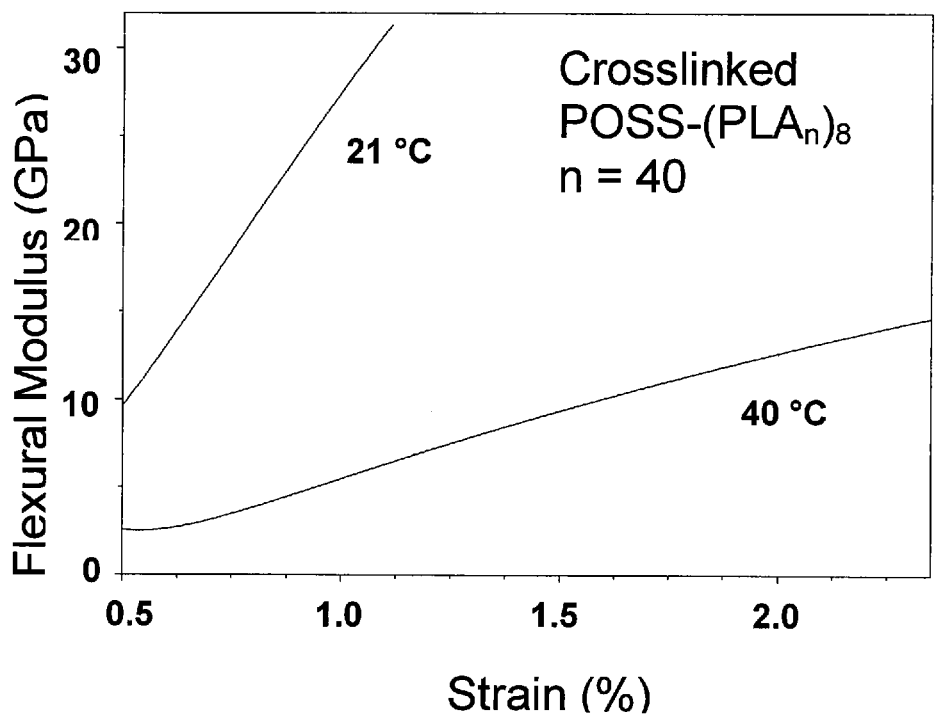
Figure 7:
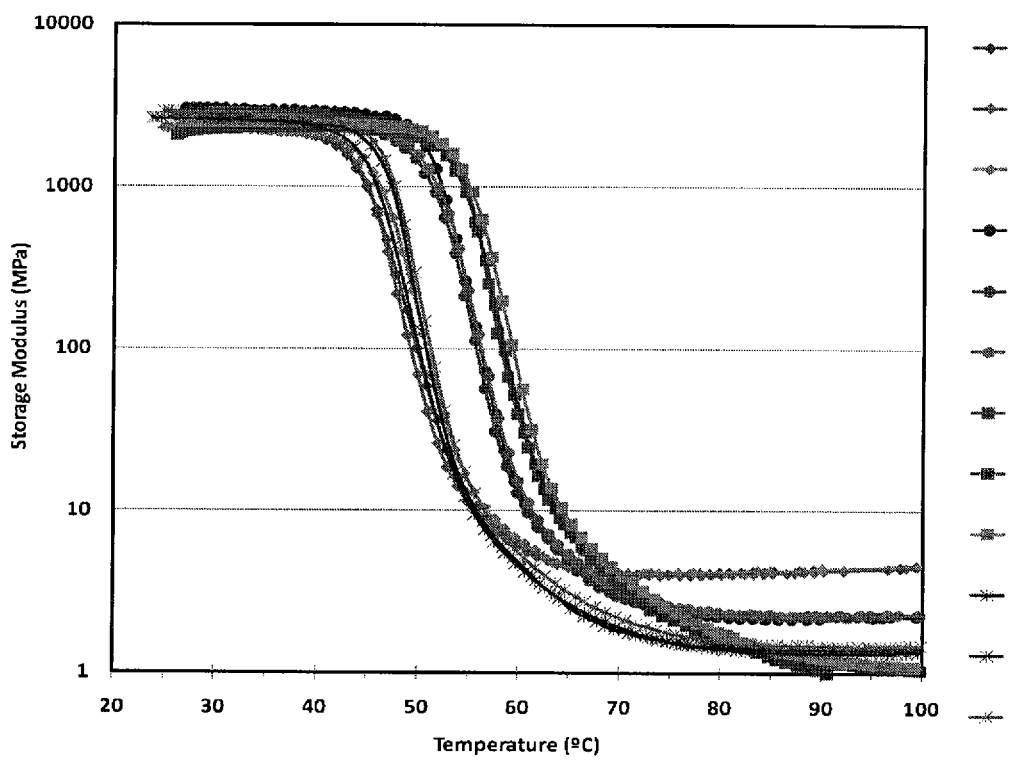
Figure 7:
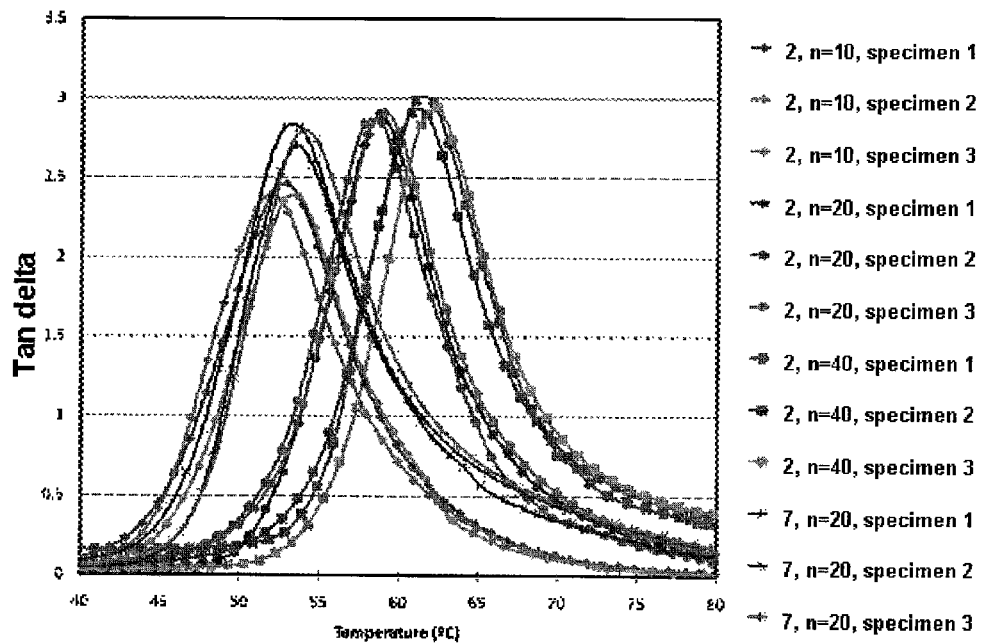
Figure 7J:
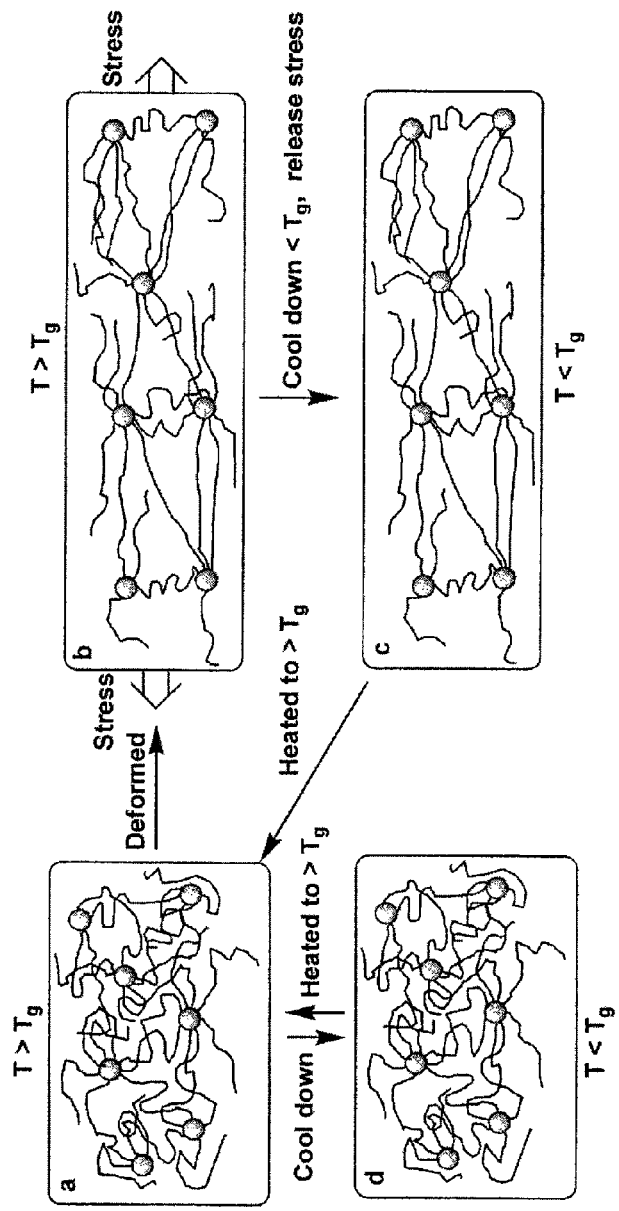

Known SMPs require low temperature for fixing their "temporary" shapes and/or high temperature for triggering the shape recovery. In addition, their performances are often limited by slow recovery rates and weak recovery stress. POSS-poly(ester-urethane) SMP can be easily deformed from a coiled permanent shape ($T_g$ ~44° C.) into a flat temporary shape when heated to 50° C. This temporary shape can be preserved at room temperature with almost no shape distortion over many months. When a 50° C. temperature was applied, however, the material recovered to its original coil shape within 1 sec. POSS-poly(ester-urethane) SMP's are transparent, owing to their amorphous polymer chain structure arrangements. Although the applicant does not intend embodiments of the invention to be limited to any particular shape, it is believed that the observed efficient shape memory behavior is due to the unique combination of the elasticity of the polylactide (PLA) chains and the rigidity of the POSS nanoparticle cores (FIG. 7J).

II. Applications of Shape Memory Polymers

In one embodiment, the present invention contemplates compositions comprising resorbable or non-resporbable POSS-SMP-based and/or Org-SMP-based smart implants. The compositions contemplated herein have numerous advantages that have the potential to revolutionize surgical interventions that currently rely on the use of more invasive, and less effective, devices including, but not limited to, metallic cages, fixators and stents. In some embodiments, the present invention contemplates methods for using these smart implants for medical conditions including but not limited to spine fusion for alleviating chronic lower back pain, vertebroplasty for treating vertebral fractures, to angioplasty for widening narrowed or obstructed blood vessels.

A. Biodegradable Polymers

The biodegradable shape memory polymers of the present invention can be used as resorbable anchors, plates and screws for orthopedic applications, some of which are mentioned above. They may also be used as dental fillers. Other biomedical applications of the shape memory polymers (SMP) include cardiovascular stents, actuators and catheters, self-tightening sutures, and resorbable drug-delivery scaffolds where temporary mechanical strength is desired. For instance, a drug-releasing and bioresorbable SMP stent will have major advantages over metallic stents (shape memory alloys, SMA) that are prevalently used today including, but not limited to, delivering drugs in a sustained manner, improving mechanical compatibility with blood vessels, and controlling biodegradability in programmable timeframes. Biodegradable embodiments of the present invention can further be applied to the manufacturing of environmentally friendly, or "green", toys.

Altehel et al., *Angew. Chem. Int. Ed.* 44, 1188-1192 (2005), incorporated herein by reference, discloses a biodegradable material of copoly-ester-urethane networks that exhibits shape memory properties. The applicants have developed an improved material with a $T_g$ close to physiological temperature (thus with minimal potential cell/tissue damages during thermal triggering), attractive physical appearance (e.g. transparent), biodegradability and tunable mechanical strength (e.g. storage modulus in the same range of cortical bone). Embodiments of the invention are illustrated in FIG. 7A. Polyhedral silsesquioxane (POSS) nanoparticles are designed as a structural anchor to grow, and mechanically strengthen, star-shape biodegradable polyesters.

B. Biomechanical Grafts

The present invention may be developed in a biodegradable material that may be further engineered with cortical-bone like mechanical properties, physiologically relevant glass transition/triggering temperatures, tunable biodegradation rates matching with normal fracture healing and spinal fusing rates, and surface functionality facilitating the materials' in vivo integration with host tissue. Therefore, these biodegradable shape memory polymers may be used, for example, as deployable synthetic bone substitutes/grafts for a wide range of orthopedic applications, including, but not limited to, craniofacial reconstruction, the repair of critical-sized bony defects due to tumor resection, the repair of skeletal trauma, the surgical fixation of hard-to-heal fractures such as osteoporotic fractures, diabetic fractures and periarticular fractures (such as tibia plateau and distal radius fractures) and minimally invasive vertebroplasty procedures. The compositions contemplated herein may further be utilized as self-expanding frames for spinal fusion applications. Synthetic bone substitutes currently comprise >50% of the multi-billion dollar spine fusion product market. It is estimated that 50 million Americans suffer lower back pain, with an increasing number of these individuals seeking surgical intervention to relieve the symptom. Because of the prevalence of cancer, osteoporosis, diabetes, degenerative disc diseases in the aging society, synthetic bone substitutes/grafts market, particularly the ones without any animal tissues, is not only an established one, but also a steadily growing one.

To be utilized as, or incorporated into, functional biomedical devices such as tissue engineering grafts, it is preferred that SMPs exhibit biocompatibility or bioactivity, biodegradability, efficient shape memory behavior near physiological temperature, appropriate mechanical properties, and bioactivities specific to their intended applications. To the best of our knowledge, no SMP reported to date can fulfill all these requirements. Embodiments of the invention disclosed herein are biodegradable, have excellent shape memory behavior, and exhibit robust mechanical strength. In order to enhance biocompatibility and bioactivity one can make chemical modifications without perturbing mechanical and shape memory properties. Specifically, one can functionalize the POSS-poly(ester-urethane) with substituents including but not limited to cell adhesive peptides, mineral-nucleating ligands and/or growth factor-retention domains to improve, for example, biological performance as a synthetic bone graft material.

It is preferable to have favorable cell-material interactions at the tissue-graft interface when integrating a synthetic graft with its tissue environment. For example, one can attach an RGD epitope on the SMP to improve the recruitment osteoblast precursor cells to the synthetic bone graft.

It is preferred to design polymer bone grafts with the ability of the graft to template the nucleation and growth of hydroxyapatite (HA), the major mineral component of bone, in situ. HA-binding peptide can act as a template for the growth of crystalline HA in vitro. It is believed that attachment of HA-binding peptide can enhance the SMP bone graft's bonding affinity to the surrounding bony tissue and its ability to template HA deposition in vivo as described in Bertozzi et al. WO Patent Application No. PCT/US 2005/43214, hereby incorporated by reference.

Fracture repair of bony defects can be promoted by the exogenous supply of osteogenic growth factor human recombinant bone morphogenetic protein 2 (rhBMP-2). In one embodiment, the present invention contemplates a method to locally retain the alkaline rhBMP-2 (isoelectric point: 9.3) on the synthetic graft by functionalizing the SMP with poly-methacrylic acid (PMA) segments. One expects the electrostatic interaction between PMA and BMP-2 to facilitate better retention and more sustained release of the osteogenic growth factor to and from the bone graft.

C. Non-Biodegradable Polymers

SMPs can also be engineered with non-biodegradable chemical content. Non-biodegradable shape memory polymers requiring shape memory efficiency superior to those of the leading commercial products (e.g. Veriflex® from Cornerstone Research Group) can be developed using some embodiments of the present invention. Traditional applications for these materials include, but are not limited to, reusable molds, transforming toys, shape-changing furniture, deployment mechanisms, custom containers, shipping/packaging, actuators, thermal sensors, smart textile products in outerwear, sportswear and self-deployable units in spacecrafts, etc.

III. SMP Control Using Glass Transition Temperatures

For previously reported biodegradable SMP, melting points ($T_m$) were utilized exclusively as the transition temperatures ($T_{trans}$) to trigger the shape memory behavior of an SMP. In contrast, the present invention contemplates a glass transition ($T_g$) that is used as the transition temperature trigger. In some embodiments, shape memory polymers comprise a $T_g$ ranging between approximately (−)60° C.-200° C., preferably between approximately 20° C.-175° C., more preferably between approximately 60° C. and 150° C. more preferably between approximately 30° C.-125° C., even more preferably between approximately, 37° C.-70° C., and most preferably between approximately between 40° C.-60° C.

Figure 10A:
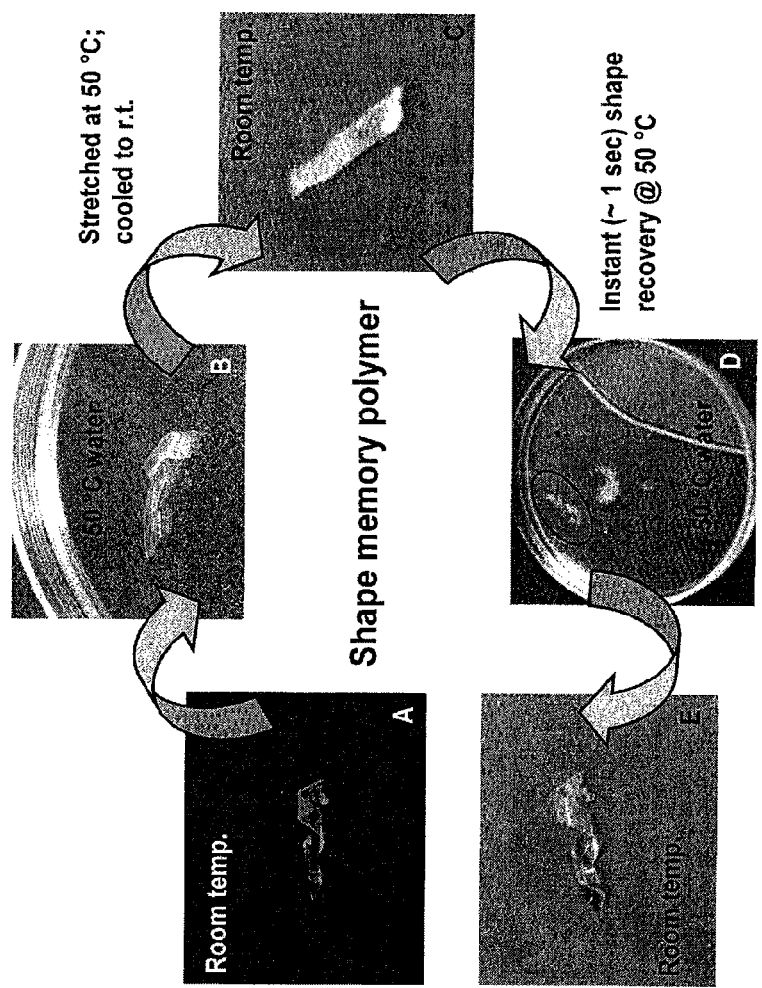
FIG. 10A shows shape memory of an embodiment of the invention.
Figure 10B:
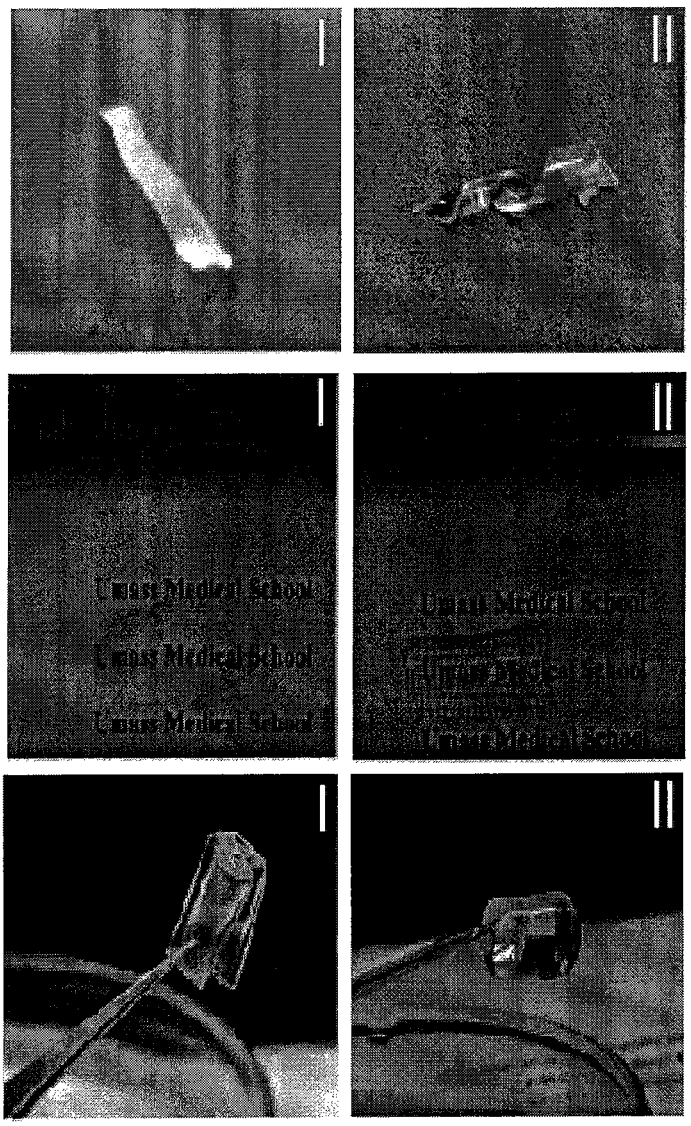
FIG. 10B shows the shape recovery from various stably held "temporary" shapes to pre-programmed "permanent" functional shapes upon thermal activation. All shape memory polymers shown are urethane-crosslinked POSS-(PLA)$_{20}$.
Figure 11:
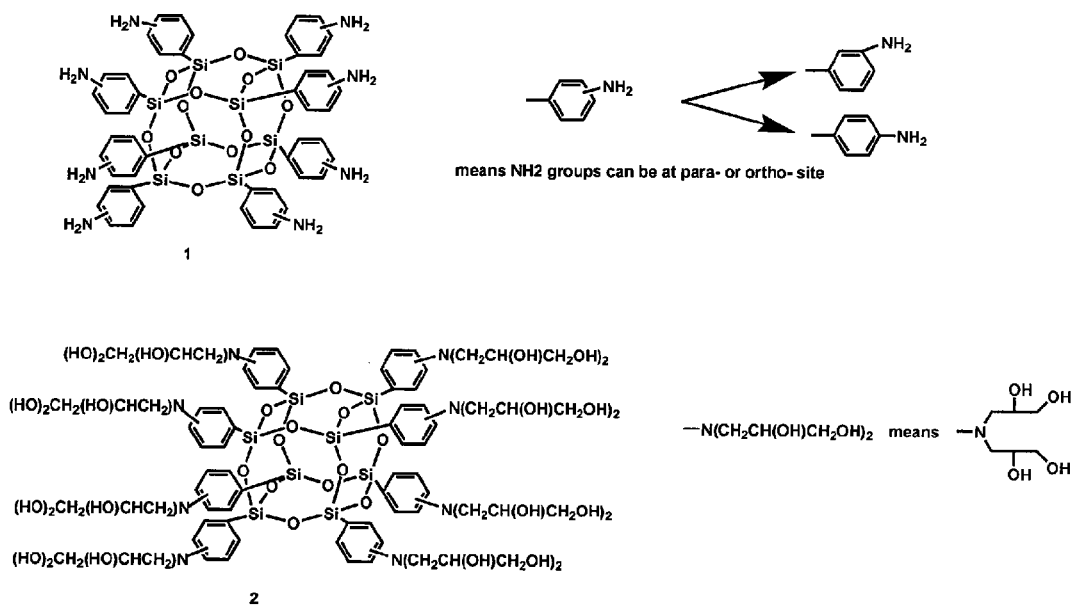
FIG. 11A illustrates a synthetic method for preparing embodiments of the invention.
FIG. 11B illustrates a synthetic method for preparing embodiments of the invention.
Figure 11:
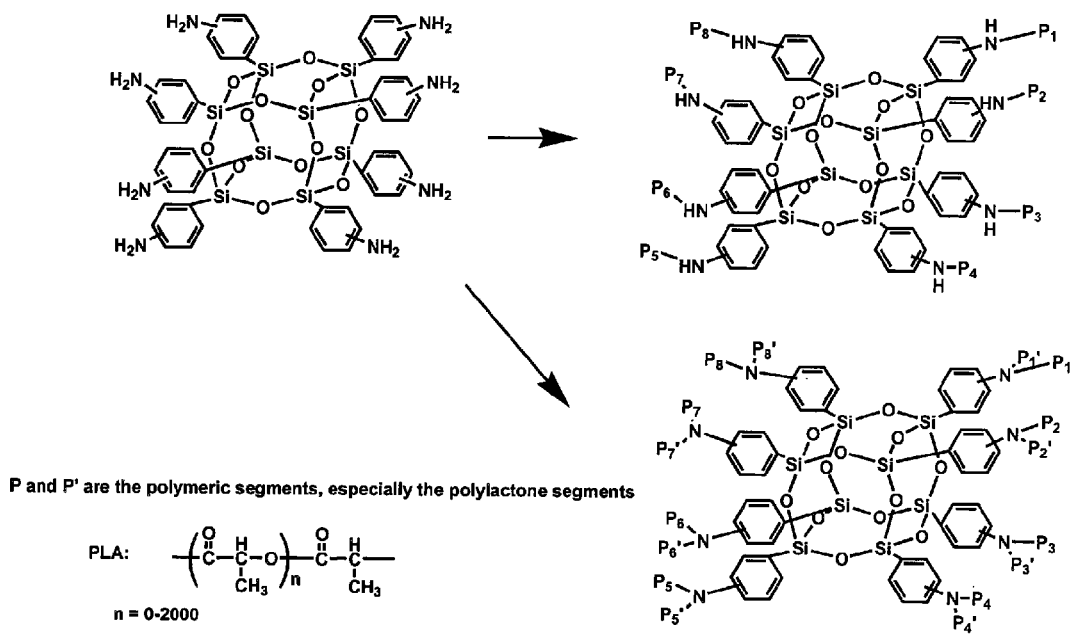

Using $T_g$ instead of $T_m$ as $T_{trans}$ has numerous advantages. First, crystallization and melting of polymeric chains (processes associated with $T_m$) are relatively slower processes than their glassy state freezing and activation (processes associated with $T_g$). Therefore, the shape fixation and recovery of a SMP system using $T_m$ as its $T_{trans}$ takes a longer time than that of the SMP using $T_g$ as $T_{trans}$. For instance, a piece of SMP with a thickness of 0.5 mm prepared in with embodiments of the invention can be fixed at its temporary shape in less than 1 second upon cooling to room temperature, and can fully recover to its original shape in less than 1 second upon raising the temperature to 50° C. (FIGS. 10A-B). Such an excellent shape memory effect within this physiologically relevant temperature range has not been achieved by any existing competitive SMPs.

Second, $T_g$ is more tunable than $T_m$. By increasing the polymeric chain lengths (e.g. via the increase of the monomer-to-POSS core feed ratio) or changing the copolymer compositions (e.g. changing the type and ratio of monomers co-polymerized), the $T_g$ value can be adjusted to the desired temperature range for specific applications. For example, the $T_g$ of crosslinked POSS-$(PLA_n)_8$ urethane can be tuned from 42.8° C. to 48° C. with the increase of the PLA chain length (attached to POSS core) from 10 to 40 (FIG. 7D).

Third, many previous polymers are semi-crystalline in nature, thus opaque in their appearances. The SMPs prepared in certain embodiments of the invention are transparent in appearance due to the fact that there are very little to no macrophase separation during crystallization (i.e., for example, they can be amorphous). For example, this is a desirable feature for ophthalmic applications.

In addition, mechanical properties of SMPs prepared in certain embodiments of the invention are unique. The flexural modulus of SMPs contemplated herein that are below the $T_{trans}$ is typically between 200 MPa and 20 GPa (FIGS. 7E-7I), within the range of those reported for human cortical bone. Given that a normal body temperature is generally 5-10° C. lower than the $T_{trans}$ of SMPs contemplated herein, these materials may be used smart bone grafts for load-bearing applications ranging from a low weight-bearing (i.e., for example, craniofacial), spinal fusion, to high weight bearing (i.e., for example, long bone segmental defects).

Thermoplastic polymers have been disclosed with POSS diol units and a diisocyanate crosslinker. U.S. Pat. No. 7,091,297 (herein incorporated by reference). However, only diisocyanates that help form a crystalline domain can be used which are usually limited to MDI or HMDI; in addition significant annealing is required to achieve steady-state crystallinity. For certain embodiments of the current invention, the material is a thermoset comprising a star-shape polyester polyol. In one embodiment, the star-shape polyester polyol is synthesized from multifunctional POSS and cyclic monomers. Alternatively, many different types of cyclic monomers are available for the synthesis and virtually all kinds of diisocyanate can be used for crosslinking with excellent SMP effect upon preparation. In addition, the $T_g$ of the final crosslinked materials is adjustable such that by changing the arm length and/or arm composition, mechanical properties of 200 MPa to 30 GPa. A $T_g$ slightly above body temperature are readily achievable. In comparison the '297 polymers are limited to mechanical properties of less than several GPa and one is limited to the melting temperature of the selected polymeric diol. For example, the $T_m$ of polycaprolactone usually is around 60° C., far exceeding body temperature.

IV. Macromer Designs

In one embodiment, the present invention contemplates a biodegradable SMP network comprising a combination of improved properties including, but not limited to: i) mechanical properties (i.e., for example, E'>2 GPa); ii) stable temporary shape fixing at room temperature and/or body temperature; iii) fast (i.e., for example, <3-22 s) and complete shape recovery within a narrow physiologically relevant temperature range (i.e., for example, <51° C.); and iv) tuneable bioactivities for biomedical applications. One structural feature of the network is a well-defined star-branched macromer comprising building blocks containing identical polymer chains which enabled high-density crosslinking, selective biofunctionalization, and more uniform response of the polymer chains to thermal stimuli. Compared to organic polyhydroxyl cores, a builder and more rigid POSS nanoparticle core is more effective in minimizing excessive global entanglement of the tethered network chains and in maximizing their participation in the shape memory process. Although it is not necessary to understand the mechanism of an invention, it is believed that a strategic use of well-defined nanoparticles to mediate polymer chain-chain interactions coupled with a bottom-up approach towards control over the structure, mechanical properties and chemical functionalities may allow optimization of SMP multiple properties for alternative applications other than those described herein.

A major roadblock in translating scaffold-based tissue engineering into clinical practice has been the lack of materials combining tissue-like mechanical and biochemical properties with clinically relevant deployability to enable their safe delivery and integration with target tissue. Engler et al., "Matrix elasticity directs stem cell lineage specification" *Cell* 126(4):677-689 634 (2006); Moroni et al., "Integrating novel technologies to fabricate smart scaffolds" *J. Biomater. Sci., Polym. Ed.* 19(5):543-572 535 (2008); Vogel et al., "Local force and geometry sensing regulate cell functions" *Nat. Rev. Mol. Cell Biol.* 7(4):265-275 236 (2006); and Chan et al., "New materials for tissue engineering: towards greater control over the biological response" *Trends Biotechnol.* 26(7):382-392 (2008). The SMPs reported here have great potential as self-fitting tissue scaffolds and implants where their unique properties could address unmet medical challenges, for instance, in the reconstruction of skeletal and craniofacial defects that are characterized with complex and irregular geometries, particularly at weight-bearing locations. Further, SMPs contemplated herein can provide unique drug delivery systems in combination with biological reconstruction.

For example, conventional pre-fabricated weightbearing scaffolds (e.g. stiff polymers and ceramics) do not readily conform to skeletal defects. On the other hand, injectable formulations that could penetrate into such defects and solidify in situ are known for toxicity concerns due to the exothermic solidification process (e.g. leading to tissue necrosis) and potential leaks. SMP scaffolds as described herein have specific advantages in that when cast in vitro with a desired size and/or shape (i.e., for example, based on an MRI or radiographic scan of a defect) may overcome limitations of known scaffolds by enabling delivery in a less invasive (i.e., for example, compressed) configuration that subsequently conforms to the defect upon a brief and safe thermal triggering (e.g. via catheter heating). Coupled with its excellent mechanical properties at body temperature, SMP implants as contemplated herein are inherently more securely anchored within the body thereby reducing the need for auxiliary metallic fixators, which often require a second surgery to remove and obscure post-operative radiographic monitoring of the osteointegration of the implant. Finally, a tunable biofunctionality and degradability of POSS-SMPs opens the possibility of locally delivering therapeutics expediting the healing of the defect while enabling the implanted scaffold to "vanish" after fulfilling its function.

A. POSS Cores Versus Organic Cores

Previous studies on dendritic and hyperbranched polymers suggest that a core architecture (i.e., for example, comprising a specific size and/or rigidity), molecular weight, and chain end composition of branched polymer systems could profoundly affect their physical properties. Matos et al., "Effect of core structure on photophysical and hydrodynamic properties of porphyrin dendrimers" *Macromolecules* 33(8): 2967-2973 (2000), and Wooley et al., "Physical-Properties of Dendritic Macromolecules—a Study of Glass-Transition Temperature. Macromolecules" 26(7):1514-1519 (1993). For example, a polyhedral oligomeric silsesquioxane (POSS) nanoparticle may be used as a core to prepare star-shaped macromer building block for the SMP network. This design has several advantages including, but not limited to: 1) a well-defined cubic geometry enabling grafting of up to eight identical polymer arms, 2) a rigidity that plays a role in controlling the grafted polymer chain motions on a molecular scale (Phillips et al., "Developments in nanoscience: polyhedral silsesquioxane (POSS)-polymers oligomeric" *Curr. Opin. Solid State Mat. Sci.* 8(1):21-29 (2004), and 3) improved biocompatibility (Kannan et al., "Polyhedral oligomeric silsesquioxane nanocomposites: The next generation material for biomedical applications" *Acc. Chem. Res.* 38(11):879-884 (2005).

Figure 16:
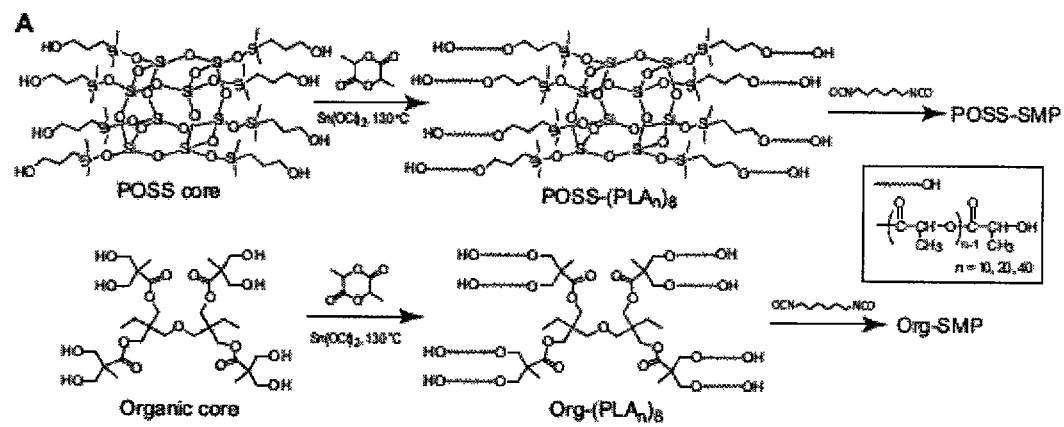
FIG. 16 illustrates exemplary embodiments for the preparation and resultant thermal mechanical properties of SMPs containing a POSS core (POSS-(PLA$_n$)$_8$) or an Organic core (Org-(PLA$_n$)$_8$)
Figure 16:
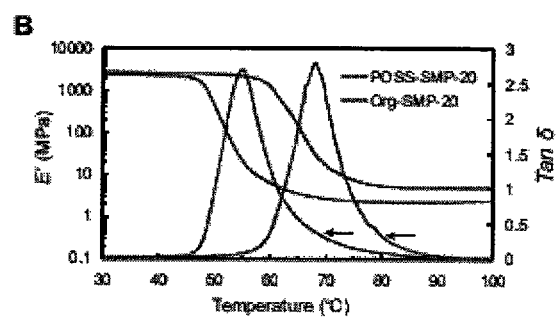

In one embodiment, polylactides (PLAs) of various lengths were grafted to the octahydroxylated POSS core via ring-opening polymerization of D,L-lactide to give star-branched macromer POSS-(PLA$_n$)$_8$ (n=10, 20, 40; representing the number of lactide repeating units) in near quantitative yields and low polydispersity. FIG. 16A and Table I.

TABLE I

GPC Characterizations Of Representative Macromer Building Blocks

| Macromer | $M_n$theo | $M_n^{NMR}$ | $M_n^{GPC}$ | PDI |
|---|---|---|---|---|
| POSS-PLA-10 | 7,245 | 7,328 | 5,528 | 1.20 |
| POSS-PLA-20 | 13,010 | 13,576 | 9,988 | 1.19 |
| POSS-PLA-40 | 24,541 | 25,788 | 19,576 | 1.36 |
| Org-PLA-10 | 6,480 | 6,264 | 4,242 | 1.14 |
| Org-PLA-20 | 12,245 | 10,948 | 8,117 | 1.23 |
| Org-PLA-40 | 23,776 | 20,389 | 16,780 | 1.26 |

$M_n^{Theo}$: theoretical number-averaged molecular weight
$M_n^{NMR}$: number-averaged molecular weight determined by 1H NMR integration.
$M_n^{GPC}$: number-averaged molecular weight determined by gel filtration chromatography.
PDI: polydispersity index determined by gel filtration chromatography.

Figure 19:
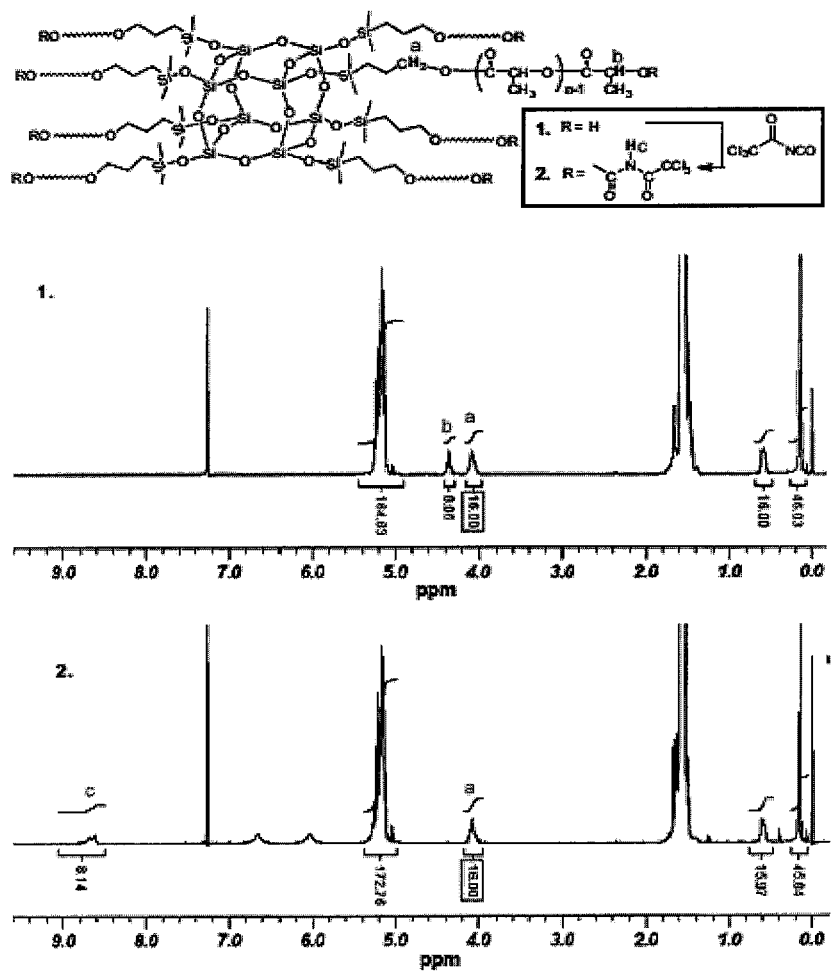
FIG. 19 presents exemplary data showing $^1$H NMR spectra for POSS-(PLA$_{20}$)$_8$ in CDCl$_3$ before and after (bottom) titration with TAI.

End group titration by $^1$H NMR confirmed the successful grafting of eight PLA arms to each core; Donovan et al., "A novel method for determination of polyester end-groups by NMR spectroscopy" *Polymer* 46(14):5005-5011 (2005); and Postma, et al. "A simple method for determining protic end-groups of synthetic polymers by H-1 NMR spectroscopy" *Polymer* 47(6):1899-1911 (2006). FIG. 19 and Table II.

TABLE II

End Group Titration By 1H NMR (Number Of —OH Per Macromer)

| Macromer | Theoretical | $^1$H NMR |
|---|---|---|
| POSS-PLA-10 | 8 | 8.15 |
| POSS-PLA-20 | 8 | 8.14 |
| POSS-PLA-40 | 8 | 6.48 |
| Org-PLA-10 | 8 | 7.98 |
| Org-PLA-20 | 8 | 7.64 |
| Org-PLA-40 | 8 | 6.53 |

The hydroxyl end groups of the macromer were then reacted with hexamethylene diisocyanate to form crosslinked POSS-SMP via urethane linkages. Table III.

TABLE III

Formulations And Gel Contents Of Urethane-Crosslinked SMPs

| Crosslinked SMPs | PLA Arm Length | Molar Ratio (POSS-PLAn) 8:HDI:3-Azido propan-1-ol | Gel Content (%) |
|---|---|---|---|
| POSS-SMP-10 | 10 | 1:4:0 | 97.0 |
| POSS-SMP-20 | 20 | 1:4:0 | 98.0 |
| POSS-SMP-40 | 40 | 1:4:0 | 98.0 |
| POSS-SMP-20-Az | 20 | 1:5:2 | 97.0 |
| Org-SMP-10 | 10 | 1:4:0 | 96.9 |
| Org-SMP-20 | 20 | 1:4:0 | 98.0 |
| Org-SMP-40 | 40 | 1:4:0 | 97.3 |

Mono- and di-functional POSS nanoparticles have been previously utilized in SMP designs wherein interactions between the particles themselves (i.e., for example, crystallization tendency of POSS) were exploited to form percolating physical crosslinks within a chemically crosslinked system. Knight et al., "Biodegradable thermoplastic polyurethanes incorporating polyhedral oligosilsesquioxane" *Biomacromolecules* 9(9):2458-2467 (2008); Lee et al., "Polycaprolactone-POSS chemical/physical double networks" *Macromolecules* 41(13):4730-4738 (2008); and Jeon et al., "Shape memory and nanostructure in poly(norbornyl-POSS) copolymers" *Polym. Int.* 49(5):453-457 (2000). Although the competitive crystallizations between POSS and polymer domains resulted in unconventional thermoplastic properties, neither the temperatures nor the broadness of the thermal transitions were suitable for biomedical applications. In one embodiment, the present invention contemplates octa-functional POSS-based macromers that are crosslinked to form an amorphous network wherein the rigid POSS cores impart controlled interactions between tethered PLA arms.

In another embodiment, the present invention contemplates an SMP comprising a flexible organic core. FIG. 16A. In one embodiment, the flexible organic cores are functionalized with PLA arms Table II and FIG. 17 (top panel). Although it is not necessary to understand the mechanism of an invention, it is believed that since a flexible organic core may be functionalized with the same PLA arms as a rigid POSS-SMP, a comparative study can determine the impact of core structure on physical properties.

B. Thermal Mechanical and Shape Memory Properties of Core Structures

Data presented herein compares thermal mechanical properties of SMPs comprising a rigid POSS core with those containing a flexible Organic core. POSS-SMP-20 and Org-SMP-20, crosslinked from POSS-(PLA20$_n$)$_8$ and Org-(PLA$_{20}$)$_8$, respectively, both possessed Gigapascal (GPa) storage moduli at body temperature. FIG. 16B. Further, both cores exhibited similar temperature-dependent viscoelastic properties, with storage modulus values sharply descending from a gigapascal (GPa) glassy state to a megapascal (MPa)-elastic plateau around their respective glass transitions. The storage modulus values of both cores decreased within a narrow transition temperature range measured as the Peak Width At Half Peak Hieght (WHPH) that is approximately <10° C. Although it is not necessary to understand the mechanism of an invention, it is believed that such a narrow glass transition reflects the formation of a homogenous network crosslinked from star-branched macromer building blocks containing identical polymer chains because a structurally homogenous network would be expected to respond more uniformly to a thermal stimuli than structurally ill-defined networks.

Figure 20:
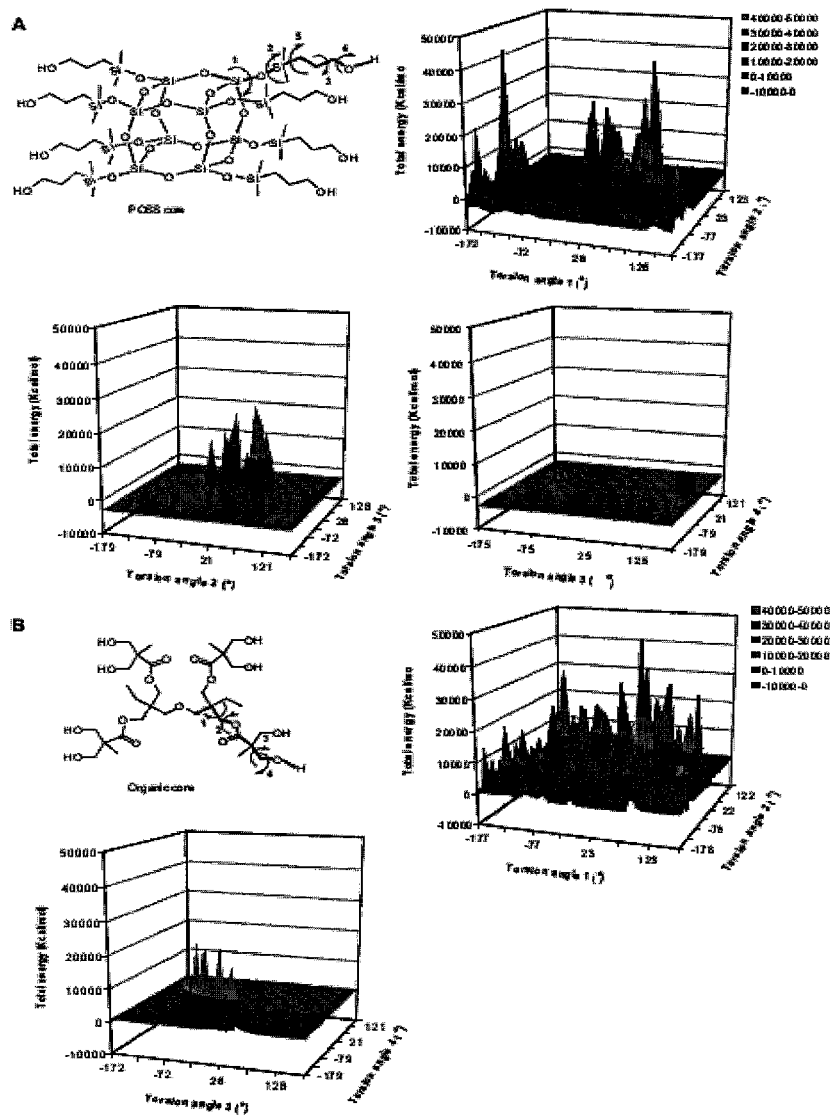
FIG. 20 presents exemplary data showing total energy contours of systemic grid scans of POSS and Organic cores.

It was observed, however, that the glass transition temperature ($T_g$) of POSS-SMP-20, was >10° C. lower than that of Org-SMP-20, and the storage modulus drop around the $T_g$ was more pronounced for POSS-SMP-20. POSS-(PLA$_{20}$)$_8$ and Org-(PLA$_{20}$)$_8$ had similar polymer chain compositions, molecular weights, and polydispersity and identical numbers of urethane crosslinking sites. Tables S1 and S2, respectively. Although it is not necessary to understand the mechanism of an invention, it is believed that these observed differences in thermal mechanical properties can be attributed to the different size and rigidity of POSS versus the organic cores. Indeed, a grid search analysis revealed more torsional freedom at each polyol branching point in the bulkier POSS core (1103-Å$^3$ molecular volume) than in the organic core (539-Å$^3$ molecular volume), suggesting that the PLA arms could distribute more homogenously in the crosslinked POSS-SMP network with less excessive chain entanglement. FIG. 20.

Figure 16C:
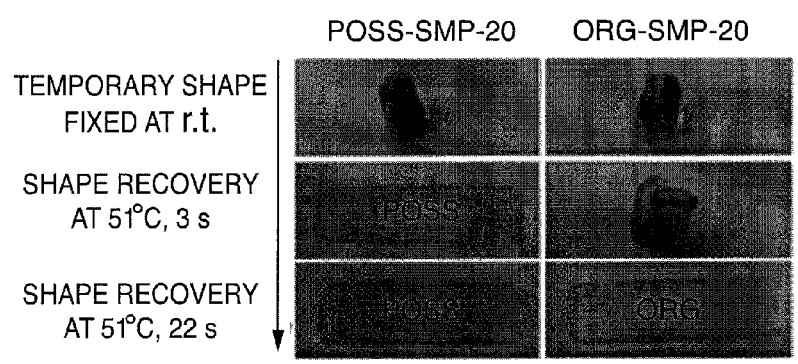
FIG. 16C: Recovery rates of POSS-SMP-20 (red arrows) vs Org-SMP-20 (blue arrows) from a identical rolled-up temporary shape (left panel) to fully extended rectangle (30.0 mm×6.0 mm×0.5 mm) in water at 51° C.

The data presented herein also examines shape memory performance of SMPs comprising different cores (i.e., for example, a rigid POSS core versus a flexible Organic core). POSS-SMP-20 and Org-SMP-20 were both cast as flat rectangle sheets (30.0 mm×6.0 mm×0.5 mm) and were subsequently rolled up into short cylinders (i.e., a temporary shape) that were stably fixed at room temperature (r.t.). Upon being immersed in water at 51° C., POSS-SMP-20 rapidly opened up and recovered its "original" flat rectangle shape while Org-SMP-20 recovered much more slowly. Both POSS-SMP-20 and Org-SMP-20 cores become stably fixed at a temporary shape within seconds upon cooling to room temperature. Although it is not necessary to understand the mechanism of an invention, it is believed that such rapid and stable shape retention indicates a complete freezing of chain segment motions below the $T_g$ in both the POSS and Organic networks. At 51° C., however, the rate of shape recovery of POSS-SMP-20 (i.e., for example, <3 s) was much faster than that of Org-SMP-20 (i.e., for example, >20 seconds respectfully. FIG. 16C. At 73° C., both POSS and Organic networks recovered original shapes at a similar rates (i.e., for example, <1 second). Although it is not necessary to understand the mechanism of an invention, it is believed that these observations suggest that increased polymeric segment motions (i.e., for example, entropy elasticity) above the $T_{trans}$ ($T_g$ in this case) may play a role in driving the shape recovery process. This differential shape memory performance data suggest that a POSS core nanostructured molecular network translates into a more rapid shape recovery at a lower triggering temperature (on a macroscopic scale) than a more flexible Organic core network.

C. Inorganic Particle Polymer Networks

Figure 29:
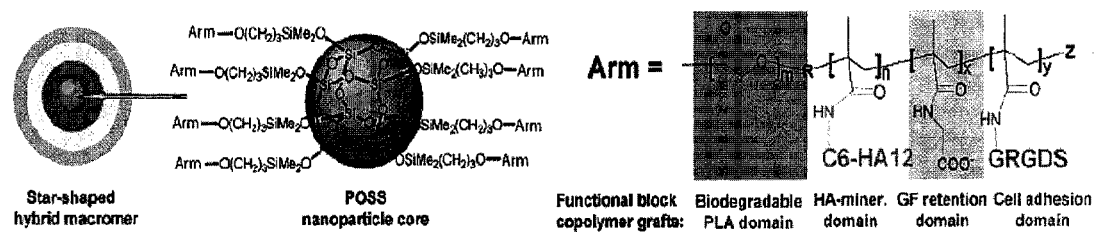
FIG. 29 illustrates the design of hybrid macromers containing a POSS nanoparticle core, a biodegradable PLA domain), an HA nucleation domain, a negatively charged growth factor retention domain and a cell adhesion domain). The block copolymer segments are sequentially grafted to POSS via ROP and RAFT polymerization.

In one embodiment, the present invention contemplates a composition comprising a shape memory polymer comprising a core and a plurality of polymer arms, wherein the core is infiltrated with inorganic particles. In one embodiment, the inorganic particle comprises a biomineral. In one embodiment, the inorganic particle comprises a paramagnetic particle. In one embodiment, the inorganic particle comprises a nanoparticle. In one embodiment, the nanoparticle comprises a mineral-polymer composite. See, FIG. 29. Although it is not necessary to understand the mechanism of an invention, it is believed that the inorganic polymer network may be useful in biomedical imaging and/or provide properties to trigger shape changes and/or provide a way to retain and release therapeutic agents.

IV. POSS Core Shape Memory Polymers

A. Siloxanes

The preparation of siloxanes, including silsesquioxanes and metallasiloxanes, are described in Purkayastha & Baruah Applied Organometallic Chemistry 2004, 18, 166-175. Silsesquioxane are compounds of an approximate formula of about $RSiO_{1.5}$, where R is any moiety but typically an alkyl, aryl, or substituted conjugate thereof. The compounds may assume a myriad of structures, including random, ladder, cage and partial cage structures (see FIG. 1B).

Silsesquioxanes are also sometimes termed ormosils (organically modified siloxanes). A preferred silsesquioxane is shown in FIG. 1A. To prepare mono-substituted silsesquioxane, there are several conventional synthetic routes. For example, the reaction of $HSiCl_3$ with $PhSiCl_3$ results in the formation of $PhH_7Si_8O_{12}$ via a co-hydrolysis reaction. A second route uses substitution reactions at a silicon center with the retention of the siloxane cage leads to structural modifications of silsesquioxane. For this reaction hydrosilylation is used as illustrated in FIG. 2.

These structures typically exhibit good insulating and permeability properties, allowing for their use as coatings for electronic and optical devices, semiconductors and liquid crystal display (LCD) devices, as well as gas separation membranes.

A variety of Polyhedral Oligomeric Silsesquioxanes (POSS) nanostructured chemicals have been prepared which contain one or more covalently bonded reactive functionalities that are suitable for polymerization, grafting, surface bonding, or other transformations. Lichtenhan, J. D. et al. U.S. Pat. No. 5,942,638 (1999); Lichtenhan, J. D. et al. *Chem. Innovat.* 1: 3 (2001), both of which are incorporated by reference. Monomers have recently become commercially available as solids or oils from Hybrid Plastics Company, Fountain Valley, Calif. A selection of POSS chemicals now exist that contain various combinations of nonreactive substituents and/or reactive functionalities. Thus, POSS nanostructured chemicals may be incorporated into common plastics via copolymerization, grafting, or blending as disclosed in Haddad et al. *Polym. Prepr.* 40: 496 (1999), incorporated herein by reference. The incorporation of POSS derivatives into polymeric materials can lead to enhancements as applied to a wide range of thermoplastics and thermoset systems. Ellsworth et al. *Polym. News* 24: 331 (1999), hereby incorporated by reference. POSS nanostructures have other use in catalyst supports and biomedical applications as scaffolds for drug delivery, imaging reagents, and combinatorial drug development.

Metallasiloxanes are siloxanes having some of the silicon atoms replaced by an appropriate metal. Incorporation of metal into a siloxane framework can lead to two and three-dimensional or linear networks. Metallasiloxane may be derived from silanediols, disilanol, silanetriols and trisilanols. For example, the transesterification reaction of $Ti(O-iPr)_4$ with sterically hindered silanediol $\{(t\text{-BuO})_3SiO\}_2Si(OH)_2$ gives cyclic siloxane of the following formula:

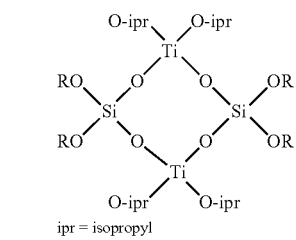

ipr = isopropyl

Similarly, cyclic dihalotitanasiloxanes $[t\text{-Bu}_2Si(O)OTiX_2]_2$ (X=Cl, Br, I) may be prepared by the direct reaction of titanium tetrachloride with $t\text{-Bu}_2Si(OH)_2$. Such compounds are made of eight-membered rings having composition $Ti_2Si_2O_4$. Both silicon and titanium atoms in the molecule exhibit regular tetrahedral geometry. Analogously, the corresponding zirconium compound $[t\text{-Bu}_2Si(O)OZrCl_2]_2$ may be prepared from the reaction between the dilithium salt of $t\text{-Bu}_2Si(OH)_2$ and $ZrCl_4$.

Cyclopentadienyl-substituted titanasiloxane $[t\text{-Bu}_2Si(O)OTiCpCl]_2$ may be prepared directly by the reaction of $CpTiCl_3$ with $t\text{-Bu}_2Si(OLi)_2$. The reaction of the silanediol $Ph_2Si(OH)_2$ with the zirconium amido derivative $Zr(NEt_2)_4$ leads to the formation of the dianonic tris-chelate metallasiloxane $[NEt_2H_2]_2[(Ph_4Si_2O_3)_3Zr]$. In the case of zirconocene, the central zirconium atom is coordinated by six oxygen atoms in a distorted octahedral geometry.

Figure 6:
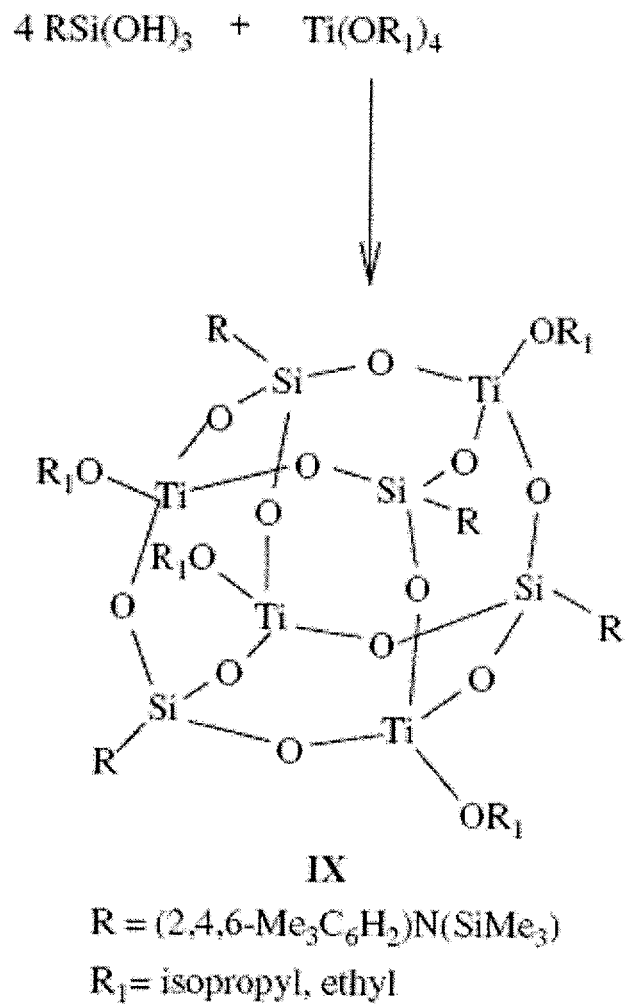
FIG. 6 shows alternative embodiments.

Disilanols may also be used as building blocks for a variety of metallasiloxanes. The disilanols are capable of chelating to form six-membered rings containing the central metal. The reactions lead to Group 4 metallasiloxanes from disilanols. In a similar manner, metallasiloxane derivatives of Group 5, Group 7, Group 9 and Main Group metals may be prepared from disilanols. Reactions of silanediol and disilanols with titanium halides or titanium amides give cyclic titanasiloxanes. Three-dimensional titanasiloxanes can be prepared by the reaction of the titanium amide with silanol or silanediol. Such reactions serve as a synthetic pathway for preparation of model compounds for titanium-doped zeolites. Cubic titanasiloxanes can be prepared by a single-step synthesis from the reaction of titanium orthoesters and silanetriols as illustrated in FIG. 6. In an analogous manner, the three-dimensional networks of aluminiumosiloxane, indiumsiloxane, galliumsiloxane, etc. may be prepared from the reaction of trisilanols and $MMe_3$ where M=Al, In, Ga, etc. In many of these networks, cubic metallasiloxanes, $M_4Si_4O_{12}$ polyhedrons, are present.

B. Synthesis of Polyhedral Oligomeric Silsesquioxanes

The preparation of oligomeric silsesquioxanes is generally described in Li et al. (2002) *Journal of Inorganic and Organometallic Polymers* 11, 123-154, incorporated herein by reference. Reactions leading to the formation of POSS may be characterized depending on the nature of the starting materials employed. One group includes the reactions giving rise to new Si—O—Si bonds with subsequent formation of the polyhedral cage framework. This class of reactions assembles polyhedral silsesquioxanes from monomers of the $XSiY_3$ type, where X is a chemically stable substituent (for example, $CH_3$, phenyl, or vinyl), and Y is a highly reactive substituent (for example, Cl, OH, or OR) as represented in Equation 1:

$$nXSiY_3 + 1.5nH_2O \rightarrow (XSiO_{1.5})_n + 3nHY \quad \text{(Equation 1).}$$

Alternatively, POSS can form from linear, cyclic, or polycyclic siloxanes that are derived from the $XSiY_3$-type monomers.

The second class of reactions involves the manipulation of the substituents at the silicon atom without affecting the silicon-oxygen skeleton of the molecule. A number of substituents may be appended to the silicon oxygen cages $[R(SiO_{1.5})]_n$ (n=8, 10, 12, and larger). Such substituents include alcohols and phenols, alkoxysilanes, chlorosilanes, epoxides, esters, fluoroalkyls, halides, isocyanates, methacrylates and acrylates, alkyl and cycloalkyl groups, nitriles, norbornenyls, olefins, phosphines, silanes, silanols, and styrenes. Many of the reactive functionalities are suitable for polymerization or copolymerization of the specific POSS derivative with other monomers. In addition to substituents with reactive functional groups, nonreactive organic functionalities may be varied to influence the solubility and compatibilization of POSS nanostructured cages with polymers, biological systems, or surfaces.

C. Multifunctional POSS Synthesis

POSS $(RSiO_{1.5})_n$, where R=H and n=8, 10, 12, 14, or 16, are structures generally formed by hydrolysis and condensation of trialkoxysilanes $(HSi(OR)3)$ or trichlorosilanes (HSiCl$_3$). For example, $(HSiO_{1.5})_n$, where n=8, 10, 12, 14, or 16, is prepared by hydrolysis of HSiCl$_3$ involving the addition of a benzene solution of HSiCl$_3$ to a mixture of benzene and $SO_3$-enriched sulfuric acid. The hydrolysis of trimethoxysilane may be carried out in cyclohexane-acetic acid in the presence of concentrated hydrochloric acid and leads to the octamer. The hydrolytic polycondensation of trifunctional monomers of type $XSiY_3$ leads to crosslinked three-dimensional networks and cis-syndiotactic (ladder-type) polymers, $(XSiO_{1.5})_n$. With increasing amounts of solvent, however, the corresponding condensed polycyclosiloxanes, POSS, and their derivatives may be formed.

The reaction rate, the degree of oligomerization, and the yield of the polyhedral compounds formed under these conditions depend on several factors. For example, POSS cages where n=4 and 6 can be obtained in nonpolar or weakly polar solvents at 0 or 20° C. However, octa(phenylsilsesquioxane), $Ph_8(SiO_{1.5})_8$, is more readily formed in benzene, nitrobenzene, benzyl alcohol, pyridine, or ethylene glycol dimethyl ether at high temperatures (e.g., 100° C.).

Figure 3:
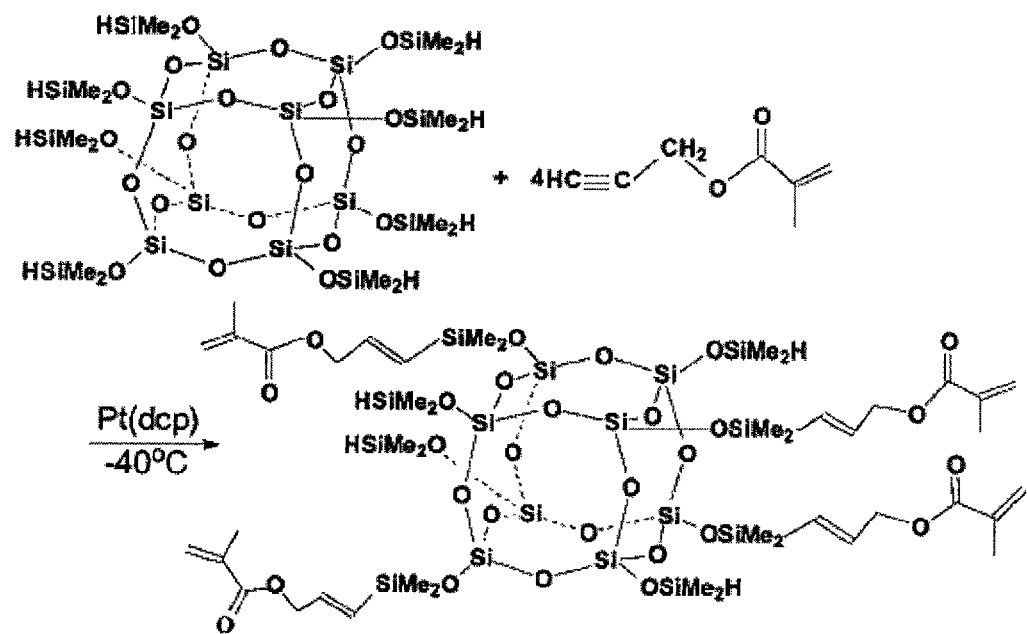
FIG. 3 shows alternative methods for making embodiments.

Multifunctional POSS derivatives can be made by the condensation of ROESi(OEt)$_3$, as described above, where ROE is a reactive group. This reaction produces an octa-functional POSS, $R'_8(SiO_{1.5})_8$. Another approach involves functionalizing POSS cages that have already been formed. For example, this may be accomplished via Pt-catalyzed hydrosilylation of alkenes or Apes with $(HSiO_{1.5})_8$ and $(HMe_2SiOSiO_{1.5})_8$ cages as shown in FIG. 3. Another example of the synthesis of multifunctional POSS derivatives is the hydrolytic condensation of modified aminosilanes as described in Fasce et al., *Macromolecules* 32: 4757 (1999), hereby incorporated by reference.

D. POSS Polymers and Copolymers

POSS units, which have been functionalized with various reactive organic groups, may be incorporated into existing polymer system through grafting or copolymerization. POSS homopolymers can also be synthesized. The incorporation of the POSS nanocluster cages into polymeric materials may result in improvements in polymer properties, including temperature and oxidation resistance, surface hardening and reductions in flammability. These shape-memory polymers, including but not limited to those disclosed in Examples V, VII and IX, may comprise materials suitable for both biomedical and non-biomedical applications.

Figure 4:
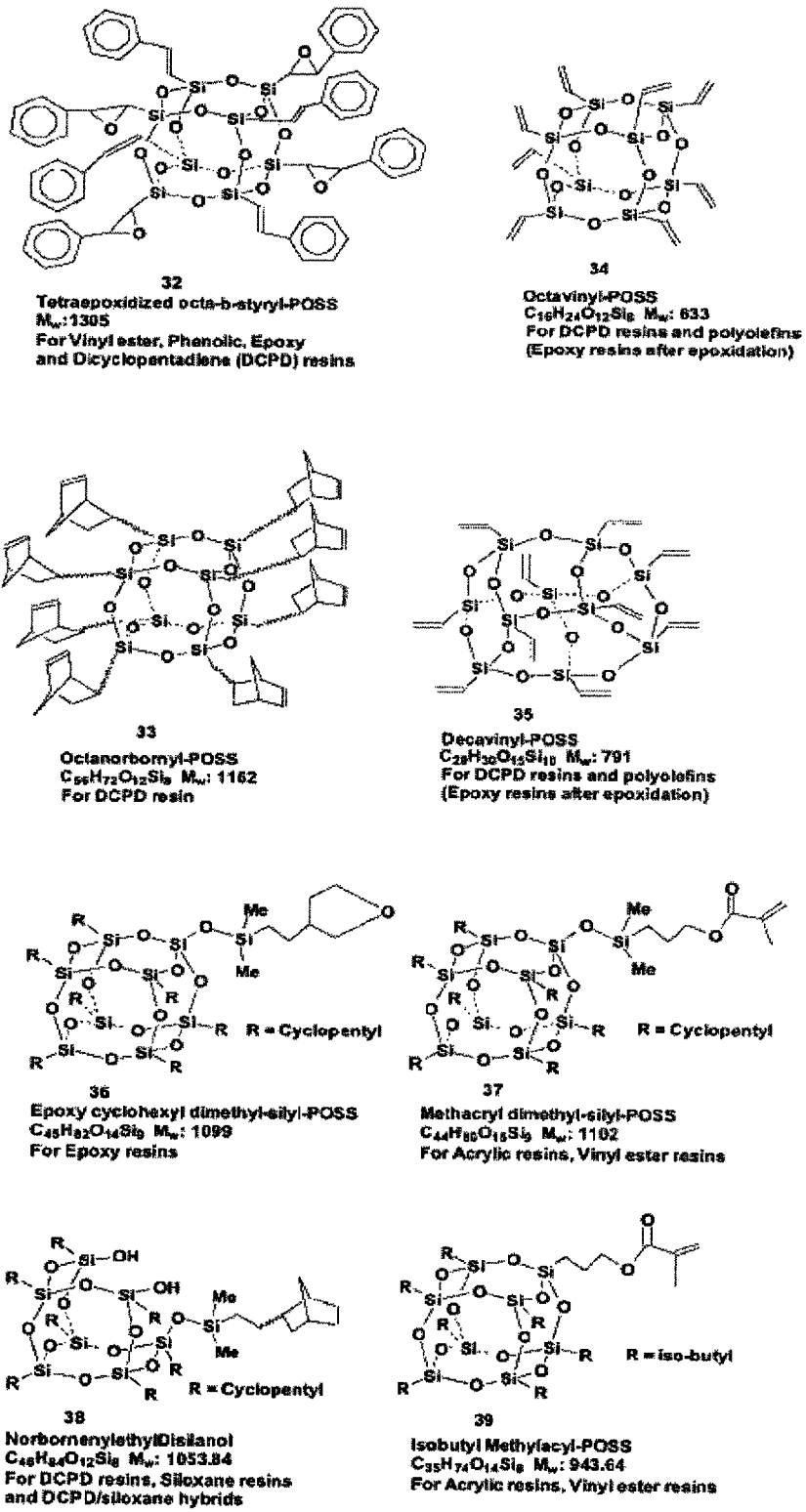
FIG. 4 shows illustrations of alternative embodiments.

Different types of substituted POSS monomers may be chemically incorporated into resins. First, monofunctional monomers can be used. Alternatively, di- or polyfunctional POSS monomers can be used. Incorporating a monofunctional POSS monomer can actually lower the resulting resin's crosslink density if the amount of the monofunctional POSS monomers in the commercial resin employed is held constant. The POSS cages with organic functions attached to its corners have typical diameters of 1.2 to 1.5 nm. Therefore, each POSS monomer occupies a substantial volume. When that POSS monomer is monosubstituted, it cannot contribute to crosslinking. A 2 mol % loading of POSS in a resin might actually occupy 6 to 20 vol % of the resin, and this occupied volume contains no crosslinks. Therefore, the average crosslink density will be lowered. Conversely, when a polyfunctional POSS monomer is employed, several bonds can be formed from the POSS cage into the matrix, thereby making the POSS cage the center of a local crosslinked network. Some examples of monofunctional and polyfunctional POSS monomers are illustrated in FIG. 4 together with the types of resins into which they may be chemically incorporated. Epoxy, vinyl ester, phenolic, and dicyclopentadiene (DCPD) resins may be made in which various POSS macromers are chemically incorporated. Besides the applications in nano-reinforced polymeric materials, there are other applications for POSS molecules as a core for building new types of dendritic macromolecules.

Figure 5:
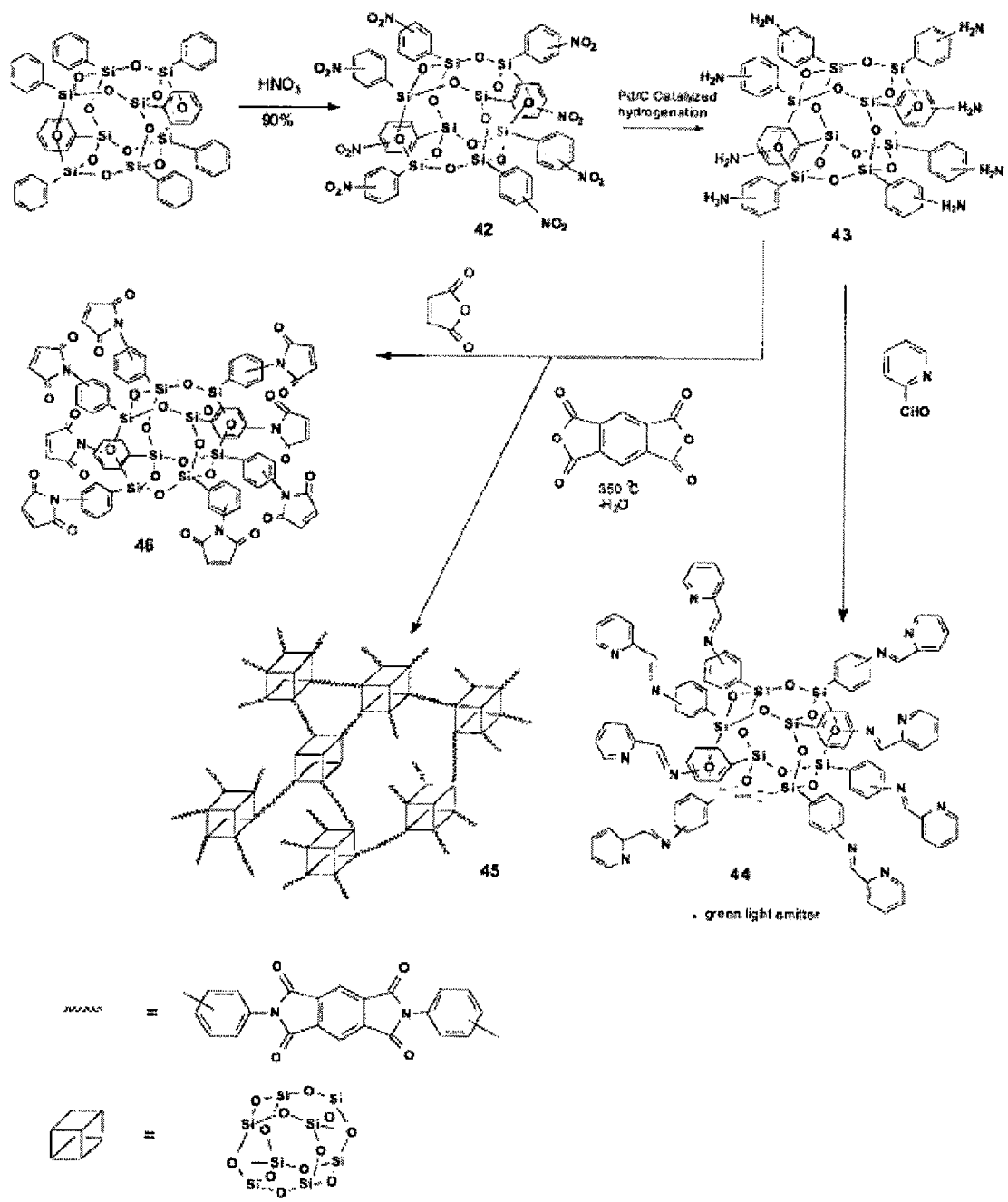
FIG. 5 shows alternative method for making embodiments.

As illustrated in FIG. 5, following the nitration of octaphenyl POSS 42 one may produce the octaaminophenyl POSS 43 by Pd/C-catalyzed hydrogenation of 42 as described in Tamaki et al., *JACS* 123, 12416-12417 (2001), incorporated herein by reference. One obtains a derivative, 44, by Schiff's base formation upon reaction of 43 with the ortho carboxaldehyde of pyridine. Furthermore, one uses the octaamino 43 with dialdehydes to make polyimide crosslinked networks. One reacts POSS 43 with maleic anhydride to make the octa-N-phenylmaleimide, 45, which could serve as a crosslinking agent in maleimide polymer chemistry.

E. Bone Implantation of POSS Polymeric and Copolymeric Composite Materials

A preferred embodiment of the present invention provides for the synthesis and use of composite materials. Biomineralized implant applications, e.g. the implantation of suitable biopolymers that contain inorganic minerals capable of being incorporated into native bone structure, offer significant improvements to subjects suffering from bone disorders and dysfunction. As described in US Patent Application Number 2004/0161444, incorporated herein by reference, inorganic minerals including but in no way limited to calcium hydroxyapatite, carbonate derivatized hydroxyapatite, and beta-tricalcium phosphate may be incorporated into biomaterials including but not limited to synthetic bone substrates. As discussed in Example X below, the present invention may be combined with said inorganic minerals to create materials and compositions suitable for use in biomedical applications. In a preferred embodiment, said inorganic minerals comprise 0.1%-90% by weight of the composite materials.

F. Tuning of Mechanical Thermal and Shape Memory Properties

Figure 17A:
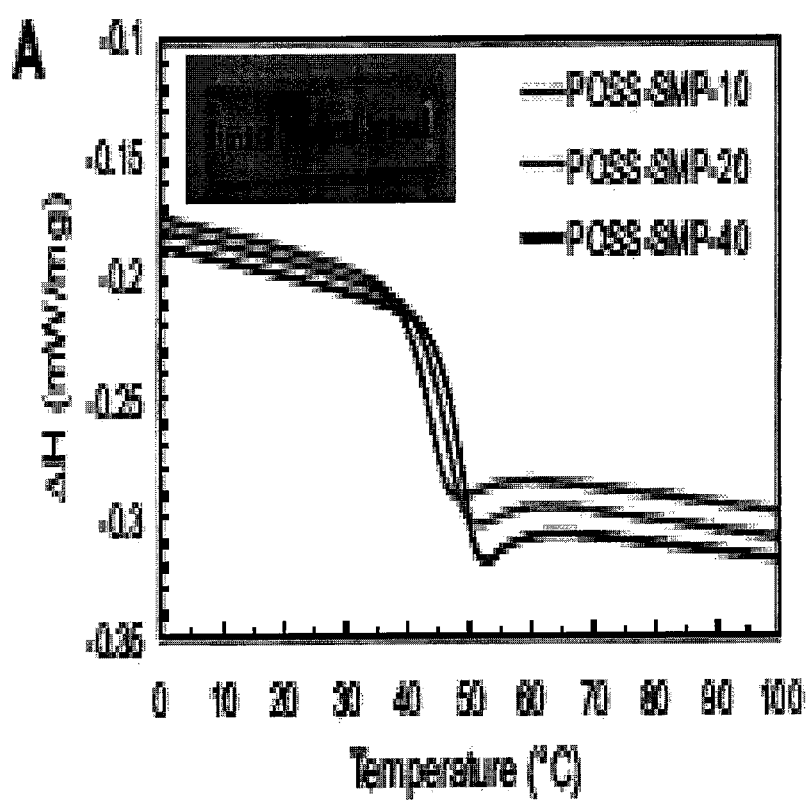
FIG. 17A: Differential scanning calorimetry (DSC) heat flow (ΔH)-Temperature curves and the transparent appearance (inset).
Figure 21:
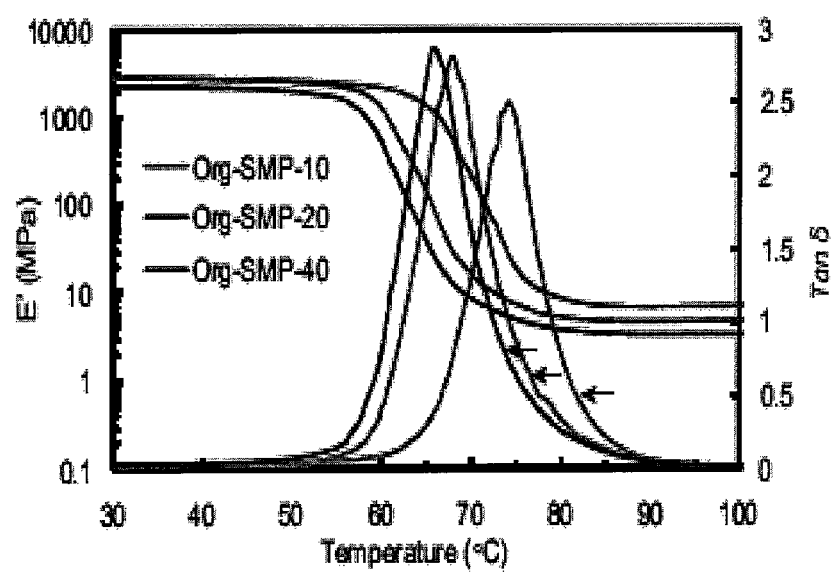
FIG. 21 presents exemplary data of storage modulus (E')-temperature and loss angle (Tan δ)-temperature (denoted by black arrows) curves of Org-SMPs with varied arm lengths.

As discussed above, the mechanical properties and biodegradation rates of POSS cores may be tuned by varying the length of crosslinked PLA arms. POSS-SMP macromers containing various PLA arm lengths (i.e., for example, n=10, 20, 40) were prepared and crosslinked. Differential scanning calorimetry (DSC) revealed a single narrow endothermic transition for each crosslinked POSS-SMP with no crystalline phase transitions detected. FIG. 17A. This observation, as well as observed optical transparency, supports an amorphous network structure where POSS cores are well-dispersed rather than crystallizing as in the case of the SMPs containing mono- or di-functional POSS. Known linear high molecular weight poly(D,L-lactides) typically have a $T_g$ of approximalte 54° C. Zhou et al. "Hydrogen bonding interaction of poly(D,L-lactide)/hydroxyapatite nanocomposites" *Chem. Mater.* 19(2):247-253 (2007). In one embodiment, the present invention contemplates POSS-SMPs exhibiting $T_g$'s ranging between approximatles 42.8° C. to 48.4° C. Although it is not necessary to understand the mechanism of an invention, it is believed that compositions comprising these lower $T_g$'s are more suitable for biomedical applications. Conventional crosslinked elastomers and the Org-SMPs have $T_g$'s that decrease as chain lengths between crosslinking point increase. FIG. 21. By contrast, the $T_g$'s of POSS-SMPs, as determined by differential scanning calorimetry, increased as the PLA chain length of the macromer increased, suggesting a more profound impact of the rigid POSS core on the chain-chain interactions within the crosslinked network than a flexible organic core. Table IV.

Structure and the Elastic Properties of Vulcanized Rubber" *Chem. Rev.* 35(1):51-75 (1944).

In one embodiment, the present invention contemplates a POSS-SMP composition comprising an extremely narrow glass transition value. In one embodiment, the glass transition value is approximately <10° C. Table IV-WHPH. In one embodiment, the POSS-SMP composition further comprises a sharp storage modulus changes of up to 3 orders of magnitude within the glass transition value. By contrast, previous SMP networks typically exhibited wide glass transitions wherein WHPH>20° C. and the modulus changes around the $T_{trans}$ are no more than 2 orders of magnitude. Lendlein et al., "Shape-memory polymers" *Angew. Chem., Int. Ed.* 41(12): 2034-2057 (2002); and Liu et al., "Review of progress in shape-memory polymers" *J. Mater. Chem.* 17(16):1543-1558 (2007); and Behl et al., "Shape-memory polymers" *Materials Today* 10(4):20-28 (2007); and Kim et al., "Polyurethanes having shape memory effects" *Polymer* 37(26):5781-5793 (1996).

Although it is not necessary to understand the mechanism of an invention, it is believed that the steep and narrow thermomechanical transitions exhibited by POSS-SMPs make it possible to achieve both temporary shape fixing and permanent shape reversion within a narrow physiologically relevant temperature range. For example, POSS-SMPs may be stably

TABLE IV

PLA Chain Length Effect On POSS-SMP $T_g$'s

| Core | $T_g^{DSC}$ (° C.)[1] | $T_g^{DMA}$ (° C.)[2] | Tan δ[3] | $E'_{37°C}$ (MPa)[4] | $E'_{85°C}$ (MPa)[5] | WHPH (° C.)[6] | $M_c$ (Dalton)[7] | $R_f$ (%)[8] | $R_r$ (%)[8] |
|---|---|---|---|---|---|---|---|---|---|
| POSS-SMP-10 | 42.8 | 51.8 ± 0.4 | 2.34 ± 0.04 | 2927.0 ± 38.3 | 4.2 ± 0.1 | 9.4 ± 0.3 | 876.9 | 96.0 | 100 |
| POSS-SMP-20 | 45.4 | 56.0 ± 0.8 | 2.68 ± 0.06 | 2286.8 ± 62.7 | 2.3 ± 62.7 | 8.7 ± 0.2 | 1563.3 | 91.6 | 100 |
| POSS-SMP-40 | 48.4 | 57.9 ± 0.5 | 2.69 ± 0.04 | 2234.7 ± 17.1 | 1.2 ± 0.1 | 9.1 ± 0.3 | 2996.3 | 100 | 95.2 (100)* |

[1] glass transition temperatures as determined from the DSC scans.
[2] glass transition temperatures as determined from the Tanδ-temperature curves;
[3] peak value of Tanδ-temperature curves.
[4] storage moduli of the glassy state determined at 37° C.;
[5] storage moduli of the elastic state determined at 85° C.
[6] peak widths at the half peak height (WHPH) of the Tanδ-temperature curves;
[7] the number-averaged molecular weight between the crosslinking points of the polymer network (Mc) calculated from $E' = \rho RT/Mc$ where ρ is the density of the polymer network (ρ = 1.27 g cm−3), R is the gas constant (R = 8.314), T is an elastic state temperature (T = 358 K), and E' is storage modulus measured at this temperature (E'85° C.).
[8] Shape fixing ratio ($R_f$) and shape recovery ratio ($R_r$) calculated from the second one-way shape memory cycle shown in FIG. 2C.
*The $R_f$ value shown in the parentheses was calculated from the third cycle.

Figure 17B:
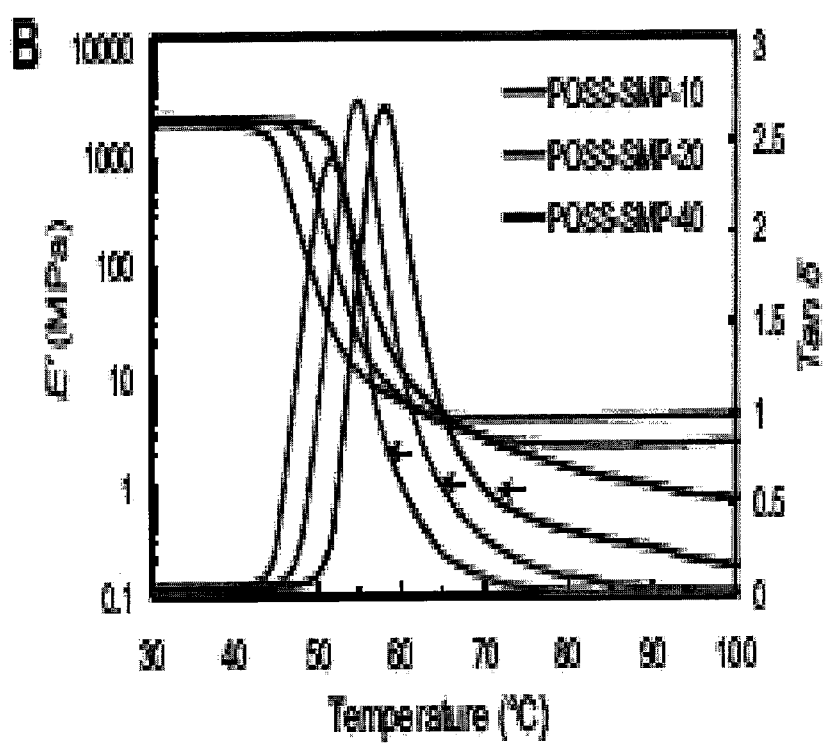
FIG. 17B: Storage modulus (E')-temperature and loss angle (Tan δ)-temperature curves (denoted by black arrows).

Dynamic mechanical analysis (DMA) revealed a similar relationship of $T_g^{DMA}$ to chain length, suggesting that the effect of POSS on chain-chain interaction become less significant with longer PLA chains. FIG. 17B.

Figure 22:
FIG. 22 presents exemplary data showing photographs of stable temporary shape fixation of POSS-SMP-20 at rt and its instant shape recovery at 51° C. White arrow: deformed at 51° C. and cool down to rt; red arrow: reheat to 51° C. Left: sample with permanent hollow cup shape (11.0 mm in diameter, 13.5 mm in height, 0.3 mm in well thickness); Right: sample with permanent grid surface pattern (scale bar: 400 mm).

POSS-SMPs strength was also measured as a function of PLA chain length and temperature using DMA. The data show that all three POSS-SMPs (e.g., wherein n=10, 20, and 40) possessed similar glassy state storage moduli (i.e., for example, approximately >2.0 Gpa) at body temperature. Table IV-$E'^{37°C}$. Interestingly, this value appears recommended for cortical bone replacement materials. Hutmacher D., "Scaffolds in tissue engineering bone and cartilage" *Biomaterials* 21(24):2529-2543 (2000). Although it is not necessary to understand the mechanism of an invention, it is believed that the observed glassy state storage moduli would allow POSS-SMPs to be used for weight-bearing in vivo applications. On the other hand, the storage modulus of POSS-SMP in an elastic state. decreased as the PLA arm length increased. Table IV-$E'^{85°C}$. This value is believed to be determined by the density of crosslinks. Flory P., "Network fixed at various temporary shapes at room and body temperatures for >1 year. Subsequently, these fixed shapes instantly (i.e., for example, within a matter of seconds) recover into their original and permanent shapes when brought to a temperature of approximately ≤51° C. FIG. 22. The shape memory behavior of POSS-SMP-20 was studied by casting with an "original" straight bar shape (70.0 mm×3.2 mm×0.5 mm). The sample was deformed at 50° C. into a temporary spiral shape, which was stably fixed at room temperature. Instant recovery to the "original" straight bar shape was observed once the spiral sample was placed in 50° C. water. The POSS-SMP-20 was also studied by casting with an "original" grid surface pattern. The surface pattern was flattened out by a hot hydraulic press and stably held at room temperature. The "original" grid surface pattern was immediately restored when the material with a distorted surface was placed on a hotplate set at 49° C. The POSS-SMP-20 was also studied by casting with an "original" hollow cup configuration. The cup-shaped SMP (diameter of 11.0 mm, height of 13.5 mm, and wall thickness of 0.3 mm) could withstand a 1.0-kg load without deformation. The cup was fold-up at ~50° C. and remained stably fixed at room temperature. Instant recovery to the "original" shape was observed once the folded cup was placed in 50° C. water.

Figure 17C:
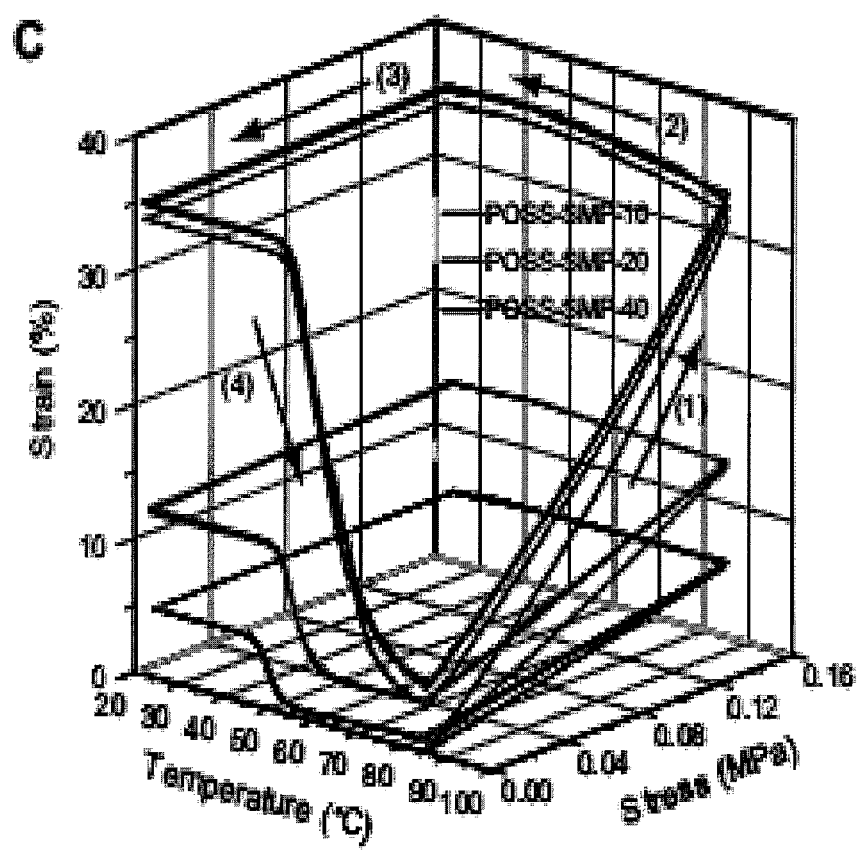
FIG. 17C: One-way shape memory cycles. Starting with 0% tensile stain at 85° C., all specimens were subjected to consecutive cycles of tensile deformation (1), cooling (2), unloading of tensile stress (3), and recovering (4). The first 4 cycles of each specimen are representatively shown.

Clinical thermal treatments employing a combination of such mild temperature and short exposure time were shown to be well tolerated by human sclera, epidermis, and bony tissues. Rem et al., "Temperature dependence of thermal damage to the sclera: Exploring the heat tolerance of the sclera for transscleral thermotherapy" *Exp. Eye Res.* 72(2):153-162 (2001); Momz A., "Studies on thermal tissue injury III. The pathology and pathogenesis of cutaneous burns. An experimental study" *Am. J. Pathol.* 23:915-941 (1947); Berman et al., "Thermally Induced Bone Necrosis in Rabbits Relation to Implant Failure in Humans" *Clin. Orthop. Relat. Res.* (186): 284-292 (1984); Eriksson et al., "Assessment of Bone Viability after Heat Trauma—a Histological, Histochemical and Vital Microscopic Study in the Rabbit" *Scand. J. Plast. Reconstr. Surg. Hand. Surg.* 18(3):261-268 (1984); and Matthews et al., "Temperatures Measured in Human Cortical Bone When Drilling" *J. Bone Jt. Surg. (Am.) A* 54(5):297-308 (1972). The above described characteristics of POSS-SMPs facilitate successful implantation applications, wherein implant materials should be delivered in a stable minimally invasive shape with a subsequent reversion into a permanent shape in vivo. Quantitative assessment of shape memory performance through stress-controlled one-way shape memory cycles verified that all POSS-SMPs exhibited a high shape fixing ratio ($R_f$>91%) and shape recovery ratio ($R_r\approx$100%), with POSS-SMP-40 achieving ~100% $R_f$ and $R_r$ after the 2nd cycle. FIG. 17C, Table IV; and Knight et al., "Biodegradable thermoplastic polyurethanes incorporating polyhedral oligosilsesquioxane" *Biomacromolecules* 9(9):2458-2467 (2008); and Behl et al., "One-Step Process for Creating Triple-Shape Capability of AB Polymer Networks" *Adv. Funct. Mater.* 19(1):102-108 (2009).

The data presented herein shows that a temperature window for deformation recovery correlated well with the glass transition process, supporting that entropy elasticity during glass transition was the driving force for shape recovery. FIG. 17C versus FIG. 17B. The corresponding PLA arm lengths of the macromer also correlated well with the number-averaged molecular weight between the crosslinking points ($M_c$), derived from an affine network model. Flory P., "Network Structure and the Elastic Properties of Vulcanized Rubber" *Chem. Rev.* 35(1):51-75 (1944); and Table IV. Although it is not necessary to understand the mechanism of an invention, it is believed that this observation suggests that almost all PLA arms were tethered by urethane crosslinks and could participate in the elastic deformation and recoiling, thereby contributing to the rapid and complete shape recovery.

G. POSS-SMP Biofunctionalization

In one embodiment, the present invention contemplates a shape memory core comprising at least one biological ligand. In one embodiment, the ligand comprises an amino acid sequence. In one embodiment, the amino acid sequence comprises an antibody. In one embodiment, the amino acid sequence comprises a biologically active protein. In one embodiment, the biologically active protein is an enzyme. In one embodiment, the biologically active protein is a peptide fragment. In one embodiment, the ligand comprises a nucleic acid sequence. In one embodiment, the nucleic acid sequence comprises messenger RNA. In one embodiment, the nucleic acid sequence comprises antisense.

Figure 18A:
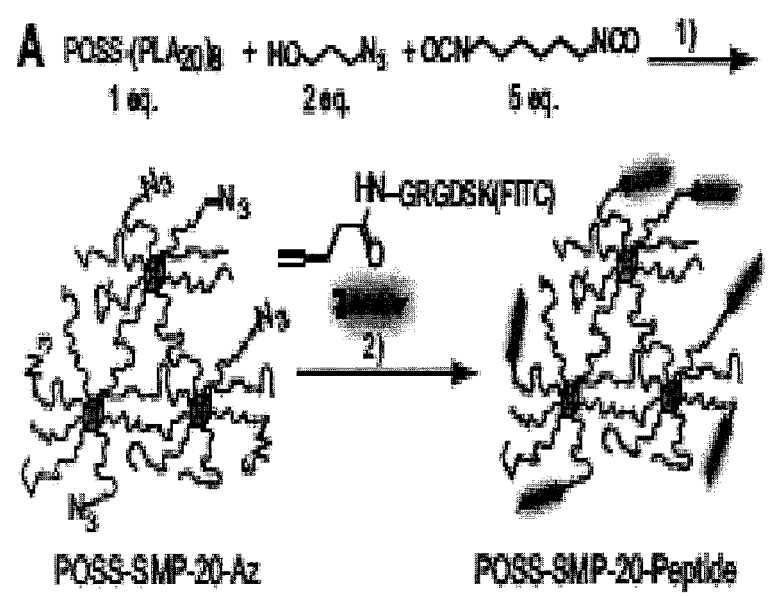
FIG. 18A: Synthetic scheme illustrating the introduction of azido groups during the covalent crosslinking of POSS-(PLA$_{20}$)$_8$ and subsequent conjugation of fluorescently labeled integrin-binding peptide to POSS-SMP via "click" chemistry: Reaction (1)—100 ppm DBTDL, CH2Cl2, Argon, rt, 12 h; 75° C., Argon, 24 h; 75° C. under vacuum, 48 h; Reaction (2)—aqueous solution of CuSO4 (2.5 mM) and L(+)-ascorbic acid sodium salt (7.5 mM), rt, 24 h.
Figure 23:
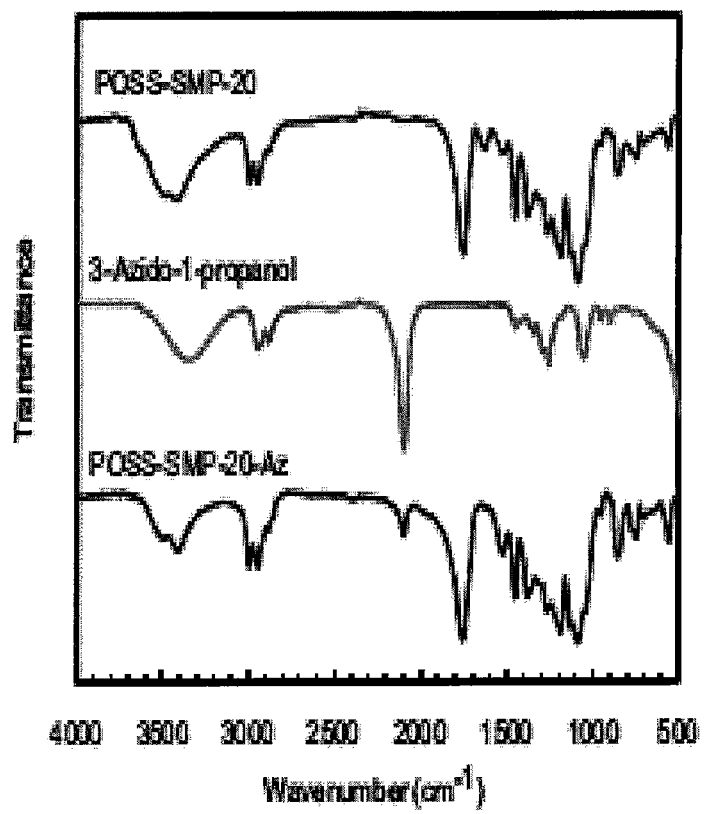
FIG. 23 presents exemplary data showing an FTIR spectra of POSS-SMP-20-Az vs. POSS-SMP-20 confirming the covalent attachment of the azido functionality (note the characteristic absorption at 2100 cm$^{-1}$). Gel extraction by chloroform was carried out with all solid specimens prior to FTIR characterizations.

To demonstrate the possibility of presenting biological ligands on POSS-SMP without compromising advantageous thermal mechanical properties, an integrin-binding peptide was covalently attached to a POSS-SMP core using a 2-step modification strategy. Schaffner et al., "Structure and function of RGD peptides involved in bone biology" *Cell. Mol. Life Sci.* 60(1):119-132 (2003); and Hersel et al., "RGD modified polymers: biomaterials for stimulated cell adhesion and beyond" *Biomaterials* 24(24):4385-4415 (2003). The first step comprises crosslinking POSS-(PLA$_{20}$)$_8$ in the presence of 3-azido-1-propan-1-ol. FIG. 18A, step (1). This reaction introduces azido end groups to make POSS-SMP-20-Az for FTIR characterizations. POSS-SMP-20-Az exhibited a storage moduli of 2.1 GPa at 37° C. and 1.2 MPa at 85° C. with a slightly reduced $T_g^{DMA}$ compared to POSS-SMP-20. FIG. 23.

Figure 18B:
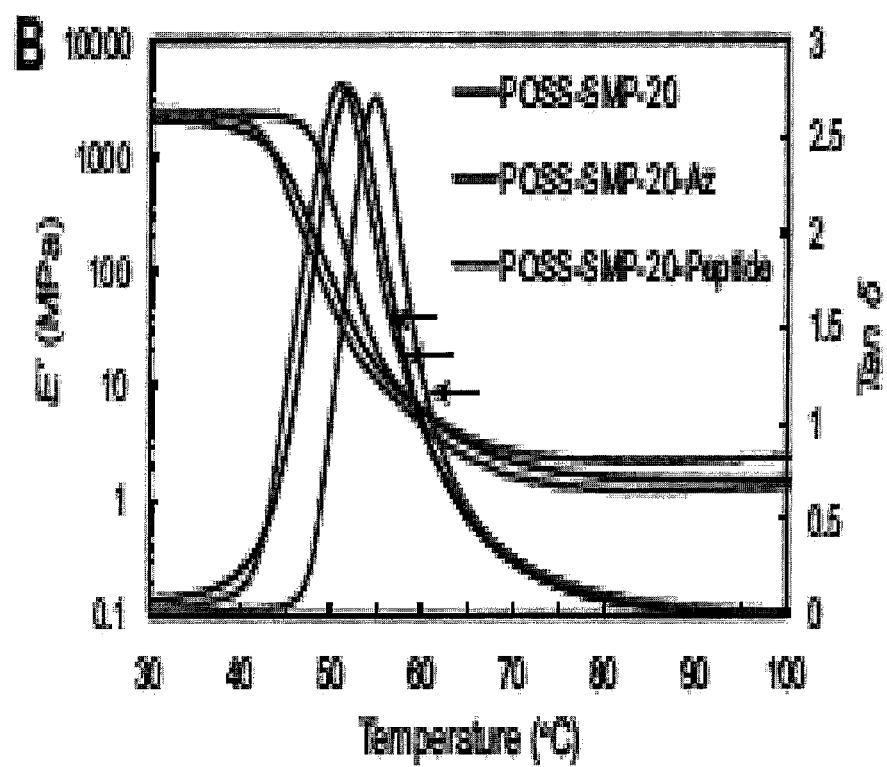
FIG. 18B: Storage modulus (E')-temperature curves and loss angle (Tan δ)-temperature curves (denoted by black arrows) of POSS-SMP-20, POSS-SMP-20-Az and POSS-SMP-20-Peptide.
Figure 18C:
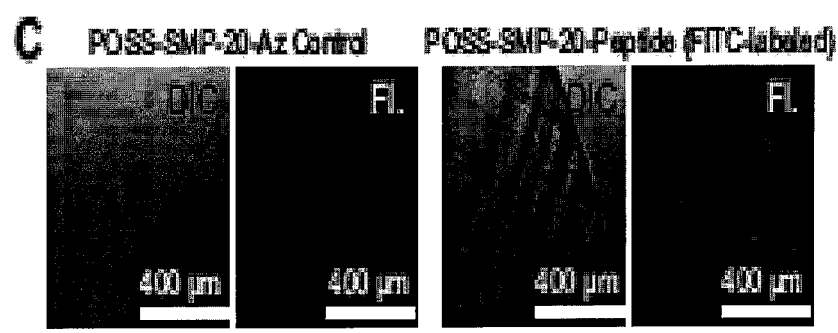
FIG. 18C: Differential interference contrast (DIC) and fluorescent (Fl) micrographs confirming the covalent conjugation of the fluorescently labeled peptide via "click" chemistry. In the negative control (left panel), POSS-SMP-20-Az was exposed to the fluorescently labelled peptide in the absence of ascorbic acid under otherwise identical reaction conditions.

These data indicate that the incorporation of the azido end groups induced a 25% reduction in urethane crosslinks, but did not deteriorate any thermal mechanical properties. FIG. 18B. Further, no notable difference in temporary shape fixing was observed. A slightly slower shape recovery, however, was observed for POSS-SMP-20-Az at 51° C., presumably due to the reduction in the number of tethered chains participating in the elastic deformation and recovery. POSS-SMP-20-Az was then coupled with a fluorescently labelled alkyne-functionalized Gly-Arg-Gly-Asp-Ser (SEQ ID NO: 1) (i.e., for example, 4-pentynoic acid-Gly-Arg-Gly-Asp-Ser-K(FTIC)-COOH) using high-fidelity "click" chemistry. FIG. 18A, step 2; and Wu et al., "Efficiency and fidelity in a click-chemistry route to triazole dendrimers by the copper(I)-catalyzed ligation of azides and alkynes" *Angew. Chem., Int. Ed.* 43(30): 3928-3932. Covalent attachment of the fluorescently labelled peptide was confirmed by fluorescence microscopy. FIG. 18C. No change in thermal mechanical properties was detected upon the attachment of the peptide to POSS-SMP-20-Az except for a minor reduction in $T_g^{DMA}$ (i.e., for example, <1° C.). FIG. 18B.

Figure 24:
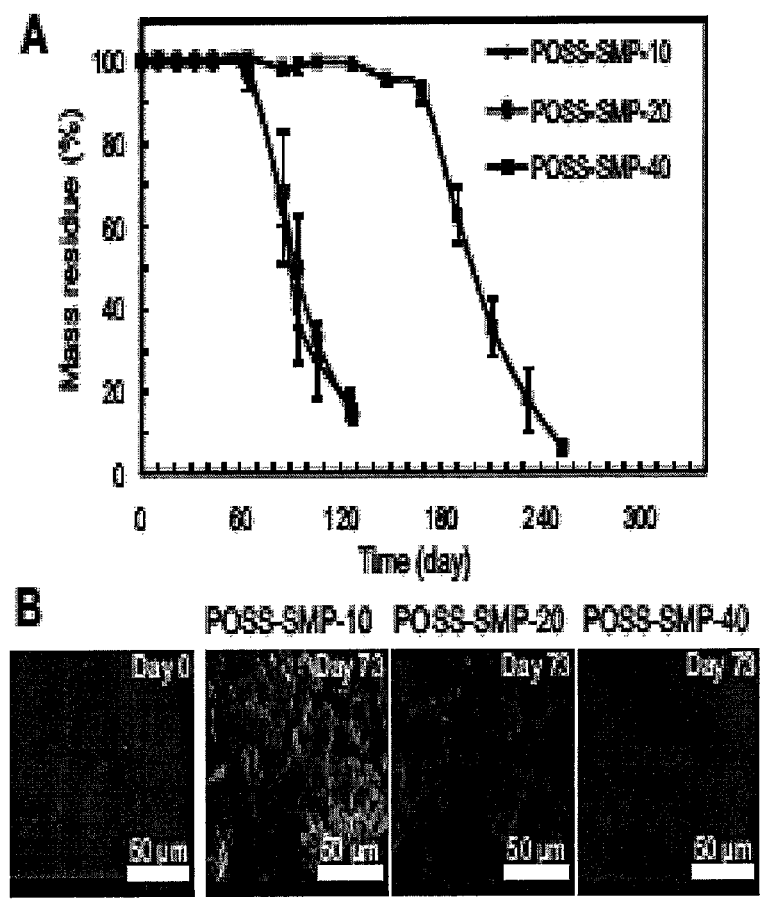
FIG. 24 presents exemplary data showing in vitro hydrolytic degradation of POSS-SMPs.

Consequently, the data suggest that this strategy can be extended to introduce a wide range of bioactive molecules to POSS-SMP while maintaining its desired physical properties. Further, POSS-SMPs can be engineered for varied hydrolytic degradation rates, e.g. 50% weight loss in 3-9 months, through the alteration of PLA chain length. FIG. 24. Together, biofunctionalization and control of degradation make it possible to prepare POSS-SMP-based tissue scaffolds and implants tailored for patient- and defect-specific biochemical environment and tissue repair/regeneration rates.

V. Organic Core Shape Memory Polymers

In one embodiment, the present invention contemplates a method for synthesizing a macromer building block. In one embodiment, the macromer building block comprises at least one hydrocarbon subunit. In one embodiment, the hydrocarbon subunit is capable of synthesizing an Org-(PLA$_n$)$_8$ macromer building block. For the purposes of illustration and without any intent to be limiting, the synthesis of the macromer building block Org-(PLA$_n$)$_8$ from a multi-hydroxylated Organic Core comprising hydrocarbon subunits is described below. FIG. 16A.

A. Acetal-Protected Organic Cores

4-Dimethylamino-pyridinium-p-toluenesulfate (DPTS) and 2,2,5-trimethyl-1,3-dioxane-5-carboxylic acid (TMDC) were prepared according to previously reported methods. TMDC (10.79 g, 61.97 mmol), di(trimethylolpropane) (DiTMP, 3.30 g, 13.18 mmol) and DPTS (3.88 g, 13.18 mmol) were dissolved and stirred in 200-mL anhydrous pyridine under N$_2$. Dicyclohexylcarbodiimide (DCC, 14.06 g, 68.17 mmol) was added after the solution became clear and stirred at r.t. for 20 h under N$_2$. The mixture was filtered and the filtrate was concentrated under vacuum. The resulting light-yellow solids were redissolved in hexane and filtered, and the filtrate was concentrated in vacuum for further purification by flash chromatography (Silica gel, Merck grade 9384, 230-400 mesh; ethyl acetate/hexane 2:3) to yield 4.5-g colorless oil ($R_f$=0.3, 40%). $^1$H NMR (400 MHz, CDCl$_3$): δ 4.15-4.12 (8H, d, J=12.0 Hz), 4.07 (8H, s), 3.62-3.59 (8H, d, J=12.0 Hz), 3.29 (4H, s), 1.49-1.43 (4H, q, J=7.4 Hz), 1.39 (12H, s), 1.33 (12H, s), 1.12 (12H, s), 0.87-0.84 (6H, t, J=7.4 Hz) ppm. $^{13}$C NMR (100 MHz, CDCl$_3$): δ 173.97, 98.27, 71.11, 66.25, 64.31, 42.56, 42.30, 25.37, 23.15, 22.32, 18.80, 7.72 ppm. HRMS for $C_{44}H_{78}NO_{17}$ [M+NH$_4^+$]: calculated 892.5270, observed 892.5273.

B. Organic Cores

Acetal-protected Organic Core (3.2 g, 3.66 mmol) described above was deprotected with 15.0 g resin (Amberlite IR-120, H+ form, 16-45 mesh) in 75-mL methanol for 15 h. After removing the resin by filtration, the filtrate was concentrated in vacuo to give colorless oil, which was redissolved in 16 mL methanol and precipitated in 100 mL anhydrous ethyl ether. The precipitate was filtered and dried under vacuum over P$_2$O$_5$ to give white powder (2.2 g, 84%). $^1$H NMR (400 MHz, CD3OD): δ 4.06 (8H, s), 3.70-3.67 (8H, d, J=10.9 Hz), 3.62-3.59 4(8H, d, J=10.9 Hz), 3.37 (4H, s), 3.31 (s) 1.54-1.49 (4H, q, J=7.4 Hz), 1.16 (12H, s), 0.94-0.90 (6H, t, J=7.4 Hz). $^{13}$C NMR (100 MHz, CD$_3$OD), δ 175.11, 70.76, 64.71, 63.99, 50.66, 42.12, 23.01, 16.20, 6.75 ppm. HRMS for $C_{32}H_{59}O_{17}$ [M+H$^+$]: calculated 715.3749, observed 715.3752.

C. Macromer Org-(PLA$_n$)$_8$

Figure 25:
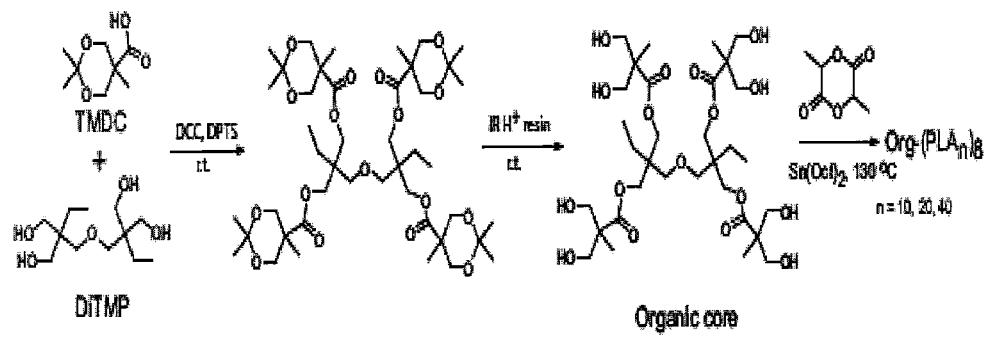
FIG. 25 presents one embodiment of a synthetic scheme of the organic core and a macromer building block Org-(PLA$_{20}$)$_8$ and associated $^1$H-NMR spectra.
Figure 25:
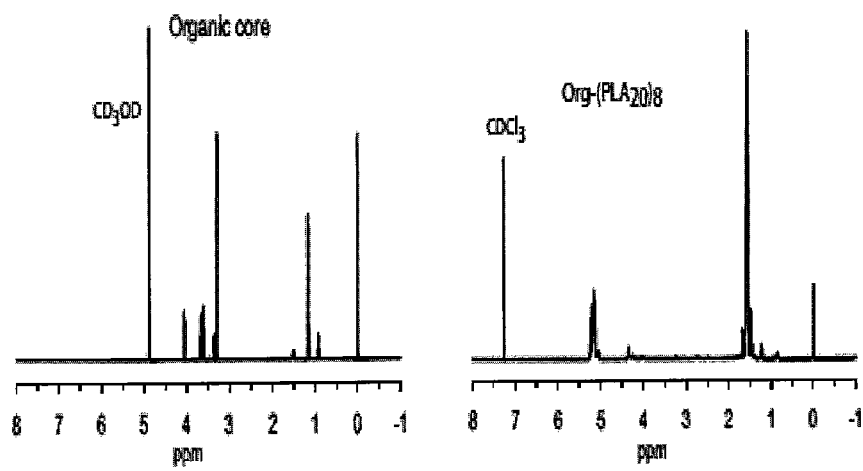

Organic macromers were prepared in the same way as POSS-(PLA$_n$)$_8$ (supra). Representatively, Organic cores (1.073 g, 1.50 mmol) and D,L-lactides (17.35 g, 120.38 mmol) were reacted at 130° C. with Sn(Oct)$_2$ (25.02 mg, 61.75 µmol) to prepare Org-(PLA$_{20}$)$_8$ in near quantitative yield. $^1$H NMR (400 MHz, CDCl$_3$): δ 5.25-5.12 (159H, m), 4.40-4.28 (16H, m), 4.24-4.20 (8H, b), 4.03 (8H, b), 3.25 (4H, s), 2.84-2.60 (OH, b), 1.75-1.71 (4H, m), 1.69-1.45 (m), 1.23 (12H, b), 0.90-0.81 (6H, m) ppm. $^{13}$C NMR (100 MHz, CDCl$_3$): δ175.31-175.19, 169.90-169.36, 72.66, 69.38-69.19, 66.87, 66.82, 46.65, 42.33, 20.70, 20.25, 16.94-16.87, 15.95, 7.68 ppm. Representative $^1$H NMR spectra and summary of GPC characterizations of the purified macromers. FIG. 25 and Table I.

VI. Bioimplantable Materials

A preferred embodiment of the present invention provides for its use as a supplement for bones that are compromised or at risk for compromise as well as tissue samples or systems that are compromised or at risk for compromise. As described in U.S. Pat. No. 6,767,928, hereby incorporated by reference, porous polymeric materials suitable for growth factor release, cellular attachment and tissue growth have been described. The present invention will find utility in these aforementioned applications due to its thermally responsive shape changes and pore recovery properties. The present invention may be further modified by attaching polymeric domains comprising multiple polymers such as block copolymers to the POSS core unit or units comprising the present invention. Such functional groups may be incorporated by methodologies that are well known to persons of ordinary skill in the art. While the present invention is in no way limited to the synthetic methods used to generate the aforementioned modified POSS domains, preferred methods include reversible addition fragmentation transfer (RAFT) and atom transfer radical polymerization (ATRP).

VI. SMP Compound Delivery Systems

The present invention contemplates a compound delivery system comprising a shape memory polymer comprising a core and a plurality of polymer arms that provide for roughly uniform distribution, and have controllable rates of compound release. In one embodiment, the shape memory polymer core comprises a POSS core. In one embodiment, the shape memory polymer core comprises an Organic core. In one embodiment, the polymer arms comprise biodegradeable (i.e., resorbable) polymers. In one embodiment, the polymer arms comprise at least one functional group capable of attaching a compound. In one embodiment, the polymers comprise non-biodegradable (i.e., non-resorbable) polymers. A variety of different polymers are described below that are useful in creating such drug delivery systems. It is not intended that any one polymer is limiting to the present invention. Note that any polymer may be attached to another polymer; for example, in one embodiment a polymer microparticle carrier attached to and/or encapsulating a compound may be attached to a polymer that is part of a shape memory polymer core.

In some embodiments, a drug delivery system contemplated herein may comprise at least one polymer selected from the group comprising gelatin, collagen, cellulose esters, dextran sulfate, pentosan polysulfate, chitin, saccharides, synthetic polyvinyl pyrrolidone, polyethylene oxide, polypropylene oxide, block polymers of polyethylene oxide and polypropylene oxide, polyethylene glycol, acrylates, acrylamides, methacrylates including, but not limited to, 2-hydroxyethyl methacrylate, poly(ortho esters), cyanoacrylates, gelatin-resorcin-aldehyde type bioadhesives, polyacrylic acid and copolymers and block copolymers thereof.

A. Compound Attachment To A Polymer

In one embodiment, the present invention contemplates a drug delivery system comprising a shape memory polymer comprising a core and a plurality of polymer arms, wherein the polymer arms attach at least one compound. In one embodiment, the compound comprises a therapeutic agent. In one embodiment, the agent comprises a small organic molecule. In one embodiment, the agent comprises an amino acid sequence. In one embodiment, the agent comprises a nucleic acid sequence. In one embodiment, amino acid sequence comprises a protein. In one embodiment, the amino acid sequence comprises a peptide fragment. In one embodiment, the amino acid sequence comprises an antibody. In one embodiment, the antibody is a polyclonal antibody. In one embodiment, the antibody is a monoclonal antibody. In one embodiment, the antibody is an Fab fragment. In one embodiment, the therapeutic agent may include, but is not limited to, anticancer agents, anti-osteoporotic agents, osteogenic agents, blasteogenic agents, anti-proliferative agents, anti-coagulation agents, and/or anti-inflammatory agents and combinations thereof.

B. Microparticle Attachment to a Polymer Arm

In one embodiment, the present invention contemplates a drug delivery system comprising a shape memory polymer comprising a core and a plurality of polymer arms, wherein the polymer arms attach at least one microparticle. In one embodiment, the microparticle comprises a therapeutic agent. In one embodiment, the agent comprises a small organic molecule. In one embodiment, the agent comprises an amino acid sequence. In one embodiment, the agent comprises a nucleic acid sequence. In one embodiment, amino acid sequence comprises a protein. In one embodiment, the amino acid sequence comprises a peptide fragment. In one embodiment, the amino acid sequence comprises an antibody. In one embodiment, the antibody is a polyclonal antibody. In one embodiment, the antibody is a monoclonal antibody. In one embodiment, the antibody is an Fab fragment. In one embodiment, the therapeutic agent may include, but is not limited to, anticancer agents, anti-osteoporotic agents, osteogenic agents, blasteogenic agents, anti-proliferative agents, anti-coagulation agents, and/or anti-inflammatory agents and combinations thereof.

Preferably, microparticles comprise liposomes, nanoparticles, microspheres, nanospheres, microcapsules, and nanocapsules. Preferably, some microparticles contemplated by the present invention comprise poly(lactide-co-glycolide), aliphatic polyesters including, but not limited to, poly-glycolic acid and poly-lactic acid, hyaluronic acid, modified polysaccharides, chitosan, cellulose, dextran, polyurethanes, polyacrylic acids, psuedo-poly(amino acids), polyhydroxybutrate-related copolymers, polyanhydrides, polymethylmethacrylate, poly(ethylene oxide), lecithin and phospholipids.

1. Liposomes

One embodiment of the present invention contemplates liposomes capable of attaching and releasing therapeutic agents described herein. Liposomes are microscopic spherical lipid bilayers surrounding an aqueous core that are made from amphiphilic molecules such as phospholipids. For example, a liposome may trap a therapeutic agent between the hydrophobic tails of the phospholipid micelle. Water soluble agents can be entrapped in the core and lipid-soluble agents can be dissolved in the shell-like bilayer. Liposomes have a special characteristic in that they enable water soluble and water insoluble chemicals to be used together in a medium without the use of surfactants or other emulsifiers. Liposomes can form spontaneously by forcefully mixing phosopholipids in aqueous media. Water soluble compounds are dissolved in an aqueous solution capable of hydrating phospholipids. Upon formation of the liposomes, therefore, these compounds are trapped within the aqueous liposomal center. The liposome wall, being a phospholipid membrane, holds fat soluble materials such as oils. Liposomes provide controlled release of incorporated compounds. In addition, liposomes can be coated with water soluble polymers, such as polyethylene glycol to increase the pharmacokinetic half-life. One embodiment of the present invention contemplates an ultra high-shear technology to refine liposome production, resulting in stable, unilamellar (single layer) liposomes having specifically designed structural characteristics. These unique properties of liposomes, allow the simultaneous storage of normally immiscible compounds and the capability of their controlled release.

In some embodiments, the present invention contemplates cationic and anionic liposomes, as well as liposomes having neutral lipids. Preferably, cationic liposomes comprise negatively-charged materials by mixing the materials and fatty acid liposomal components and allowing them to charge-associate. Clearly, the choice of a cationic or anionic liposome depends upon the desired pH of the final liposome mixture. Examples of cationic liposomes include lipofectin, lipofectamine, and lipofectace.

One embodiment of the present invention contemplates a drug delivery system comprising a shape memory polymer comprising a core and a plurality of polymer arms, wherein the polymer arms are attached to at least one liposome encapsulating a therapeutic agent that provides controlled release of the at least one therapeutic agent. Preferably, liposomes that are capable of controlled release: i) are biodegradable and non-toxic; ii) carry both water and oil soluble compounds; iii) solubilize recalcitrant compounds; iv) prevent compound oxidation; v) promote protein stabilization; vi) control hydration; vii) control compound release by variations in bilayer composition such as, but not limited to, fatty acid chain length, fatty acid lipid composition, relative amounts of saturated and unsaturated fatty acids, and physical configuration; viii) have solvent dependency; iv) have pH-dependency and v) have temperature dependency.

The compositions of liposomes are broadly categorized into two classifications. Conventional liposomes are generally mixtures of stabilized natural lecithin (PC) that may comprise synthetic identical-chain phospholipids that may or may not contain glycolipids.

Special liposomes may comprise: i) bipolar fatty acids; ii) the ability to attach antibodies for tissue-targeted therapies; iii) coated with materials such as, but not limited to lipoprotein and carbohydrate; iv) multiple encapsulation and v) emulsion compatibility.

Liposomes may be easily made in the laboratory by methods such as, but not limited to, sonication and vibration. Alternatively, compound-delivery liposomes are commercially available. For example, Collaborative Laboratories, Inc. are known to manufacture custom designed liposomes for specific delivery requirements.

2. Microspheres, Microparticles and Microcapsules

Microspheres and microcapsules are useful in drug delivery systems due to their ability to maintain a generally uniform distribution, provide stable controlled compound release and are economical to produce and dispense.

Microspheres are obtainable commercially (Prolease®, Alkerme's: Cambridge, Mass.). Alternatively, a freeze dried polymer composition comprising at least one therapeutic agent is homogenized in a suitable solvent and sprayed to manufacture microspheres in the range of 20 to 90 µm. Techniques are then followed that maintain sustained release integrity during phases of purification, encapsulation and storage. Scott et al., "Improving Protein Therapeutics With Sustained Release Formulations" *Nature Biotechnology* 16:153-157 (1998).

Modification of microsphere composition by integrating biodegradable polymers can provide an ability to control the rate of therapeutic agent release. Miller et al., "Degradation Rates of Oral Resorbable Implants (Polylactates and Polyglycolates): Rate Modification and Changes in PLA/PGA Copolymer Ratios" *J. Biomed. Mater. Res.*, 11:711-719 (1977).

Alternatively, a sustained and/or controlled release microsphere preparation is prepared using an in-water drying method, where an organic solvent solution of a biodegradable polymer metal salt is first prepared. Subsequently, a dissolved or dispersed therapeutic agent is added to the biodegradable polymer metal salt solution. The weight ratio of a therapeutic agent to a biodegradable polymer metal salt may for example be about 1:100000 to about 1:1, preferably about 1:20000 to about 1:500 and more preferably about 1:10000 to about 1:500. Next, an organic solvent solution containing a biodegradable polymer metal salt and therapeutic agent is poured into an aqueous phase to prepare an oil/water emulsion. The solvent in the oil phase is then evaporated off to provide microspheres. Finally, these microspheres are then recovered, washed and lyophilized. Thereafter, the microspheres may be heated under reduced pressure to remove the residual water and organic solvent.

Other methods useful in producing microspheres that are compatible with a biodegradable polymer metal salt and therapeutic agent mixture are: i) phase separation during a gradual addition of a coacervating agent; ii) an in-water drying method or phase separation method, where an antiflocculant is added to prevent particle agglomeration and iii) by a spray-drying method.

In one embodiment, the present invention contemplates a microsphere or microcapsule capable of delivering a controlled release of a therapeutic agent for a duration of approximately between 1 day and 6 months. In one embodiment, the microsphere or microparticle may be colored to allow the medical practitioner the ability to see the medium clearly as it is dispensed. In another embodiment, the microsphere or microcapsule may be clear. In another embodiment, the microsphere or microparticle is impregnated with a radio-opaque fluoroscopic dye.

Controlled release microcapsules may be produced by using known encapsulation techniques such as centrifugal extrusion, pan coating and air suspension. Such microspheres and/or microcapsules can be engineered to achieve desired release rates. For example, Oliosphere® (Macromed) is a controlled release microsphere system. These particular microsphere's are available in uniform sizes ranging between 5-500 μm and composed of biocompatible and biodegradable polymers.

Specific polymer compositions of a microsphere can control therapeutic agent release rates such that custom-designed microspheres are possible, including effective management of a burst effect. For example, ProMaxx® (Epic Therapeutics, Inc.) is a commercially available protein-matrix microsphere delivery system. The system is aqueous in nature and is adaptable to standard pharmaceutical delivery models. In particular, ProMaxx® comprises bioerodible protein microspheres that deliver both small and macromolecular drugs, and may be customized regarding both microsphere size and desired release characteristics.

In one embodiment, a microsphere or microparticle comprises a pH sensitive encapsulation material that is stable at a pH less than the pH of the internal mesentery. The typical range in the internal mesentery is pH 7.6 to pH 7.2. Consequently, the microcapsules should be maintained at a pH of less than 7. However, if pH variability is expected, the pH sensitive material can be selected based on the different pH criteria needed for the dissolution of the microcapsules. An encapsulated compound, therefore, can be selected for the pH environment in which dissolution is desired and stored in a pH preselected to maintain stability. Examples of pH sensitive material useful as encapsulants are Eudragit® L-100 or S-100 (Rohm GMBH), hydroxypropyl methylcellulose phthalate, hydroxypropyl methylcellulose acetate succinate, polyvinyl acetate phthalate, cellulose acetate phthalate, and cellulose acetate trimellitate. In one embodiment, lipids comprise the inner coating of the microcapsules. In these compositions, these lipids may be, but are not limited to, partial esters of fatty acids and hexitiol anhydrides, and edible fats such as triglycerides. Lew C. W., "Controlled-Release pH Sensitive Capsule And Adhesive System And Method" U.S. Pat. No. 5,364,634 (herein incorporated by reference).

In one embodiment, the present invention contemplates a microparticle comprising a gelatin, or other polymeric cation having a similar charge density to gelatin (i.e., poly-L-lysine) and is used as a complex to form a primary microparticle. A primary microparticle is produced as a mixture of the following composition: i) Gelatin (60 bloom, type A from porcine skin), ii) chondroitin 4-sulfate (0.005%-0.1%), iii) glutaraldehyde (25%, grade 1), and iv) 1-ethyl-3-(3-dimethylaminopropyl)-carbodiimide hydrochloride (EDC hydrochloride), and ultra-pure sucrose (Sigma Chemical Co., St. Louis, Mo.). The source of gelatin is not thought to be critical; it can be from bovine, porcine, human, or other animal source. Typically, the polymeric cation is between 19,000-30,000 daltons. Chondroitin sulfate is then added to the complex with sodium sulfate, or ethanol as a coacervation agent.

Following the formation of a microparticle, a therapeutic agent may be directly bound to the surface of the microparticle or indirectly attached using a "bridge" or "spacer". For example, amino groups of gelatin lysine groups are easily derivatized to provide sites for direct coupling of a compound. Alternatively, spacers (i.e., for example, linking molecules and derivatizing moieties on targeting ligands) such as avidin-biotin are also useful to indirectly couple targeting ligands to the microparticles. Stability of the microparticle is controlled by the amount of glutaraldehyde-spacer crosslinking induced by the EDC hydrochloride. A controlled release medium is also empirically determined by the final density of glutaraldehyde-spacer crosslinks.

In one embodiment, the present invention contemplates microparticles formed by spray-drying a composition comprising fibrinogen or thrombin with a therapeutic agent. Preferably, these microparticles are soluble and the selected protein (i.e., fibrinogen or thrombin) creates the walls of the microparticles. Consequently, therapeutic agents may be incorporated within, and/or between, the protein walls of the microparticle. Heath et al., "Microparticles And Their Use In Wound Therapy" U.S. Pat. No. 6,113,948 (herein incorporated by reference). Following the application of microparticles to living tissue, the subsequent reaction between the fibrinogen and thrombin creates a tissue sealant thereby releasing the incorporated compound into the immediate surrounding area.

One having ordinary skill in the art will understand that the shape of the microspheres need not be exactly spherical, but only represent very small particles. In one embodiment, microparticles may be comprised of a biocompatible and/or biodegradable material selected from the group consisting of polylactide, polyglycolide and copolymers of lactide/glycolide (PLGA), hyaluronic acid, modified polysaccharides and any other well known material.

VII. Pharmaceutical Compositions and/or Formulations

The present invention further provides pharmaceutical compositions (e.g., comprising a therapeutic drug as described above). The pharmaceutical compositions of the present invention may be administered by surgical implantation.

Pharmaceutical compositions and formulations contemplated herein may include sterile compositions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, gels, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with semi-solid carriers or finely divided solid carriers or both, and then, if necessary, shaping the product.

Agents that enhance uptake of oligonucleotides at the cellular level may also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or, anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with a therapeutic drug of the formulation.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models or based on the examples described herein. In general, dosage is from 0.01 µg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the oligonucleotide is administered in maintenance doses, ranging from 0.01 µg to 100 g per kg of body weight, once or more daily, to once every 20 years.

EXAMPLES

The following examples are provided in order to demonstrate and further illustrate certain preferred embodiments and aspects of the present invention and are not to be construed as limiting the scope thereof.

Example I

Silicon-Based Nanoparticles

Silicon-based nanoparticles are chosen as the structural and mechanical anchor for grafting block copolymers to generate star-shaped macromer building blocks of the synthetic bone substitute. As described in FIG. 7A, octakis(dimethylsiloxy) octasilsesquioxane (POSS) was hydrosilylated by allyl alcohol catalyzed by platinum divinyltetramethyldisiloxane, Pt(dvs), to form a octahedral hydroxylated POSS core as shown in FIG. 7A (1) following precipitation in acetone/ether and repeated washing with toluene (90% yield). Grafting of biodegradable polylactide (PLA) arms to 1 was achieved by ring opening polymerization (ROP) of cyclic racemic lactide (5, 10 or 20 eq. relative to the number of OH's in 1). The polymerization was catalyzed by stannous octoate (0.2 wt %), which was added to the optically clear melt of lactides at 115° C. under nitrogen. Macromers 2 (POSS-(PLA$_n$)$_8$, wherein n=10, 20 and 40), were obtained in >90% yield. $^1$H NMR (FIG. 7B) revealed expected increase of proton intensity within the PLA repeat (elements e and f of the disclosed NMR spectra) relative to those of the POSS core (a, b, c and d of the disclosed NMR spectra) as the polyester chain grew from n=10 to n=20. The varying PLA lengths should result in different in vivo biodegradation rates. Molecular weight distribution of 2 (FIG. 7C) was determined by gel permeation chromatography (GPC) using two 5-mm PLGel MiniMIX-D column (Polymer Labs) in THF on a Varian HPLC system equipped with an evaporative light scattering detector. The system was calibrated using polystyrene standards and a Polymer Labs Galaxie Cirrus AIA GPC Software.

Figure 8A:
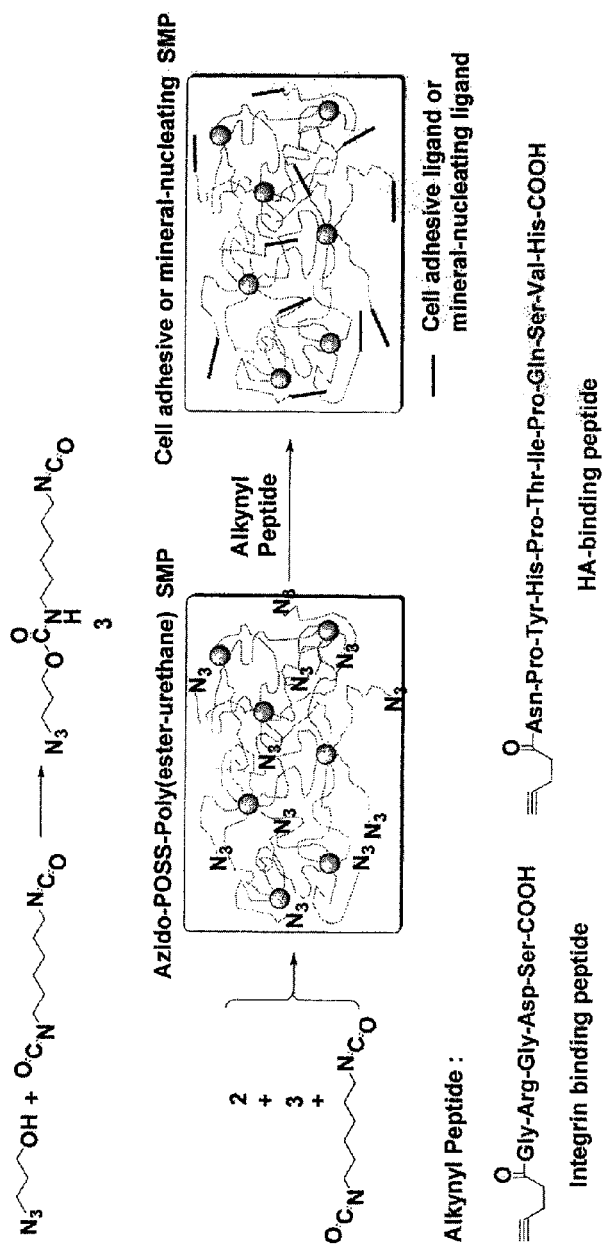
FIG. 8A illustrates a synthetic method for attaching bioactive peptides of preferred embodiments, where the mineral nucleating peptide is HA-binding peptide (SEQ ID No.: 1) and the cell adhesive ligand is (SEQ ID No.: 2).
Figure 8B:
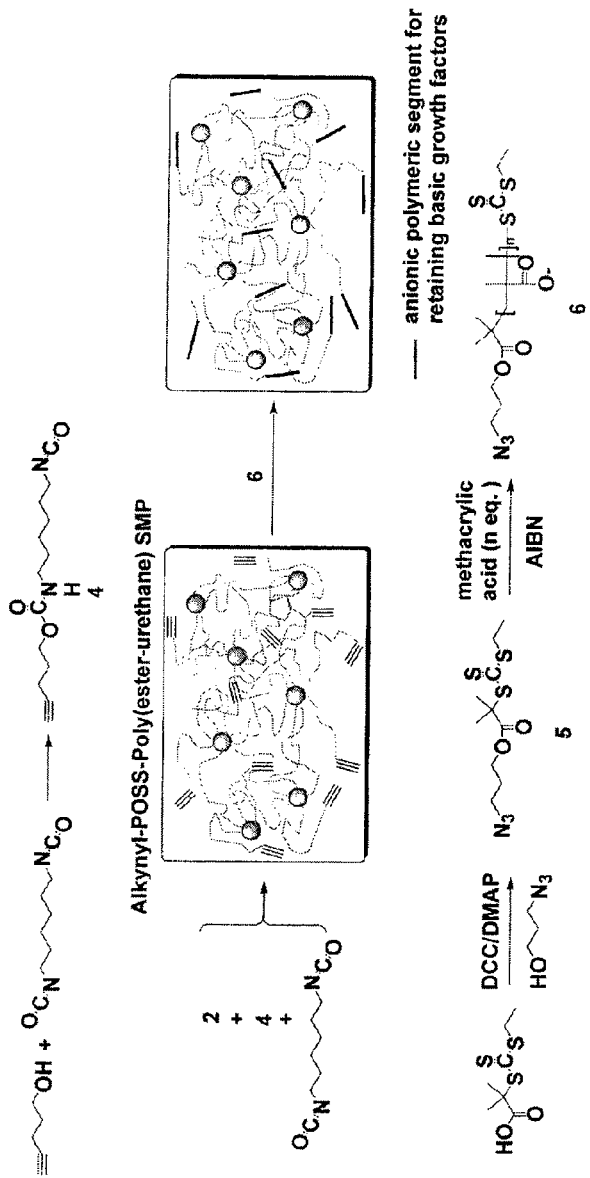
FIG. 8B illustrates a synthetic method for attaching anionic growth factor-retention domains to the POSS-poly(ester-urethane) SMP.
Figure 8:
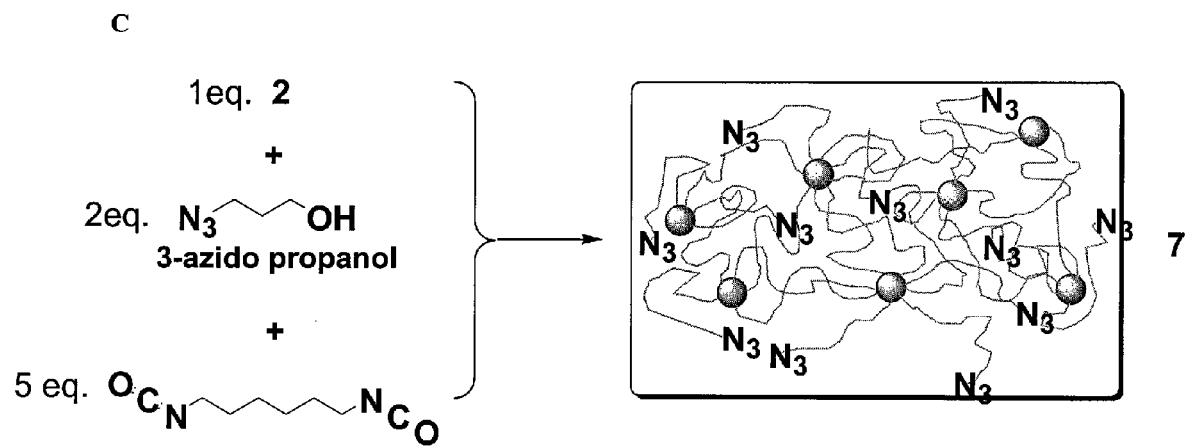
FIG. 8C illustrates a synthetic method for preparing embodiments of the invention.
FIG. 8D shows the Fourier transform infrared (FTIR) spectrum of crosslinked macromers of the present invention and 3-azido propanol (FIG. 8C).
FIG. 8E illustrates a synthetic route for the attachment of CTA-1 to macromer 2 and the subsequent grafting of pHEMA to the macromer CTA by RAFT polymerization.
FIG. 8F shows data of GPC characterization of macromer 2, macromer CTA and the POSS-(PLA$_n$-co-pHEMA$_m$)$_8$ obtained via RAFT (n=20, m=200). Polydispersity ($M_w/M_n$) was determined using a PLGel Mixed-D column on a Varian HPLC equipped with an evaporative light scattering detector.
FIG. 8G illustrates one of the strategies of making functional shape memory polymers as an embodiment of the invention.
FIG. 8H illustrates examples of the molecules generalized in FIG. 8G.
Figure 8:
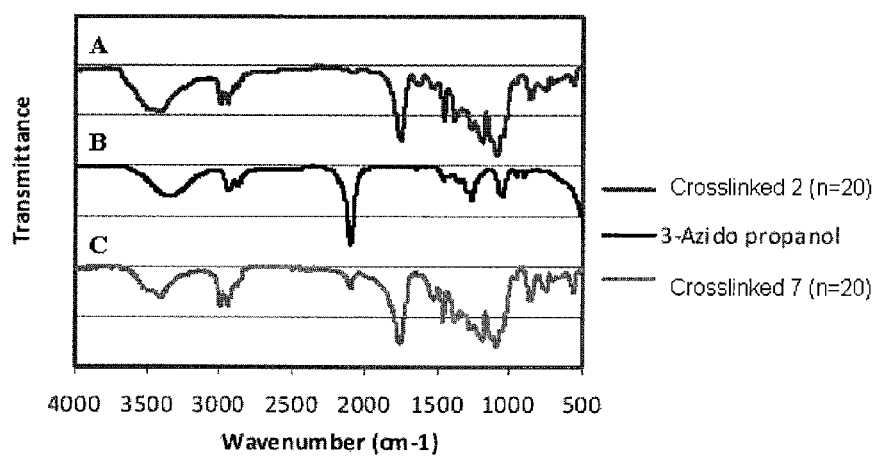
Figure 8:
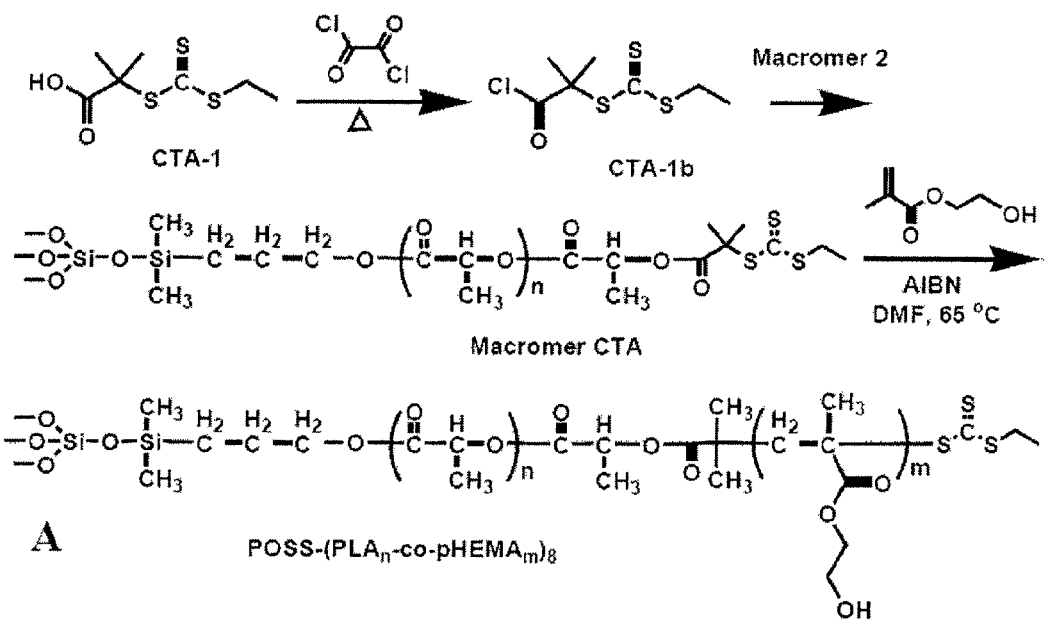
Figure 8:
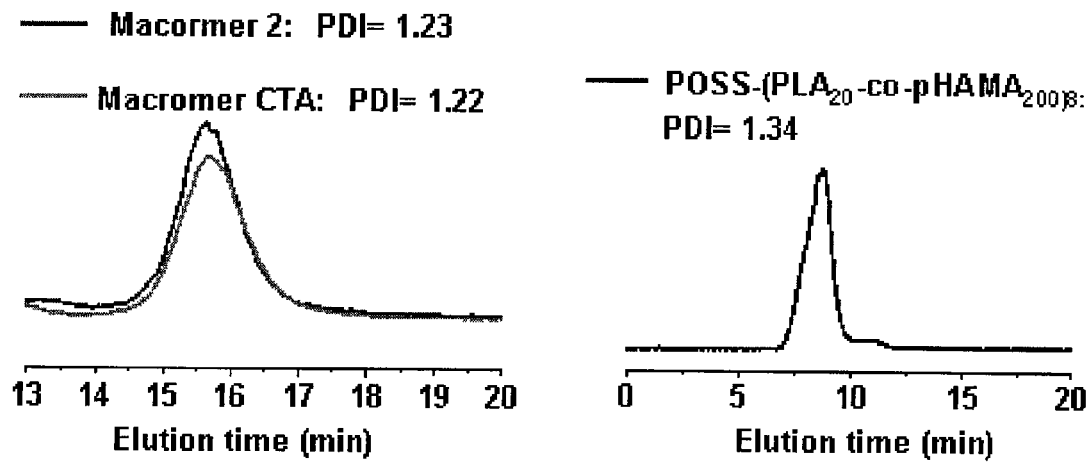
Figure 8G:
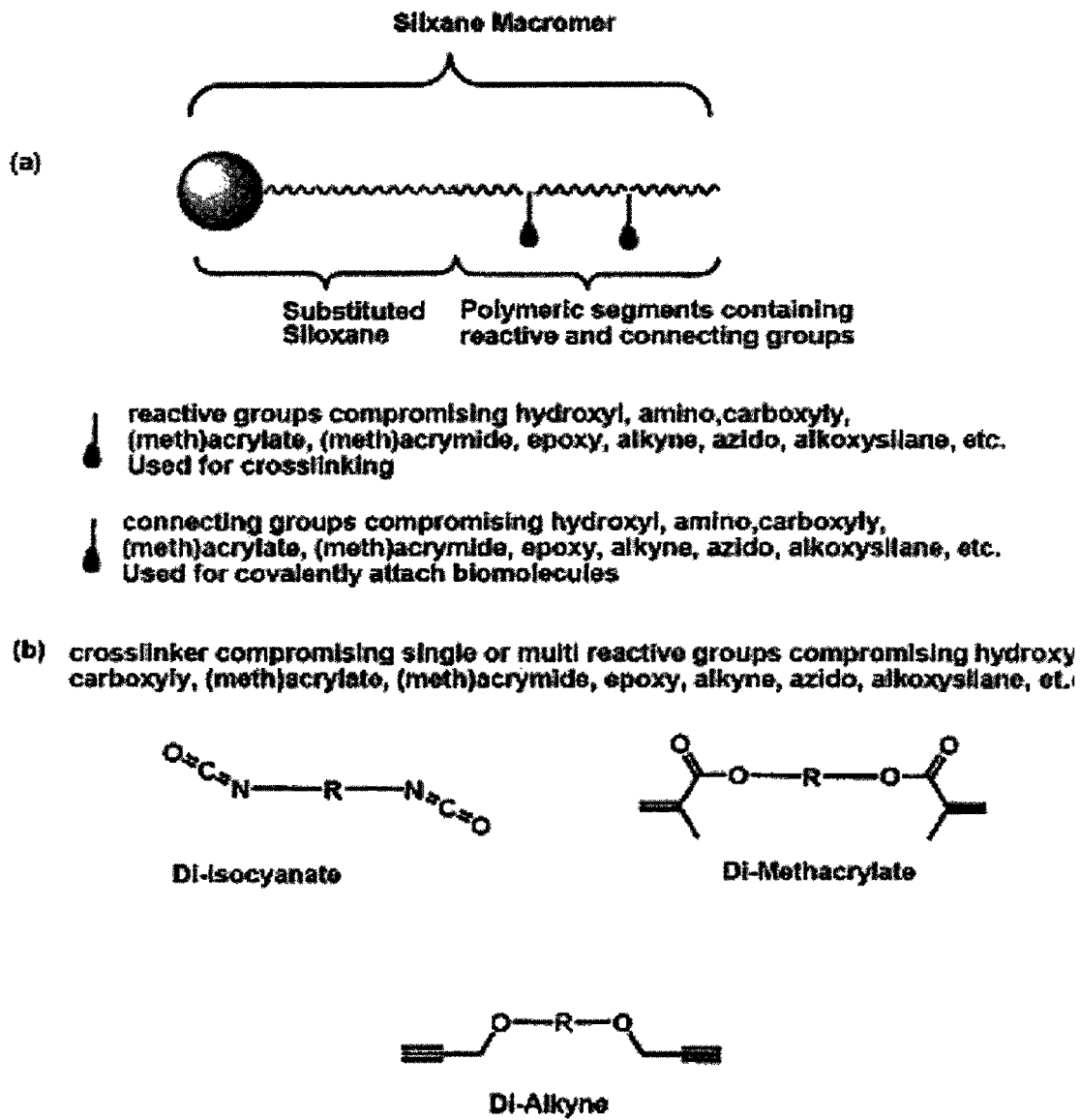
Figure 8H:
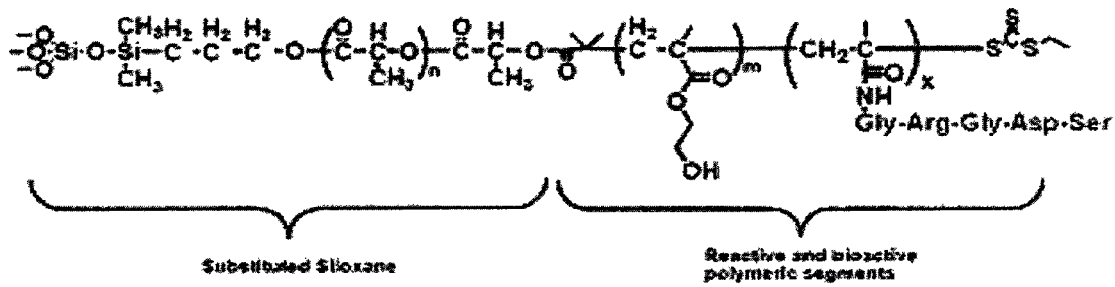
Figure 8H:
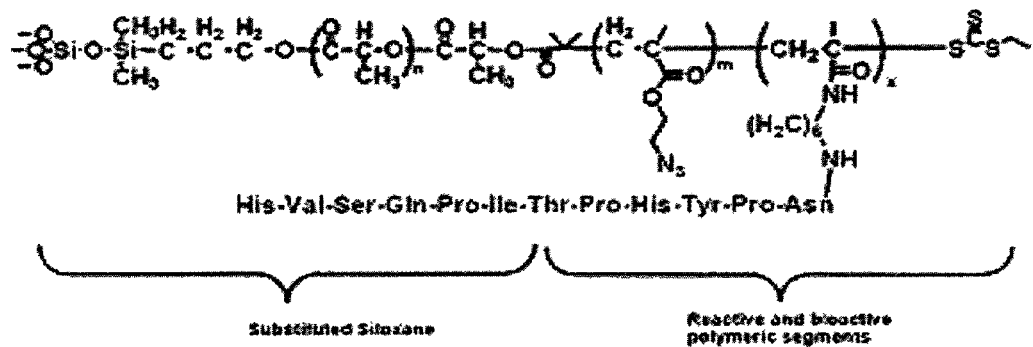
Figure 8H:
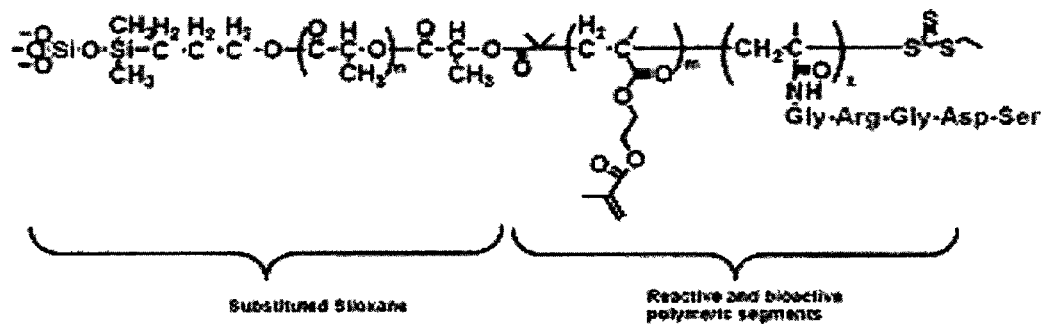
Figure 9A:
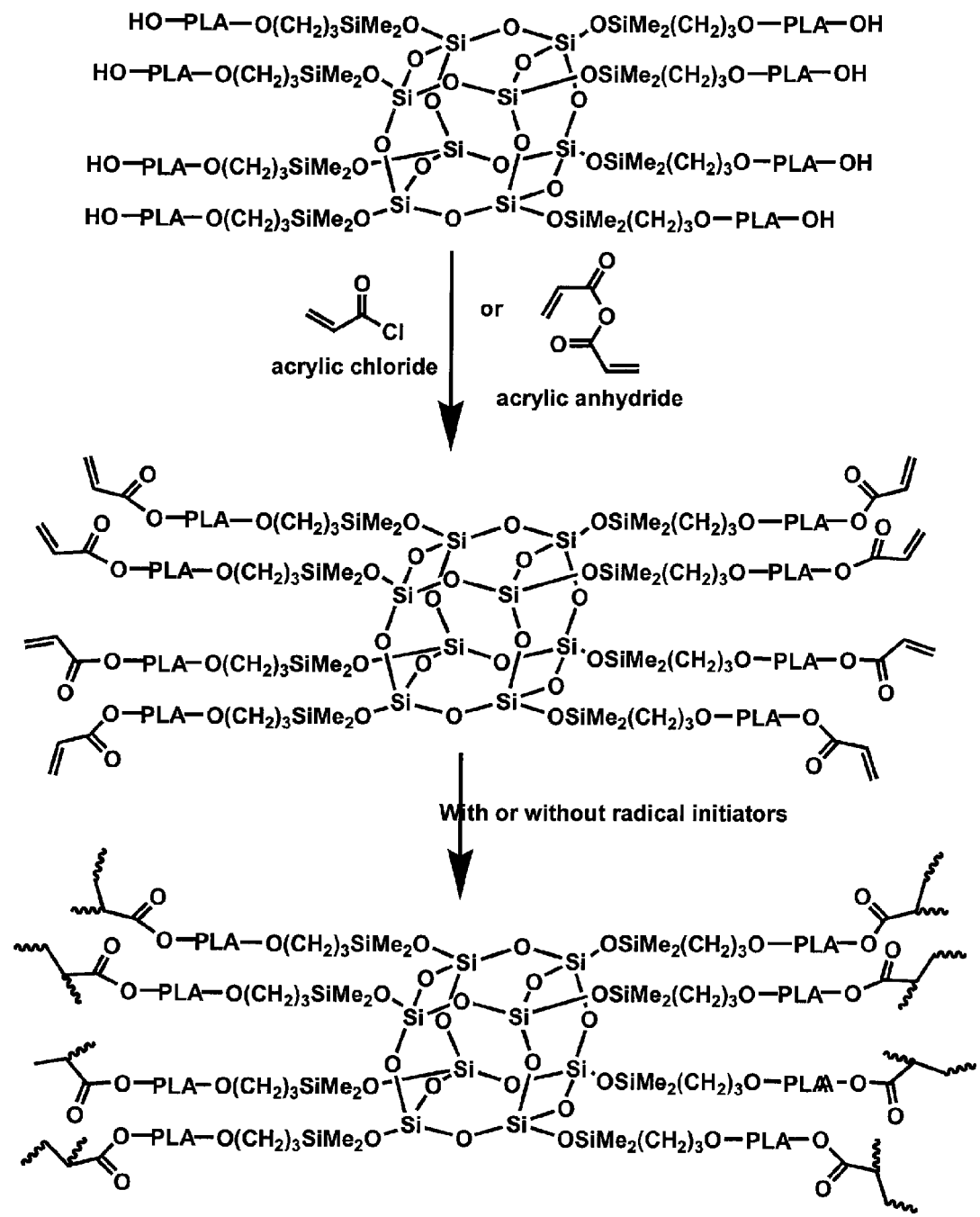
FIG. 9A illustrates a synthetic method for making embodiments of the invention.
Figure 9B:
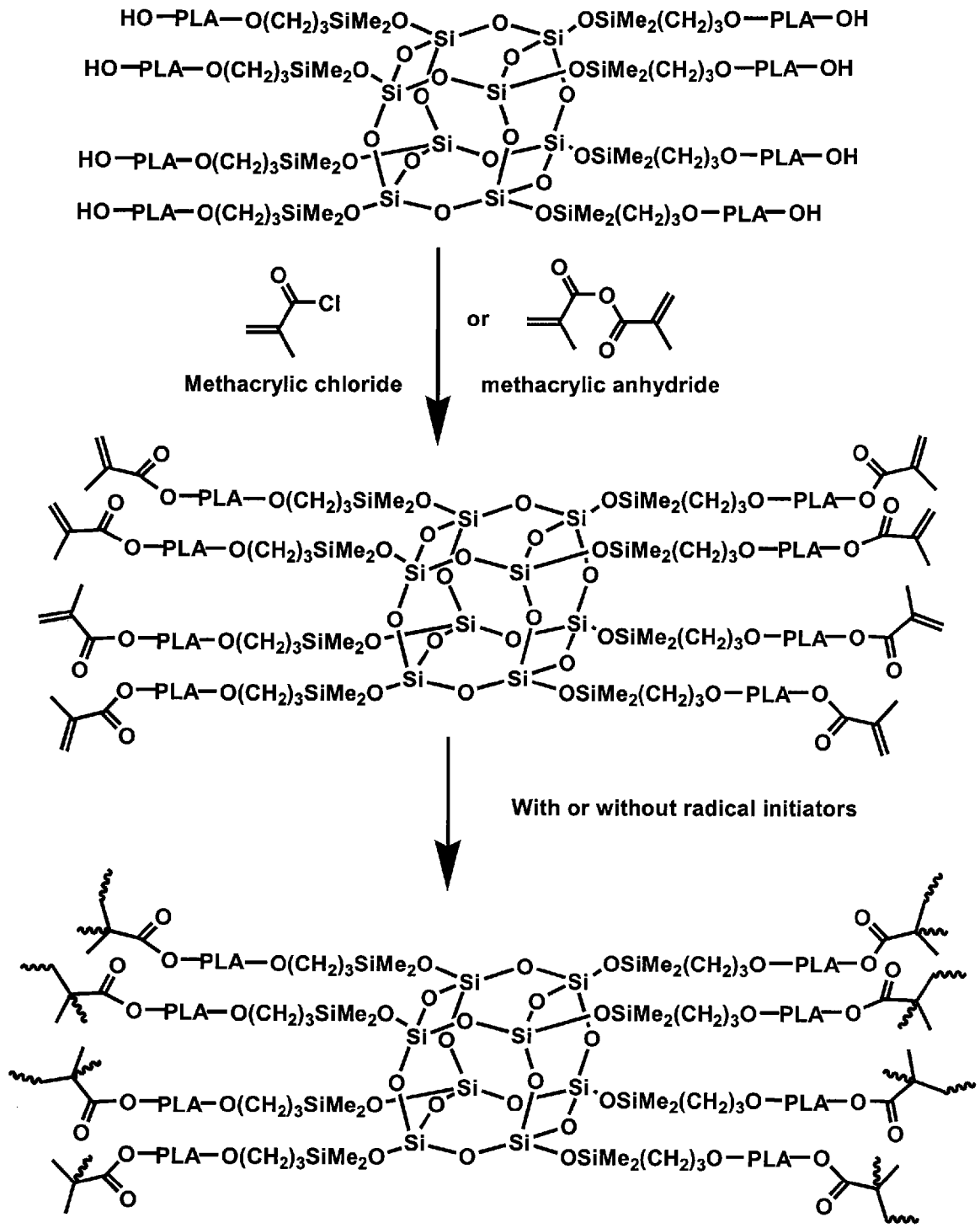
FIG. 9B illustrates another synthetic method for making embodiments of the invention.

Additional methods for synthesizing the functional shape memory polymers and macromer structures of the present invention are illustrated in FIGS. 8G and 8H.

Example II

Crosslinking of Biodegradable POSS-(PLA$_n$)$_8$ and Characterization of their Thermal and Mechanical Properties Star-shaped macromer 2 (FIG. 7A) was crosslinked by diisocyanates to form the SMP which were cast into desirable "permanent" shapes, in one case (FIG. 10A), a coil such as a stretched out helix that maintains its stable temporary shape at rt for >1 yr, but instantly (~1 sec) restores its permanent helical shape upon heat activation at 50 deg C., and in other cases, a folded cup that maintains its stable temporary shape at rt, but immediately restores the permanent cup shape (hollow cup) when exposed to a 50 deg C. water bath, or a flat sheet with surface grid patterns wherein a permanent surface grid pattern can be "erased" under compression above the Tg and maintains "patternless" upon cooling to rt wherein the surface grid pattern is immediately restored upon heat activation, (FIG. 10B). The $T_g$'s of the hybrid SMP, as determined by differential scanning calorimetry (DSC), are close to body temperature and can be fine-tuned by manipulating the grafted PLA chain lengths. The $T_g$'s ranged from 42.8° C. to 48.4° C. with the PLA segment grew from 10 to 40 repeating units (FIG. 7D). The storage and flexural moduli of the SMP are in the GPa range at both room temperature and body temperature, close to those exhibited by human cortical bone. The moduli of the SMP are tunable by PLA chain lengths and decreased with increasing temperature (FIG. 7E-7I).

Example III

Demonstration of the Temporary Shape Fixation Stability and Shape Recovery Efficiency of Urethane-Crosslinked POSS-(PLA$_n$)$_8$ Bulk urethane-crosslinked POSS-(PLA$_n$)$_8$ with varying permanent shapes, sizes and surface patterns can be fabricated using the solution casting method. Examples of the bulk materials with pre-programmed permanent shapes are shown in FIGS. 10A and 10B. These materials can be deformed into any desired temporary shapes or surface patterns beyond their glass transition temperatures, and can be held stably at these temporary shapes for months to years upon cooling to room temperature, without slowly creeping back to their permanent shapes (FIG. 10B). As soon the thermal stimuli are re-applied, however; these materials instantaneously (~1 sec) returned to their pre-programmed permanent shapes or surface patterns (FIGS. 10A and 10B). Such stable shape fixation at room or body temperatures as well as the high shape recovery efficiency is consistent with the modulus-temperature data shown in FIGS. 7E-7I.

Example IV

Synthetic Modification of POSS-Poly(Ester-Urethane) SMP

In certain embodiments, the applicants can introduce new functionlization sites through the modification of the crosslinker rather than the star-shaped macromer 2. As shown in FIG. 8, one uses azido-isocyanate 3 (route 8A) or alkynyl-isocyanate 4 (route 8B) along with the diisocyanate to crosslink star-shaped macromer 2 to form azido-POSS-poly (ester-urethane) or alkynyl-POSS-poly(ester-urethane), respectively. By keeping the stoichiometric ratio of 3 or 4 to diisocyanate low, one keeps the majority of the eight terminal hydroxyls of 2 crosslinked as usual, thus maintaining its shape memory behavior. One introduces a small amount of azido- or alkynyl-groups to the graft (e.g. by coupling 3 or 4 to one of the terminal hydroxyls of macromer 2 via urethane linkages), and allows the introduction of the RGD peptide, HA-binding peptide or PMA functionalized with the complimentary reactive sites by a coupling reaction between the azido group and the alkyne group. One can carry this reaction out under very mild conditions, and it is tolerant to other functional groups including peptide side chains and polar carboxylates that are richly present in PMA. One couples an alkyne-terminated RGD-containing pentapeptide and an alkyne-terminated 12mer HA-binding peptide to the exposed azido groups of the polymer grafts to generate cell adhesive and/or HA-nucleating SMP (FIG. 8A).

Figure 2:
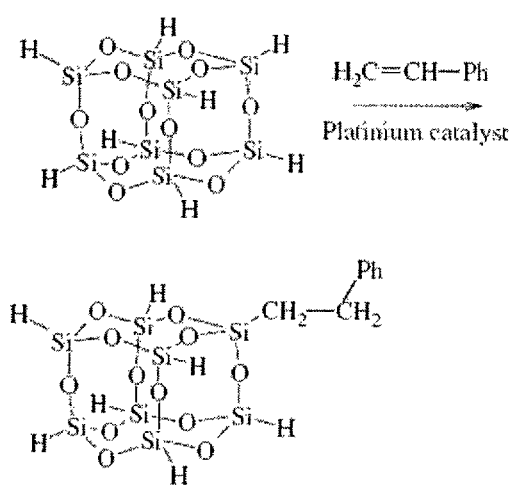
FIG. 2 shows a preferred method of making embodiments.

As shown in FIG. 8C, 1 eq. macromer 2, 2 eq. 3-diazo-propanol and 5 eq. hexamethylene diisocyanate were mixed in 5 eq. dichloromethane with the addition of 100 ppm dibutyltin dilaurate as the catalyst. The solution was stirred for 2 hour and then poured into Teflon molds to evaporate the solvent at room temperature overnight under nitrogen. The materials were further crosslinked for another 24 h at 75° C. and 48 h at 75° C. under vacuum. The crosslinked material 7 were soaked in chloroform for 12 h to remove any un-reacted monomers and soluble components. The FTIR of crosslinked 7 (FIG. 8D) shows characteristic absorption for the azido functionality (~2200 cm-1).

One can introduce an rhBMP-2-retention domain by the attachment of azido-terminated polymethacrylic acid 6 to the alkynyl-POSS-poly(ester-urethane) SMP (FIG. 8B). One prepares the azido-PMA 6 by reversible addition fragmentation transfer (RAFT) polymerization of methacrylic acid initiated by the azido-RAFT agent 5 as disclosed in Quemener et al., Chem. Comm., 5051-5053 (2006), incorporated herein by reference.

One can further functionalize the shape memory polymer by the attachment of small molecule CTA-1 via acyl chloride intermediate CTA-1b (FIG. 8E) to the hydroxyl termini of macromer 2 to enable subsequent RAFT polymerization. The attachment of CTA-1 to macromer 2 was accomplished in 92% yield (FIG. 8E). Briefly, oxalyl chloride (1.455 g) was reacted with CTA-1(0.4662 g, 2.078 mmol) under N2 for 2 h at rt and then 3 h at 55° C. The volatile was removed under vacuum before macromer 2 (n=20, Mw/Mn=1.23, 0.5695 g) in 15 mL THF was added. The reaction proceeded at 55° C. for 12 h before the volatile was removed by distillation. The resulting red oil was dissolved in 30 mL ethyl acetate, washed with 100 mL saturated NaHCO3 aq. solution, dried with anhydrous MgSO4, and precipitated in 100 mL hexane. The yellow solid was further purified by dissolving in THF and precipitating in hexane 3 times. Drying under vacuum at 40° C. yielded spectroscopically pure macromer CTA (n=20, 0.5308 g, 92%). 1H NMR (400 MHz, CDCl3): d 5.24-5.12 (172H, br), 5.12-5.05 (8H, q, J=7.0 Hz), 4.10 (16H, t, J=6.6 Hz), 3.27 (16H, q, J=7.4 Hz), 1.74 and 1.70 (48H, s), 1.68-1.49 (560H, br), 0.60 (16H, t, J=8.6 Hz), 0.16-0.05 (48H, s) ppm. 13C NMR (100 MHz, CDCl3): d 221.44, 172.22, 170.23-169.28, 69.52-68.89, 67.78, 55.71, 31.29, 25.39 and 25.13, 22.26, 16.96-16.76, 13.47, 13.04, −0.32 ppm. GPC characterization using two 5-mm PLGel MiniMIX-D columns confirmed that narrow molecular weight distribution of macromer 2 (PDI=1.23, red trace, FIG. 10) was retained upon attachment of the CTA (PDI=1.22, green trace, FIG. 8F).

The efficiency for macromer CTA to initiate RAFT was illustrated by grafting 200 repeating HEMA units to each arm of the macromer. A 5-mL N,N-dimethylformamide (DMF) solution of macromer CTA (n=20, PDI=1.22, 161.0 mg, 0.01 mM), AIBN (3.3 mg, 0.02 mM), and HEMA (2.080 g, 16.0 mM) was placed in a 25-mL Schlenc flask, degassed with 3 freeze-evacuate-thaw cycles, and reacted at 65° C. under N2 for 10 h. The reaction mixture was precipitated in cold ethyl ether to yield yellow solid, which was further purified by precipitation in DMF/ethyl ether 3 times to give POSS-(PLA20-co-pHEMA200)$_8$ (1.3 g, 65%). GPC characterization revealed a narrow molecular weight distribution (PDI=1.34, blue trace, FIG. 8F), indicating the achievement of a well-controlled RAFT initiated by the macromer CTA. 1H NMR integration suggested a 222,000 molecular weight for POSS-(PLA20-co-pHEMA200)$_8$, confirming an average of 200 repeating HEMA units in each grafted pHEMA arm. 1H NMR (400 MHz, CD3OD): d 5.20 (260H, br), 4.04 (5505H, br), 3.78 (5505H, br), 2.17-1.87 (5505H, br), 1.62-1.49 (780H, br), 1.32 (330H, br), 1.17 and 0.94 (8041H, br), 0.21 (4811, br) ppm. As expected, the integrations for the proton signals corresponding to the inner core structure of the macromer were lower than theoretical values due to the limited motion of the core in the NMR solvent.

Example V

In Vitro Bioactivities of the SMP Bone Grafts

One may determine the HA-nucleating capacity induced by the HA-binding peptide attached to the SMP graft in vitro by the method disclosed herein or as appropriately modified. One soaks a graft in a HA-mineralization solution consisting of 5 mM $Na_2HPO_4$ and 10 mM $CaCl_2$ precursor ions. One retrieves the grafts after being incubated at 37° C. for 2, 12, 24 and 48 h. One washes and freeze-dries the retrieved grafts for scanning and transmission electron microscopy analyses. One examines the morphology and crystallinity of the templated HA-mineral growth on both the surface and at the cross-section of the graft.

One examines the role of the GRGDS peptide (SEQ ID NO: 1) functionalized on the SMP graft in promoting cell attachment by comparing the rate of cell attachment, the morphology, and the spreading of the attached cells in the early culture (2, 4, 12 and 24 hours) of mouse osteoblast-like MC3T3-E1 cells on crosslinked POSS-poly(ester-urethane) 2 vs. on crosslinked cell adhesive POSS-poly(ester-urethane) substrates. Fast attachment and good spreading of MC3T3-E1 indicates good initial cell-material interactions.

One determines the biological activity of rhBMP-2 pre-absorbed to and released from the SMP graft functionalized with the PMA domains by testing its ability to convert the differentiation pathway of mouse C2C12 myoblasts (which have zero/low endogenous background of BMP-2) into the osteoblast lineage. One plates C2C12 cells in low mitogen medium (5% FBS). One adds, the graft (5×5×1 mm) pre-absorbed with rhBMP-2 (0-0.5 µg/graft) to the culture. One adds an appropriate dose of BMP-2 (300 ng/mL) for converting C2C12 into osteoblast lineage to a positive control culture. At 2 and 4 days, one fixes the cell layers with 2% paraformaldehyde and stains for alkaline phosphatase (ALP), a marker for osteoblast differentiation, following standard protocol. Positive ALP staining indicates osteoblast differentiation.

Example VI

Angioplasty of an Arthoscloritic Plaque

One molds the materials disclosed in Examples 2 and 3 into a tubular web stent. The stent is coated with a material that degrades artherosclerotic plague a described in U.S. Pat. No. 7,195,640. One places the stent into a position in the cardiovascular system subject to atherosclerosis. The stent shape expands upon exposure to body temperature and degrades over time.

Example VII

In Vitro Hydrolytic Degradation of Urethane-Crosslinked POSS-$(PLA_n)_8$SMP

The hydrolytic degradation of urethane-crosslinked macromer 2 was examined in PBS (pH 7.4) at 37° C. over a course of 9 months. The extent of degradation as a function of PLA chain lengths was monitored as the weight loss of the material over time (FIG. 12A). As expected, the crosslinked macromers with shorter PLA (n=10, 20) led to faster degradation, losing >50% of mass in 3 months, whereas significant mass reduction was not detected with that containing longer PLA (n=40) until after 6 months. SEM micrographs (FIGS. 12B-G) confirmed that the material containing shorter PLA (n=10, 20) degraded to generate high porosity by day 73 whereas little degradation was detected for the one with longer PLA (n=40). The tunable degradation rate matching with normal fracture healing and spine fusion rate (2-6 months) combined with the tunable cortical bone-like mechanical properties of the crosslinked macromers support the notion that the shape memory polymer can be engineered for orthopedic applications.

Example VIII

Preliminary In Vivo Evaluation of POSS-PLA Macromer Toxicity

Figure 13:
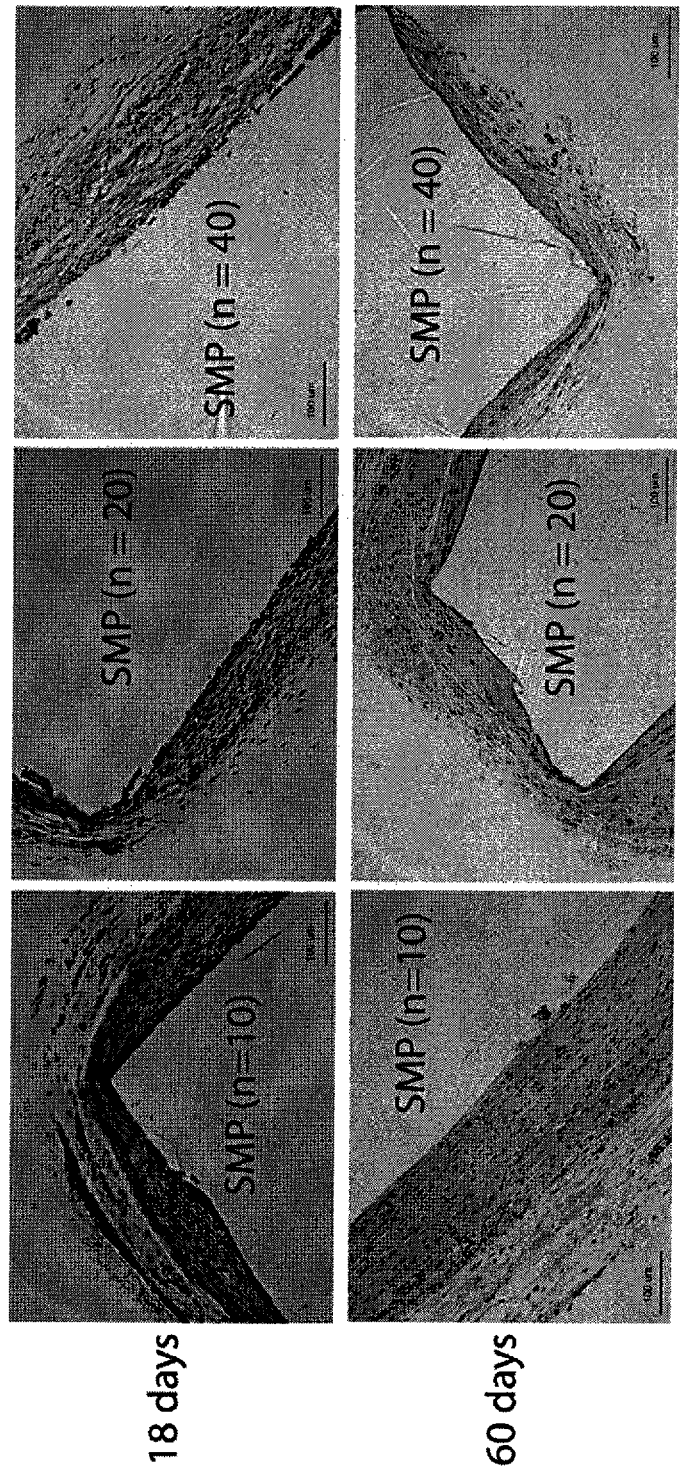
FIG. 13 shows images of the retrieved urethane-crosslinked POSS-(PLA)$_n$ (n=10, 20, 40) after 18-60 days of subcutaneous implantation under the rib cage of rats. All sections are 6 µm in thickness, and stained by hematoxylin and eosin. Double arrows indicate normal fibrous tissue encapsulation of the implants.

In vivo implantation of a shape memory polymer containing urethane-crosslinked POSS-PLA motifs into a mammalian subject. Subcutaneous implantation of urethane-crosslinked (POSS-$PLA_n)_8$ (n=10, 20, 40) under rat rib cages led to negligible inflammatory response, suggesting excellent biocompatibility of the shape memory polymers. See, FIG. 13. All sections shown are 6 µm in thickness, and stained by hematoxylin and eosin. Normal fibrous tissue encapsulation (indicated by double arrows) were observed in all cases. These results are suggestive of the efficacy of the present invention in biomaterials compatible with the natural tissue environment as well as biomaterials that are resistant to, e.g., immunological rejection.

Example IX

In Vivo Time Course of Tissue Response to Subcutaneously Implanted Urethane-Crosslinked POSS-PLA Macromer (POSS-SMPs)

Briefly, in each rat a small ventral incision was made to create a subcutaneous pocket to place a thin disc (Φ~5 mm; 1-mm thick) of POSS-SMP of a given PLA arm lengths (POSS-SMP-10, POSS-SMP-20, POSS-SMP-40) or commercial amorphous PLA (Mw 75-120 kD, Aldrich) pellets of the same weight. Each implant was retrieved at 4-, 18-, 60-, or 164-day post-op for histology. Heart, kidney, lung, liver, spleen and the rib cage were collected from 164-day post-op rats for the examination of potential systemic side effects of implant degradation.

Subcutaneous explants and retrieved organs were fixed in periodate-lysine-paraformaldehyde fixative at 4° C. for 1 and 2 days, respectively. Subcutaneous explants were stained for Ki67, a marker for cell proliferation, and with H&E for pathological assessment. Retrieved organs were stained with H&E. All histology slides were blind-assessed by a pathologist. The number of lymphocytes, macrophages, mast cells, eosinophils, and neutrophils were tallied in 5 randomly selected areas (40× field of view, FOV), and reported as average ±standard deviation. Blood vessel counts were reported in the most active 40× FOVs.

Figure 28A:
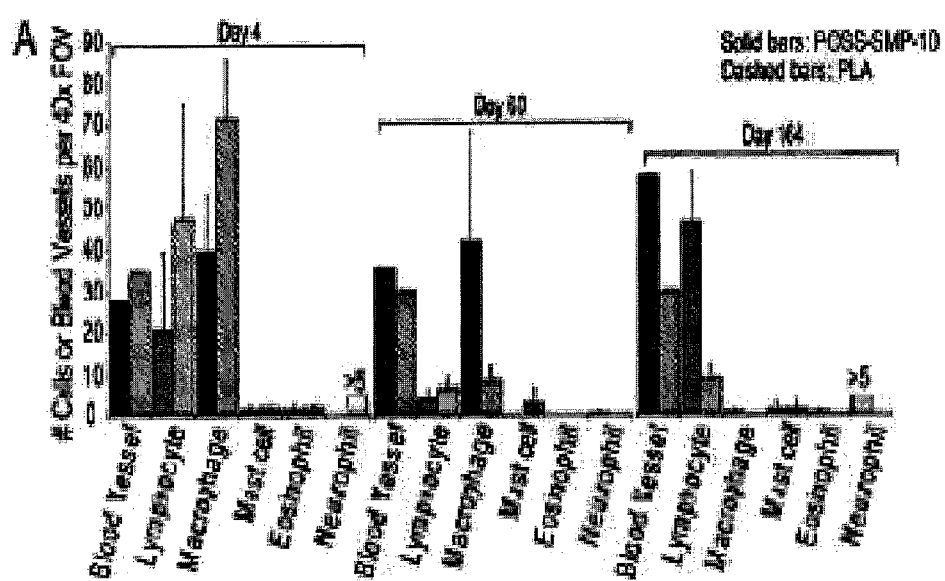
FIG. 28A: Immunogenicity of POSS-SMP-10 vs. PLA over time.

POSS-SMPs elicited normal tissue response to foreign biomaterials shortly after the subcutaneous implantation (day 4) as indicated by fibrous tissue encapsulation and inflammatory response (likely resulting from the surgery). The numbers of blood vessels, macrophages (acute/chronic inflammation), neutrophils (marker of acute inflammation), and lymphocytes (marker of chronic inflammation) detected within the fibrous tissue surrounding POSS-SMPs were much less than those detected from the PLA fibrous capsule, suggesting that both the acute and chronic inflammatory responses elicited by freshly implanted POSS-SMPs were milder than those of the PLA control. See, FIG. 28A. A declining proliferative (Ki67+) cell index and the number of lymphocytes by day 60 supported that the initial inflammatory response was largely acute in nature. See, Table V.

TABLE V

Percent Of Proliferating Cells per 40x FOV (Ki67+)

| | Day 4 | Day 60 | Day 164 |
| --- | --- | --- | --- |
| POSS-SMP-10 | >80% | 25% | 25-30% |
| PLA | >80% | 0% | 0% |

Figure 28B:
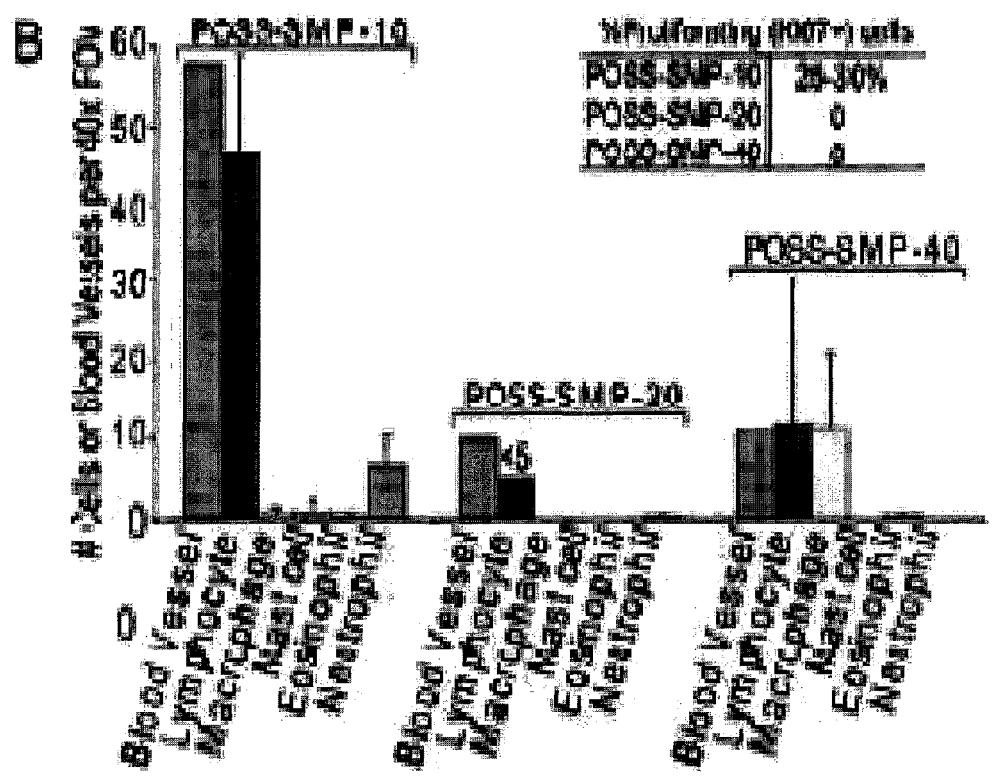
FIG. 28B: Tissue responses of POSS-SMPs on Day 164
Figure 28C:
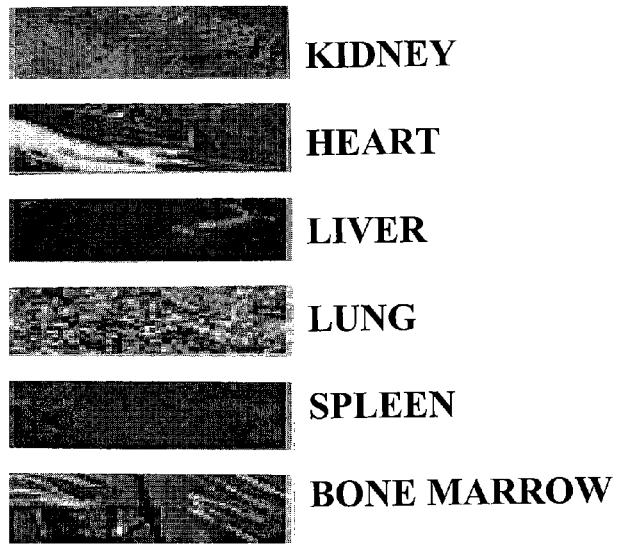
FIG. 28C: Hemotoxylin & eosin stains of vital organs retrieved from rats receiving POSS-SMP-10 for 164 days (500×) revealing no systemic side effects.

As the materials degraded in vivo, a second acute and chronic inflammatory response, indicated by an increase in the counts of blood vessels, lymphocytes and neutrophils, was elicited. See, FIG. 28A. The extent of the response positively correlated with the rate of degradation, with the most profound increases observed with the fastest degrading POSS-SMP-10 by day 164. See, FIG. 28B. It is worth noting, however, the degradation did not lead to allergic reactions as evidenced by the zero-to-low counts of mast cells and eosinophils. Finally, assessment of kidney, heart, liver, lung, and scavenger organs (spleen, bone marrow) revealed no detrimental systemic side effects of the degradation products, suggesting that the degradation-induced acute and chronic responses were local. See, FIG. 28C.

These data suggest that in vitro degradation rates of POSS-SMPs can be tuned by altering the length of PLA chains grafted to the POSS cores. POSS-SMPs elicited normal tissue responses to foreign biomaterials upon subcutaneous implantation while its degradation induced a later localized inflammatory response with minimal allergic reactions and no negative systemic effects on vital organs.

Example IX

Preparation of Porous Urethane-Crosslinked POSS-(PLA$_n$)$_8$ and its Retained Thermal Responsive Shape Memory Behavior Macroporous urethane-crosslinked POSS-(PLA$_n$)$_8$ scaffold can be fabricated by many methods including salt-leaching, porogen leaching, thermally induced phase separation, and solid freeform fabrication techniques, etc. The porous scaffold shown in FIG. 14 was prepared by the salt-leaching method. Briefly, the shape memory polymer crosslinking components (1 eq POSS-(PLA)$_{20}$, 4 eq hexamethylenediisocyanate, and 100 ppm dibutyltin dilaurate) were stirred in 2.5 times (w/w) CH$_2$Cl$_2$ at room temperature for 2 hours, before sodium chloride salt (70% w/w) was added and mixed thoroughly while the solvent was being evaporated under nitrogen. The mixture was left under nitrogen atmosphere overnight at room temperature before it was further crosslinked at 75° C. under nitrogen for 24 hours and at 75° C. under vacuum for 48 hours to remove any residual volatiles. The sodium chloride salt was removed by washing the composite in water under stirring for 24 hours. The scaffold was then freeze dried for 24 hours.

Figure 14:
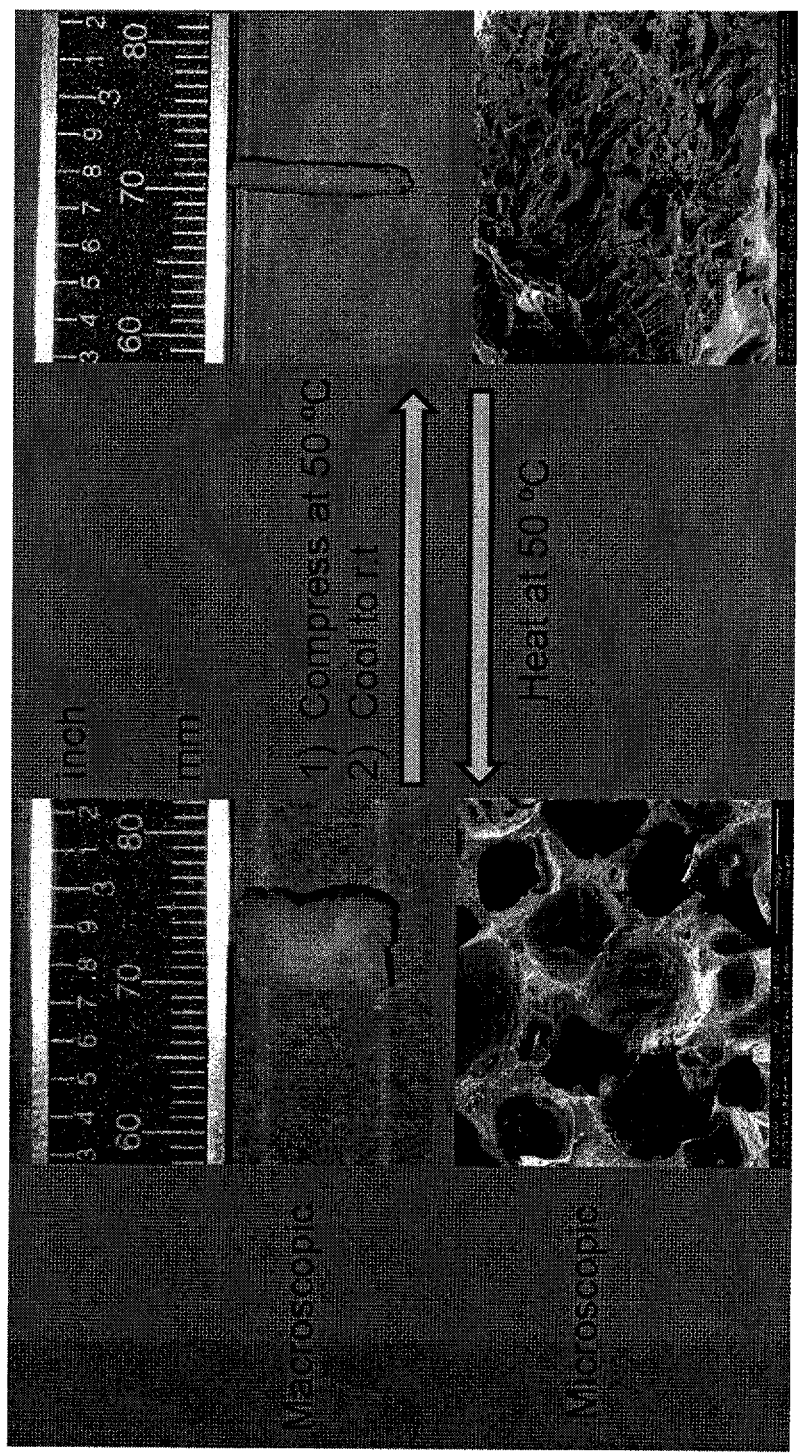
FIG. 14 shows a sample of a porous shape memory polymer collapsed under compression and reopened upon thermal stimulation, both macroscopically and microscopically as indicated by the scanning electron microscopy (SEM) image.
Figure 15:
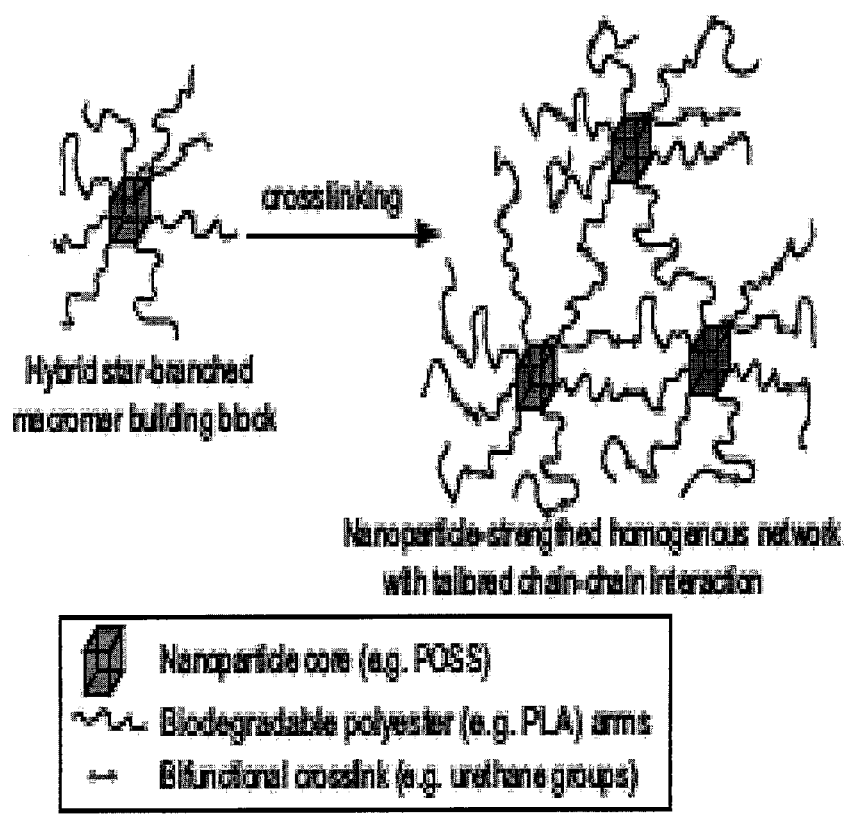
FIG. 15 depicts one embodiment of a nanostructured shape memory polymer network.

As shown in FIG. 14, the porous bulk material prepared using this method retained the thermal responsive shape memory behavior as illustrated by the collapse of the pores upon compression at 50° C., and the subsequent re-opening of the collapsed pores when the 50° C. thermal stimulation is reapplied to the compressed material. Such behavior is supported by the evidence of both thermal responsive macroscopic shape change and microscopic pore recovery as shown by the scanning electron micrographs (FIG. 14).

Example X

Preparation of Urethane-Crosslinked POSS-(PLA$_n$)$_8$/Tricalcium Phosphate (TCP) Composite A varying content of inorganic minerals can be incorporated with the shape memory polymer to fabricate composite material. For instance, the shape memory polymer crosslinking components (1 eq POSS-(PLA)$_{20}$, 4 eq hexamethylenediisocyanate, and 100 ppm dibutyltin dilaurate) were stirred in 2.5 times (w/w) CH$_2$Cl$_2$ at room temperature for 2 hours, before tricalcium phosphate (50% w/w) was added and mixed thoroughly while the solvent was being evaporated under nitrogen. The mixture was left under nitrogen atmosphere overnight at room temperature before it was further crosslinked at 75° C. under nitrogen for 24 h and at 75° C. under vacuum for 48 hours to remove any residual volatiles. The resulting dense composite was obtained with excellent structural integration between the biomineral and the polymer matrix.

Example XI

Preparation and Characterization of POSS-SMPs, Org-SMPs and Azido-Functionalized POSS-SMP-20-Az In a typical procedure, POSS-(PLA$_n$)$_8$ or Org-(PLA$_n$)$_8$, hexamethylene diisocyanate (HDI, ≥98.0%, Fluka) and 3-azidopropan-1-ol were mixed (molar ratios shown in Table III) in 2.5 times (wt/wt) dichloromethane. Catalytic amount (100 ppm) dibutyltin dilaurate (DBTDL, ≥95%, Aldrich) was added. The solution was stirred for 2 h at rt before being poured into Teflon molds. The solvent was evaporated at rt overnight under Ar, and the material was further crosslinked at 75° C. under Ar for 24 h. The final product was heated at 75° C. under vacuum for 48 h to remove residue volatiles. The complete conversion of HDI to urethane crosslinks was confirmed by the disappearance of the FTIR absorption at 2280 cm-1 (for isocyanate) upon crosslinking. FIG. 23. To determine the efficiency of crosslinking, POSS-SMPs were extracted in chloroform (100 mL/g) for 12 h and then dried under vacuum for 24 h. Gel content, defined by the ratio of dry weight before and after the solvent extraction, was calculated. Table III.

Example X

Preparation of POSS-SMP-20-Peptide

A specimen of POSS-SMP-20-Az (30.0 mm×6.0 mm×0.5 mm) was immersed into a 50-mL aqueous solution of (4-pentynoic acid)-Gly-Arg-Gly-Asp-Ser-Lys(FTIC)-COOH (BiomerTechnology, CA; 1.0 mg/mL), to which 0.8 mL CuSO$_4$ aqueous solution (2.5 mM) was added. The mixture was degassed under argon for 1 h before 0.8 mL of degassed solution of L(+)-ascorbic acid sodium salt (7.5 mM) was injected. The reaction was carried out at rt under argon for 24 h. The peptide-modified specimen was washed with water and ethanol for 1 h, respectively, and dried wider vacuum.

Example XI

Dynamic Thermal Mechanical Analysis (DMA)

The dynamic mechanical properties of POSS-SMPs and Org-SMPs were determined on a Q800 DMA (TA Instruments) equipped with tensile film clamps. Specimens with dimension of 30.0 mm×6.0 mm×0.5 mm were used for testing. The temperature was ramped from rt to 110° C. at a heating rate of 2.0° C./min. 0.02% strain amplitude and 1.0-Hz frequency were applied. Three specimens were tested for each sample.

Example XII

Nuclear Magnetic Resonance (NMR)

The NMR spectra were recorded on a Varian Mercury 400 MHz spectrometer at 298K. Chemical shifts were reported in parts per million (ppm) highfield from an internal standard, tetramethylsilane (TMS) in deuterated solvents (CDCl$_3$ or CD3OD).

Example XIII

Gel Permeation Chromatography (GPC)

The GPC characterization of star-branched macromers was carried out on a Varian Prostar HPLC system equipped with two 5-mm PLGel MiniMIX-D columns (Polymer Laboratory, Amherst, Mass.) and a PL-ELS2100 evaporative light scattering detector (Polymer Laboratory, Amherst, Mass.). THF was used as an eluent at a flow rate of 0.3 mL/min at rt. The number-averaged molecular weight (Mn) and the polydispersity index (PDI) were calculated by Cirrus AIA GPC Software using narrow dispersed poly(methyl methacrylate) as calibration standards.

Example IVX

High Resolution Mass Spectrometry (HRMS)

HRMS spectra were recorded on a Waters Q-Tof Premier mass spectrometer using electrospray ionization (ESI). Samples in methanol or methanol/water mixture (50:50) (1.0 ng/mL) were injected. Octahydroxylated POSS core was analyzed within 10 min of preparation.

Example XV

Fourier Transformed Infrared Spectroscopy (FTIR)

FTIR spectra were taken on a Nicolet IR 100 spectrometer (Thermo Electron Corporation) with 2-$cm^{-1}$ spectral resolution. Liquid samples were coated on NaCl salt window and the solid samples were mold-pressed into transparent discs with KBr, respectively.

Example XVI

End-Group Titration

Figure 26:
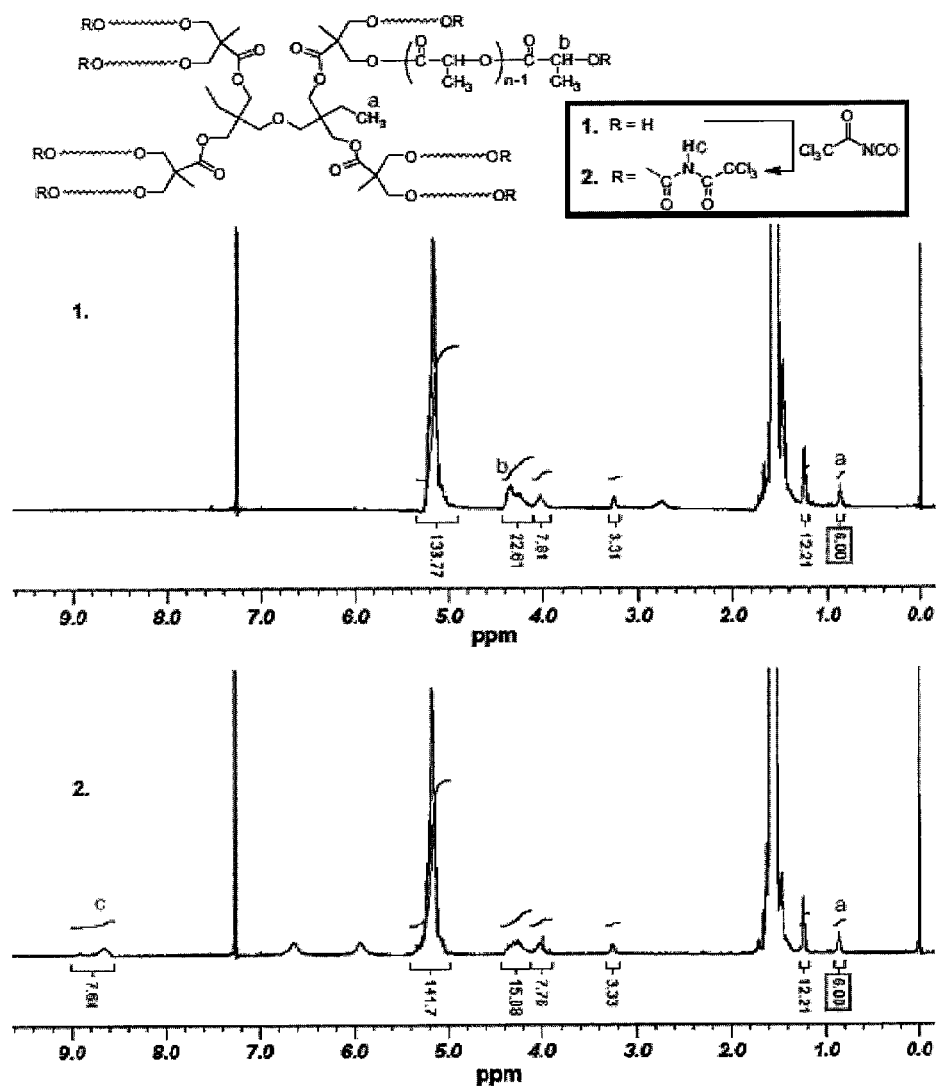
FIG. 26 presents exemplary data showing an $^1$H NMR spectra for an Org-(PLA$_{20}$)$_8$ in CDCl$_3$ before and after (bottom) titration with TAI.
Figure 27:
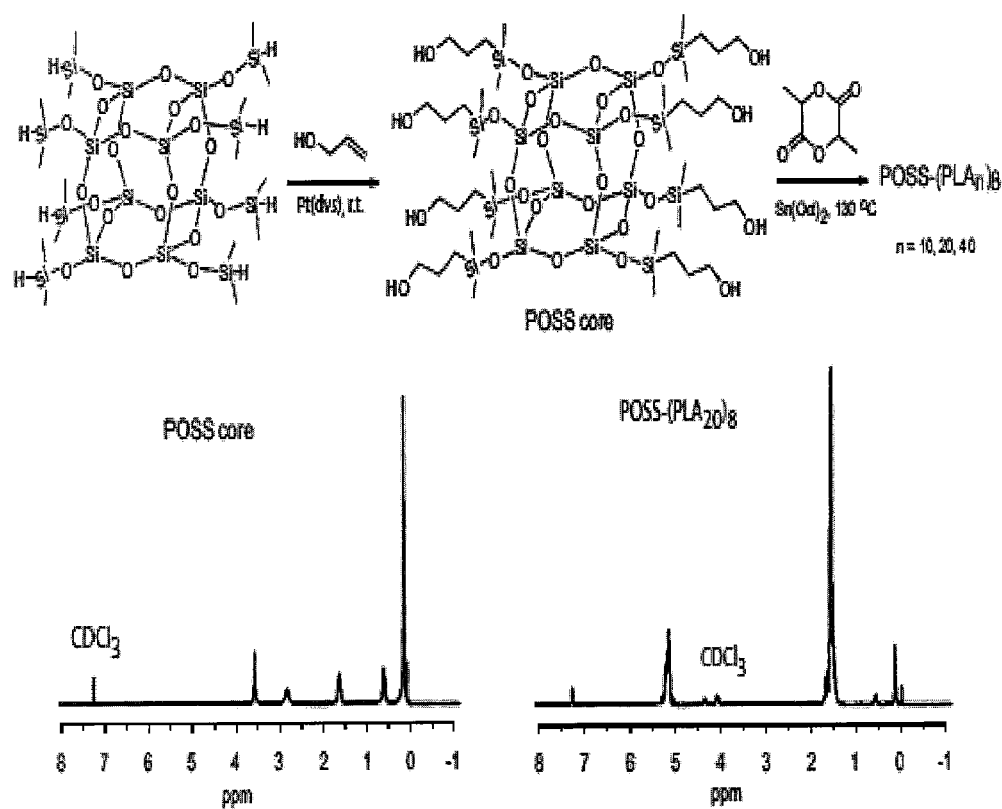
FIG. 27 presents exemplary data showing a synthetic scheme of a POSS core and macromer building block POSS-(PLA$_{20}$)$_8$ and associated $^1$H-NMR spectra.

To quantify the number of hydroxyl end groups per macromer, integration of end group proton signals by $^1$H NMR was carried out. Due to the overlap of the —CH(CH$_3$)—OH proton signals with those of the backbone protons in Org-(PLA$_n$)$_8$, hydroxyl groups were reacted with trichloroacetyl isocyanate (TAI) in situ to generate a more down-field shifted imidic proton signal for integration. This TAI titration method were successfully used to quantitatively determine protic end-groups in various synthetic polymers. Donovan et al., "A novel method for determination of polyester end-groups by NMR spectroscopy" *Polymer* 46(14):5005-5011 (2005); and Postma et al., "A simple method for determining protic end-groups of synthetic polymers by H-1 NMR spectroscopy" *Polymer* 47(6):1899-1911 (2006). In these cases, the number of hydroxyl (—OH) end-groups per macromer was determined by $^1$H NMR integration of the imidic protons of the derivatized end groups [—O—C(O)—NH—COCCl$_3$] ($\delta$-8-9 ppm). Briefly, ~15 mg macromer sample was dissolved in 1.0-mL CDCl$_3$ in an NMR tube, to which 30-mg TAI was added and allowed to react at room temperature for 1 h. $^1$H NMR spectra were taken before and after the 1-3 h reactin with TAI. The average number of —OH groups per macromer was calculated from the integration of the imidic proton signal (—O—C(O)—NH—COCCl$_3$; $\delta$-8-9 ppm) normalized against that of the methylene proton signal of the core —Si(CH$_3$)$_2$CH$_2$CH$_2$CH$_2$—O—C(O) in POSS-(PLA$_n$)$_8$ (FIG. 19) or the methyl protons of the core —[CH$_2$C(CH$_2$CH$_3$)(CH$_2$OCOR)$_2$]$_2$ in Org-(PLA$_n$)$_8$ (FIG. 26). The results are summaried in Table II.

Example XVII

Energy Minimization and Systemic Grid Scans

Using COMPASS force field and Discover Smart Minimizer (steepest descent method followed by conjugate gradient method and Newton method) of the Materials Studio 4.4 (Accelrys), energy-minimized structures of POSS core (3-D molecular volume: 1103.39 Å3) and the Organic core (3-D molecular volume: 539.334 Å3) were calculated in vacuum and used in subsequent grid scans. Systemic grid scans (10°/step) of torsion angles 1-5 of the POSS core and torsion angles 1-4 of the organic core were carried out using Universal force field in the Conformers Module (Materials Studio 4.4, Accelrys) to gain insights into the rotational freedom of the branching point of the respective anchors, as well as the total energy contours of the grid scans. FIG. 20A and FIG. 20B.

Example XVIII

Differential Scanning Calorimetry (DSC)

The glass transition temperatures ($T_g$ DSC) of POSS-SMPs were determined on a Q-20 DSC (TA Instruments). Each sample (~10 mg) was scanned from –50° C. to 120° C. (10° C./min), held at 120° C. for 2 min, cooled to –50° C. (10° C./min), held at 120° C. for 2 min, and re-heated to 120° C. (10° C./min). A constant nitrogen flow of 50 mL/min was applied. The $T_g$ DSC was determined as the midpoint of the inflection tangent of the second heating curve. Indium, gallium and tin were used as standards for the temperature calibration. Heat flow ($\Delta H$) versus temperature curves were also constructed. FIG. 17A.

Example IXX

Thermomechanical Properties of Org-SMPs as a Function of PLA Chain Length

The dynamic mechanical properties of the Org-SMP were determined on a Q800 DMA (TA Instruments) equipped with tensile film clamps following the same protocol applied to POSS-SMPs. Samples with dimension of 30.0 mm×6.0 mm×0.5 mm were used for testing. The temperature was ramped from rt to 110° C. at a heating rate of 2.0° C./min. 0.02% strain amplitude and 1.0-Hz frequency were applied. Three specimens were tested for each sample. The storage modulus (E') and loss angle (Tan $\delta$) versus temperature curves are also shown. FIG. 21.

Example XX

Stress-Controlled Cyclic Thermal Mechanical Testing

The testing was carried out on Q800 DMA using a tensile fixture. Specimens (30.0 mm×6.0 mm×0.5 mm) were first equilibrated at 85° C. for 10 min, and then cooled down to rt prior to testing. A preload force of 1-mN was applied to each specimen. Temperature was first raised to 85° C. (10° C./min) and kept isothermal for 5 min. The specimen was deformed at 85° C. at a stress ramping rate of 0.02-MPa/min from its "permanent" shape at the beginning of the Nth testing cycle, $\epsilon_p$(N-1), to the elongated shape under a final tensile stress of 0.16-MPa. The temperature were then cooled to rt with the stress kept constant at 0.16-MPa, and the sample length was recorded as $\epsilon_l$(N) (the strained sample length at the lower temperature at the Nth cycle). After being held at rt for 2 min, the applied stress was released to the 1-mN preload force, and the sample length was recorded as $\epsilon_u$(N) (the sample length at the lower temperature after unloading the tensile stress at the Nth cycle). Finally, the temperature was ramped from rt to 85° C. at a heating rate of 2.0° C./min and kept isothermal for 2 min, and the final sample length was recorded as $\epsilon_p$(N) (the recovered length at the Nth cycle or "permanent" length at the beginning of the (N+1)$^{th}$ cycle). At least 4 cycles were recorded for each specimen (all specimens showed nearly identical behavior after the 2nd or 3rd cycle. FIG. 17C. The strain fixing ratio (R$_f$) and the strain recovery ratio (R$_r$) in a given cycle N were determined using the following formulas:

$$R_f(N) = \frac{\varepsilon_u(N) - \varepsilon_p(N-1)}{\varepsilon_l(N) - \varepsilon_p(N-1)}$$

$$R_r(N) = \frac{\varepsilon_u(N) - \varepsilon_p(N)}{\varepsilon_u(N) - \varepsilon_p(N-1)}$$

Example XXI

Demonstration of Shape Memory Properties of POSS-SMP-20 Cast with Different Permanent Shapes Cup-shaped POSS-SMP-20 and surface-patterned POSS-SMP-20 were fabricated in proper molds according to Example TBD. Their shape memory responses are also presented. FIG. 22.

Example XXI

In vitro Hydrolytic Degradation of POSS-SMPs

Pre-weighed POSS-SMPs were incubated in PBS (100 mL/g) at 37° C. The specimens (n=3) were retrieved at various time points, weighed and then returned to fresh PBS. The morphology of POSS-SMPs retrieved at various time points were examined by scanning electron microscope (SEM).

To determine the hydrolytic degradation of POSS-SMPs, samples were incubated in PBS (100 mL/g) at 37° C. and retrieved at pre-determined time points. They were washed with deionized water and freeze-dried to determine the residue masses. The samples were then returned to a fresh PBS (100 mL/g) and incubated at 37° C. The percentage (%) of mass residue, defined as the residue dry mass at a given time point over the original dry weight of the sample, was plotted over time. The morphology of the crosslinked POSS-SMPs retrieved from PBS at various time points were examined on a Quanta 200 FEG MKII SEM (FEI Inc.). The samples were sputter-coated with Au and imaged under high vacuum at 10 kV.

In Vitro Results

The data show that POSS-SMPs exhibited PLA chain length-dependent in vitro hydrolytic degradation. FIG. 24A. Whereas POSS-SMP-10 and POSS-SMP-20 lost 50% of their original masses in 3 months in PBS (with substantial increase in scaffold porosity. FIG. 24B. POSS-SMP-40 reached 50% degradation in 7 months. These observations agree well with the observed dependence of T$_g$ on PLA arm length, supporting that a more densely packed chain structure in POSS-SMP-40 as a result of longer PLA arms and less POSS disruption is more resistant to hydrolytic degradation.

In sum, POSS-SMPs reached 50% degradation in 3-7 months upon incubation in PBS at 37° C., with the degradation rate correlating with the PLA chain length of the macromer building block. POSS-SMP-10 degraded the fastest, with significant increase in its porosity.

We claim:
1. A composition comprising a crosslinked network made from molecules of the following formula:
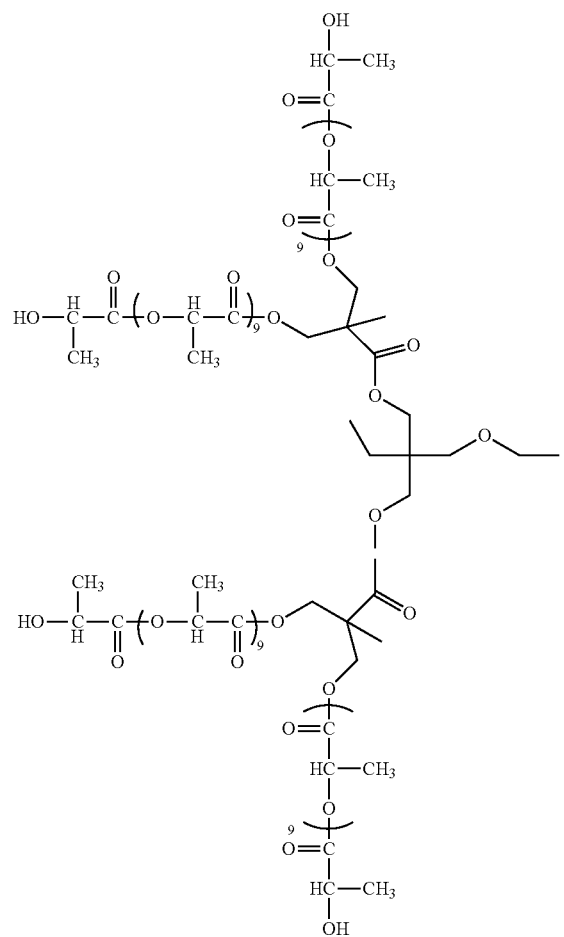
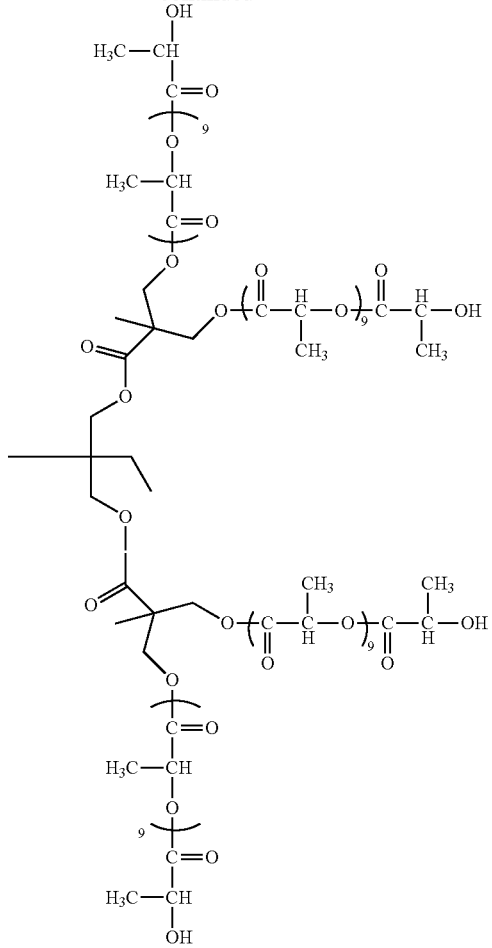
wherein the crosslinkable groups of the polymeric arms shown in the formula are crosslinked to form a network.
2. A composition comprising a crosslinked network made from molecules of the following formula:
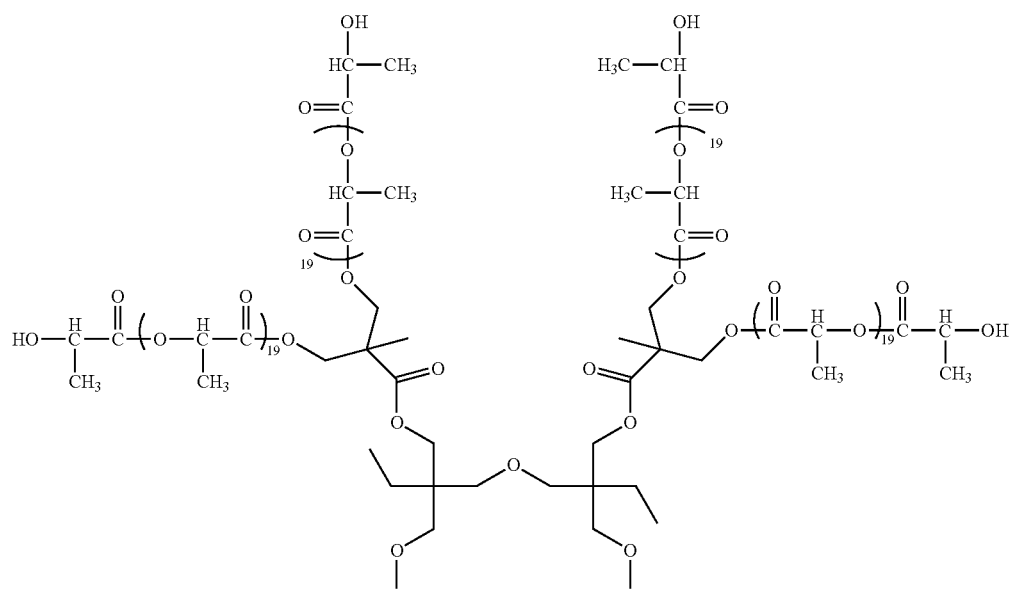

101
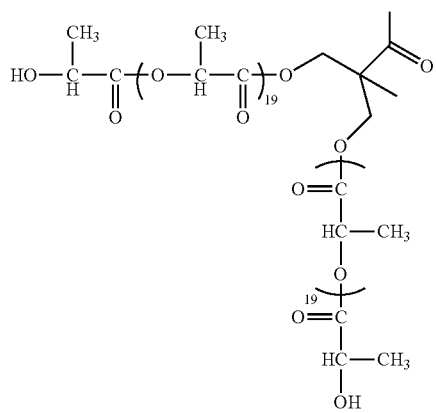
102
-continued
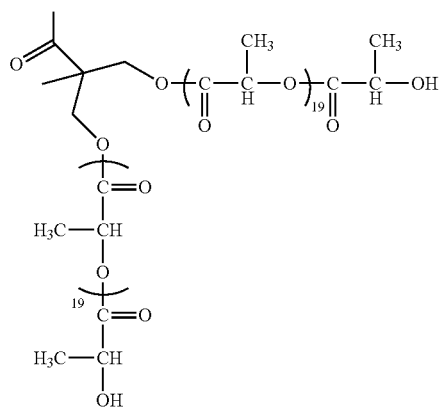
wherein the crosslinkable groups of the polymeric arms shown in the formula are crosslinked to form a network.
3. A composition comprising a crosslinked network made from molecules of the following formula:
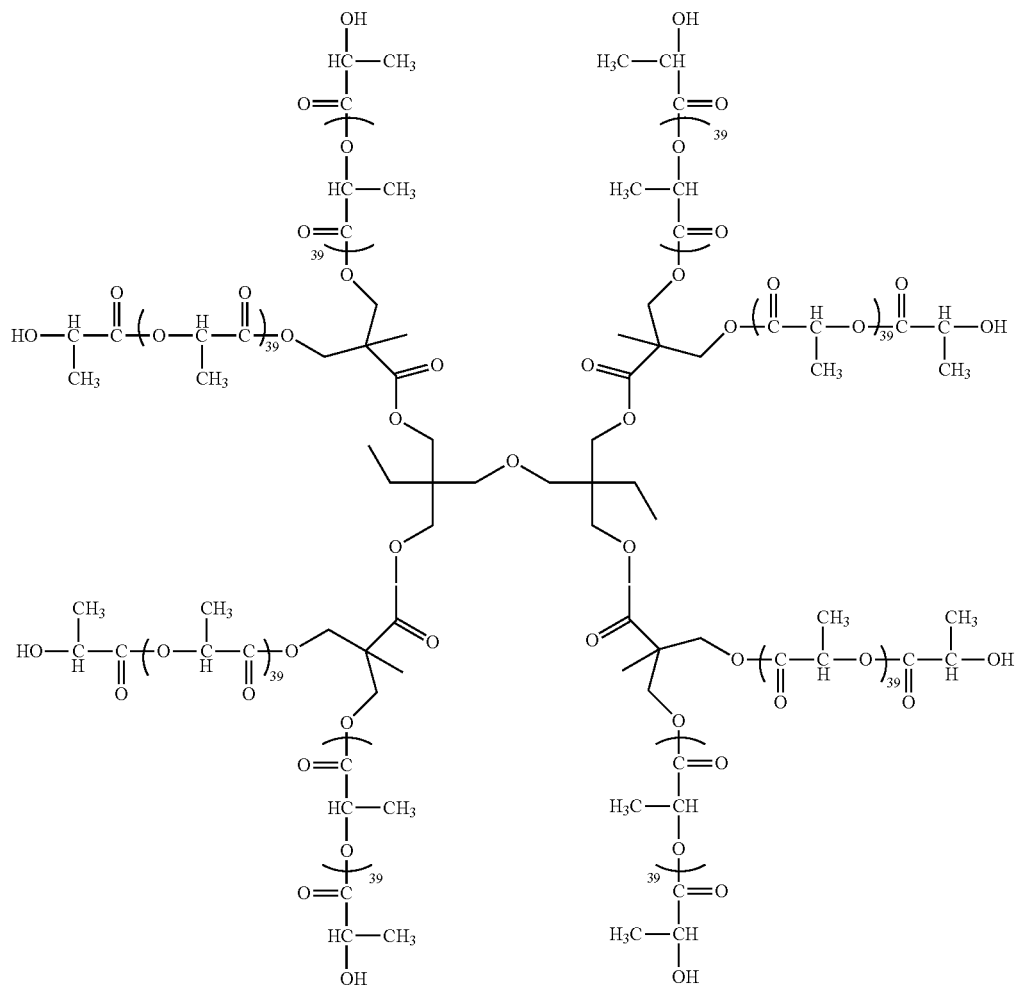
wherein the crosslinkable groups of the polymeric arms shown in the formula are crosslinked to form a network.

4. A composition comprising a crosslinked network made from molecules of the following formula:
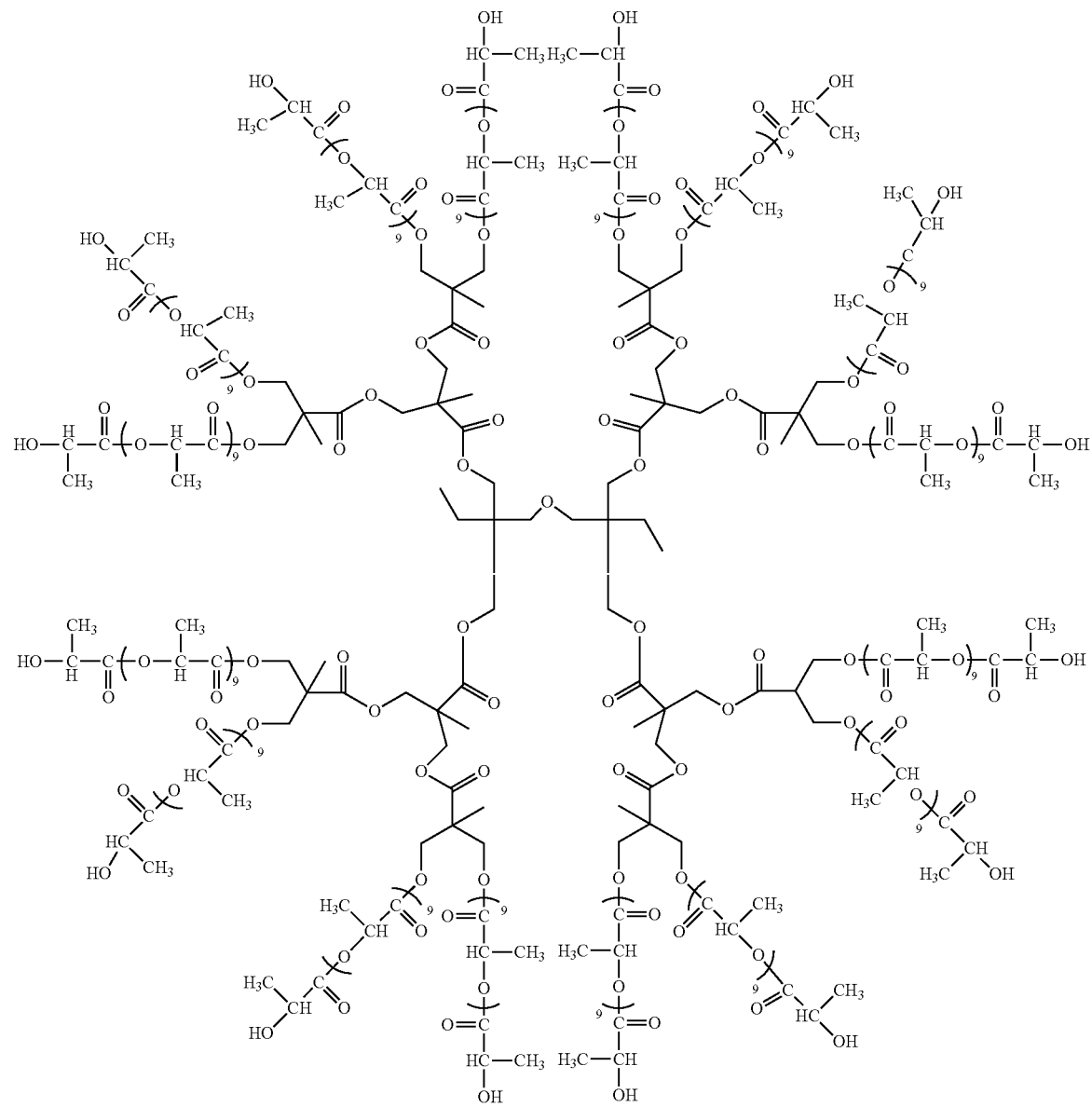
wherein the crosslinkable groups of the polymeric arms shown in the formula are crosslinked to form a network.

5. A composition comprising a crosslinked network made from molecules of the following formula:
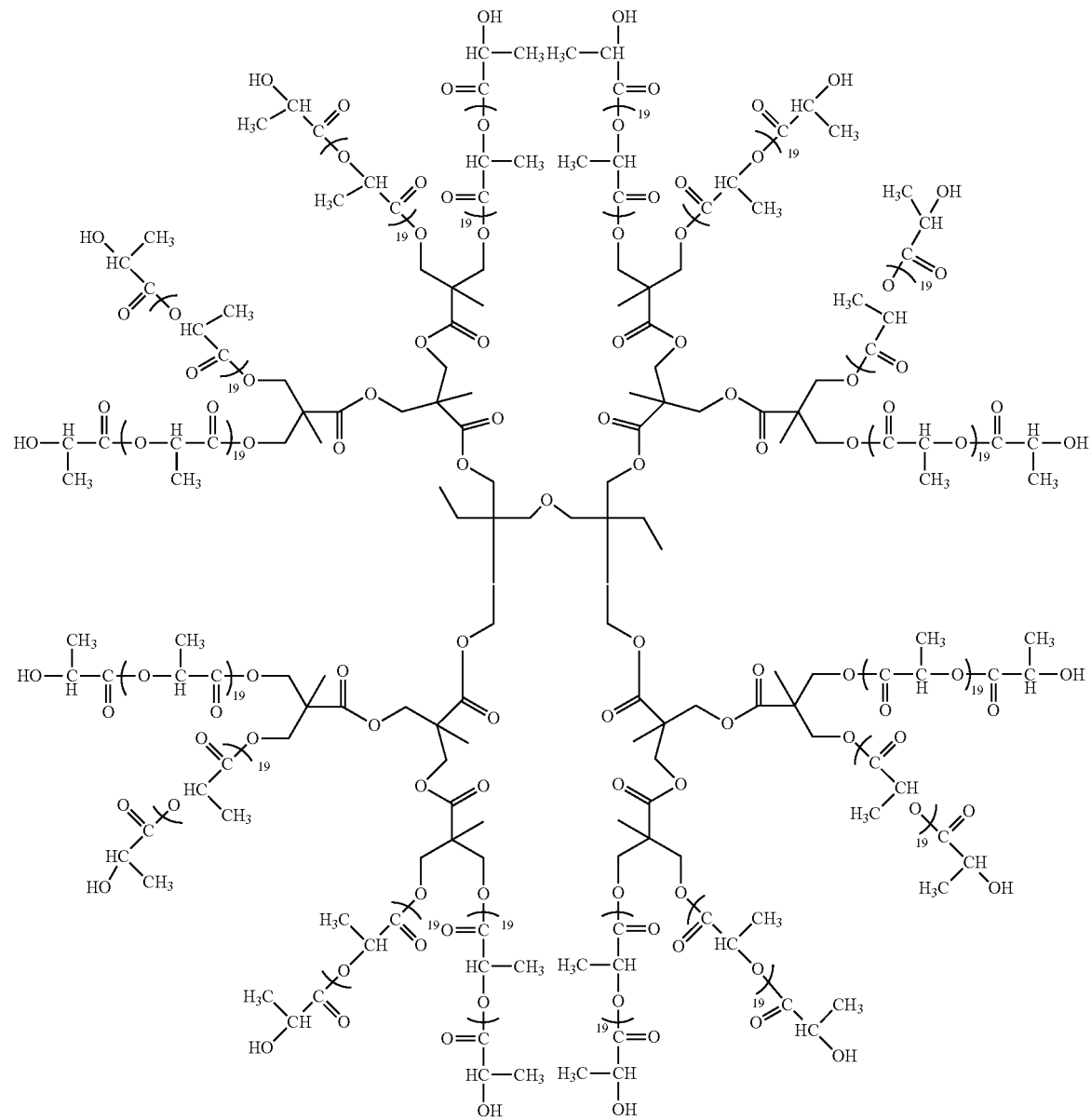
wherein the crosslinkable groups of the polymeric arms shown in the formula are crosslinked to form a network.

6. A composition comprising a crosslinked network made from molecules of the following formula:
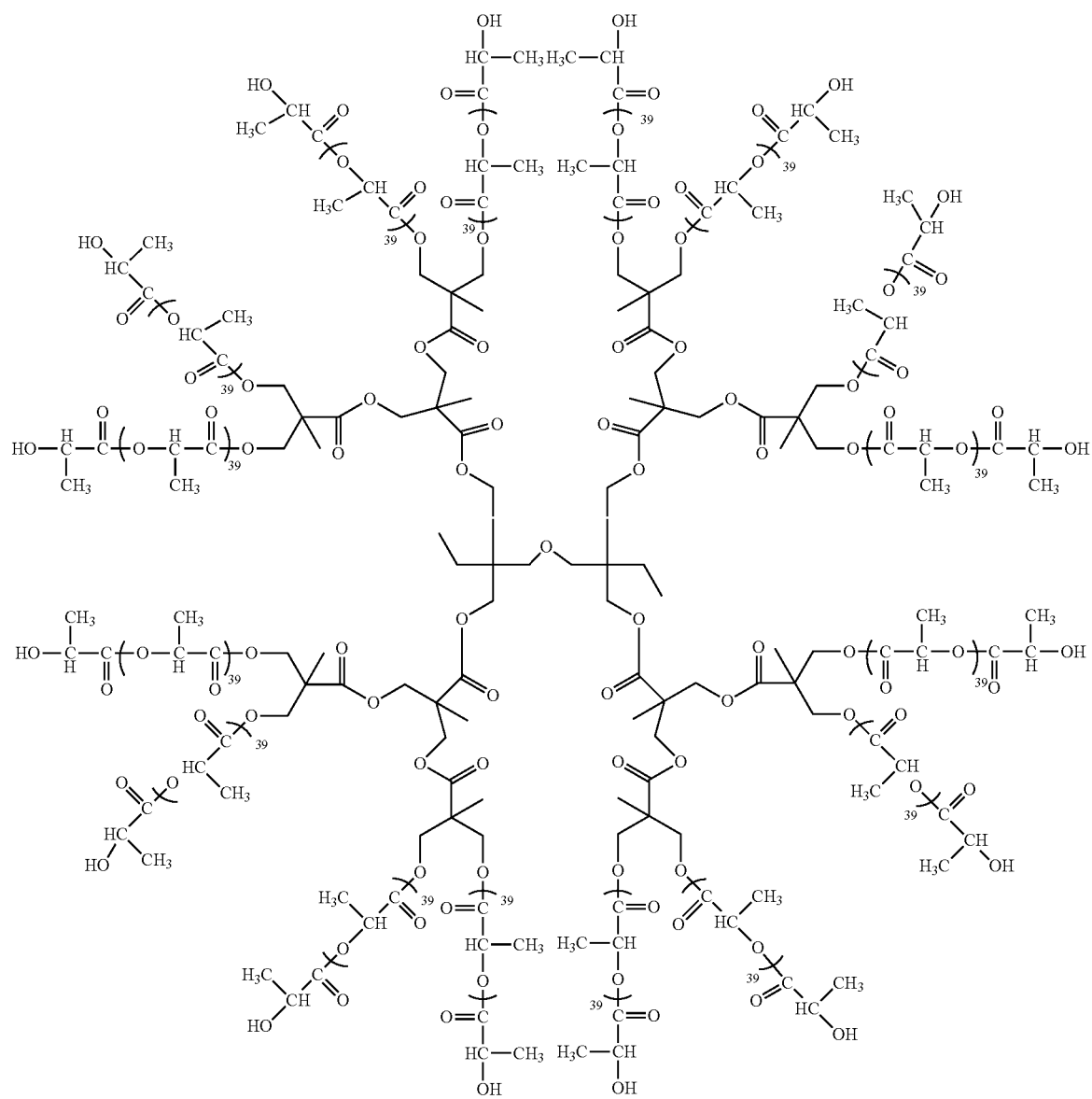
wherein the crosslinkable groups of the polymeric arms shown in the formula are crosslinked to form a network.
7. A composition comprising a crosslinked network made from molecules of the following formula:

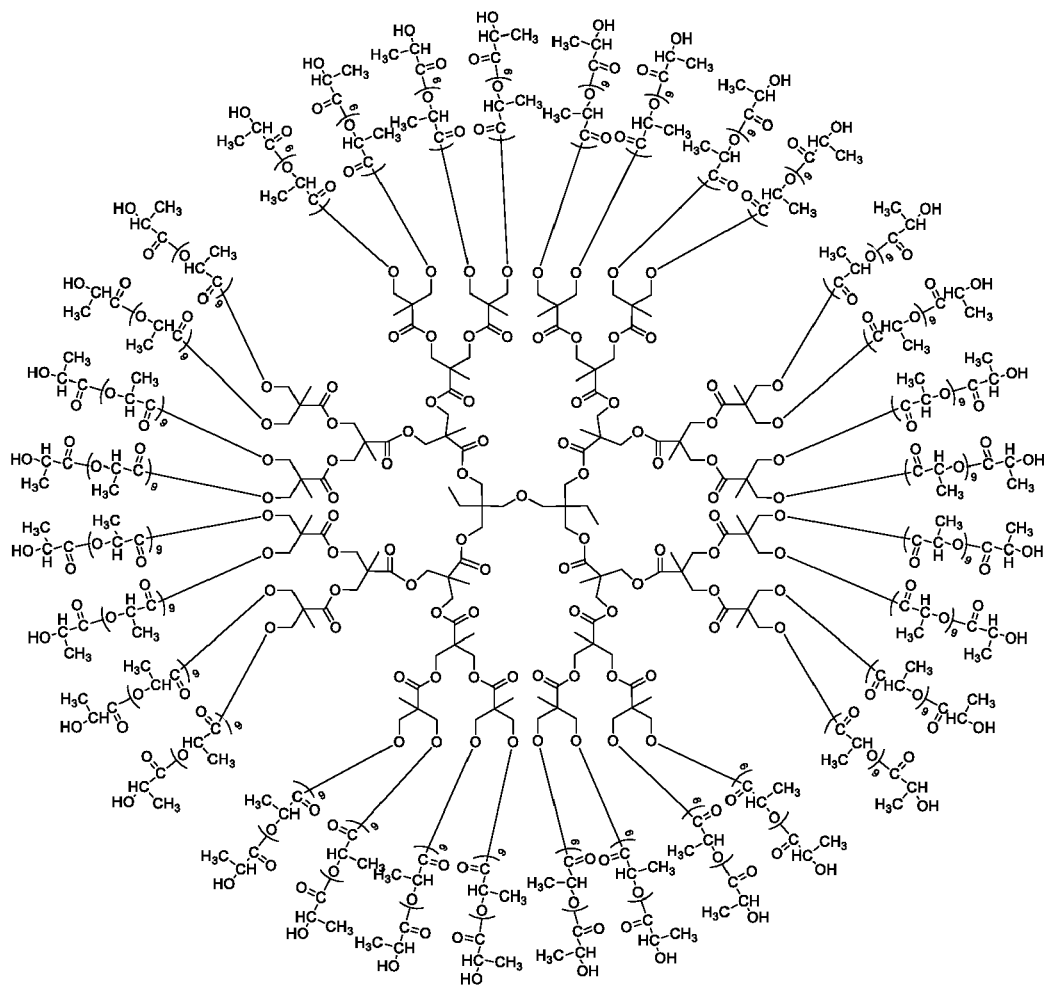

wherein the crosslinkable groups of the polymeric arms shown in the formula are crosslinked to form a network.

8. A composition comprising a crosslinked network made from molecules of the following formula:

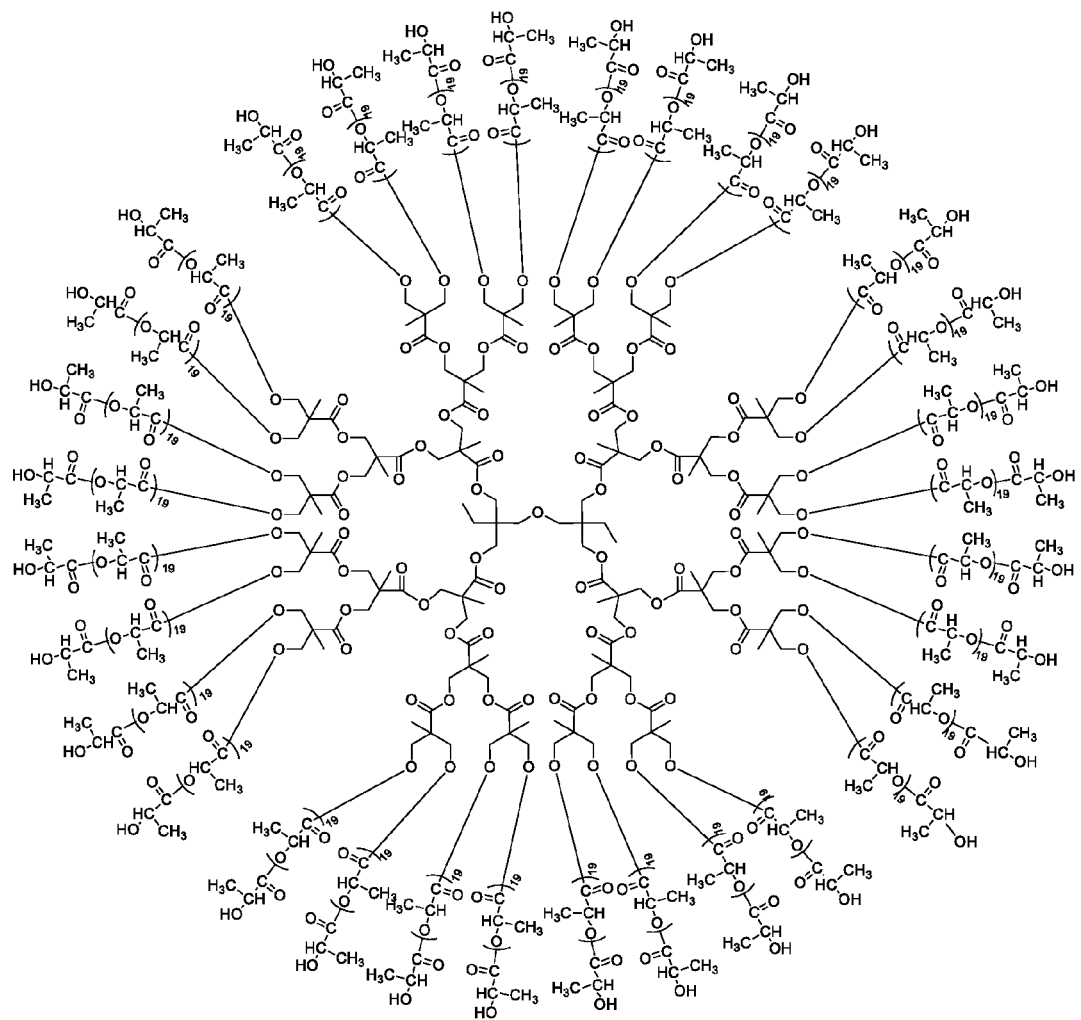

wherein the crosslinkable groups of the polymeric arms shown in the formula are crosslinked to form a network.

9. A composition comprising a crosslinked network made from molecules of the following formula:

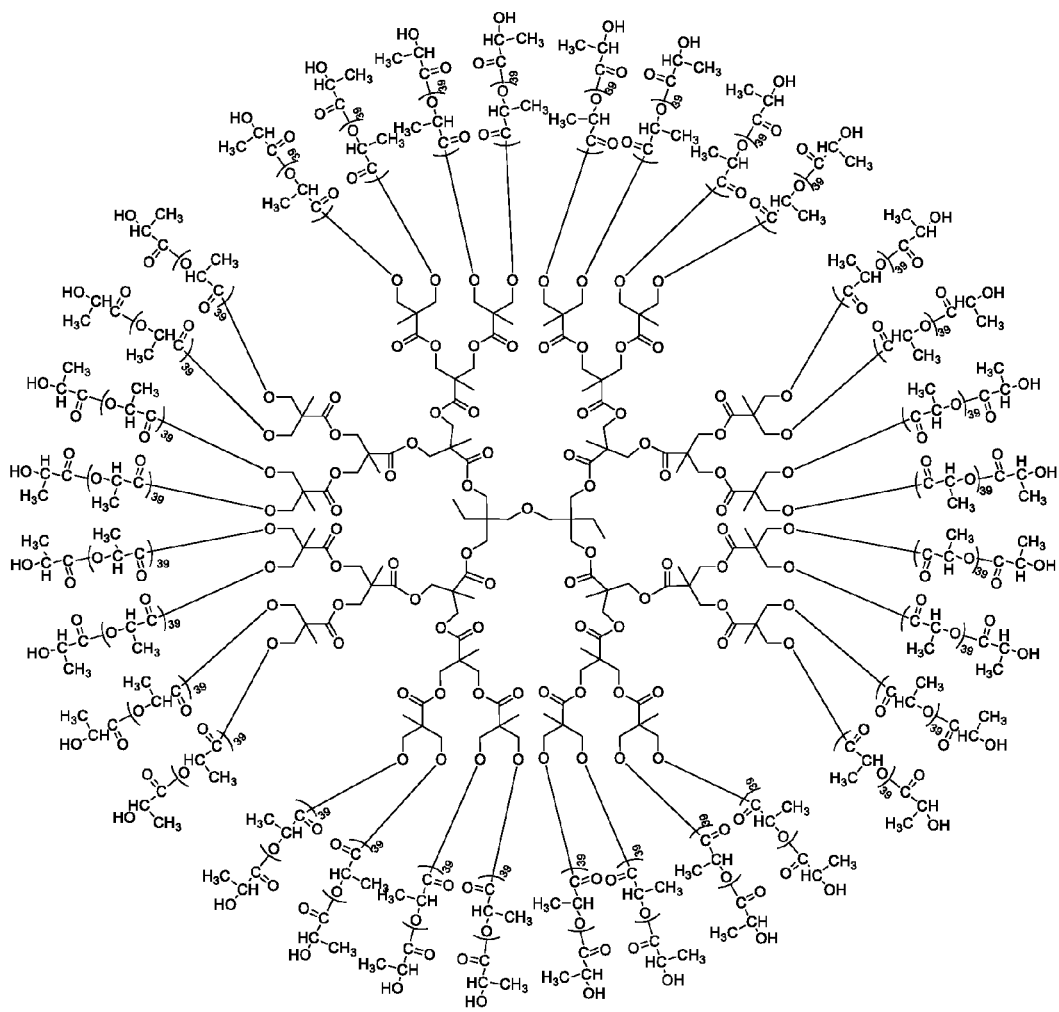

wherein the crosslinkable groups of the polymeric arms shown in the formula are crosslinked to form a network.

* * * * *